United States Patent
Steichen et al.

(10) Patent No.: US 12,281,142 B2
(45) Date of Patent: Apr. 22, 2025

(54) RECOMBINANT HIV Env POLYPEPTIDES AND THEIR USE

(71) Applicants: International AIDS Vaccine Initiative, Inc., New York, NY (US); The Scripps Research Institute, La Jolla, CA (US)

(72) Inventors: Jon M. Steichen, La Jolla, CA (US); William R. Schief, La Jolla, CA (US)

(73) Assignees: International AIDS Vaccine Initiative, Inc., New York, NY (US); The Scripps Research Institute, La Jolla, CA (US)

( * ) Notice: Subject to any disclaimer, the term of this patent is extended or adjusted under 35 U.S.C. 154(b) by 512 days.

(21) Appl. No.: 17/335,244

(22) Filed: Jun. 1, 2021

(65) Prior Publication Data
US 2021/0363195 A1 Nov. 25, 2021

Related U.S. Application Data

(63) Continuation-in-part of application No. PCT/US2019/063903, filed on Dec. 1, 2019.

(60) Provisional application No. 62/774,178, filed on Dec. 1, 2018.

(51) Int. Cl.
*C07K 14/16* (2006.01)
*A61K 9/51* (2006.01)
*A61K 38/00* (2006.01)
*A61K 39/21* (2006.01)
*C07K 16/10* (2006.01)
*C12N 7/00* (2006.01)

(52) U.S. Cl.
CPC .......... *C07K 14/162* (2013.01); *A61K 9/5169* (2013.01); *A61K 39/21* (2013.01); *C07K 16/1063* (2013.01); *C12N 7/00* (2013.01); *A61K 38/00* (2013.01); *C07K 2317/565* (2013.01); *C12N 2740/16134* (2013.01)

(58) Field of Classification Search
None
See application file for complete search history.

(56) References Cited

U.S. PATENT DOCUMENTS

2005/0064392 A1  3/2005  Hoxie et al.

FOREIGN PATENT DOCUMENTS

WO  2017/165674 A1  9/2017

*Primary Examiner* — Nicole Kinsey White
(74) *Attorney, Agent, or Firm* — Duane Morris LLP; Thomas J. Kowalski

(57) ABSTRACT

The present disclosure relates to recombinant HIV Env polypeptides and their use in the treatment and prevention of HIV/AIDS.

16 Claims, 23 Drawing Sheets
Specification includes a Sequence Listing.

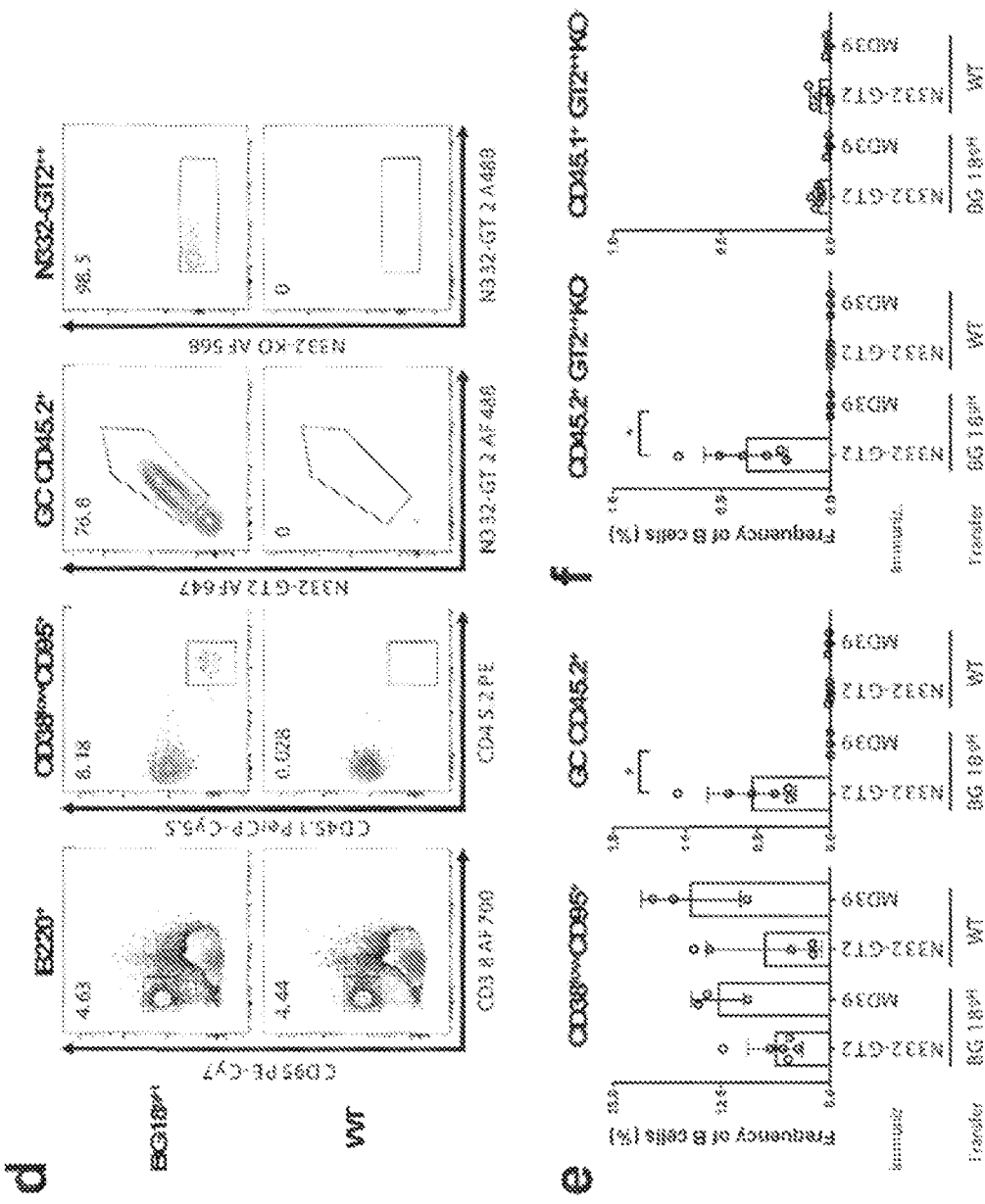

Figure 5 a

| | BG18* | BG18.11 (MinBG18) | BG18.6 | BG18 HC VL3-1 LC | BG18 HC VL3-21 LC | BG18 HC VL2-4 LC |
|---|---|---|---|---|---|---|
| CNE20 | | | | | 0.041 | 0.762 |
| 6535.3 | | 0.019 | | 0.01 | 0.049 | 0.104 |
| 1006_11_C3_1601 | | 0.033 | >50 | | 0.083 | >50 |
| 6811.v7.c18 | | 0.016 | | 0.012 | 0.063 | 0.033 |
| Du156.12 | | 0.016 | 0.62 | 0.029 | 0.206 | 0.152 |
| Q23.17 | | 0.024 | | 0.004 | 0.148 | 0.113 |
| P1981_C5_3 | | 0.019 | 4 | 0.015 | 0.101 | |
| T250-4 | | | >50 | | >50 | 0.184 |
| X2131_C1_B5 | | 0.028 | >50 | 0.016 | 0.427 | >50 |
| Ce1172_H1 | | 0.327 | >50 | 0.02 | 0.358 | 6.12 |
| 191084 B7-19 | | 0.072 | >50 | 0.034 | 0.647 | 5.6 |
| 6244_13_B5_4576 | | 0.073 | >50 | 0.042 | >50 | >50 |
| 3301.v1.c24 | | 0.037 | >50 | 0.067 | 0.296 | >50 |
| ZM135M.PL10a | | 0.068 | >50 | 0.03 | 2.08 | >50 |
| 246F C1G | | 0.0 | >50 | 0.029 | >50 | >50 |
| A07412M1.vrc12 | | 0.6 | >50 | 0.088 | >50 | >50 |
| T251-18 | | 0.057 | >50 | 0.13 | >50 | >50 |
| 0815.v3.c3 | | >50 | >50 | 4.7 | >50 | >50 |
| 3817.v2.c59 | | >50 | >50 | 0.508 | >50 | >50 |
| T278-50 | | >50 | >50 | 2 | >50 | >50 |
| 62357_14_D3_4589 | | >50 | >50 | 2 | >50 | >50 |
| TRJO4551.58 | | >50 | >50 | >50 | >50 | >50 |
| CAP210.2.00.E8 | | >50 | >50 | >50 | >50 | >50 |
| 0842.d12 | | 0.047 | 0.104 | 0.048 | 0.188 | 0.511 |
| geomean IC50 | 0.031 | | | | | |
| breadth (%) | 100 | 66.7 | 31.8 | 87.5 | 50 | 37.5 |

IC50 (μg/mL): <0.01, 0.01–0.1, 0.1–1, 1–30, >50, Not tested

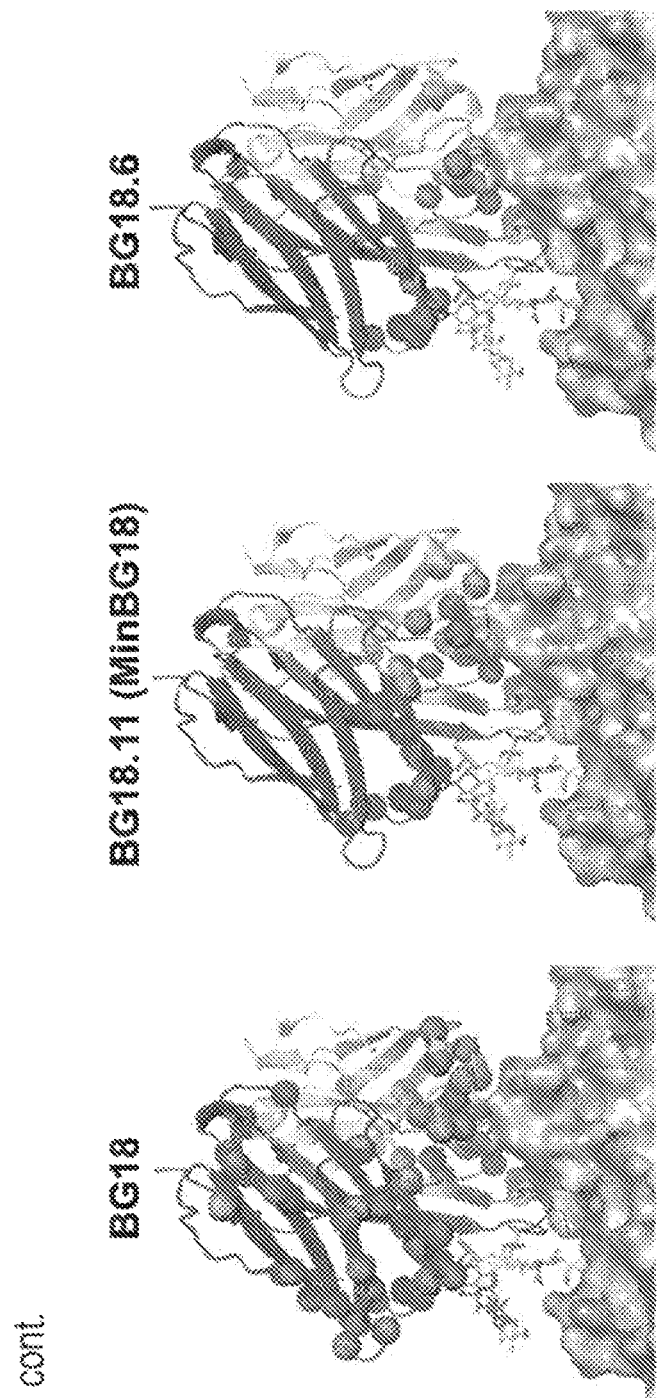
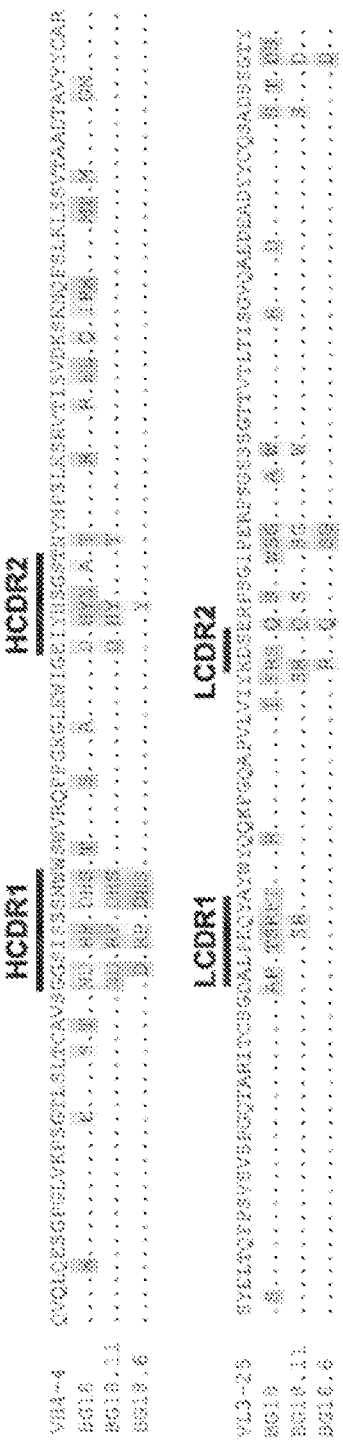
Figure 5 cont.

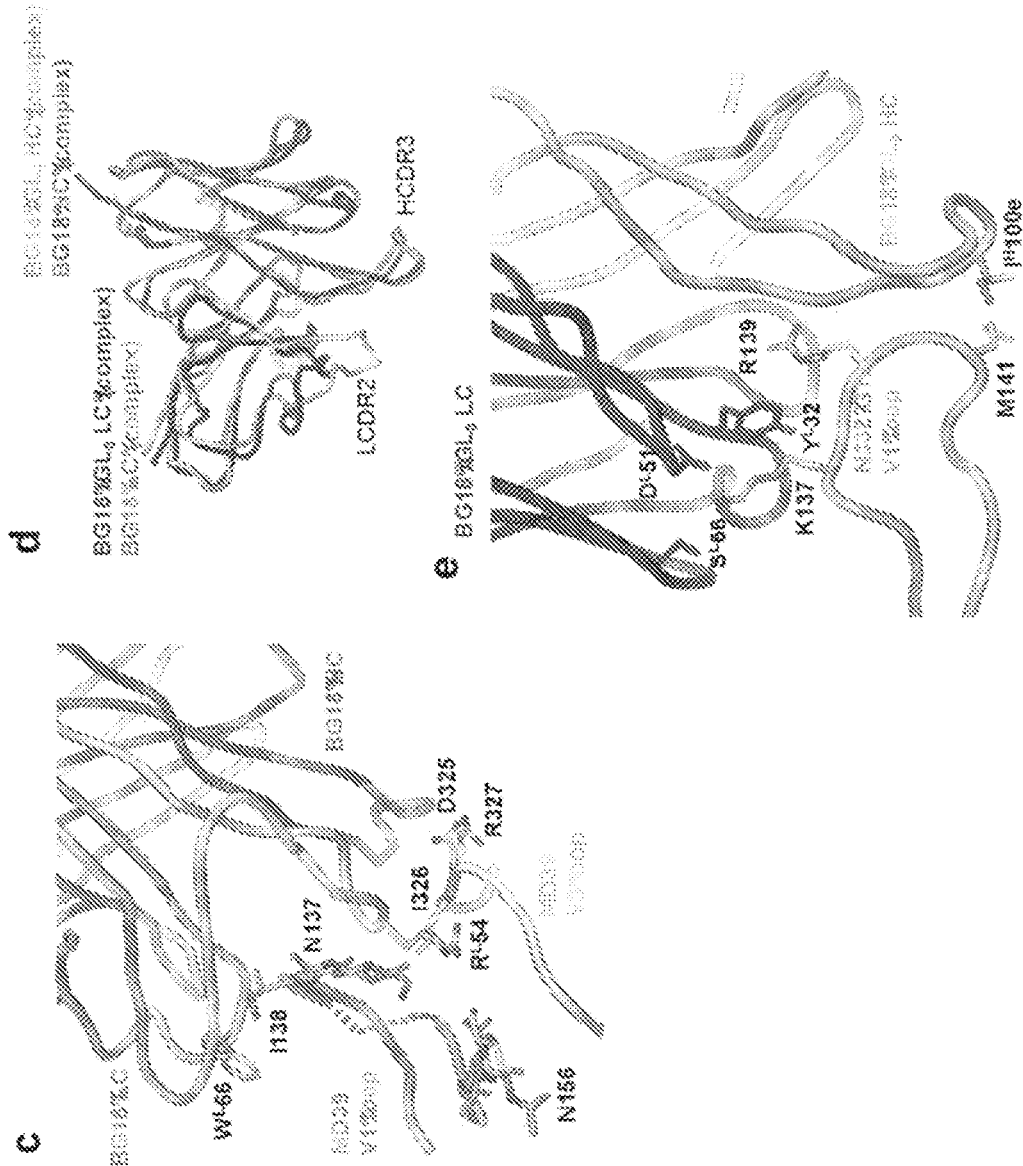

Figure 9 a

| Map | BG505_MD64_N332-GT2 + BG18 iGL | BG505_MD39 + BG18 |
|---|---|---|
| Data collection | | |
| Microscope | FEI Titan Krios | FEI Titan Krios |
| Voltage (kV) | 300 | 300 |
| Detector | Gatan K2 Summit | Gatan K2 Summit |
| Recording mode | Counting | Counting |
| Magnification (incl. post-magnification) | 46,543 | 46,543 |
| Movie micrograph pixelsize (Å) | 1.03 | 1.03 |
| Dose rate (e-/[(camera pixel)^s]) | 8.51 | 5.17 |
| Number of frames per movie micrograph | 40 | 48 |
| Frame exposure time (ms) | 250 | 250 |
| Movie micrograph exposure time (s) | 10 | 12 |
| Total dose (e-/Å²) | 85 | 62 |
| Defocus range (μm) | 0.5-2.5 | 1.0-2.5 |
| EM data processing | | |
| Number of movie micrographs | 1,031 | 691 |
| Number of molecular projection images in map | 46,273 | 46,306 |
| Symmetry | C3 | C3 |
| Map resolution (FSC 0.143; Å) | 3.65 | 4.43 |
| Local resolution range (Å) | 3.6-6.4 | 4.2-7.2 |
| Map sharpening B-factor (Å²) | -46 | -302 |
| Structure Building and Validation | | |
| Number of atoms in deposited model | | |
| gp120 | 10,461 | 10,281 |
| gp41 | 3,075 | 2,761 |
| Fab Fv | 5,325 | 5,421 |
| glycans | 1,188 | 1,877 |
| MolProbity score | 1.94 | 2.00 |
| Clashscore | 7.09 | 7.71 |
| Map correlation coefficient | 0.65 | 0.61 |
| EMRinger score | 1.78 | 1.95 |
| RMSD from ideal | | |
| Bond length (Å) | 0.010 | 0.010 |
| Bond angles (°) | 1.00 | 1.11 |
| Ramachandran plot | | |
| Favored (%) | 90.16 | 89.02 |
| Allowed (%) | 9.84 | 10.98 |
| Outliers (%) | 0.00 | 0.00 |
| Side chain rotamer outliers (%) | 0 | 0 |

| | BG18 iGL | BG18 mature |
|---|---|---|
| Fv:gp120 | 969.1 | 1725.2 |
| HC:gp120 | 618.1 | 982.0 |
| %total | 63.8% | 56.9% |
| LC:gp120 | 351.0 | 743.2 |
| %total | 36.2% | 43.1% |
| HCDR3:gp120 | 618.2 | 607.7 |
| %HC | 100% | 61.9% |
| %total | 63.8% | 35.2% |
| | | |
| Fv:glycans | 272.8 | 1024.6 |
| %total | 28.1% | 59.4% |
| HC:glycans | 252.4 | 764.3 |
| %HC | 40.8% | 77.8% |
| %total | 26.0% | 44.3% |
| LC:glycans | 20.4 | 260.3 |
| %LC | 5.8% | 35.0% |
| %total | 2.1% | 15.1% |
| HCDR3:glycans | 252.4 | 390.9 |
| %HCDR3 | 40.8% | 64.3% |
| %HC | 40.8% | 39.8% |
| %total | 26.0% | 22.7% |
| | | |
| Fv:N332 (HC/LC) | 272.8 (252.4/20.4) | 594.8 (535.3/59.5) |
| %total | 28.1% | 34.5% |
| Fv:N392 (HC/LC) | 0 (0/0) | 319.8 (232.0/87.8) |
| %total | 0% | 18.5% |
| Fv:N137 | No glycan | 146.2 (0/146.2) |
| %total | No glycan | 8.5% |

Figure 12 a

Data from flow cytometry

| Sample | Spleen | CountBright Beads | B cells | CD45.2 | CD45.1 GT2+KO- | CD45.2 GT2+KO- |
|---|---|---|---|---|---|---|
| 1 | WT 5000 #1 | 25461 | 5.45E+05 | 50 | 167 | 0 |
| 2 | WT 5000 #2 | 27841 | 5.88E+05 | 50 | 231 | 0 |
| 3 | BG18ᵘᶜᵃ 5000 #1 | 16925 | 6.30E+05 | 83 | 185 | 4 |
| 4 | BG18ᵘᶜᵃ 5000 #2 | 23162 | 6.71E+05 | 72 | 185 | 5 | b

Exact number in the flow cytometry sample (5 x 10^6 cells stained)

| Beads multipl. factor | Exact B cells | Exact CD45.2 | Exact CD45.1 GT2+KO- | Exact CD45.2 GT2+KO- |
|---|---|---|---|---|
| 2.08 | 1.13E+06 | 104 | 348 | 0 |
| 1.92 | 1.13E+06 | 96 | 443 | 0 |
| 3.33 | 2.10E+06 | 276 | 616 | 13 |
| 2.29 | 1.54E+06 | 165 | 423 | 11 | c

Exact total number in the spleen

| Total splenocytes (Nucleocounter) | Spleen multipl. factor | Total B cells | Total CD45.2 | Frequency CD45.2 | Total CD45.1 GT2+KO- | Frequency CD45.1 binders | Total CD45.2 GT2+KO- | Frequency CD45.2 binders | Ratio (binders per million of B cells) |
|---|---|---|---|---|---|---|---|---|---|
| 23.8E+06 | 5.96 | 6.76E+06 | 621 | 0.009% | 2073 | 0.031% | 0 | 0% | 0 |
| 31.3E+06 | 6.25 | 7.05E+06 | 600 | 0.009% | 2770 | 0.039% | 0 | 0% | 0 |
| 23.8E+06 | 4.76 | 9.99E+06 | 1316 | 0.013% | 2932 | 0.029% | 63 | 5% | 6 |
| 23.8E+06 | 6.75 | 1.04E+07 | 1113 | 0.011% | 2859 | 0.026% | 77 | 7% | 7 |

SEQUENCE LISTING

<160> NUMBER OF SEQ ID NOS: 111

<210> SEQ ID NO 1
<211> LENGTH: 856
<212> TYPE: PRT
<213> ORGANISM: Human Immunodeficiency Virus

<400> SEQUENCE: 1

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365
```

```
Pro Glu Ile Val Thr His Ser Phe Asn Cys Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
                420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
770                 775                 780

Leu Gly Arg Arg Gly Trp Glu Ala Leu Lys Tyr Trp Trp Asn Leu Leu
```

```
               785                 790                 795                 800
Gln Tyr Trp Ser Gln Glu Leu Lys Asn Ser Ala Val Ser Leu Leu Asn
                    805                 810                 815

Ala Thr Ala Ile Ala Val Ala Glu Gly Thr Asp Arg Val Ile Glu Val
                820                 825                 830

Val Gln Gly Ala Cys Arg Ala Ile Arg His Ile Pro Arg Arg Ile Arg
            835                 840                 845

Gln Gly Leu Glu Arg Ile Leu Leu
        850                 855

<210> SEQ ID NO 2
<211> LENGTH: 860
<212> TYPE: PRT
<213> ORGANISM: Human Immunodeficiency Virus

<400> SEQUENCE: 2

Met Arg Val Met Gly Ile Gln Arg Asn Cys Gln His Leu Phe Arg Trp
1               5                   10                  15

Gly Thr Met Ile Leu Gly Met Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Gly Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Val Met Ile Arg
            260                 265                 270

Ser Glu Asn Ile Thr Asn Asn Ala Lys Asn Ile Leu Val Gln Phe Asn
        275                 280                 285

Thr Pro Val Gln Ile Asn Cys Thr Arg Pro Asn Asn Thr Arg Lys
    290                 295                 300
```

-continued

```
Ser Ile Arg Ile Gly Pro Gly Gln Ala Phe Tyr Ala Thr Gly Asp Ile
305                 310                 315                 320

Ile Gly Asp Ile Arg Gln Ala His Cys Thr Val Ser Lys Ala Thr Trp
            325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
            355                 360                 365

Val Thr Thr His Ser Phe Asn Cys Gly Gly Glu Phe Phe Tyr Cys Asn
            370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
            405                 410                 415

Ile Lys Gln Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly
            435                 440                 445

Leu Ile Leu Thr Arg Asp Gly Gly Ser Thr Asn Ser Thr Thr Glu Thr
450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
            485                 490                 495

Arg Ala Lys Arg Val Val Gly Arg Glu Lys Arg Ala Val Gly Ile
            500                 505                 510

Gly Ala Val Phe Leu Gly Phe Leu Gly Ala Ala Gly Ser Thr Met Gly
            515                 520                 525

Ala Ala Ser Met Thr Leu Thr Val Gln Ala Arg Asn Leu Leu Ser Gly
530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
            565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Asn Val Pro Trp Asn
            595                 600                 605

Ser Ser Trp Ser Asn Arg Asn Leu Ser Glu Ile Trp Asp Asn Met Thr
            610                 615                 620

Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Glu Lys Asn Glu Gln Asp
            645                 650                 655

Leu Leu Ala Leu Asp Lys Trp Ala Ser Leu Trp Asn Trp Phe Asp Ile
            660                 665                 670

Ser Asn Trp Leu Trp Tyr Ile Lys Ile Phe Ile Met Ile Val Gly Gly
            675                 680                 685

Leu Ile Gly Leu Arg Ile Val Phe Ala Val Leu Ser Val Ile His Arg
            690                 695                 700

Val Arg Gln Gly Tyr Ser Pro Leu Ser Phe Gln Thr His Thr Pro Asn
705                 710                 715                 720

Pro Arg Gly Leu Asp Arg Pro Glu Arg Ile Glu Glu Glu Asp Gly Glu
```

```
                        725                 730                 735
Gln Asp Arg Gly Arg Ser Thr Arg Leu Val Ser Gly Phe Leu Ala Leu
                740                 745                 750

Ala Trp Asp Asp Leu Arg Ser Leu Cys Leu Phe Cys Tyr His Arg Leu
                755                 760                 765

Arg Asp Phe Ile Leu Ile Ala Ala Arg Ile Val Glu Leu Leu Gly His
                770                 775                 780

Ser Ser Leu Lys Gly Leu Arg Leu Gly Trp Glu Gly Leu Lys Tyr Leu
785                 790                 795                 800

Trp Asn Leu Leu Ala Tyr Trp Gly Arg Glu Leu Lys Ile Ser Ala Ile
                805                 810                 815

Asn Leu Phe Asp Thr Ile Ala Ile Ala Val Ala Glu Trp Thr Asp Arg
                820                 825                 830

Val Ile Glu Ile Gly Gln Arg Leu Cys Arg Ala Phe Leu His Ile Pro
                835                 840                 845

Arg Arg Ile Arg Gln Gly Leu Glu Arg Ala Leu Leu
                850                 855                 860

<210> SEQ ID NO 3
<211> LENGTH: 634
<212> TYPE: PRT
<213> ORGANISM: Human Immunodeficiency Virus

<400> SEQUENCE: 3

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
                20                  25                  30

Thr Glu Lys His Asn Val Trp Ala Thr His Ala Cys Val Pro Thr Asp
            35                  40                  45

Pro Asn Pro Gln Glu Ile His Leu Glu Asn Val Thr Glu Glu Phe Asn
        50                  55                  60

Met Trp Lys Asn Asn Met Val Glu Gln Met His Glu Asp Ile Ile Ser
65              70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240
```

```
Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630

<210> SEQ ID NO 4
<211> LENGTH: 634
<212> TYPE: PRT
```

<213> ORGANISM: Artificial Sequence
<220> FEATURE:
<223> OTHER INFORMATION: Artificial Polypeptide

<400> SEQUENCE: 4

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Asn Leu Leu Ser Asn Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Phe
        275                 280                 285

Gly Asp Ile Ile Gly Asp Ile Arg Met Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Val Leu
    370                 375                 380

Pro Cys Arg Ile Lys Gln Ile Ile Asn Met Trp Gln Arg Ile Gly Gln
```

```
                385                 390                 395                 400
Ala Met Tyr Ala Pro Pro Ile Gln Gly Val Ile Arg Cys Val Ser Asn
                    405                 410                 415
Ile Thr Gly Leu Ile Leu Thr Arg Asp Gly Gly Ser Thr Asn Ser Thr
                    420                 425                 430
Thr Glu Thr Phe Arg Pro Gly Gly Gly Asp Met Arg Asp Asn Trp Arg
                    435                 440                 445
Ser Glu Leu Tyr Lys Tyr Lys Val Val Lys Ile Glu Pro Leu Gly Val
                    450                 455                 460
Ala Pro Thr Arg Cys Lys Arg Val Gly Arg Arg Arg Arg
465                 470                 475                 480
Arg Ala Val Gly Ile Gly Ala Val Ser Leu Gly Phe Leu Gly Ala Ala
                    485                 490                 495
Gly Ser Thr Met Gly Ala Ala Ser Met Thr Leu Thr Val Gln Ala Arg
                    500                 505                 510
Asn Leu Leu Ser Gly Ile Val Gln Gln Gln Ser Asn Leu Leu Arg Ala
                    515                 520                 525
Pro Glu Pro Gln Gln His Leu Leu Lys Asp Thr His Trp Gly Ile Lys
                    530                 535                 540
Gln Leu Gln Ala Arg Val Leu Ala Val Glu His Tyr Leu Arg Asp Gln
545                 550                 555                 560
Gln Leu Leu Gly Ile Trp Gly Cys Ser Gly Lys Leu Ile Cys Cys Thr
                    565                 570                 575
Asn Val Pro Trp Asn Ser Ser Trp Ser Asn Arg Asn Leu Ser Glu Ile
                    580                 585                 590
Trp Asp Asn Met Thr Trp Leu Gln Trp Asp Lys Glu Ile Ser Asn Tyr
                    595                 600                 605
Thr Gln Ile Ile Tyr Gly Leu Leu Glu Glu Ser Gln Asn Gln Gln Glu
                    610                 615                 620
Lys Asn Glu Gln Asp Leu Leu Ala Leu Asp
625                 630

<210> SEQ ID NO 5
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 5

Ala Glu Asn Leu Trp Val Thr Val Tyr Tyr Gly Val Pro Val Trp Lys
1               5                   10                  15
Asp Ala Glu Thr Thr Leu Phe Cys Ala Ser Asp Ala Lys Ala Tyr Glu
                    20                  25                  30
Thr Glu Lys His Asn Val Trp Ala Thr His Ala Cys Val Pro Thr Asp
                    35                  40                  45
Pro Asn Pro Gln Glu Ile His Leu Glu Asn Val Thr Glu Glu Phe Asn
                    50                  55                  60
Met Trp Lys Asn Asn Met Val Glu Gln Met His Glu Asp Ile Ile Ser
65                  70                  75                  80
Leu Trp Asp Gln Ser Leu Lys Pro Cys Val Lys Leu Thr Pro Leu Cys
                    85                  90                  95
Val Thr Leu Gln Cys Thr Asn Tyr Ala Pro Asn Leu Leu Ser Asn Met
                    100                 105                 110
Arg Gly Glu Ile Lys Asn Cys Ser Phe Asn Met Thr Thr Glu Leu Arg
```

-continued

```
            115                 120                 125
Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Phe
        275                 280                 285

Gly Asp Val Leu Gly Asp Val Arg Met Ala His Cys Asn Ile Ser Lys
290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540
```

```
Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
610                 615                 620

Lys Asn Glu Gln Asp Leu Leu Ala Leu Asp
625                 630

<210> SEQ ID NO 6
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 6

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Leu Ser Asn Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270
```

Thr Val Lys Ser Ile Arg Ile Gly Pro Gly Gln Ala Phe Tyr Tyr Phe
            275                 280                 285

Gly Asp Val Leu Gly His Val Arg Met Ala His Cys Asn Ile Ser Lys
        290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630

<210> SEQ ID NO 7
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 7

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Arg Ser Met Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Phe
        275                 280                 285

Gly Asp Val Leu Gly Asp Val Arg Met Ala His Cys Asn Ile Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415
```

-continued

Ile Thr Gly Leu Ile Leu Thr Arg Asp Gly Ser Thr Asn Ser Thr
            420                 425                 430

Thr Glu Thr Phe Arg Pro Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Val Gly Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630

<210> SEQ ID NO 8
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 8

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Arg Ser Met Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

```
Gln Ile Asn Glu Asn Gln Gly Asn Arg Ser Asn Ser Asn Lys Glu
145                 150                 155                 160

Tyr Arg Leu Ile Asn Cys Asn Thr Ser Ala Ile Thr Gln Ala Cys Pro
            165                 170                 175

Lys Val Ser Phe Glu Pro Ile Pro Ile His Tyr Cys Ala Pro Ala Gly
                180                 185                 190

Phe Ala Ile Leu Lys Cys Lys Asp Lys Lys Phe Asn Gly Thr Gly Pro
            195                 200                 205

Cys Pro Ser Val Ser Thr Val Gln Cys Thr His Gly Ile Lys Pro Val
        210                 215                 220

Val Ser Thr Gln Leu Leu Leu Asn Gly Ser Leu Ala Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
                260                 265                 270

Thr Val Lys Ser Ile Arg Ile Gly Pro Gly Gln Ala Phe Tyr Tyr Phe
            275                 280                 285

Gly Asp Val Leu Gly His Val Arg Met Ala His Cys Asn Ile Ser Lys
        290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
        370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
        450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
                500                 505                 510

Asn Leu Leu Ser Gly Ile Val Gln Gln Ser Asn Leu Leu Arg Ala
                515                 520                 525

Pro Glu Pro Gln Gln His Leu Leu Lys Asp Thr His Trp Gly Ile Lys
            530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
```

-continued

```
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630

<210> SEQ ID NO 9
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 9

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Arg Ser Met Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Ser Asn Asn
            260                 265                 270

Thr Val Lys Ser Ile Arg Ile Gly Pro Gly Gln Ala Phe Tyr Tyr Phe
        275                 280                 285

Gly Asp Val Leu Gly His Val Arg Met Ala His Cys Asn Ile Ser Lys
```

```
            290                 295                 300
Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Val Val Gly Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630

<210> SEQ ID NO 10
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 10

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
```

```
                    20                  25                  30
Thr Glu Lys His Asn Val Trp Ala Thr His Ala Cys Val Pro Thr Asp
                35                  40                  45

Pro Asn Pro Gln Glu Ile His Leu Glu Asn Val Thr Glu Glu Phe Asn
            50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Arg Ser Met Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
        130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
        210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Ser Asn Asn
            260                 265                 270

Thr Val Lys Ser Ile Arg Ile Gly Pro Gly Gln Ala Phe Tyr Tyr Phe
        275                 280                 285

Gly Asp Val Leu Gly His Val Arg Met Ala His Cys Asn Ile Ser Lys
        290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
        370                 375                 380

Pro Cys Trp Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445
```

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
                500                 505                 510

Asn Leu Leu Ser Gly Ile Val Gln Gln Gln Ser Asn Leu Leu Arg Ala
            515                 520                 525

Pro Glu Pro Gln Gln His Leu Leu Lys Asp Thr His Trp Gly Ile Lys
        530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
                580                 585                 590

Trp Asp Asn Met Thr Trp Leu Gln Trp Asp Lys Glu Ile Ser Asn Tyr
            595                 600                 605

Thr Gln Ile Ile Tyr Gly Leu Leu Glu Glu Ser Gln Asn Gln Gln Glu
        610                 615                 620

Lys Asn Glu Gln Asp Leu Leu Ala Leu Asp
625                 630

<210> SEQ ID NO 11
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 11

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Asn Leu Arg Ser Asp Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

-continued

```
Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Phe
        275                 280                 285

Gly Asp Val Leu Gly Asp Val Asp Met Ala Lys Cys Thr Ile Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Val Gly Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Ser Asn Leu Leu Arg Ala
        515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590
```

-continued

```
Trp Asp Asn Met Thr Trp Leu Gln Trp Asp Lys Glu Ile Ser Asn Tyr
            595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630

<210> SEQ ID NO 12
<211> LENGTH: 634
<212> TYPE: PRT
<213> ORGANISM: Artificial Sequence
<220> FEATURE:
<223> OTHER INFORMATION: Artificial Polypeptide

<400> SEQUENCE: 12

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Glu Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Glu
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Arg Ser Met Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Phe
        275                 280                 285

Gly Asp Val Leu Gly Asp Val Arg Met Ala His Cys Asn Ile Ser Lys
    290                 295                 300

Ala Thr Trp Asn Glu Thr Leu Gly Lys Val Val Lys Gln Leu Arg Lys
305                 310                 315                 320
```

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
        515                 520                 525

Pro Glu Pro Gln Gln His Leu Leu Lys Leu Thr Val Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp
625                 630

<210> SEQ ID NO 13
<211> LENGTH: 819
<212> TYPE: PRT
<213> ORGANISM: Artificial Sequence
<220> FEATURE:
<223> OTHER INFORMATION: Artificial Polypeptide

<400> SEQUENCE: 13

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

```
Pro Asn Pro Gln Glu Ile His Leu Glu Asn Val Thr Glu Glu Phe Asn
 50                  55                  60
Met Trp Lys Asn Asn Met Val Glu Gln Met His Glu Asp Ile Ile Ser
 65                  70                  75                  80
Leu Trp Asp Gln Ser Leu Lys Pro Cys Val Lys Leu Thr Pro Leu Cys
                 85                  90                  95
Val Thr Leu Gln Cys Thr Asn Tyr Ala Pro Lys Leu Arg Ser Met Met
            100                 105                 110
Arg Gly Glu Ile Lys Asn Cys Ser Phe Asn Met Thr Thr Glu Leu Arg
            115                 120                 125
Asp Lys Lys Gln Lys Val Tyr Ser Leu Phe Tyr Arg Leu Asp Val Val
130                 135                 140
Gln Ile Asn Glu Asn Gln Gly Asn Arg Ser Asn Asn Ser Asn Lys Glu
145                 150                 155                 160
Tyr Arg Leu Ile Asn Cys Asn Thr Ser Ala Ile Thr Gln Ala Cys Pro
                165                 170                 175
Lys Val Ser Phe Glu Pro Ile Pro Ile His Tyr Cys Ala Pro Ala Gly
            180                 185                 190
Phe Ala Ile Leu Lys Cys Lys Asp Lys Lys Phe Asn Gly Thr Gly Pro
            195                 200                 205
Cys Pro Ser Val Ser Thr Val Gln Cys Thr His Gly Ile Lys Pro Val
210                 215                 220
Val Ser Thr Gln Leu Leu Leu Asn Gly Ser Leu Ala Glu Glu Glu Val
225                 230                 235                 240
Ile Ile Arg Ser Glu Asn Ile Thr Asn Asn Ala Lys Asn Ile Leu Val
                245                 250                 255
Gln Leu Asn Thr Pro Val Gln Ile Asn Cys Thr Arg Pro Asn Asn Asn
            260                 265                 270
Thr Val Lys Ser Ile Arg Ile Gly Pro Gly Gln Ala Phe Tyr Tyr Phe
            275                 280                 285
Gly Asp Val Leu Gly Asp Val Arg Met Ala His Cys Asn Ile Ser Lys
290                 295                 300
Ala Thr Trp Asn Glu Thr Leu Gly Lys Val Val Lys Gln Leu Arg Lys
305                 310                 315                 320
His Phe Gly Asn Asn Thr Ile Ile Arg Phe Ala Gln Ser Ser Gly Gly
                325                 330                 335
Asp Leu Glu Val Thr Thr His Ser Phe Asn Cys Gly Gly Glu Phe Phe
            340                 345                 350
Tyr Cys Asn Thr Ser Gly Leu Phe Asn Ser Thr Trp Ile Ser Asn Thr
            355                 360                 365
Ser Val Gln Gly Ser Asn Ser Thr Gly Ser Asn Asp Ser Leu Ile Leu
370                 375                 380
Pro Cys Arg Ile Lys Gln Ile Ile Asn Met Trp Gln Arg Ile Gly Gln
385                 390                 395                 400
Ala Met Tyr Ala Pro Pro Ile Gln Gly Val Ile Arg Cys Val Ser Asn
                405                 410                 415
Ile Thr Gly Leu Ile Leu Thr Arg Asp Gly Gly Ser Thr Asn Ser Thr
            420                 425                 430
Thr Glu Thr Phe Arg Pro Gly Gly Gly Asp Met Arg Asp Asn Trp Arg
            435                 440                 445
Ser Glu Leu Tyr Lys Tyr Lys Val Val Lys Ile Glu Pro Leu Gly Val
450                 455                 460
Ala Pro Thr Arg Cys Lys Arg Arg Val Val Gly Ser His Ser Gly Ser
```

```
            465                 470                 475                 480
    Gly Gly Ser Gly Ser Gly Gly His Ala Ala Val Gly Ile Gly Ala Val
                        485                 490                 495

Ser Leu Gly Phe Leu Gly Ala Ala Gly Ser Thr Met Gly Ala Ala Ser
                        500                 505                 510

Met Thr Leu Thr Val Gln Ala Arg Asn Leu Pro Ser Gly Ile Val Gln
                        515                 520                 525

Gln Gln Ser Asn Leu Leu Arg Ala Pro Glu Pro Gln Gln His Leu Leu
                        530                 535                 540

Lys Asp Thr His Trp Gly Ile Lys Gln Leu Gln Ala Arg Val Leu Ala
    545                 550                 555                 560

Val Glu His Tyr Leu Arg Asp Gln Gln Leu Leu Gly Ile Trp Gly Cys
                        565                 570                 575

Ser Gly Lys Leu Ile Cys Cys Thr Asn Val Pro Trp Asn Ser Ser Trp
                        580                 585                 590

Ser Asn Arg Asn Leu Ser Glu Ile Trp Asp Asn Met Thr Trp Leu Gln
                        595                 600                 605

Trp Asp Lys Glu Ile Ser Asn Tyr Thr Gln Ile Ile Tyr Gly Leu Leu
                        610                 615                 620

Glu Glu Ser Gln Asn Gln Gln Glu Lys Asn Glu Gln Asp Leu Leu Ala
    625                 630                 635                 640

Leu Asp Gly Ser Gly Gly Leu Ser Glu Arg Met Leu Lys Ala Leu Asn
                        645                 650                 655

Asp Gln Leu Asn Arg Glu Leu Tyr Ser Ala Tyr Leu Tyr Phe Ala Met
                        660                 665                 670

Ala Ala Tyr Phe Glu Asp Leu Gly Leu Glu Gly Phe Ala Asn Trp Met
                        675                 680                 685

Lys Ala Gln Ala Glu Glu Ile Gly His Ala Leu Arg Phe Tyr Asn
                        690                 695                 700

Tyr Ile Tyr Asp Lys Asn Gly Arg Val Glu Leu Asp Glu Ile Pro Lys
    705                 710                 715                 720

Pro Pro Lys Glu Trp Glu Ser Pro Leu Lys Ala Phe Glu Ala Ala Tyr
                        725                 730                 735

Glu His Glu Lys Phe Ile Ser Lys Ser Ile Tyr Glu Leu Ala Ala Leu
                        740                 745                 750

Ala Glu Glu Lys Asp Tyr Ser Thr Arg Ala Phe Leu Glu Trp Phe
                        755                 760                 765

Ile Asn Glu Gln Val Glu Glu Ala Ser Val Lys Lys Ile Leu Asp
    770                 775                 780

Lys Leu Lys Phe Ala Lys Asp Ser Pro Gln Ile Leu Phe Met Leu Asp
    785                 790                 795                 800

Lys Glu Leu Ser Ala Arg Ala Pro Lys Leu Pro Gly Leu Leu Met Gln
                        805                 810                 815

Gly Gly Glu

<210> SEQ ID NO 14
<211> LENGTH: 811
<212> TYPE: PRT
<213> ORGANISM: Artificial Sequence
<220> FEATURE:
<223> OTHER INFORMATION: Artificial Polypeptide

<400> SEQUENCE: 14

Ala Glu Asn Leu Trp Val Thr Val Tyr Tyr Gly Val Pro Val Trp Lys
    1                   5                   10                  15
```

-continued

```
Asp Ala Glu Thr Thr Leu Phe Cys Ala Ser Asp Ala Lys Ala Tyr Glu
             20                  25                  30

Thr Glu Lys His Asn Val Trp Ala Thr His Ala Cys Val Pro Thr Asp
         35                  40                  45

Pro Asn Pro Gln Glu Ile His Leu Glu Asn Val Thr Glu Glu Phe Asn
 50                  55                  60

Met Trp Lys Asn Asn Met Val Glu Gln Met His Glu Asp Ile Ile Ser
 65                  70                  75                  80

Leu Trp Asp Gln Ser Leu Lys Pro Cys Val Lys Leu Thr Pro Leu Cys
                 85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430
```

Thr Glu Thr Phe Arg Pro Gly Gly Asp Met Arg Asp Asn Trp Arg
            435                 440                 445

Ser Glu Leu Tyr Lys Tyr Lys Val Val Lys Ile Glu Pro Leu Gly Val
450                 455                 460

Ala Pro Thr Arg Cys Lys Arg Val Val Gly Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
                500                 505                 510

Asn Leu Leu Ser Gly Ile Val Gln Gln Gln Ser Asn Leu Leu Arg Ala
                515                 520                 525

Pro Glu Pro Gln Gln His Leu Leu Lys Asp Thr His Trp Gly Ile Lys
530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
                580                 585                 590

Trp Asp Asn Met Thr Trp Leu Gln Trp Asp Lys Glu Ile Ser Asn Tyr
                595                 600                 605

Thr Gln Ile Ile Tyr Gly Leu Leu Glu Glu Ser Gln Asn Gln Gln Glu
                610                 615                 620

Lys Asn Glu Gln Asp Leu Leu Ala Leu Asp Gly Ser Gly Gly Leu Ser
625                 630                 635                 640

Glu Arg Met Leu Lys Ala Leu Asn Asp Gln Leu Asn Arg Glu Leu Tyr
                645                 650                 655

Ser Ala Tyr Leu Tyr Phe Ala Met Ala Ala Tyr Phe Glu Asp Leu Gly
                660                 665                 670

Leu Glu Gly Phe Ala Asn Trp Met Lys Ala Gln Ala Glu Glu Ile
                675                 680                 685

Gly His Ala Leu Arg Phe Tyr Asn Tyr Ile Tyr Asp Lys Asn Gly Arg
690                 695                 700

Val Glu Leu Asp Glu Ile Pro Lys Pro Lys Glu Trp Glu Ser Pro
705                 710                 715                 720

Leu Lys Ala Phe Glu Ala Ala Tyr Glu His Glu Lys Phe Ile Ser Lys
                725                 730                 735

Ser Ile Tyr Glu Leu Ala Ala Leu Ala Glu Glu Glu Lys Asp Tyr Ser
                740                 745                 750

Thr Arg Ala Phe Leu Glu Trp Phe Ile Asn Glu Gln Val Glu Glu Glu
                755                 760                 765

Ala Ser Val Lys Lys Ile Leu Asp Lys Leu Lys Phe Ala Lys Asp Ser
770                 775                 780

Pro Gln Ile Leu Phe Met Leu Asp Lys Glu Leu Ser Ala Arg Ala Pro
785                 790                 795                 800

Lys Leu Pro Gly Leu Leu Met Gln Gly Gly Glu
                805                 810

<210> SEQ ID NO 15
<211> LENGTH: 804
<212> TYPE: PRT
<213> ORGANISM: Artificial Sequence
<220> FEATURE:
<223> OTHER INFORMATION: Artificial Polypeptide

<400> SEQUENCE: 15

```
Ala Glu Asn Leu Trp Val Thr Val Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65              70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Arg Ser Met Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Ser Asn Asn
            260                 265                 270

Thr Val Lys Ser Ile Arg Ile Gly Pro Gly Gln Ala Phe Tyr Tyr Phe
        275                 280                 285

Gly Asp Val Leu Gly His Val Arg Met Ala His Cys Asn Ile Ser Lys
290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380

Pro Cys Trp Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
```

```
                        405                 410                 415
Ile Thr Gly Leu Ile Leu Thr Arg Asp Gly Ser Thr Asn Ser Thr
                420                 425                 430

Thr Glu Thr Phe Arg Pro Gly Gly Asp Met Arg Asp Asn Trp Arg
            435                 440                 445

Ser Glu Leu Tyr Lys Tyr Lys Val Val Lys Ile Glu Pro Leu Gly Val
450                 455                 460

Ala Pro Thr Arg Cys Lys Arg Glu Val Gly Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
                500                 505                 510

Asn Leu Leu Ser Gly Ile Val Gln Gln Gln Ser Asn Leu Leu Arg Ala
                515                 520                 525

Pro Glu Pro Gln Gln His Leu Leu Lys Asp Thr His Trp Gly Ile Lys
            530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
                580                 585                 590

Trp Asp Asn Met Thr Trp Leu Gln Trp Asp Lys Glu Ile Ser Asn Tyr
            595                 600                 605

Thr Gln Ile Ile Tyr Gly Leu Leu Glu Glu Ser Gln Asn Gln Gln Glu
            610                 615                 620

Lys Asn Glu Gln Asp Leu Leu Ala Leu Asp Gly Ser Gly Gly Leu Ser
625                 630                 635                 640

Lys Asp Ile Ile Lys Leu Leu Asn Glu Gln Val Asn Lys Glu Met Gln
                645                 650                 655

Ser Ser Asn Leu Tyr Met Ser Met Ser Ser Trp Cys Tyr Thr His Ser
                660                 665                 670

Leu Asp Gly Ala Gly Leu Phe Leu Phe Asp His Ala Ala Glu Glu Tyr
            675                 680                 685

Glu His Ala Lys Lys Leu Ile Ile Phe Leu Asn Glu Asn Asn Val Pro
            690                 695                 700

Val Gln Leu Thr Ser Ile Ser Ala Pro Glu His Lys Phe Glu Gly Leu
705                 710                 715                 720

Thr Gln Ile Phe Gln Lys Ala Tyr Glu His Glu Gln His Ile Ser Glu
            725                 730                 735

Ser Ile Asn Asn Ile Val Asp His Ala Ile Lys Ser Lys Asp His Ala
                740                 745                 750

Thr Phe Asn Phe Leu Gln Trp Tyr Val Ala Glu Gln His Glu Glu Glu
            755                 760                 765

Val Leu Phe Lys Asp Ile Leu Asp Lys Ile Glu Leu Ile Gly Asn Glu
770                 775                 780

Asn His Gly Leu Tyr Leu Ala Asp Gln Tyr Val Lys Gly Ile Ala Lys
785                 790                 795                 800

Ser Arg Lys Ser

<210> SEQ ID NO 16
<211> LENGTH: 634
```

```
<212> TYPE: PRT
<213> ORGANISM: Artificial Sequence
<220> FEATURE:
<223> OTHER INFORMATION: Artificial Polypeptide

<400> SEQUENCE: 16

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Tyr Ala Pro Lys Leu Arg Ser Met Met
            100                 105                 110

Arg Gly Glu Ile Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Gln Asn Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Ser Val Gln Ile Asn Cys Thr Arg Pro Ser Asn Asn
            260                 265                 270

Thr Val Lys Ser Ile Arg Ile Gly Pro Gly Gln Ala Phe Tyr Tyr Phe
        275                 280                 285

Gly Asp Val Leu Gly His Val Arg Met Ala His Cys Asn Ile Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Leu Ile Leu
    370                 375                 380
```

-continued

Pro Cys Trp Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
            405                 410                 415

Ile Thr Gly Leu Ile Leu Thr Arg Asp Gly Gly Ser Thr Asn Ser Thr
        420                 425                 430

Thr Glu Thr Phe Arg Pro Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Thr Val Gly Arg Arg Arg Arg Arg
465                 470                 475                 480

Arg Ala Ala Gly Ile Gly Ala Ser Ser Asp Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
            515                 520                 525

Pro Glu Pro Gln Gln His Leu Leu Lys Asp Thr His Trp Gly Ile Lys
530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
            595                 600                 605

Thr Gln Ile Ile Tyr Gly Leu Leu Glu Glu Ser Gln Asn Gln Gln Glu
        610                 615                 620

Lys Asn Glu Gln Asp Leu Leu Ala Leu Asp
625                 630

<210> SEQ ID NO 17
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 17

Gln Val Gln Leu Arg Glu Ser Gly Pro Gly Leu Val Lys Pro Ser Glu
1               5                   10                  15

Thr Leu Ser Leu Ser Cys Thr Val Ser Asn Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Asn Gly Ala Thr Thr Tyr Asn Pro Ser Leu
    50                  55                  60

Arg Ser Arg Val Arg Ile Glu Leu Asp Gln Ser Ile Pro Arg Phe Ser
65                  70                  75                  80

Leu Lys Met Thr Ser Met Thr Ala Ala Asp Thr Gly Met Tyr Tyr Cys
                85                  90                  95

Ala Arg Asn Ala Ile Arg Ile Tyr Gly Val Val Ala Leu Gly Glu Trp
            100                 105                 110

```
Phe His Tyr Gly Met Asp Val Trp Gly Gln Gly Thr Ala Val Thr Val
            115                 120                 125
Ser Ser
    130

<210> SEQ ID NO 18
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 18

Ser Ser Glu Leu Thr Gln Pro Pro Ser Val Ser Val Ser Pro Gly Gln
1               5                   10                  15

Thr Ala Arg Ile Thr Cys Ser Gly Ala Pro Leu Thr Ser Arg Phe Thr
            20                  25                  30

Tyr Trp Tyr Arg Gln Lys Pro Gly Gln Ala Pro Val Leu Ile Ile Ser
        35                  40                  45

Arg Ser Ser Gln Arg Ser Ser Gly Trp Ser Gly Arg Phe Ser Ala Ser
    50                  55                  60

Trp Ser Gly Thr Thr Val Thr Leu Thr Ile Arg Gly Val Gln Ala Asp
65                  70                  75                  80

Asp Glu Ala Asp Tyr Tyr Cys Gln Ser Ser Thr Ser Asp Ser Tyr
                85                  90                  95

Lys Met Phe Gly Gly Gly Thr Lys Leu Thr Val Leu
            100                 105

<210> SEQ ID NO 19
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 19

Gln Val Gln Leu Gln Glu Ser Gly Pro Gly Leu Val Lys Pro Ser Gly
1               5                   10                  15

Thr Leu Ser Leu Thr Cys Ala Val Ser Asn Asp Ser Arg Pro Ser Asp
            20                  25                  30

His Ser Trp Ser Trp Val Arg Gln Pro Pro Gly Lys Gly Leu Glu Trp
        35                  40                  45

Ile Gly Asp Ile His Tyr Ser Gly Ser Thr Thr Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Thr Val Thr Val
            115                 120                 125

Ser Ser
    130

<210> SEQ ID NO 20
<211> LENGTH: 108
<212> TYPE: PRT
<213> ORGANISM: Artificial Sequence
```

<220> FEATURE:
<223> OTHER INFORMATION: Artificial Polypeptide

<400> SEQUENCE: 20

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Ser Arg Tyr Ala
            20                  25                  30

Tyr Trp Tyr Gln Gln Lys Pro Gly Gln Ala Pro Val Leu Val Ile Ser
        35                  40                  45

Arg Asp Ser Gln Arg Ser Ser Gly Ile Ser Gly Arg Phe Ser Gly Ser
    50                  55                  60

Trp Ser Gly Thr Thr Val Thr Leu Thr Ile Ser Gly Val Gln Ala Glu
65              70                  75                  80

Asp Glu Ala Asp Tyr Tyr Cys Gln Ser Ser Asp Ser Ser Asp Thr Tyr
                85                  90                  95

Lys Val Phe Gly Gly Gly Thr Lys Leu Thr Val Leu
            100                 105

<210> SEQ ID NO 21
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 21

Gln Val Gln Leu Gln Glu Ser Gly Pro Gly Leu Val Lys Pro Ser Gly
1               5                   10                  15

Thr Leu Ser Leu Thr Cys Ala Val Ser Gly Asp Ser Arg Pro Ser Asp
            20                  25                  30

His Ser Trp Ser Trp Val Arg Gln Pro Pro Gly Lys Gly Leu Glu Trp
        35                  40                  45

Ile Gly Glu Ile Tyr Tyr Ser Gly Ser Thr Asn Tyr Asn Pro Ser Leu
    50                  55                  60

Lys Ser Arg Val Thr Ile Ser Val Asp Lys Ser Lys Asn Gln Phe Ser
65              70                  75                  80

Leu Lys Leu Ser Ser Val Thr Ala Ala Asp Thr Ala Val Tyr Tyr Cys
                85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Thr Val Thr Val
        115                 120                 125

Ser Ser
    130

<210> SEQ ID NO 22
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 22

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

-continued

Tyr Trp Tyr Gln Gln Lys Pro Gly Gln Ala Pro Val Leu Val Ile Tyr
            35                  40                  45

Arg Asp Ser Gln Arg Pro Ser Gly Ile Ser Gly Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Thr Tyr
                 85                  90                  95

Lys Val Phe Gly Gly Gly Thr Lys Leu Thr Val Leu
                100                 105

<210> SEQ ID NO 23
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 23

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
            85                  90                  95

Ala Arg Asn Ala Ile Thr Ile Phe Gly Val Val Ile Ile Gly Glu Tyr
                100                 105                 110

Tyr Tyr Tyr Gly Met Asp Val Trp Gly Gln Gly Thr Thr Val Thr Val
            115                 120                 125

Ser Ser
 130

<210> SEQ ID NO 24
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 24

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

```
Trp Val Phe Gly Gly Gly Thr Lys Leu Thr Val Leu
            100                 105

<210> SEQ ID NO 25
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 25

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ala Ile Thr Ile Phe Gly Val Val Ile Leu Gly Glu Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 26
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 26

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105

<210> SEQ ID NO 27
<211> LENGTH: 130
<212> TYPE: PRT
<213> ORGANISM: Artificial Sequence
<220> FEATURE:
<223> OTHER INFORMATION: Artificial Polypeptide
```

<400> SEQUENCE: 27

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ala Ile Thr Ile Phe Gly Val Val Ala Leu Gly Glu Tyr
                100                 105                 110

Tyr Tyr Tyr Gly Met Asp Val Trp Gly Gln Gly Thr Thr Val Thr Val
                115                 120                 125

Ser Ser
    130

<210> SEQ ID NO 28
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 28

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
                100                 105

<210> SEQ ID NO 29
<211> LENGTH: 129
<212> TYPE: PRT
<213> ORGANISM: Artificial Sequence
<220> FEATURE:
<223> OTHER INFORMATION: Artificial Polypeptide

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asn Ala Ile Thr Ile Phe Gly Val Val Ala Leu Gly Glu Tyr Tyr
             100                 105                 110

Tyr Tyr Gly Met Asp Val Trp Gly Gln Gly Thr Thr Val Thr Val Ser
             115                 120                 125

Ser

<210> SEQ ID NO 30
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 30

Gln Val Gln Leu Val Gln Ser Gly Ala Glu Val Lys Lys Pro Gly Ser
 1               5                   10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Ala Ile Thr Ile Phe Gly Val Val Ala Leu Gly Glu Tyr
             100                 105                 110

Tyr Tyr Tyr Gly Met Asp Val Trp Gly Gln Gly Thr Thr Val Thr Val
             115                 120                 125

Ser Ser
    130

<210> SEQ ID NO 31
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 31

Glu Val Gln Leu Val Gln Ser Gly Ala Glu Val Lys Lys Pro Gly Glu
 1               5                   10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

```
Leu Gln Trp Ser Ser Leu Lys Ala Ser Asp Thr Ala Met Tyr Tyr Cys
                85                  90                  95

Ala Arg Asn Ala Ile Thr Ile Phe Gly Val Val Ala Leu Gly Glu Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 32
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Ala Ile Thr Ile Phe Gly Val Val Ala Leu Gly Glu Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 33
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Ile Thr Ile Phe Gly Val Val Ala Leu Gly Glu Tyr
```

```
                100              105              110
Tyr Tyr Tyr Gly Met Asp Val Trp Gly Gln Gly Thr Thr Val Thr Val
        115              120              125
Ser Ser
    130

<210> SEQ ID NO 34
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 34

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Trp Val Phe Gly Gly Gly Thr Lys Leu Thr Val Leu
            100                 105

<210> SEQ ID NO 35
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 35

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Lys Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Asp Asp Tyr Tyr Cys Tyr Ser Ala Asp Tyr Ser Gly Asn His
                85                  90                  95

Trp Val Phe Gly Gly Gly Thr Lys Leu Thr Val Leu
            100                 105

<210> SEQ ID NO 36
<211> LENGTH: 107
<212> TYPE: PRT
<213> ORGANISM: Artificial Sequence
<220> FEATURE:
<223> OTHER INFORMATION: Artificial Polypeptide

<400> SEQUENCE: 36
```

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Trp
                85                  90                  95

Val Phe Gly Gly Gly Thr Lys Leu Thr Val Leu
                100                 105

<210> SEQ ID NO 37
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 37

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
                100                 105

<210> SEQ ID NO 38
<211> LENGTH: 111
<212> TYPE: PRT
<213> ORGANISM: Artificial Sequence
<220> FEATURE:
<223> OTHER INFORMATION: Artificial Polypeptide

<400> SEQUENCE: 38

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
```

Asn Asn Phe Trp Val Phe Gly Gly Gly Thr Lys Leu Thr Val Leu
            85                  90                  95
            100                 105                 110

<210> SEQ ID NO 39
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 39

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gln Arg Thr Ile Phe Gly Val Val Ile Leu Phe Asn Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 40
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 40

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105

<210> SEQ ID NO 41
<211> LENGTH: 130
<212> TYPE: PRT
<213> ORGANISM: Artificial Sequence
<220> FEATURE:

<223> OTHER INFORMATION: Artificial Polypeptide

<400> SEQUENCE: 41

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Leu Leu Thr Ser Phe Gly Val Val Ile Phe Ser Gln His
                100                 105                 110

Lys Ser Tyr Gly Met Asp Val Trp Gly Gln Gly Thr Thr Val Thr Val
            115                 120                 125

Ser Ser
    130

<210> SEQ ID NO 42
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 42

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105

<210> SEQ ID NO 43
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 43

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp

```
            35                  40                  45
Ile Gly Glu Ile Tyr His Ser Gly Ser Thr Asn Tyr Asn Pro Ser Leu
         50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Ser Ile Thr Ile Phe Gly Val Val Ile Leu Gln Asp Tyr
                100                 105                 110

Tyr Tyr Tyr Gly Met Asp Val Trp Gly Gln Gly Thr Thr Val Thr Val
                115                 120                 125

Ser Ser
130
```

<210> SEQ ID NO 44
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 44

```
Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
                 20                  25                  30

Tyr Trp Tyr Gln Gln Lys Pro Gly Gln Ala Pro Val Leu Val Ile Tyr
             35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Trp Val Phe Gly Gly Gly Thr Lys Leu Thr Val Leu
                100                 105
```

<210> SEQ ID NO 45
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 45

```
Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Gly Lys Gly Leu Glu Trp
             35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95
```

```
Ala Arg Glu Arg Asp Thr Ile Phe Gly Val Val Ser Leu Arg Val Tyr
                100                 105                 110

Tyr Tyr Tyr Gly Met Asp Val Trp Gly Gln Gly Thr Thr Val Thr Val
            115                 120                 125

Ser Ser
    130

<210> SEQ ID NO 46
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 46

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105

<210> SEQ ID NO 47
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 47

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Lys Asp Thr Ile Phe Gly Val Val Ile Ile Gly Glu Tyr
                100                 105                 110

Tyr Tyr Tyr Gly Met Asp Val Trp Gly Gln Gly Thr Thr Val Thr Val
            115                 120                 125

Ser Ser
    130

<210> SEQ ID NO 48
```

```
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 48

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105

<210> SEQ ID NO 49
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 49

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser Ile Thr Ile Phe Gly Val Val Ile Ile Leu Glu Asp
            100                 105                 110

Tyr Tyr Tyr Gly Met Asp Val Trp Gly Gln Gly Thr Thr Val Thr Val
        115                 120                 125

Ser Ser
    130

<210> SEQ ID NO 50
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 50

Ser Tyr Glu Leu Thr Gln Pro Pro Ser Val Ser Val Ser Pro Gly Gln
1               5                   10                  15
```

-continued

```
Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
                35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105
```

<210> SEQ ID NO 51
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 51

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
                35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gln Arg Ala Ile Phe Gly Val Val Ile Ile Arg Glu Asp
            100                 105                 110

Tyr Tyr Tyr Gly Met Asp Val Trp Gly Gln Gly Thr Thr Val Thr Val
        115                 120                 125

Ser Ser
    130
```

<210> SEQ ID NO 52
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 52

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
                35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
65                  70                  75                  80
```

```
Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105

<210> SEQ ID NO 53
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 53

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Arg Leu Arg Val Phe Gly Val Val Ile Phe Leu Tyr Gly
            100                 105                 110

Tyr Tyr Tyr Gly Met Asp Val Trp Gly Gln Gly Thr Thr Val Thr Val
        115                 120                 125

Ser Ser
    130

<210> SEQ ID NO 54
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 54

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105

<210> SEQ ID NO 55
<211> LENGTH: 130
<212> TYPE: PRT
```

<213> ORGANISM: Artificial Sequence
<220> FEATURE:
<223> OTHER INFORMATION: Artificial Polypeptide

<400> SEQUENCE: 55

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Arg Lys Arg Phe Phe Gly Val Val Ile Met Asp Glu Ser
            100                 105                 110

Tyr Tyr Tyr Gly Met Asp Val Trp Gly Gln Gly Thr Thr Val Thr Val
        115                 120                 125

Ser Ser
    130
```

<210> SEQ ID NO 56
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 56

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105
```

<210> SEQ ID NO 57
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 57

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30
```

```
Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Gly Val Lys Ile Phe Gly Val Val Ile Ile Arg Glu Ala
                100                 105                 110

Tyr Tyr Tyr Gly Met Asp Val Trp Gly Gln Gly Thr Thr Val Thr Val
                115                 120                 125

Ser Ser
    130

<210> SEQ ID NO 58
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 58

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
             35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Trp Val Phe Gly Gly Gly Thr Lys Leu Thr Val Leu
                100                 105

<210> SEQ ID NO 59
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 59

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
```

```
                    85                  90                  95
Ala Arg Asp Gly Ile Lys Ile Phe Gly Val Val Ile Met Gly Glu Ala
                100                 105                 110
His Tyr Tyr Gly Met Asp Val Trp Gly Gln Gly Thr Thr Val Thr Val
            115                 120                 125
Ser Ser
    130

<210> SEQ ID NO 60
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 60

Ser Tyr Glu Leu Thr Gln Pro Pro Ser Val Ser Val Ser Pro Gly Gln
1               5                   10                  15
Thr Ala Arg Ile Thr Cys Ser Gly Asp Ala Leu Pro Lys Gln Tyr Ala
            20                  25                  30
Tyr Trp Tyr Gln Gln Lys Pro Gly Gln Ala Pro Val Leu Val Ile Tyr
        35                  40                  45
Lys Asp Ser Glu Arg Pro Ser Gly Ile Pro Glu Arg Phe Ser Gly Ser
50                  55                  60
Ser Ser Gly Thr Thr Val Thr Leu Thr Ile Ser Gly Val Gln Ala Glu
65                  70                  75                  80
Asp Glu Ala Asp Tyr Tyr Cys Gln Ser Ala Asp Ser Ser Gly Thr Tyr
                85                  90                  95
Trp Val Phe Gly Gly Gly Thr Lys Leu Thr Val Leu
            100                 105

<210> SEQ ID NO 61
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 61

Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Ser
            20                  25                  30
Asn Trp Trp Ser Trp Val Arg Gln Pro Pro Gly Lys Gly Leu Glu Trp
        35                  40                  45
Ile Gly Glu Ile Tyr His Ser Gly Ser Thr Asn Tyr Asn Pro Ser Leu
50                  55                  60
Lys Ser Arg Val Thr Ile Ser Val Asp Lys Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Lys Gly Arg Gly Thr Ile Phe Gly Val Val Arg Phe Tyr Glu Asn
            100                 105                 110
Tyr Tyr Tyr Gly Met Asp Val Trp Gly Gln Gly Thr Thr Val Thr Val
        115                 120                 125
Ser Ser
    130
```

<210> SEQ ID NO 62
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 62

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Trp Val Phe Gly Gly Gly Thr Lys Leu Thr Val Leu
            100                 105
```

<210> SEQ ID NO 63
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 63

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Lys Ala Leu Asn Thr Ile Phe Gly Val Val Thr Leu Thr Gln Tyr
            100                 105                 110

Tyr Tyr Tyr Gly Met Asp Val Trp Gly Gln Gly Thr Thr Val Thr Val
        115                 120                 125

Ser Ser
    130
```

<210> SEQ ID NO 64
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 64

```
Ser Tyr Glu Leu Thr Gln Pro Pro Ser Val Ser Val Ser Pro Gly Gln
```

```
                 1               5                  10                 15
            Thr Ala Arg Ile Thr Cys Ser Gly Asp Ala Leu Pro Lys Gln Tyr Ala
                            20                  25                  30

Tyr Trp Tyr Gln Gln Lys Pro Gly Gln Ala Pro Val Leu Val Ile Tyr
                        35                  40                  45

Lys Asp Ser Glu Arg Pro Ser Gly Ile Pro Glu Arg Phe Ser Gly Ser
                    50                  55                  60

Ser Ser Gly Thr Thr Val Thr Leu Thr Ile Ser Gly Val Gln Ala Glu
            65                  70                  75                  80

Asp Glu Ala Asp Tyr Tyr Cys Gln Ser Ala Asp Ser Ser Gly Thr Tyr
                                85                  90                  95

Trp Val Phe Gly Gly Gly Thr Lys Leu Thr Val Leu
                            100                 105

<210> SEQ ID NO 65
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 65

Gln Val Gln Leu Gln Glu Ser Gly Pro Gly Leu Val Lys Pro Ser Gly
            1               5                   10                  15

Thr Leu Ser Leu Thr Cys Ala Val Ser Gly Gly Ser Ile Ser Ser Ser
                            20                  25                  30

Asn Trp Trp Ser Trp Val Arg Gln Pro Pro Gly Lys Gly Leu Glu Trp
                        35                  40                  45

Ile Gly Glu Ile Tyr His Ser Gly Ser Thr Asn Tyr Asn Pro Ser Leu
                    50                  55                  60

Lys Ser Arg Val Thr Ile Ser Val Asp Lys Ser Lys Asn Gln Phe Ser
            65                  70                  75                  80

Leu Lys Leu Ser Ser Val Thr Ala Ala Asp Thr Ala Val Tyr Tyr Cys
                            85                  90                  95

Ala Arg Gly Arg Ile Thr Ile Phe Gly Val Val Thr Leu Arg Gly Tyr
                            100                 105                 110

Tyr Tyr Tyr Gly Met Asp Val Trp Gly Gln Gly Thr Thr Val Thr Val
                    115                 120                 125

Ser Ser
                130

<210> SEQ ID NO 66
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 66

Ser Tyr Glu Leu Thr Gln Pro Pro Ser Val Ser Val Ser Pro Gly Gln
            1               5                   10                  15

Thr Ala Arg Ile Thr Cys Ser Gly Asp Ala Leu Pro Lys Gln Tyr Ala
                            20                  25                  30

Tyr Trp Tyr Gln Gln Lys Pro Gly Gln Ala Pro Val Leu Val Ile Tyr
                        35                  40                  45

Lys Asp Ser Glu Arg Pro Ser Gly Ile Pro Glu Arg Phe Ser Gly Ser
                    50                  55                  60
```

```
Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Trp Val Phe Gly Gly Gly Thr Lys Leu Thr Val Leu
            100                 105
```

<210> SEQ ID NO 67
<211> LENGTH: 130
<212> TYPE: PRT
<213> ORGANISM: Artificial Sequence
<220> FEATURE:
<223> OTHER INFORMATION: Artificial Polypeptide

<400> SEQUENCE: 67

```
Gln Val Gln Leu Gln Glu Ser Gly Pro Gly Leu Val Lys Pro Ser Gly
  1               5                  10                  15

Thr Leu Ser Leu Thr Cys Ala Val Ser Gly Gly Ser Ile Ser Ser Ser
                 20                  25                  30

Asn Trp Trp Ser Trp Val Arg Gln Pro Pro Gly Lys Gly Leu Glu Trp
             35                  40                  45

Ile Gly Glu Ile Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Ile His Asn Ser Phe Gly Val Val Ser Leu Asp Gln Asn
                100                 105                 110

Tyr Tyr Tyr Gly Met Asp Val Trp Gly Gln Gly Thr Thr Val Thr Val
            115                 120                 125

Ser Ser
    130
```

<210> SEQ ID NO 68
<211> LENGTH: 108
<212> TYPE: PRT
<213> ORGANISM: Artificial Sequence
<220> FEATURE:
<223> OTHER INFORMATION: Artificial Polypeptide

<400> SEQUENCE: 68

```
Ser Tyr Glu Leu Thr Gln Pro Pro Ser Val Ser Val Ser Pro Gly Gln
  1               5                  10                  15

Thr Ala Arg Ile Thr Cys Ser Gly Asp Ala Leu Pro Lys Gln Tyr Ala
                 20                  25                  30

Tyr Trp Tyr Gln Gln Lys Pro Gly Gln Ala Pro Val Leu Val Ile Tyr
             35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Trp Val Phe Gly Gly Gly Thr Lys Leu Thr Val Leu
            100                 105
```

<210> SEQ ID NO 69

```
<211> LENGTH: 132
<212> TYPE: PRT
<213> ORGANISM: Artificial Sequence
<220> FEATURE:
<223> OTHER INFORMATION: Artificial Polypeptide

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Gln Gln Gly Lys Arg Ile Tyr Gly Val Val Ser Phe Gly Asp
            100                 105                 110

Tyr Tyr Tyr Tyr Tyr Tyr Met Asp Val Trp Gly Lys Gly Thr Thr Val
        115                 120                 125

Thr Val Ser Ser
    130

<210> SEQ ID NO 70
<211> LENGTH: 109
<212> TYPE: PRT
<213> ORGANISM: Artificial Sequence
<220> FEATURE:
<223> OTHER INFORMATION: Artificial Polypeptide

<400> SEQUENCE: 70

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Trp Val Phe Gly Gly Gly Thr Lys Leu Thr Val Leu
            100                 105

<210> SEQ ID NO 71
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 71

Cys Thr Asn Val Thr Asn Asn Ile Thr Asp Asp Met Arg Gly Glu Leu
1               5                   10                  15
```

```
<210> SEQ ID NO 72
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 72

Cys Thr Asn Tyr Ala Pro Asn Leu Leu Ser Asn Met Arg Gly Glu Leu
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 73

Cys Thr Asn Tyr Ala Pro Asn Leu Leu Ser Asn Met Arg Gly Glu Ile
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 74

Cys Thr Asn Tyr Ala Pro Lys Leu Leu Ser Asn Met Arg Gly Glu Ile
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 75

Cys Thr Asn Tyr Ala Pro Lys Leu Arg Ser Met Met Arg Gly Glu Ile
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 76

Cys Thr Asn Tyr Ala Pro Asn Leu Arg Ser Asp Met Arg Gly Glu Ile
1               5                   10                  15

<210> SEQ ID NO 77
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 77

Thr Arg Pro Asn Asn Asn Thr
1               5
```

```
<210> SEQ ID NO 78
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 78

Thr Arg Pro Ser Asn Asn Thr
1               5

<210> SEQ ID NO 79
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 79

Thr Gly Asp Ile Ile Gly Asp Ile Arg Gln Ala His Cys Asn Val Ser
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 80

Phe Gly Asp Ile Ile Gly Asp Ile Arg Met Ala His Cys Asn Val Ser
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 81

Phe Gly Asp Val Leu Gly Asp Val Arg Met Ala His Cys Asn Ile Ser
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 82

Phe Gly Asp Val Leu Gly His Val Arg Met Ala His Cys Asn Ile Ser
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Artificial Polypeptide

<400> SEQUENCE: 83

Phe Gly Asp Val Leu Gly Asp Val Asp Met Ala Lys Cys Thr Ile Ser
1               5                   10                  15

<210> SEQ ID NO 84
```

```
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 84

Ser Ile Thr Leu Pro Cys Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 85

Ser Ile Val Leu Pro Cys Arg
1               5

<210> SEQ ID NO 86
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 86

Ser Leu Ile Leu Pro Cys Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 87

Ser Leu Ile Leu Pro Cys Trp
1               5

<210> SEQ ID NO 88
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 88

Ala Arg Asn Ala Ile Thr Ile Phe Gly Val Val Ile Ile Gly Glu Tyr
1               5                   10                  15

Tyr Tyr Tyr Gly Met Asp Val
            20

<210> SEQ ID NO 89
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 89

Ala Arg Glu Gly Phe Thr Ile Phe Gly Val Val Thr Phe Ser Glu Gly
1               5                   10                  15
```

```
Tyr Tyr Tyr Gly Met Asp Val
            20

<210> SEQ ID NO 90
<211> LENGTH: 21
<212> TYPE: PRT
<213> ORGANISM: Artificial Sequence
<220> FEATURE:
<223> OTHER INFORMATION: Artificial Polypeptide

<400> SEQUENCE: 90

Ala Arg Asp Arg Gly Arg Glu Trp Glu Leu Glu Ser Tyr Tyr Tyr Tyr
1               5                   10                  15

Tyr Tyr Met Asp Val
            20

<210> SEQ ID NO 91
<211> LENGTH: 21
<212> TYPE: PRT
<213> ORGANISM: Artificial Sequence
<220> FEATURE:
<223> OTHER INFORMATION: Artificial Polypeptide

<400> SEQUENCE: 91

Ala Lys Asp Ile Glu Ser Arg Tyr Phe Asp Trp Asp Asn Tyr Tyr Tyr
1               5                   10                  15

Tyr Gly Met Asp Val
            20

<210> SEQ ID NO 92

<400> SEQUENCE: 92

000

<210> SEQ ID NO 93

<400> SEQUENCE: 93

000

<210> SEQ ID NO 94
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 94

Ala Arg Asn Ala Ile Arg Ile Tyr Gly Val Val Ala Leu Gly Glu Trp
1               5                   10                  15

Phe His Tyr Gly Met Asp Val
            20

<210> SEQ ID NO 95
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 95

Ala Arg Asn Ala Ile Thr Ile Phe Gly Val Val Ile Leu Gly Glu Tyr
1               5                   10                  15

Tyr Tyr Tyr Gly Met Asp Val
```

```
<210> SEQ ID NO 96
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 96

Ala Arg Asn Ala Ile Thr Ile Phe Gly Val Val Ala Leu Gly Glu Tyr
1               5                   10                  15

Tyr Tyr Tyr Gly Met Asp Val
            20

<210> SEQ ID NO 97
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 97

Ala Arg Gly Gln Arg Thr Ile Phe Gly Val Val Ile Leu Phe Asn Tyr
1               5                   10                  15

Tyr Tyr Tyr Gly Met Asp Val
            20

<210> SEQ ID NO 98
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 98

Ala Arg Asp Leu Leu Thr Ser Phe Gly Val Val Ile Phe Ser Gln His
1               5                   10                  15

Lys Ser Tyr Gly Met Asp Val
            20

<210> SEQ ID NO 99
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 99

Ala Arg Asp Ser Ile Thr Ile Phe Gly Val Val Ile Leu Gln Asp Tyr
1               5                   10                  15

Tyr Tyr Tyr Gly Met Asp Val
            20

<210> SEQ ID NO 100
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 100

Ala Arg Glu Arg Asp Thr Ile Phe Gly Val Val Ser Leu Arg Val Tyr
1               5                   10                  15
```

Tyr Tyr Tyr Gly Met Asp Val
            20

<210> SEQ ID NO 101
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 101

Ala Arg Asp Lys Asp Thr Ile Phe Gly Val Val Ile Ile Gly Glu Tyr
1               5                   10                  15

Tyr Tyr Tyr Gly Met Asp Val
            20

<210> SEQ ID NO 102
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 102

Ala Arg Gly Ser Ile Thr Ile Phe Gly Val Val Ile Ile Leu Glu Asp
1               5                   10                  15

Tyr Tyr Tyr Gly Met Asp Val
            20

<210> SEQ ID NO 103
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 103

Ala Arg Glu Gln Arg Ala Ile Phe Gly Val Val Ile Ile Arg Glu Asp
1               5                   10                  15

Tyr Tyr Tyr Gly Met Asp Val
            20

<210> SEQ ID NO 104
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 104

Ala Arg Ala Arg Leu Arg Val Phe Gly Val Val Ile Phe Leu Tyr Gly
1               5                   10                  15

Tyr Tyr Tyr Gly Met Asp Val
            20

<210> SEQ ID NO 105
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 105

Ala Arg Asp Arg Lys Arg Phe Phe Gly Val Val Ile Met Asp Glu Ser
1               5                   10                  15

```
Tyr Tyr Tyr Gly Met Asp Val
            20

<210> SEQ ID NO 106
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 106

Ala Arg Asp Gly Val Lys Ile Phe Gly Val Val Ile Ile Arg Glu Ala
1               5                   10                  15

Tyr Tyr Tyr Gly Met Asp Val
            20

<210> SEQ ID NO 107
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 107

Ala Arg Asp Gly Ile Lys Ile Phe Gly Val Val Ile Met Gly Glu Ala
1               5                   10                  15

His Tyr Tyr Gly Met Asp Val
            20

<210> SEQ ID NO 108
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 108

Ala Lys Gly Arg Gly Thr Ile Phe Gly Val Val Arg Phe Tyr Glu Asn
1               5                   10                  15

Tyr Tyr Tyr Gly Met Asp Val
            20

<210> SEQ ID NO 109
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 109

Ala Lys Ala Leu Asn Thr Ile Phe Gly Val Val Thr Leu Thr Gln Tyr
1               5                   10                  15

Tyr Tyr Tyr Gly Met Asp Val
            20

<210> SEQ ID NO 110
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 110

Ala Arg Gly Arg Ile Thr Ile Phe Gly Val Val Thr Leu Arg Gly Tyr
```

```
1               5                  10                 15
Tyr Tyr Tyr Gly Met Asp Val
            20

<210> SEQ ID NO 111
<211> LENGTH: 23
<212> TYPE: PRT
<213> ORGANISM: Artificial Sequence
<220> FEATURE:
<223> OTHER INFORMATION: Artificial Polypeptide

<400> SEQUENCE: 111

Ala Arg Asp Ile His Asn Ser Phe Gly Val Val Ser Leu Asp Gln Asn
1               5                  10                 15

Tyr Tyr Tyr Gly Met Asp Val
            20
```

RECOMBINANT HIV Env POLYPEPTIDES AND THEIR USE

RELATED APPLICATIONS AND INCORPORATION BY REFERENCE

This application is a continuation-in-part of international patent application Serial No. PCT/US2019/063903 filed Dec. 1, 2019, which published as Publication No. WO 2020/113199 on Jun. 4, 2020, which claims priority to U.S. Provisional Application No. 62/774,178 filed Dec. 1, 2018. Reference is made to international patent application Serial No. PCT/US2021/30063 filed Apr. 30, 2021.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been filed electronically in ASCII format and is hereby incorporated by reference in its entirety. Said ASCII copy is named Y796901062SL.txt and is 164 bytes in size.

FIELD OF THE INVENTION

The field of the invention generally relates to recombinant HIV Env polypeptides and their use in the treatment and prevention of HIV/AIDS.

BACKGROUND OF THE INVENTION

HIV broadly neutralizing antibodies (bnAbs) have been isolated from infected individuals, but their induction by vaccination remains a major unmet need for global health. The majority of HIV bnAbs engage the HIV Env trimer with long immunoglobulin heavy chain complementarity determining region 3 (HCDR3) loops that reach through the glycan shield to contact relatively conserved epitopes on the underlying protein surface. A key barrier to inducing long-HCDR3 bnAbs is the priming of appropriate naive B cells that occur at very low frequency in the human repertoire and generally have very low or no detectable affinity for HIV Env. Furthermore, the field lacks methods to design appropriate priming immunogens. Thus, there remains a need for the development of immunogenic compositions capable of eliciting the production of broadly neutralizing antibodies.

Citation or identification of any document in this application is not an admission that such document is available as prior art to the present invention.

SUMMARY OF THE INVENTION

In one aspect, described herein are isolated polypeptides which may comprise a variant HIV Env gp120 polypeptide.

In one aspect, described herein are recombinant HIV Env trimers which may comprise an antigenic polypeptide.

In one aspect, described herein are nanoparticles which may comprise an antigenic polypeptide.

In one aspect, described herein are isolated polynucleotides encoding the isolated polypeptides, HIV ENV trimmers, and nanoparticles.

In one aspect, described herein are RNA replicons which may comprise an isolated polynucleotide.

In one aspect, described herein are recombinant viruses which may comprise an isolated polynucleotide.

In one aspect, described herein are vectors which may comprise an isolated polynucleotide.

In one aspect, described herein are methods of producing an antigenic polypeptide, HIV ENV trimmer, or nanoparticle.

In one aspect, described herein are liposomes and VLPs which may comprise an antigenic polypeptide.

In one aspect, described herein are pharmaceutical compositions which may comprise an antigenic polypeptide, recombinant HIV Env trimer, nanoparticle, polynucleotide, recombinant virus, VLP, or liposome.

In one aspect, described herein are immunogenic compositions which may comprise an antigenic polypeptide, recombinant HIV Env trimer, nanoparticle, polynucleotide, recombinant virus, VLP, or liposome.

In one aspect, described herein are methods for generating an immune response to HIV Env gp120 in a subject, which may comprise administering to the subject an effective amount of an immunogenic composition.

In one aspect, described herein are methods of reducing the likelihood of HIV infection in a subject exposed to HIV which may comprise administering to the subject an effective amount of an immunogenic composition or pharmaceutical composition.

In one aspect, described herein are methods of reducing the risk of a subject becoming infected with HIV which may comprise administering to the subject in need thereof an effective amount of an immunogenic composition or pharmaceutical composition.

In one aspect, described herein are methods of preventing HIV infection which may comprise administering to a subject in need thereof an effective amount of an immunogenic composition or pharmaceutical composition.

In one aspect, described herein are methods of treating HIV/AIDS which may comprise administering to a subject in need thereof an effective amount of an immunogenic composition or pharmaceutical composition described herein.

In one aspect, described herein are isolated antibodies which may comprise a VH and a VK described herein.

In one aspect, described herein are methods of identifying a vaccine candidate variant HIV Env polypeptide using an antibody described herein.

In a first embodiment, the invention relates to an isolated polypeptide which may comprise a variant HIV Env gp120 polypeptide, wherein the variant HIV Env gp120 polypeptide may comprise one or more of
  (a) a V1 loop which may comprise positions 131-154, wherein the V1 loop may comprise an amino acid sequence of
    (i) CTNVTNNITDDMRGEL (SEQ ID NO: 71) which may comprise 0, 1, 2, 3, 4, or 5 insertions, deletions, and/or substitutions,
    (ii) CTNYAPNLLSNMRGEL (SEQ ID NO: 72) which may comprise 0, 1, 2, 3, 4, or 5 insertions, deletions, and/or substitutions, (iii) CTNYAPNLLSNMRGEI (SEQ ID NO: 73) which may comprise 0, 1, 2, 3, 4, or 5 insertions, deletions, and/or substitutions,
(iv) CTNYAPKLLSNMRGEI (SEQ ID NO: 74) which may comprise 0, 1, 2, 3, 4, or 5 insertions, deletions, and/or substitutions,
(v) CTNYAPKLRSMMRGEI (SEQ ID NO: 75) which may comprise 0, 1, 2, 3, 4, or 5 insertions, deletions, and/or substitutions, or
(vi) CTNYAPNLRSDMRGEI (SEQ ID NO: 76) which may comprise 0, 1, 2, 3, 4, or 5 insertions, deletions, and/or substitutions;
(b) a V3 loop which may comprise positions 297-334, wherein positions 297-303 of the V3 loop may comprise an amino acid sequence of
(i) TRPNNNT (SEQ ID NO: 77) which may comprise 0, 1, 2, 3, 4, or 5 insertions, deletions, and/or substitutions, or
(ii) TRPSNNT (SEQ ID NO: 78) which may comprise 0, 1, 2, 3, 4, or 5 insertions, deletions, and/or substitutions;
(c) a V3 loop which may comprise positions 297-334, wherein positions 319-334 of the V3 loop may comprise an amino acid sequence of
(i) TGDIIGDIRQAHCNVS (SEQ ID NO: 79) which may comprise 0, 1, 2, 3, 4, or 5 insertions, deletions, and/or substitutions,
(ii) FGDIIGDIRMAHCNVS (SEQ ID NO: 80) which may comprise 0, 1, 2, 3, 4, or 5 insertions, deletions, and/or substitutions,
(iii) FGDVLGDVRMAHCNIS (SEQ ID NO: 81) which may comprise 0, 1, 2, 3, 4, or 5 insertions, deletions, and/or substitutions,
(iv) FGDVLGHVRMAHCNIS (SEQ ID NO: 82) which may comprise 0, 1, 2, 3, 4, or 5 insertions, deletions, and/or substitutions, or
(v) FGDVLGDVDMAKCTIS (SEQ ID NO: 83) which may comprise 0, 1, 2, 3, 4, or 5 insertions, deletions, and/or substitutions; and
(d) a β19 sheet which may comprise positions 413-419, wherein the β19 sheet may comprise an amino acid sequence of
(i) SITLPCR (SEQ ID NO: 84) which may comprise 0, 1, 2, 3, 4, or 5 insertions, deletions, and/or substitutions,
(ii) SIVLPCR (SEQ ID NO: 85) which may comprise 0, 1, 2, 3, 4, or 5 insertions, deletions, and/or substitutions,
(iii) SLILPCR (SEQ ID NO: 86) which may comprise 0, 1, 2, 3, 4, or 5 insertions, deletions, and/or substitutions, or
(iv) SLILPCW (SEQ ID NO: 87) which may comprise 0, 1, 2, 3, 4, or 5 insertions, deletions, and/or substitutions;
wherein HIV Env gp120 polypeptide positions correspond to the HXB2 reference.

In a second embodiment, the invention relates to an isolated polypeptide which may comprise a variant HIV Env gp120 polypeptide, wherein the variant HIV Env gp120 polypeptide may comprise
(a) a V1 loop which may comprise positions 131-154, wherein the V1 loop may comprise an amino acid sequence of
(i) CTNVTNNITDDMRGEL (SEQ ID NO: 71) which may comprise 0, 1, 2, 3, 4, or 5 insertions, deletions, and/or substitutions,
(ii) CTNYAPNLLSNMRGEL (SEQ ID NO: 72) which may comprise 0, 1, 2, 3, 4, or 5 insertions, deletions, and/or substitutions,
(iii) CTNYAPNLLSNMRGEI (SEQ ID NO: 73) which may comprise 0, 1, 2, 3, 4, or 5 insertions, deletions, and/or substitutions,
(iv) CTNYAPKLLSNMRGEI (SEQ ID NO: 74) which may comprise 0, 1, 2, 3, 4, or 5 insertions, deletions, and/or substitutions,
(v) CTNYAPKLRSMMRGEI (SEQ ID NO: 75) which may comprise 0, 1, 2, 3, 4, or 5 insertions, deletions, and/or substitutions, or
(vi) CTNYAPNLRSDMRGEI (SEQ ID NO: 76) which may comprise 0, 1, 2, 3, 4, or 5 insertions, deletions, and/or substitutions;
(b) a V3 loop which may comprise positions 297-334, wherein positions 297-303 of the V3 loop may comprise an amino acid sequence of
(i) TRPNNNT (SEQ ID NO: 77) which may comprise 0, 1, 2, 3, 4, or 5 insertions, deletions, and/or substitutions, or
(ii) TRPSNNT (SEQ ID NO: 78) which may comprise 0, 1, 2, 3, 4, or 5 insertions, deletions, and/or substitutions;
(c) a V3 loop which may comprise positions 297-334, wherein positions 319-334 of the V3 loop may comprise an amino acid sequence of
(i) TGDIIGDIRQAHCNVS (SEQ ID NO: 79) which may comprise 0, 1, 2, 3, 4, or 5 insertions, deletions, and/or substitutions,
(ii) FGDIIGDIRMAHCNVS (SEQ ID NO: 80) which may comprise 0, 1, 2, 3, 4, or 5 insertions, deletions, and/or substitutions,
(iii) FGDVLGDVRMAHCNIS (SEQ ID NO: 81) which may comprise 0, 1, 2, 3, 4, or 5 insertions, deletions, and/or substitutions,
(iv) FGDVLGHVRMAHCNIS (SEQ ID NO: 82) which may comprise 0, 1, 2, 3, 4, or 5 insertions, deletions, and/or substitutions, or
(v) FGDVLGDVDMAKCTIS (SEQ ID NO: 83) which may comprise 0, 1, 2, 3, 4, or 5 insertions, deletions, and/or substitutions; and
(d) a β19 sheet which may comprise positions 413-419, wherein the β19 sheet may comprise an amino acid sequence of
(i) SITLPCR (SEQ ID NO: 84) which may comprise 0, 1, 2, 3, 4, or 5 insertions, deletions, and/or substitutions,
(ii) SIVLPCR (SEQ ID NO: 85) which may comprise 0, 1, 2, 3, 4, or 5 insertions, deletions, and/or substitutions,
(iii) SLILPCR (SEQ ID NO: 86) which may comprise 0, 1, 2, 3, 4, or 5 insertions, deletions, and/or substitutions, or
(iv) SLILPCW (SEQ ID NO: 87) which may comprise 0, 1, 2, 3, 4, or 5 insertions, deletions, and/or substitutions;
wherein HIV Env gp120 polypeptide positions correspond to the HXB2 reference.

In a third embodiment, the invention relates to an isolated polypeptide which may comprise a variant HIV Env gp120 polypeptide, wherein the variant HIV Env gp120 polypeptide may comprise one or more of
(a) a V1 loop which may comprise positions 131-154, wherein the V1 loop may comprise an amino acid sequence of (i)
CTNVTNNITDDMRGEL, (SEQ ID NO: 71)

(ii)
CTNYAPNLLSNMRGEL, (SEQ ID NO: 72)

(iii)
CTNYAPNLLSNMRGEI, (SEQ ID NO: 73)

(iv)
CTNYAPKLLSNMRGEI, (SEQ ID NO: 74)

(v)
CTNYAPKLRSMMRGEI, (SEQ ID NO: 75)
or (vi)
CTNYAPNLRSDMRGEI; (SEQ ID NO: 76)

(b) a V3 loop which may comprise positions 297-334, wherein positions 297-303 of the V3 loop may comprise an amino acid sequence of (i)
TRPNNNT, (SEQ ID NO: 77)
or (ii)
TRPSNNT; (SEQ ID NO: 78)

(c) a V3 loop which may comprise positions 297-334, wherein positions 319-334 of the V3 loop may comprise an amino acid sequence of (i)
TGDIIGDIRQAHCNVS, (SEQ ID NO: 79)

(ii)
FGDIIGDIRMAHCNVS, (SEQ ID NO: 80)

(iii)
FGDVLGDVRMAHCNIS, (SEQ ID NO: 81)

(iv)
FGDVLGHVRMAHCNIS, (SEQ ID NO: 82)
or (v)
FGDVLGDVDMAKCTIS; (SEQ ID NO: 83)

and
(d) a β19 sheet which may comprise positions 413-419, wherein the β19 sheet may comprise an amino acid sequence of (i)
SITLPCR, (SEQ ID NO: 84)

(ii)
SIVLPCR, (SEQ ID NO: 85)

(iii)
SLILPCR, (SEQ ID NO: 86)
or (iv)
SLILPCW; (SEQ ID NO: 87)

wherein HIV Env gp120 polypeptide positions correspond to the HXB2 reference.

In a fourth embodiment, the invention relates to an isolated polypeptide which may comprise a variant HIV Env gp120 polypeptide, wherein the variant HIV Env gp120 polypeptide may comprise (a) a V1 loop which may comprise positions 131-154, wherein the V1 loop may comprise an amino acid sequence of (i)
CTNVTNNITDDMRGEL, (SEQ ID NO: 71)

(ii)
CTNYAPNLLSNMRGEL, (SEQ ID NO: 72)

(iii)
CTNYAPNLLSNMRGEI, (SEQ ID NO: 73)

(iv)
CTNYAPKLLSNMRGEI, (SEQ ID NO: 74)

(v)
CTNYAPKLRSMMRGEI, (SEQ ID NO: 75)
or (vi)
CTNYAPNLRSDMRGEI; (SEQ ID NO: 76)

(b) a V3 loop which may comprise positions 297-334, wherein positions 297-303 of the V3 loop may comprise an amino acid sequence of (i)
TRPNNNT, (SEQ ID NO: 77)
or (ii)
TRPSNNT; (SEQ ID NO: 78)

(c) a V3 loop which may comprise positions 297-334, wherein positions 319-334 of the V3 loop may comprise an amino acid sequence of (i)
TGDIIGDIRQAHCNVS, (SEQ ID NO: 79)

(ii)
FGDIIGDIRMAHCNVS, (SEQ ID NO: 80)

(iii)
FGDVLGDVRMAHCNIS, (SEQ ID NO: 81)

-continued (iv)
FGDVLGHVRMAHCNIS, (SEQ ID NO: 82)
or (v)
FGDVLGDVDMAKCTIS; (SEQ ID NO: 83)

and
(d) a β19 sheet which may comprise positions 413-419, wherein the β19 sheet may comprise an amino acid sequence of (i)
SITLPCR, (SEQ ID NO: 84)

(ii)
SIVLPCR, (SEQ ID NO: 85)

(iii)
SLILPCR, (SEQ ID NO: 86)
or (iv)
SLILPCW; (SEQ ID NO: 87)

wherein HIV Env gp120 polypeptide positions correspond to the HXB2 reference.

In a fifth embodiment, the invention relates to an isolated polypeptide which may comprise a variant HIV Env gp120 polypeptide, wherein the variant HIV Env gp120 polypeptide may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of (a) CTNYAPKLLSNMRGEI (SEQ ID NO: 74), TRPNNNT (SEQ ID NO: 77), FGDVLGHVRMAHCNIS (SEQ ID NO: 82), and SLILPCR (SEQ ID NO: 86), respectively,
(b) CTNYAPKLRSMMRGEI (SEQ ID NO: 75), TRPNNNT (SEQ ID NO: 77), FGDVLGDVRMAHCNIS (SEQ ID NO: 81), and SLILPCR (SEQ ID NO: 86), respectively,
(c) CTNYAPKLRSMMRGEI (SEQ ID NO: 75), TRPNNNT (SEQ ID NO: 77), FGDVLGHVRMAHCNIS (SEQ ID NO: 82), and SLILPCR (SEQ ID NO: 86), respectively,
(d) CTNYAPKLRSMMRGEI (SEQ ID NO: 75), TRPSNNT (SEQ ID NO: 78), FGDVLGHVRMAHCNIS (SEQ ID NO: 82), and SLILPCR (SEQ ID NO: 86), respectively,
(e) CTNYAPKLRSMMRGEI (SEQ ID NO: 75), TRPSNNT (SEQ ID NO: 78), FGDVLGHVRMAHCNIS (SEQ ID NO: 82), and SLILPCW (SEQ ID NO: 87), respectively,
(f) CTNYAPNLRSDMRGEI (SEQ ID NO: 76), TRPNNNT (SEQ ID NO: 77), FGDVLGDVDMAKCTIS (SEQ ID NO: 83), and SLILPCR (SEQ ID NO: 86), respectively,
(g) CTNYAPKLLSNMRGEI (SEQ ID NO: 74) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively,
(h) CTNYAPKLRSMMRGEI (SEQ ID NO: 75) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGDVRMAHCNIS (SEQ ID NO: 81) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively,
(i) CTNYAPKLRSMMRGEI (SEQ ID NO: 75) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively,
(j) CTNYAPKLRSMMRGEI (SEQ ID NO: 75) which may comprise 0, 1, 2, 3, 4, or 5 insertions, deletions, and/or substitutions, TRPSNNT (SEQ ID NO: 78) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively,
(k) CTNYAPKLRSMMRGEI (SEQ ID NO: 75) which may comprise 0, 1, 2, 3, 4, or 5 insertions, deletions, and/or substitutions, TRPSNNT (SEQ ID NO: 78) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCW (SEQ ID NO: 87) which may comprise 0, 1, 2, 3, 4, or 5 insertions, deletions, and/or substitutions, respectively, or
(l) CTNYAPNLRSDMRGEI (SEQ ID NO: 76) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGDVDMAKCTIS (SEQ ID NO: 83) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively, wherein HIV Env gp120 polypeptide positions correspond to the HXB2 reference.

In a sixth embodiment, the invention relates to an isolated polypeptide which may comprise a variant HIV Env gp120 polypeptide, wherein the variant HIV Env gp120 polypeptide may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLLSNMR-GEI (SEQ ID NO: 74), TRPNNNT (SEQ ID NO: 77), FGDVLGHVRMAHCNIS (SEQ ID NO: 82), and SLILPCR (SEQ ID NO: 86), respectively, wherein HIV Env gp120 polypeptide positions correspond to the HXB2 reference.

In a seventh embodiment, the invention relates to an isolated polypeptide which may comprise a variant HIV Env gp120 polypeptide, wherein the variant HIV Env gp120 polypeptide may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPNNNT (SEQ ID NO: 77), FGDVLGDVRMAHCNIS (SEQ ID NO: 81), and SLILPCR (SEQ ID NO: 86), respectively, wherein HIV Env gp120 polypeptide positions correspond to the HXB2 reference.

In an eighth embodiment, the invention relates to an isolated polypeptide which may comprise a variant HIV Env gp120 polypeptide, wherein the variant HIV Env gp120 polypeptide may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPNNNT (SEQ ID NO: 77), FGDVLGHVRMAHCNIS (SEQ ID NO: 82), and SLILPCR (SEQ ID NO: 86), respectively, wherein HIV Env gp120 polypeptide positions correspond to the HXB2 reference.

In an ninth embodiment, the invention relates to an isolated polypeptide which may comprise a variant HIV Env gp120 polypeptide, wherein the variant HIV Env gp120 polypeptide may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPSNNT (SEQ ID NO: 78), FGDVLGHVRMAHCNIS (SEQ ID NO: 82), and SLILPCR (SEQ ID NO: 86), respectively, wherein HIV Env gp120 polypeptide positions correspond to the HXB2 reference.

In a tenth embodiment, the invention relates to an isolated polypeptide which may comprise a variant HIV Env gp120 polypeptide, wherein the variant HIV Env gp120 polypeptide may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPSNNT (SEQ ID NO: 78), FGDVLGHVRMAHCNIS (SEQ ID NO: 82), and SLILPCW (SEQ ID NO: 87), respectively, wherein HIV Env gp120 polypeptide positions correspond to the HXB2 reference.

In an eleventh embodiment, the variant HIV Env gp120 polypeptide may comprise N332.

In a twelfth embodiment, the N-terminal residue of the variant HIV Env gp120 polypeptide is one of HIV Env positions 1-35.

In a thirteenth embodiment, the C-terminal residue of the variant HIV Env gp120 polypeptide is one of HIV Env positions 503-512.

In a fourteenth embodiment, the variant HIV Env gp120 polypeptide is a variant of the BG505, BG505 N332, BG505 MD39, BG505 MD64, BG505 MD39 N332, BG505 MD39 11mutB, or BG505 MD39 17mutE gp120 polypeptide.

In a fifteenth embodiment, the variant HIV Env gp120 polypeptide is a variant of the BG505 MD39 N332 gp120 polypeptide.

In a sixteenth embodiment, the variant HIV Env gp120 polypeptide is a variant of the BG505 MD64 N332 gp120 polypeptide.

In a seventeenth embodiment, the invention relates to an isolated polypeptide which may comprise
(a) an amino acid sequence having at least about 80%, at least about 90%, at least about 95%, at least about 97%, at least about 99%, or 100% sequence identity to the amino acid sequence of BG505 MD39 N332-GT1,
(b) an amino acid sequence having at least about 80%, at least about 90%, at least about 95%, at least about 97%, at least about 99%, or 100% sequence identity to the amino acid sequence of BG505 MD39 N332-GT2,
(c) an amino acid sequence having at least about 80%, at least about 90%, at least about 95%, at least about 97%, at least about 99%, or 100% sequence identity to the amino acid sequence of BG505 MD39 N332-GT3,
(d) an amino acid sequence having at least about 80%, at least about 90%, at least about 95%, at least about 97%, at least about 99%, or 100% sequence identity to the amino acid sequence of BG505 MD39 N332-GT4,
(e) an amino acid sequence having at least about 80%, at least about 90%, at least about 95%, at least about 97%, at least about 99%, or 100% sequence identity to the amino acid sequence of BG505 MD39 N332-GT5, or
(f) an amino acid sequence having at least about 80%, at least about 90%, at least about 95%, at least about 97%, at least about 99%, or 100% sequence identity to the amino acid sequence of BG505 MD39 N332-GT2-KO.

In an eighteenth embodiment, the invention relates to an isolated polypeptide which may comprise an amino acid sequence having at least about 80%, at least about 90%, at least about 95%, at least about 97%, at least about 99%, or 100% sequence identity to the amino acid sequence of BG505 MD39 N332-GT1.

In an nineteenth embodiment, the invention relates to an isolated polypeptide which may comprise an amino acid sequence having at least about 80%, at least about 90%, at least about 95%, at least about 97%, at least about 99%, or 100% sequence identity to the amino acid sequence of BG505 MD39 N332-GT2.

In a twentieth embodiment, the invention relates to an isolated polypeptide which may comprise an amino acid sequence having at least about 80%, at least about 90%, at least about 95%, at least about 97%, at least about 99%, or 100% sequence identity to the amino acid sequence of BG505 MD39 N332-GT3.

In a twenty first embodiment, the invention relates to an isolated polypeptide which may comprise an amino acid sequence having at least about 80%, at least about 90%, at least about 95%, at least about 97%, at least about 99%, or 100% sequence identity to the amino acid sequence of BG505 MD39 N332-GT4.

In a twenty second embodiment, the invention relates to an isolated polypeptide which may comprise an amino acid sequence having at least about 80%, at least about 90%, at least about 95%, at least about 97%, at least about 99%, or 100% sequence identity to the amino acid sequence of BG505 MD39 N332-GT5.

In a twenty third embodiment, the invention relates to an isolated polypeptide which may comprise an amino acid sequence having at least about 80%, at least about 90%, at least about 95%, at least about 97%, at least about 99%, or 100% sequence identity to the amino acid sequence of BG505 MD64 N332-GT2.

In a twenty fourth embodiment, the invention relates to an isolated polypeptide which may comprise a variant HIV Env polypeptide, wherein the variant HIV Env polypeptide may comprise
  (a) the amino acid sequence of BG505 MD39 N332-GT1,
  (b) the amino acid sequence of BG505 MD39 N332-GT2,
  (c) the amino acid sequence of BG505 MD39 N332-GT3,
  (d) the amino acid sequence of BG505 MD39 N332-GT4,
  (e) the amino acid sequence of BG505 MD39 N332-GT5, or
  (f) the amino acid sequence of BG505 MD39 N332-GT2-KO.

In a twenty fifth embodiment, the invention relates to an isolated polypeptide which may comprise a variant HIV Env polypeptide, wherein the variant HIV Env gp120 polypeptide may comprise the amino acid sequence of BG505 MD39 N332-GT1.

In a twenty sixth embodiment, the invention relates to an isolated polypeptide which may comprise a variant HIV Env polypeptide, wherein the variant HIV Env gp120 polypeptide may comprise the amino acid sequence of BG505 MD39 N332-GT2.

In a twenty seventh embodiment, the invention relates to an isolated polypeptide which may comprise a variant HIV Env polypeptide, wherein the variant HIV Env gp120 polypeptide may comprise the amino acid sequence of BG505 MD39 N332-GT3.

In a twenty eighth embodiment, the invention relates to an isolated polypeptide which may comprise a variant HIV Env polypeptide, wherein the variant HIV Env gp120 polypeptide may comprise the amino acid sequence of BG505 MD39 N332-GT4.

In a twenty ninth embodiment, the invention relates to an isolated polypeptide which may comprise a variant HIV Env polypeptide, wherein the variant HIV Env gp120 polypeptide may comprise the amino acid sequence of BG505 MD39 N332-GT5.

In a thirtieth embodiment, the invention relates to an isolated polypeptide which may comprise a variant HIV Env polypeptide, wherein the variant HIV Env gp120 polypeptide may comprise the amino acid sequence of BG505 MD64 N332-GT2.

In a thirty first embodiment, the variant HIV Env polypeptide may comprise K137 and H325.

In a thirty second embodiment, the variant HIV Env polypeptide may comprise K137 and P325.

In a thirty third embodiment, the variant HIV Env polypeptide may comprise K137, M141 and H325.

In a thirty fourth embodiment, the variant HIV Env polypeptide may comprise K137, R139, M141, and H325.

In a thirty fifth embodiment, the variant HIV Env polypeptide may comprise K137 and P325.

In a thirty sixth embodiment, the variant HIV Env polypeptide may comprise K137, M141, and P325.

In a thirty seventh embodiment, the variant HIV Env polypeptide may comprise K137, R139, M141, and P325.

In a thirty eighth embodiment, the isolated polypeptide specifically binds to the BG18 antibody.

In a thirty ninth embodiment, the isolated polypeptide specifically binds to an antibody selected from the group consisting of BG18.11 and BG18.6.

In a fortieth embodiment, the isolated polypeptide specifically binds to an antibody selected from the group consisting of BG18 iGL0, BG18 iGL1, and BG18 iGL2.

In a forty first embodiment, the isolated polypeptide specifically binds to an antibody selected from the group consisting of PRE1, PRE2, PRE3, PRE4, PRE5, PRE6, PRE7, PRE8, PRE9, PRE10, PRE11, PRE12, PRE13, PRE14, and PRE1S.

In a forty second embodiment, the isolated polypeptide specifically binds to the PG121 iGL antibody.

In a forty third embodiment, the isolated polypeptide specifically binds to an antibody which may comprise the VH and VL of
  (a) VH4-59 and BG18 iGL, respectively;
  (b) VH1-69 and BG18 iGL, respectively;
  (c) VH5-51 and BG18 iGL, respectively;
  (d) VH3-33 and BG18 iGL, respectively;
  (e) VH3-23 and BG18 iGL, respectively;
  (f) BG18 iGL1 and VL3-19, respectively;
  (g) BG18 iGL1 and VL3-10, respectively;
  (h) BG18 iGL1 and VL3-1, respectively;
  (i) BG18 iGL1 and VL3-21, respectively; or
  (j) BG18 iGL1 and VL2-8, respectively.

In a forty fourth embodiment, the isolated polypeptide may comprise a gp140.

In a forty fifth embodiment, the isolated polypeptide may comprise a gp160.

In a forty sixth embodiment, a recombinant HIV Env trimer may comprise the isolated polypeptide.

In a forty seventh embodiment, the recombinant HIV Env trimer is a homotrimer.

In a forty eight embodiment, the recombinant HIV Env trimer of is a heterotrimer.

In a forty ninth embodiment, the recombinant HIV Env trimer may comprise gp120-gp41 heterodimers.

In a fiftieth embodiment, the recombinant HIV Env trimer may comprise gp120-gp41 heterodimers wherein the heterodimers are covalently linked.

In a fifty first embodiment, the recombinant HIV Env trimer may comprise gp120-gp41 fusions.

In a fifty second embodiment, the recombinant HIV Env trimer may be a stabilized trimer.

In a fifty third embodiment, the recombinant HIV Env trimer may be a SOSIP, NFL or UFO trimer.

In a fifty fourth embodiment, the recombinant HIV Env trimer may be a SOSIP trimer.

In a fifty fifth embodiment, a nanoparticle may comprise the isolated polypeptide.

In a fifty sixth embodiment, the nanoparticle may be a ferritin nanoparticle, an encapsulin nanoparticle, a Sulfur Oxygenase Reductase (SOR) nanoparticle, a lumazine synthase nanoparticle or a pyruvate dehydrogenase nanoparticle.

In a fifty seventh embodiment, the nanoparticle may comprise N332-GT1, N332-GT2, N332-GT3, N332-GT4, or N332-GT5.

In a fifty eighth embodiment, the nanoparticle may be a ferritin nanoparticle.

In a fifty ninth embodiment, the nanoparticle may be a ferritin nanoparticle having at least about 80%, at least about 90%, at least about 95%, at least about 97%, at least about 99%, or 100% sequence identity to the amino acid sequence of the amino acid sequence of SEQ ID NO. 13 or 15.

In a sixtieth embodiment, nanoparticle may be a ferritin nanoparticle which may comprise the amino acid sequence of SEQ ID NO. 13 or 15.

In a sixty first embodiment, an isolated polynucleotide encodes an isolated polypeptide, a recombinant HIV Env trimer, or a nanoparticle.

In a sixty second embodiment, the isolated polynucleotide is a DNA.

In a sixty third embodiment, the isolated polynucleotide is an mRNA.

In a sixty fourth embodiment, the mRNA may comprise a modified nucleotide.

In a sixty fifth embodiment, the invention relates to an RNA replicon which may comprise the isolated polynucleotide.

In a sixty sixth embodiment, the invention relates to an isolated vector which may comprise the polynucleotide.

In a sixty seventh embodiment, the vector is a viral vector.

In a sixty eighth embodiment, the invention relates to a recombinant virus which may comprise the polynucleotide.

In a sixty ninth embodiment, the recombinant virus may be a recombinant adeno-associated virus (AAV).

In a seventieth embodiment, the invention relates to a host cell which may comprise the polynucleotide or the vector.

In a seventy first embodiment, the host cell may be selected from the group consisting of E. coli, Pseudomonas, Bacillus, Streptomyces, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

In a seventy second embodiment, the invention relates to a method of producing the isolated polypeptide, recombinant HIV Env trimer, or the nanoparticle which may comprise, culturing the host cell of so that the polynucleotide is expressed and the isolated polypeptide, recombinant HIV Env trimer, or nanoparticle is produced.

In a seventh third embodiment, the invention relates to a VLP which may comprise the polypeptide.

In a seventy fourth embodiment, the invention relates to a liposome which may comprise the polypeptide.

In a seventy fifth embodiment, the invention relates to a pharmaceutical composition which may comprise the isolated polypeptide, recombinant HIV Env trimer, the nanoparticle, the polynucleotide, the vector, the recombinant virus, VLP, or the liposome of and a pharmaceutically acceptable excipient.

In a seventy sixth embodiment, the invention relates to an immunogenic composition which may comprise the isolated polypeptide, recombinant HIV Env trimer, the nanoparticle, the polynucleotide, the vector, the recombinant virus, VLP, or the liposome and a pharmaceutically acceptable excipient.

In a seventy seventh embodiment, the immunogenic composition may comprise an adjuvant.

In a seventy eighth embodiment, the adjuvant may comprise lecithin.

In a seventy ninth embodiment, the adjuvant may comprise alum.

In an eightieth embodiment, the adjuvant may comprise saponin, cholesterol and phospholipid.

In an eighty first embodiment, the adjuvant may comprise carbomer homopolymer and lecithin.

In an eighty second embodiment, the immunogenic composition is capable of eliciting a BG18 like response.

In an eighty third embodiment, the immunogenic composition is capable of eliciting a BG18 like response in a human subject.

In an eighty fourth embodiment, the immunogenic composition is capable of eliciting a BG18 like response in BG18gH B cell adoptive transfer recipient mice.

In an eighty fifth embodiment, the immunogenic composition is capable of eliciting the production of an antibody that binds to N332-GT2.

In an eighty sixth embodiment, the immunogenic composition is capable of eliciting the production of an antibody that binds to N332-GT2 with a higher affinity than to N332-GT2-KO.

In an eighty seventh embodiment, the immunogenic composition is capable of eliciting the production of a broadly neutralizing antibody in a subject.

In an eighty eighth embodiment, the invention relates to a method for eliciting an immune response to HIV Env gp120 in a subject, which may comprise administering to the subject an effective amount of the immunogenic composition, thereby generating the immune response.

In an eighty ninth embodiment, the subject may be a human.

In a ninetieth embodiment, the subject may be a non-human primate.

In a ninety first embodiment, the subject may be a BG18gH B cell adoptive transfer recipient mouse.

In a ninety second embodiment, the subject may be a mouse.

In a ninety third embodiment, the invention relates to a method of reducing the likelihood of HIV infection in a subject exposed to HIV which may comprise administering to the subject an effective amount of the immunogenic composition, or the pharmaceutical composition.

In a ninety fourth embodiment, the invention relates to a method of reducing the risk of a subject becoming infected with HIV which may comprise administering to the subject in need thereof an effective amount of the immunogenic composition, or the pharmaceutical composition.

In a ninety fifth embodiment, the invention relates to a method of preventing HIV infection which may comprise administering to a subject in need thereof an effective amount of the immunogenic composition, or the pharmaceutical composition.

In a ninety sixth embodiment, the invention relates to a method of treating HIV/AIDS which may comprise administering to a subject in need thereof an effective amount of the immunogenic composition, or the pharmaceutical composition.

In a ninety seventh embodiment, the invention relates to a immunogenic composition may comprise the isolated polypeptide.

In a ninety eighth embodiment, the immunogenic composition may comprise the recombinant HIV Env trimer.

In a ninety ninth embodiment, the immunogenic composition may comprise the nanoparticle.

In a one hundredth embodiment, the immunogenic composition may comprise the polynucleotide.

In a one hundred and first embodiment, the immunogenic composition may comprise the vector.

In a one hundred and second embodiment, the pharmaceutical composition may comprise the recombinant virus In a one hundred and third embodiment, the method may comprise administering at least one additional therapeutic agent.

In a one hundred and fourth embodiment, the additional therapeutic agent may comprise an antiretroviral agent.

In a one hundred and fifth embodiment, the additional therapeutic agent may comprise a broadly neutralizing anti-HIV antibody.

In a one hundred and sixth embodiment, the subject may be a human.

In a one hundred and seventh embodiment, the subject may be a non-human primate.

In a one hundred and eighth embodiment, the invention relates to an isolated antibody which may comprise
(a) the VHCDR1, VH CDR2, and VH CDR3 of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VH4-595, VH1-69, VH5-51, VH3-33, or VH3-23; and
(b) the VL CDR1, VL CDR2, and VL CDR3 of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VL3-10, VL3-19, VL3-1, VL3-21, or VL2-8.

In a one hundred and ninth embodiment, the invention relates to an isolated antibody which may comprise the VH CDR1, VH CDR2, VH CDR3, VL CDR1, VL CDR2, and VL CDR3 of BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, or PRE15.

In a one hundred and tenth embodiment, the invention relates to an isolated antibody which may comprise the 3 VH CDRs and 3 VL CDRs of
(a) VH4-59 and BG18 iGL, respectively;
(b) VH1-69 and BG18 iGL, respectively;
(c) VH5-51 and BG18 iGL, respectively;
(d) VH3-33 and BG18 iGL, respectively;
(e) VH3-23 and BG18 iGL, respectively;
(f) BG18 iGL1 and VL3-19, respectively;
(g) BG18 iGL1 and VL3-10, respectively;
(h) BG18 iGL1 and VL3-1, respectively;
(i) BG18 iGL1 and VL3-21, respectively; or
(j) BG18 iGL1 and VL2-8, respectively.

In a one hundred and eleventh embodiment, the invention relates to an isolated antibody which may comprise
(a) the VH of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VH4-595, VH1-69, VH5-51, VH3-33, or VH3-23; and
(b) the VL of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VL3-10, VL3-19, VL3-1, VL3-21, or VL2-8.

In a one hundred and twelfth embodiment, the invention relates to an isolated antibody which may comprise the VH and VL of BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, or PRE15.

In a one hundred and thirteenth embodiment, the invention relates to an isolated antibody which may comprise the VH and VL of
(a) VH4-59 and BG18 iGL, respectively;
(b) VH1-69 and BG18 iGL, respectively;
(c) VH5-51 and BG18 iGL, respectively;
(d) VH3-33 and BG18 iGL, respectively;
(e) VH3-23 and BG18 iGL, respectively;
(f) BG18 iGL1 and VL3-19, respectively;
(g) BG18 iGL1 and VL3-10, respectively;
(h) BG18 iGL1 and VL3-1, respectively;
(i) BG18 iGL1 and VL3-21, respectively; or
(j) BG18 iGL1 and VL2-8, respectively.

In a one hundred and fourteenth embodiment, the invention relates to an method for identifying a vaccine candidate variant HIV Env gp120 polypeptide, the method which may comprise
(a) providing a library which may comprise a plurality of variant HIV Env gp120 polypeptides;
(b) contacting the library with an antibody; and
(c) identifying a variant HIV Env gp120 polypeptide that specifically binds to the antibody.

In a one hundred and fifteenth embodiment, the plurality of variant HIV Env gp120 polypeptides comprise variants of a parental HIV Env gp120 polypeptide which may comprise one or more amino acid substitutions at a region selected from the V1 loop which may comprise positions 131-154, V3 loop which may comprise positions 297-334, and $\beta 19$ sheet which may comprise positions 413-419, wherein HIV Env gp120 polypeptide positions correspond to the HXB2 reference.

In a one hundred and sixteenth embodiment, the parental HIV Env gp120 polypeptide may comprise BG505, BG505 N332, BG505 MD39, BG505 MD39 N332, BG505 MD39 11mutB, or BG505 MD39 17mutE gp120 polypeptide.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 5. Minimally mutated BG18 variants and alternate VL variants by structural model-guided design. a) Neutralization IC50s on a panel of 24 BG18-sensitive pseudoviruses by less mutated variants of BG18 and variants of BG18 containing alternate LCs as indicated. One variant (BG18.11, "minBG18") is only 11% mutated in VHVL and was found to be 59% as broad as BG18 and had similar potency to BG18. Another variant with 6% mutation in VHVL (BG18.6) neutralized 26% of the viruses. IC50 values for BG18 were taken from Freund et al15. For testing alternate LCs (VL3-1, VL3-21, VL2-8), BG18 somatic mutations were incorporated into each LC and paired with the mature BG18 HC. b) The model from FIG. 4a is shown with VHVL somatic mutations (red spheres) in BG18, BG18.11 and BG18.6. The essential VH mutations are localized to the HCDR1, whereas the VL mutations are localized to the LCDR2 and LCDR3. c) VH/VL sequences of less mutated variants of BG18. VH4-4, BG18 VH, BG18.11 VH, BG18.6 VH, VL3-25, BG18 VL, BG18.11 VL, and BG18.6 VL comprise the amino acid sequences of SEQ ID NO: [VH4-4], 17, 19, 21, [VL3-25], 18, 20, and 22 respectively.

FIG. 9. Cryo-EM statistics. a) Data collection, processing, building and validation statistics. b) Summary of buried solvent accessible surface area between Fabs and Env trimer in high resolution cryo-EM datasets. Area values are totals buried on both Fab and Env and are stated in units of A2. No glycan, gene lacks PNGS consensus sequence.

DETAILED DESCRIPTION OF THE INVENTION

Figure 1:
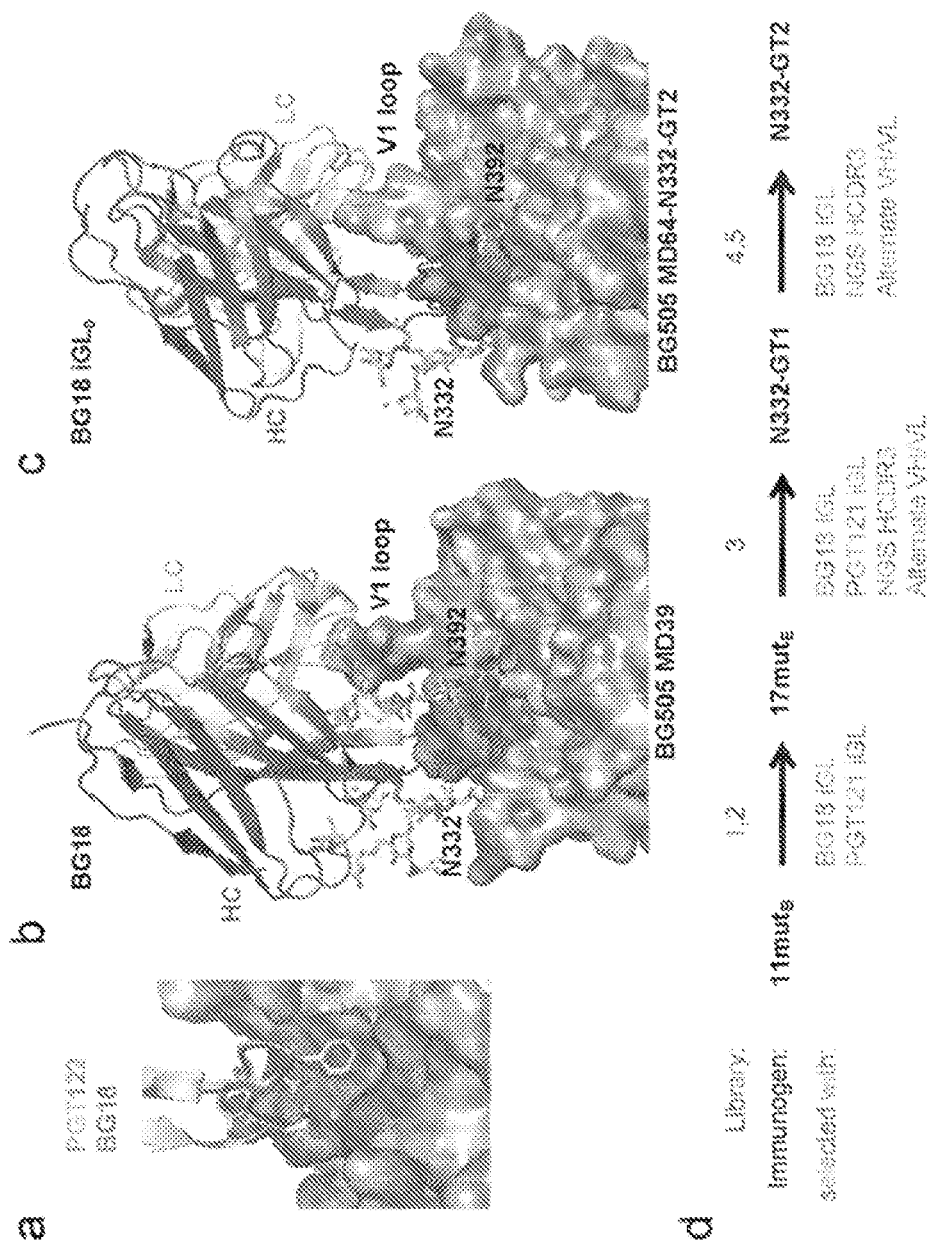
FIG. 1. Structural and biophysical properties of BG18 germline targeting trimers. a) HCDR3 structural alignment of unliganded BG18 (PDB:5UD9) to PGT122 bound to BG505 SOSIP (PDB:4TVP). BG505 SOSIP is shown as a gray surface and the HCDR3s of BG18 and PGT122 are shown in purple and green, respectively. Conserved residues contacted by the HCDR3 (G324, D325, I326, R327, Q328, H330, T415, and P417) are colored red. b) Cryo-EM derived structure of BG18 bound to BG505 MD39. MD39 is colored gray with the N332 and N392 glycans shown as green sticks. The BG18 HC and LC are colored purple and cyan, respectively. Red indicates conserved contact residues as in a). c) Cryo-EM derived structure of BG18 iGL0 in complex with BG505 N332-GT2 with MD64 stabilizing mutations 19. N332-GT2 is colored gray with the N332 and N392 glycans shown as green sticks. The BG18 iGL0 HC and LC are colored purple and cyan, respectively. The same residues as in a) and c) are colored red. d) Schematic of the N332-GT1 and -GT2 directed evolution design process. e) BG505 MD39 N332-GT binding affinities (KD) for BG18 iGL0-2 (red), BG18 iGL1 with alternate germline VL (blue open symbols) or VH genes (blue filled symbols), and BG18 iGL variants containing NGS-derived HCDR3s (pre1-15) (black). Dashed line indicates the limit of detection.
Figure 1:
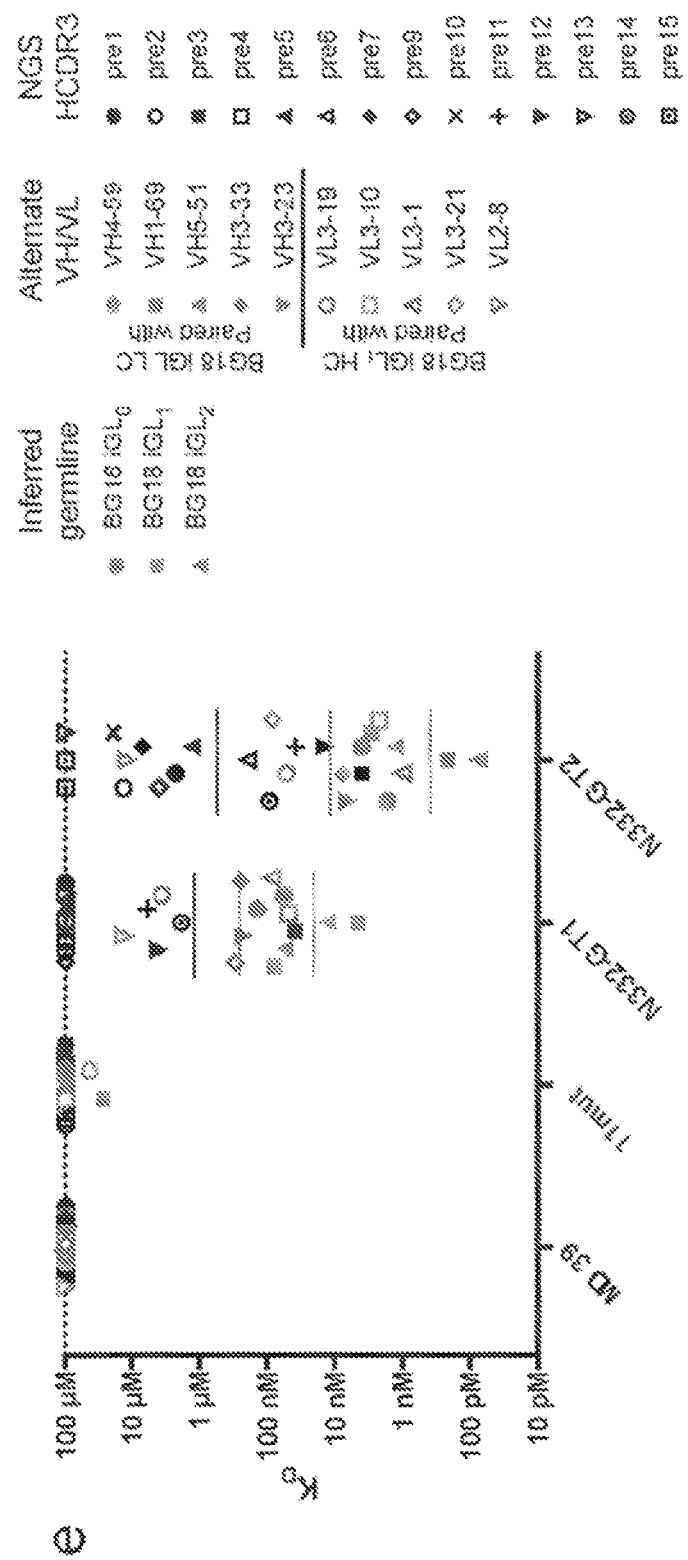

In one aspect, provided herein are HIV Env variant polypeptides and immunogenic compositions which may comprise thereof that are capable of eliciting the formation of antibodies with binding properties similar to the BG18 broadly neutralizing antibody. The inventors used next generation sequencing (NGS) and bioinformatics to identify in HIV-uninfected donors germline encoded heavy chain CDRs that share key properties with the heavy chain CDR3-dependent broadly neutralizing anti-HIV antibody (bnAb) BG18. BG18 inferred-germline (iGL) variants with the NGS-derived HCDR3 loops were used in a structural-model-guided, multitarget mammalian-display selection to identify variant Env polypeptides, including variant Env trimers that bind to diverse BG18 iGL antibodies and potential BG18 precursor antibodies. The N332-GT trimers were used to elicit an immune response. The inventors found that the variant Env polypeptides disclosed herein were capable of inducing the formation of BG18-like antibodies. As such, the HIV Env variant polypeptides and immunogenic compositions disclosed herein have the potential to elicit a protective broadly neutralizing response against HIV.

To facilitate an understanding of the present invention, a number of terms and phrases are defined below.

The terms "human immunodeficiency virus" or "HIV," as used herein, refer generally to a retrovirus that is the causative agent for acquired immunodeficiency syndrome (AIDS), variants thereof (e.g., simian acquired immunodeficiency syndrome, SAIDS), and diseases, conditions, or opportunistic infections associated with AIDS or its variants, and includes HIV-Type 1 (HIV-1) and HIV-Type 2 (HIV-2) of any clade or strain therein, related retroviruses (e.g., simian immunodeficiency virus (SIV)), and variants thereof (e.g., engineered retroviruses, e.g., chimeric HIV viruses, e.g., simian-human immunodeficiency viruses (SHIVs)). In some embodiments, an HIV virus is an HIV-Type-1 virus. Previous names for HIV include human T-lymphotropic virus-Ill (HTLV-III), lymphadenopathy-associated virus (LAV), and AIDS-associated retrovirus (ARV).

Acquired immune deficiency syndrome ("AIDS") is a disease caused by the human immunodeficiency virus, or HIV.

As used herein, the term "envelope glycoprotein" or "Env" refers to the glycoprotein that is expressed on the surface of the envelope of HIV virions and the surface of the plasma membrane of HIV infected cells. "Envelope glycoprotein" or "Env" encompass, but are not limited to, native Env, an isoform of Env, or a recombinant variant of Env (e.g., SOSIP) derived from an HIV isolate. Env is the sole virally encoded gene product on the surface of the virus and, as such, is the only target of neutralizing antibodies. Env is a trimer of heterodimers composed of two non-covalently associated subunits: the receptor-binding gp120 and the fusion machinery-containing gp41. Each subunit is derived from a gp160 precursor glycoprotein following cleavage by cellular furins. HIV-1 gp120 binds the CD4 molecule on the surface of human target T cells to initiate the viral entry process, and following co-receptor engagement, fusion is mediated by gp41. gp140 env is the uncleaved ectodomain of gp160. In some embodiments, the Env is a BG505, 92BR020, JR-FL, YU-2, or JR-CSF Env polypeptide. In some embodiments, the Env is a BG505 Env polypeptide. UniProtKB accession number Q2N0S5-1, Q2N0S6-1, and Q2N0S7-1 provide BG505 env gp160 polypeptide sequences. In some embodiments, the Env is a well-ordered Env trimer. In some embodiments, the BG505 Env polypeptide has the amino acid sequence of SEQ ID NO: 2.

The term "well-ordered Env trimer" or "well-ordered trimer" as used herein refers to an envelope glycoprotein trimer which may comprise three cleaved gp140 polypeptides that closely mimic the quaternary structure of the Env ectodomain on the surface of the envelope of HIV or SIV virions and the surface of the plasma membrane of HIV or SIV infected cells. In one embodiment, the gp140 polypeptides comprise MPER. In one embodiment, the well-ordered trimer may comprise three MPERs. In one embodiment, the gp120 and gp41 ectodomain is linked by a covalent linkage, for example, a disulfide bond. In one embodiment, the gp140 polypeptide may comprise one or more mutations to promote trimer formation. In one embodiment, the gp140 polypeptide may comprise one or more Cys substitutions to promote disulfide formation. In one embodiment, the well-ordered trimer is a SOSIP gp140 trimer. Well-ordered SOSIP trimers have been disclosed in US Patent Appl. Pub. No. 2014/0212458, and Sanders, R. W. et al., PLoS Pathog. 9, e1003618 (2013), each of which is incorporated by reference herein in its entirety. In one embodiment, a well-ordered trimer is formed from a clade A Env. In one embodiment, a well-ordered trimer is formed from a clade B Env. In one embodiment, a well-ordered trimer is formed from a clade C Env. In one embodiment, a well-ordered trimer is formed from a circulating recombinant form Env, wherein 'circulating recombinant form' (CRF) refers to a hybrid virus which may comprise a combination of genetic material from different subtypes. In one embodiment, a well-ordered trimer is Du156.12 SOSIP which may comprise MPER. In one embodiment, a well-ordered Env trimer is a native flexibly linked (NFL) trimer as described in Sharna, et al., Cell Reports, 11(4):539-50 (2015). In one embodiment, a well-ordered Env trimer is a DS-SOSIP as described in Chuang G Y, et al., J. Virology, 91(10). pii: e02268-16

(2017). In one embodiment, a well-ordered trimer is formed from an SIV Env. In one embodiment, a well-ordered trimer is an SIV Env SOSIP. In one embodiment, a well-ordered trimer is formed from an Env which may comprise a mutation (e.g., substitution or deletion) in the CD4 binding site. In one embodiment, a well-ordered trimer is formed from an Env which may comprise a mutation (e.g., substitution or deletion) in the CD4 binding site wherein the mutation reduces or disrupts the binding between Env and CD4. In one embodiment, a well-ordered trimer is a CRF or C108 SOSIP. See, e.g., Andrabi R., et al, Immunity 43(5): 959-973 (2015). In some embodiments, the gp120 and gp41 ectodomain is linked by a peptide linker, for example, a Gly-Ser linker, as described in Georgiev I S, et al., J. Virology 89(10): 5318-5329 (2015). In some embodiments, the well-ordered Env trimer is stable.

The term "antibody" means an immunoglobulin molecule (or a group of immunoglobulin molecules) that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies which may comprise two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), affybodies, Fab fragments, F(ab')$_2$ fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclasses (isotypes) thereof (e.g. IgG$_1$, IgG$_2$, IgG$_3$, IgG$_4$, IgA$_1$ and IgA$_2$), of immunoglobulin molecule, based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated or fused to other molecules such as toxins, radioisotopes, other polypeptides etc.

As used herein, the terms "antigen-binding domain," "antigen-binding region," "antigen-binding site," and similar terms refer to the portion of antibody molecules, which may comprise the amino acid residues that confer on the antibody molecule its specificity for the antigen (e.g., HIV Env MPER). The antigen-binding region can be derived from any animal species, such as mouse and humans.

As used herein, the terms "variable region" or "variable domain" are used interchangeably and are common in the art. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen (e.g., HIV Env MPER). In certain embodiments, the variable region may comprise 3 CDRs (CDR1, CDR2, and CDR3) and 4 framework regions (FR1, FR2, FR3, and FR4) in the order of FR1-CDR1-FR2-CDR2-FR3-CDR3-FR4 from the N terminus to the C terminus. In certain embodiments, the variable region is a human variable region. In certain embodiments, the variable region may comprise human CDRs and human framework regions (FRs). In certain embodiments, the variable region may comprise CDRs and framework regions (FRs) wherein one or more of the CDRs were modified by a substitution, deletion, or insertion relative to the CDRs of a parental antibody. In certain embodiments, the variable region may comprise CDRs and framework regions (FRs) wherein one or more of the FRs were modified by a substitution, deletion, or insertion relative to the FRs of a parental antibody. In certain embodiments, the variable region may comprise CDRs and framework regions (FRs) wherein one or more of the CDRs and one or more of the FRs were modified by a substitution, deletion, or insertion relative to the CDRs and FRs of a parental antibody. In certain embodiments, the parental antibody is PGZL1. In certain embodiments, the variable region may comprise human CDRs and primate (e.g., non-human primate) framework regions (FRs).

A skilled artisan understands that there are several methods for determining CDRs. One approach is based on cross-species sequence variability (i.e., Kabat E A, et al., Sequences of Proteins of Immunological Interest, (5th ed., 1991, National Institutes of Health, Bethesda Md.) ("Kabat"). Another approach is based on crystallographic studies of antigen-antibody complexes (Al-lazikani B., et al, J. Mol. Biol. 273:927-948 (1997)) ("Chothia"). In addition, combinations of these two approaches are sometimes used in the art to determine CDRs. In some embodiments, the CDR sequences are identified according to Kabat. In some embodiments, the CDR sequences are identified according to Chothia. It is understood that the identification of CDRs in a variable region also identifies the FRs as the sequences flanking the CDRs.

The Kabat numbering system is generally used when referring to a residue in the variable domain (approximately residues 1-107 of the light chain and residues 1-113 of the heavy chain) (e.g., Kabat E A, et al., Sequences of Immunological Interest. (5th Ed., 1991, National Institutes of Health, Bethesda, Md.) ("Kabat").

The amino acid position numbering as in Kabat, refers to the numbering system used for heavy chain variable domains or light chain variable domains of the compilation of antibodies in Kabat E A, et al. (Sequences of Immunological Interest. (5th Ed., 1991, National Institutes of Health, Bethesda, Md.), "Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software, available, for example, at bioinf.org.uk/abs/software. In some embodiments, the CDR sequences are identified according to Kabat. In some embodiments, the CDR sequences are identified according to Chothia. In some embodiments, the CDR sequences are identified according to AbM. In some embodiments, the VH CDR3 sequence is identified according to Kabat. In some embodiments, the VH CDR3 sequence is identified according to Chothia. In some embodiments, the VH CDR3 sequence is identified according to AbM.

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The terms "VL" and "VL domain" are used interchangeably to refer to the light chain variable region of an antibody.

The terms "VH" and "VH domain" are used interchangeably to refer to the heavy chain variable region of an antibody.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')$_2$, and Fv fragments, linear antibodies, and single chain antibodies.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')$_2$, Fv), single chain (scFv) mutants, fusion proteins which may comprise an antibody portion, and any other modified immunoglobulin molecule which may comprise an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "polyclonal antibody" describes a composition of different (diverse) antibody molecules, which are capable of binding to or reacting with several different specific antigenic determinants on the same or on different antigens. Usually, the variability of a polyclonal antibody is primarily located in the so-called variable regions of the polyclonal antibody, in particular in the CDR regions. In the present disclosure, a mixture of two or more polyclonal antibodies (a polycomposition) is produced in one mixture from a polyclonal polycomposition cell line, which is produced from two or more parental polyclonal cell lines each expressing antibody molecules, which are capable of binding to a distinct target, but it may also be a mixture of two or more polyclonal antibodies produced separately. A mixture of monoclonal antibodies providing the same antigen/epitope coverage as a polyclonal antibody described herein will be considered as an equivalent of a polyclonal antibody.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g., mouse) with the desired specificity, affinity, and capability, while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following. In certain embodiments, an antibody described herein binds to N332-GT1, N332-GT2, N332-GT3, N332-GT4, or N332-GT5 with a $K_D$ of at least about 0.1 □M or less, at least about 0.01 □M or less, at least about 1 nM or less, or at least about 0.1 nM or less. In certain embodiments, an anti-HIV antibody described herein binds to N332-GT1, N332-GT2, N332-GT3, N332-GT4, or N332-GT5 with a $K_D$ of at least about 0.01 □M or less. In one embodiment, an anti-HIV antibody described herein is capable of binding to cells that express functional, well-ordered HIV-1 membrane Env trimers. In one embodiment, an anti-HIV antibody described herein is capable of binding to cells that display N332-GT1, N332-GT2, N332-GT3, N332-GT4, or N332-GT5 in a flow cytometry assay. In one embodiment, an anti-HIV antibody described herein is capable of binding to N332-GT1, N332-GT2, N332-GT3, N332-GT4, or N332-GT5 in biolayer interferometry (BLI) assay. In one embodiment, an anti-HIV antibody described herein is capable of binding to N332-GT1, N332-GT2, N332-GT3, N332-GT4, or N332-GT5 in ELISA. In one embodiment, an anti-HIV antibody described herein is capable of binding Env trimers from detergent-solubilized HIV-1 virions in an ELISA assay. In one embodiment, an anti-HIV antibody described herein is capable of binding Env trimers from detergent-solubilized HIV-1 virions in a BN-PAGE gel mobility-shift assay.

"Or better" when used herein to refer to binding affinity refers to a stronger binding between a molecule and its binding partner. "Or better" when used herein refers to a stronger binding, represented by a smaller numerical $K_D$ value. For example, an antibody, which has an affinity for an antigen of "0.6 nM or better", the antibody's affinity for the antigen is <0.6 nM, i.e. 0.59 nM, 0.58 nM, 0.57 nM etc. or any value less than 0.6 nM.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), ELISA, biolayer interferometry (BLI), flow cytometry or other assays known in the art. In a specific embodiment, molecules that immunospecifically bind to an antigen bind to the antigen with a $K_D$ that is at least 2 logs, 2.5 logs, 3 logs, or 4 logs lower than the $K_D$ when the molecules bind non-specifically to another antigen. In one example, the antibody may specifically bind to cells that express functional, well-ordered HIV-1 membrane Env trimers. In one example, the antibody may specifically bind to cells that display MPER-TM peptide. In one example, the antibody may specifically bind to the MPER peptide. In one example, the antibody may specifically bind to the MPER peptide in biolayer interferometry (BLI) assay. In one example, the antibody may specifically bind to the MPER peptide in ELISA assay. In one example the antibody may specifically bind to Env trimers from detergent-solubilized HIV-1 virions. In one example, the antibody may specifically bind to Env trimers from detergent-solubilized HIV-1 virions in an ELISA assay. In one example, the antibody may specifically bind to Env trimers from detergent-solubilized HIV-1 virions in a BN-PAGE gel mobility-shift assay. The antibody may bind to N332-GT1, N332-GT2, N332-GT3, N332-GT4, or N332-GT5 with a $K_D$ at least 2 logs, 2.5 logs, 3 logs, or 4 logs lower than $K_D$ of binding to other viral or non-viral polypeptides. An antibody that specifically binds to Env encompass, but are not limited to, antibodies that specifically bind to native Env, an isoform of Env, or a variant of Env (e.g., SOSIP) derived from an HIV isolate.

By "preferentially binds," it is meant that the antibody specifically binds to an epitope more readily than it would bind to a related, similar, homologous, or analogous epitope. Thus, an antibody, which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "broadly neutralizing antibody" or "bnAb," as used herein, with respect to HIV (e.g., HIV-1), refers to an antibody that recognizes HIV Env of more than one isolate or strain of HIV and inhibits or prevents receptor binding of target cells as evaluated in an in vitro neutralization assay. In one embodiment, a broadly neutralizing antibody inhibits infection of a susceptible target cell by HIV. In one embodiment, a broadly neutralizing antibody specifically binds an HIV Env and inhibits infection of a susceptible target cell (e.g., TZM-bl) by an HIV pseudovirus which may comprise an Env polypeptide. HIV pseudovirus neutralization assays have been disclosed in the art, for example, in Walker L. M., et al., Nature 477, 466-470 (2011), Li M., et al., J. Virol. 79:10108-10125 (2005), each of which is incorporated herein by reference in its entirety for all purposes. In one embodiment, a broadly neutralizing antibody neutralizes 2, 3, 4, 5, 6, 7, 8, 9, or more HIV strains or pseudoviruses. In one embodiment, a broadly neutralizing antibody neutralizes 2, 3, 4, 5, 6, 7, 8, 9, or more HIV strains or pseudoviruses that belong to the same or different clades. In one embodiment, a broadly neutralizing antibody is capable of neutralizing HIV strains or pseudoviruses from at least two different clades. In one embodiment, a broadly neutralizing antibody is capable of neutralizing at least one clade B strain or pseudovirus and one clade C strain or pseudovirus. In one embodiment, a broadly neutralizing antibody is capable of neutralizing more than one clade B strain or pseudovirus and more than one clade C strain or pseudovirus. In one embodiment, a broadly neutralizing antibody is capable of neutralizing an HIV strain or pseudovirus from at least one, at least two, at least three, at least four, at least five, at least six, at least seven, at least eight, at least nine, at least ten, or at least eleven clades represented in the 130-member indicator virus panel. In one embodiment, a broadly neutralizing antibody is capable of neutralizing an HIV strain or pseudovirus from at least one, at least two, at least three, at least four, at least five, at least six, at least seven, at least eight, at least nine, at least ten, at least eleven, at least twelve, at least thirteen, at least fourteen, or all fifteen clades selected from the group consisting of clades A, A (T/F), AC, ACD, B, B (T/F), BC, C, C (T/F), CD, CRF01_AE, CRF01_AE (T/F), CRF02_AG, D, and G. In one embodiment, a broadly neutralizing antibody is capable of neutralizing an HIV strain or pseudovirus from at least one, at least two, at least three, at least four, at least five, at least six, at least seven, at least eight, at least nine, at least ten, or all eleven clades selected from the group consisting of clades A, AC, ACD, AE, AG, B, BC, C, CD, D, G.

In one embodiment, the breadth of neutralization is tested on an indicator virus panel which may comprise cross-clade HIV isolates. In one embodiment, the virus panel may comprise the 9 cross-clade isolates of 92TH021, JRCSF, C22, 94UG103, 92BR020, Du156.12, HIV-2, HIV-2C1, and HIV-2C4. In one embodiment, the virus panel may comprise the 130 cross-clade isolates of NIH-065_191955 All, NIH-063_0330.v4.c3, NIH-066_191084 B7.19, NAC_BG505, NIH-057_MS208.A1, NIH-064_0260.v5.c1, NAC_KNH1144, NAC_94UG103, NAC_92RW020, NIH-060_Q769ENVd22, NIH-058_Q23ENV17, NIH- 056_Q168ENVa2, NIH-061_Q259ENVd2.17, NIH-059_Q461ENVe2, NIH-117_T278.5, NIH-100_6041.v3.c23, NIH-099_3301.v1.c24, NIH-102_6545.v4.c1, NIH-101_6540.v4.c1, NIH-103_0815.v3.c3, NIH-104_3103.v3.c10, NIH-073_C3347.c11, NIH-080_BJOX025000.01.1, NIH-075_CNE8, NAC_92TH021, NIH-081_BJOX028000.10.3, NIH-078_BJOX015000.11.5, NIH-079_BJOX010000.06.2, NIH-074_C4118.c09, NIH-069_C1080.c03, NIH-077_BJOX009000.02.4, NIH-068_620345.c01, NIH-076_CNE5, NIH-070_R2184.c04, NIH-072_R3265.c06, NIH-071_R1166.c01, NIH-115_928.28, NIH-118_T255.34, NIH-116_T263.8, NIH-108_T235.47, NIH-114_T257.31, NIH-107_T251.18, NIH-106_T250.4, NIH-119_T211.9, NAC_MN, NAC_HxB2, NIH-012_1012.11.TC21.3257, NAC_ADA, NAC_WITO.33, NIH-006_AC10.0.29, NIH-003_SC422661.8, NAC_89.6, NAC_BaL.26, NAC_RHPA4.7, NIH-014_6244.13.B5.4567, NAC_TRJO.58, NAC_92BR020, NIH-008_WEAU.d15.410.787, NAC_REJO.67, NIH-009_1006.11.C3.1601, NAC_SS1196.1, NAC_YU2, NAC_JRCSF, NAC_JRFL, NIH-004_PVO.4, NAC_DH12, NIH-005_TRO.11, NAC_SF162, NIH-011_1056.10.TA11.1826, NIH-016_SC05.8C11.2344, NIH-013_6240.08.TA5.4622, NIH-007_CAAN5342.A2, NIH-010_1054.07.TC4.1499, NIH-001_6535.3, NIH-015_62357.14.D3.4589, NIH-002_QHO692 0.42, NIH-050_CNE21, NIH-054_CNE53, NIH-055_CNE58, NIH-048_CNE19, NIH-053_CNE52, NIH-051_CNE17, NIH-052_CNE30, NIH-049_CNE20, NIH-030_HIV-0013095.2.11, NIH-026_ZM135M.PL10a, NIH-017_Du156.12, NIH-019_Du422.1, NIH-018_Du172.17, NIH-032_HIV-16845.2.22, NIH-039_Ce2060 G9, NAC_931N905, NIH-029_HIV-001428.2.42, NIH-041_BF1266.431a, NIH-023_ZM249M.PL1, NIH-031_HIV-16055.2.3, NIH-043_ZM249M.B10, NIH-025_ZM109F.PB4, NIH-040_Ce703010054 2A2, NIH-036_Ce2010 F5, NIH-020_ZM197M.PB7, NIH-044_ZM247F.F7, NIH-046_1394C9G1(Rev.), NIH-047_Ce704809221 1B3, NAC_IAVIC22, NIH-034_Ce0393 C3, NIH-045_7030102001E5(Rev.), NIH-021_ZM214M.PL15, NIH-024_ZM53M.PB12, NIH-035_Ce1176 A3, NIH-022_ZM233M.PB6, NIH-027_CAP45.G3, NIH-042_ZM246F.D5, NHI-028_CAP210.E8, NIH-038_Ce1172 H1, NIH-095_6480.v4.c25, NIH-096_6952.v1.c20, NIH-097_6811.v7.c18, NIH-094_3817.v2.c59, NIH-098_89.F1 2 25, NIH-089_3016.v5.c45, NIH-090_A07412M1.vrc12, NIH-091_231965.c01, NIH-086_X2131 C1 B5, NIH-082_X1193 c1, NIH-084_X1254 c3, NIH-083_P0402 c2 11, NIH-087_P1981 C5 3, NIH-088_X1632 S2 B10, and NIH-085_X2088 c9. In one embodiment, a broadly neutralizing antibody is capable of neutralizing at least 4, 5, 6, 7, 8 or 9 of the cross-clade HIV isolates in the 9-member indicator virus panel. In one embodiment, a broadly neutralizing antibody is capable of neutralizing at least 6 of the cross-clade HIV isolates in the 9-member indicator virus panel. In one embodiment, a broadly neutralizing antibody is capable of neutralizing at least about 50%, 60%, 70%, 80%, 90%, 95%, or 100% of cross-clade HIV isolates in the 130-member indicator virus panel. In one embodiment, a broadly neutralizing antibody is capable of neutralizing at least about 60% of cross-clade HIV isolates in the 130-member indicator virus panel. In one embodiment, a broadly neutralizing antibody is capable of neutralizing at least about 70% of cross-clade HIV isolates in the 130-member indicator virus panel. In one embodiment, a broadly neutralizing antibody is capable of neutralizing at least about 75% of cross-clade HIV isolates in the 130-member indicator virus panel. In one embodiment, a broadly neutralizing antibody is capable of neutralizing at least about 80% of cross-clade HIV isolates in the 130-member indicator virus panel. In one embodiment, a broadly neutralizing antibody is capable of neutralizing at least about 90% of cross-clade HIV isolates in the 130-member indicator virus panel. In one embodiment, a broadly neutralizing antibody is capable of neutralizing at least about 95% of cross-clade HIV isolates in the 130-member indicator virus panel. In one embodiment, a broadly neutralizing antibody is capable of neutralizing at least about 98% of cross-clade HIV isolates in the 130-member indicator virus panel. In one embodiment, a broadly neutralizing antibody is capable of neutralizing at least about 100% of cross-clade HIV isolates in the 130-member indicator virus panel.

The phrase "substantially similar," or "substantially the same", as used herein, denotes a sufficiently high degree of similarity between two numeric values (generally one associated with an antibody described herein and the other associated with a reference/comparator antibody) such that one of skill in the art would consider the difference between the two values to be of little or no biological and/or statistical significance within the context of the biological characteristic measured by said values (e.g., $K_D$ values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition, which is "isolated" is a polypeptide, antibody, polynucleotide, vector, cell, or composition, which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition, which is isolated is substantially pure.

As used herein, "substantially pure" refers to material, which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides described herein are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin S., et al, Proc. Natl. Acad. Sci., 87:2264-2268 (1990), as modified in Karlin S., et al., Proc. Natl. Acad. Sci., 90:5873-5877 (1993), and incorporated into the NBLAST and XBLAST programs (Altschul S F, et al., Nucleic Acids Res., 25:3389-3402 (1991)). In certain embodiments, Gapped BLAST can be used as described in Altschul S F, et al., Nucleic Acids Res. 25:3389-3402 (1997). BLAST-2, WU-BLAST-2 (Altschul S F, et al., Methods in Enzymology, 266:460-480 (1996)), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman (Advances in Applied Mathematics 2: 482 489 (1981)) to find the best segment of homology between two sequences. When using Bestfit or any other sequence alignment program to determine whether a particular sequence is, for instance, 95% identical to a reference sequence described herein, the parameters are set such that the percentage of identity is calculated over the full length of the reference nucleotide sequence and that gaps in identity of up to 5% of the total number of nucleotides in the reference sequence are allowed.

In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies described herein do not abrogate the binding of the polypeptide or antibody containing the amino acid sequence, to the antigen(s). Methods of identifying nucleotide and amino acid conservative substitutions, which do not eliminate antigen binding are well-known in the art (see, e.g., Brummell D A, et al., Biochem. 32: 1180-1 187 (1993); Kobayashi et al., Protein Eng. 12(10):879-884 (1999); and Burks E A, et al., Proc. Natl. Acad. Sci. USA 94: 412-417 (1997)).

As used herein, the terms "treatment" or "therapy" (as well as different forms thereof, including curative or palliative) refer to treatment of an infected person. As used herein, the term "treating" includes alleviating or reducing at least one adverse or negative effect or symptom of a condition, disease or disorder. This condition, disease or disorder can be HIV infection.

Terms such as "treating" or "treatment" or "to treat" or "alleviating" or "to alleviate" refer to therapeutic measures that cure, slow down, lessen symptoms of, and/or halt progression of a diagnosed pathologic condition or disorder, such as HIV or AIDS. Thus, those in need of treatment include those already diagnosed with or suspected of having the disorder. In certain embodiments, a subject is successfully "treated" for the disorder according to the methods described herein if the patient shows one or more of the following: a reduction in the number of or complete absence of viral load; a reduction in the viral burden; inhibition of or an absence of the virus into peripheral organs; relief of one or more symptoms associated with the disorder; reduced morbidity and mortality; improvement in quality of life; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

As used herein, the terms "prevention" or "prophylaxis" refer to preventing a subject from becoming infected with, or reducing the risk of a subject from becoming infected with, or halting transmission of, or the reducing the risk of transmission of a virus. Prophylactic or preventative measures refer to measures that prevent and/or slow the development of a targeted pathological condition or disorder. Thus, those in need of prophylactic or preventative measures include those prone to have the disorder and those in whom the disorder is to be prevented. In one embodiment, prevention encompasses passive immunization of a subject in need thereof which may comprise administering an effective amount of an antibody described herein.

As employed above and throughout the disclosure the term "effective amount" refers to an amount effective, at dosages, and for periods of time necessary, to achieve the desired result with respect to the treatment of the relevant disorder, condition, or side effect. An "effective amount" can be determined empirically and in a routine manner, in relation to the stated purpose. It will be appreciated that the effective amount of components of the present invention will vary from patient to patient not only with the particular vaccine, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors, which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

The term "therapeutically effective amount" refers to an amount of an antibody, recombinant virus, immunoconjugate, or other drug effective to "treat" a disease or disorder in a subject or mammal. To the extent an antibody can prevent growth and/or kill existing cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "subject," "individual," and "patient" are used interchangeably herein, and refer to an animal, for example a human, to whom treatment, including prophylactic treatment, with the antibody or pharmaceutical composition according to the present disclosure, is provided. In one embodiment, the subject, individual, or patient has been infected with HIV. In one embodiment, the subject, individual, or patient suffers from AIDS. In one embodiment, the subject, individual, or patient has been exposed to HIV. In one embodiment, the subject, individual, or patient is at risk of being exposed to HIV.

Administration "in combination with" one or more further therapeutic agents includes simultaneous (concurrent) or consecutive administration in any order.

The terms "pharmaceutically composition," "pharmaceutical formulation," "pharmaceutically acceptable formulation," or "pharmaceutically acceptable composition" all of which are used interchangeably, refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. "Pharmaceutically acceptable" or "pharmaceutical formulation" refers to a preparation, which is in such form as to permit the biological activity of the active ingredient to be effective, and which contains no additional components, which are unacceptably toxic to a subject to which the formulation would be administered. The formulation can be sterile.

The term "antiretroviral therapy" or "ART," as used herein, refers to any of the therapies used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include, but are not limited to, lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine (ETR), delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir (RTV), darunavir (DRV), atazanavir sulfate (ATV), nelfinavir mesylate (NFV), enfuvirtide (T-20), maraviroc and raltegravir. ART drugs can also include antibodies that target HIV proteins or cellular proteins associated with disease progression. Also included are immune-based therapies, such as IL-2, IL-12, and alpha-epibromide. Each of these drugs can be administered alone or in combination with any other ART drug or any HIV-specific neutralizing antibody, such as a broadly neutralizing antibody, which is incorporated by reference herein in its entirety for all purposes.

The term "reservoir activator," as used herein, refers to an agent capable of activating a viral reservoir (e.g., an HIV reservoir). In one embodiment, a reservoir activator may comprise a histone deacytelase (HDAC) inhibitor (e.g., romidepsin, vorinostat, and panobinostat), immunologic activator (e.g., cytokines and TLR agonists), or a dedicated small molecule drug.

The term "immunomodulator," as used herein, refers to an agent, such as an antibody or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Immunomodulators include, but are not limited to immune checkpoint inhibitors, for example, a PD-1, PD-L1, LAG-3, or TIGIT antagonist. In one embodiment, an immunomodulator used in the methods described herein may comprise an anti-PD-1 antibody, anti-PD-L1 antibody, anti-LAG3 antibody, or an anti-TIGIT antibody. An immunomodulator can be administered in conjunction with (e.g., prior to, concurrently with, or subsequent to, or within the context of a treatment regimen that includes the administration of a broadly neutralizing antibody described herein.

As used in this specification and the appended claims, the singular forms "a," "an," and "the" include plural referents unless the content clearly dictates otherwise. Thus, for example, reference to "a cell" includes a combination of two or more cells, and the like.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein when referring to a measurable value such as an amount, a temporal duration, and the like, is meant to encompass variations of up to ±20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope described herein are approximations, the numerical values set forth in the specific examples are reported as precisely as possible. Any numerical value, however, inherently contain certain errors necessarily resulting from the standard deviation found in their respective testing measurements.

It is understood that wherever embodiments are described herein with the language "comprising," otherwise analogous embodiments described in terms of "consisting of" and/or "consisting essentially of" are also provided.

In one aspect, provided herein are isolated polypeptides derived from an HIV Env polypeptide. In some embodiments, an isolated polypeptide described herein may comprise a variant gp160 polypeptide. In some embodiments, an isolated polypeptide described herein may comprise a variant gp140 polypeptide. In some embodiments, an isolated polypeptide described herein may comprise a variant gp120 polypeptide. It is understood that in some embodiments, a variant gp160 or gp140 polypeptide described herein may comprise a variant gp120 polypeptide described herein.

In some embodiments, an isolated polypeptide described herein is capable of binding to a BG18 inferred-germline (iGL) variant antibody or a BG18-like native antibody described herein. In some embodiments, the BG18 iGL is BG18 iGL0, BG18 iGL1, BG18 iGL2.

In some embodiments, a variant HIV Env gp120 polypeptide described herein may comprise one or more of (a) a V1 loop which may comprise positions 131-154, wherein the V1 loop may comprise an amino acid sequence of CTNVTNNITDDMRGEL (SEQ ID NO: 71) which may comprise 0, 1, 2, 3, 4, or 5 insertions, deletions, and/or substitutions, CTNYAPNLLSNMRGEL (SEQ ID NO: 72) which may comprise 0, 1, 2, 3, 4, or 5 insertions, deletions, and/or substitutions, CTNYAPNLLSNMRGEI (SEQ ID NO: 73) which may comprise 0, 1, 2, 3, 4, or 5 insertions, deletions, and/or substitutions, CTNYAPKLLSNMRGEI (SEQ ID NO: 74) which may comprise 0, 1, 2, 3, 4, or 5 insertions, deletions, and/or substitutions, CTNYAPKLRSMMRGEI (SEQ ID NO: 75) which may comprise 0, 1, 2, 3, 4, or 5 insertions, deletions, and/or substitutions, or CTNYAPNLRSDMRGEI (SEQ ID NO: 76) which may comprise 0, 1, 2, 3, 4, or 5 insertions, deletions, and/or substitutions;

(b) a V3 loop which may comprise positions 297-334, wherein positions 297-303 of the V3 loop may comprise an amino acid sequence of TRPNNNT (SEQ ID NO: 77) which may comprise 0, 1, 2, 3, 4, or 5 insertions, deletions, and/or substitutions, or TRPSNNT (SEQ ID NO: 78) which may comprise 0, 1, 2, 3, 4, or 5 insertions, deletions, and/or substitutions;

(c) a V3 loop which may comprise positions 297-334, wherein positions 319-334 of the V3 loop may comprise an amino acid sequence of TGDIIGDIRQAHCNVS (SEQ ID NO: 79) which may comprise 0, 1, 2, 3, 4, or 5 insertions, deletions, and/or substitutions, FGDIIGDIRMAHCNVS (SEQ ID NO: 80) which may comprise 0, 1, 2, 3, 4, or 5 insertions, deletions, and/or substitutions, FGDVLGDVRMAHCNIS (SEQ ID NO: 81) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, or FGDVLGDVDMAKCTIS (SEQ ID NO: 83) which may comprise 0, 1, 2, 3, 4, or 5 insertions, deletions, and/or substitutions; and (d) a β19 sheet which may comprise positions 413-419, wherein the β19 sheet may comprise an amino acid sequence of SITLPCR (SEQ ID NO: 84) which may comprise 0, 1, 2, 3, 4, or 5 insertions, deletions, and/or substitutions, SIVLPCR (SEQ ID NO: 85) which may comprise 0, 1, 2, 3, 4, or 5 insertions, deletions, and/or substitutions, SLILPCR (SEQ ID NO: 86) which may comprise 0, 1, 2, 3, 4, or 5 insertions, deletions, and/or substitutions, or SLILPCW (SEQ ID NO: 87) which may comprise 0, 1, 2, 3, 4, or 5 insertions, deletions, and/or substitutions;

wherein HIV Env gp120 polypeptide positions correspond to the HXB2 reference (SEQ ID NO: 1).

In some embodiments, a variant HIV Env gp120 polypeptide described herein may comprise (a) a V1 loop which may comprise positions 131-154, wherein the V1 loop may comprise an amino acid sequence of CTNVTNNITDDMRGEL (SEQ ID NO: 71) which may comprise 0, 1, 2, 3, 4, or 5 insertions, deletions, and/or substitutions, CTNYAPNLLSNMRGEL (SEQ ID NO: 72) which may comprise 0, 1, 2, 3, 4, or 5 insertions, deletions, and/or substitutions, CTNYAPNLLSNMRGEI (SEQ ID NO: 73) which may comprise 0, 1, 2, 3, 4, or 5 insertions, deletions, and/or substitutions, CTNYAPKLLSNMRGEI (SEQ ID NO: 74) which may comprise 0, 1, 2, 3, 4, or 5 insertions, deletions, and/or substitutions, CTNYAPKLRSMMRGEI (SEQ ID NO: 75) which may comprise 0, 1, 2, 3, 4, or 5 insertions, deletions, and/or substitutions, or CTNYAPNLRSDMRGEI (SEQ ID NO: 76) which may comprise 0, 1, 2, 3, 4, or 5 insertions, deletions, and/or substitutions;

(b) a V3 loop which may comprise positions 297-334, wherein positions 297-303 of the V3 loop may comprise an amino acid sequence of TRPNNNT (SEQ ID NO: 77) which may comprise 0, 1, 2, 3, 4, or 5 insertions, deletions, and/or substitutions, or TRPSNNT (SEQ ID NO: 78) which may comprise 0, 1, 2, 3, 4, or 5 insertions, deletions, and/or substitutions;
- (c) a V3 loop which may comprise positions 297-334, wherein positions 319-334 of the V3 loop comprise an amino acid sequence of TGDIIGDIRQAHCNVS (SEQ ID NO: 79) which may comprise 0, 1, 2, 3, 4, or 5 insertions, deletions, and/or substitutions, FGDIIGDIRMAHCNVS (SEQ ID NO: 80) which may comprise 0, 1, 2, 3, 4, or 5 insertions, deletions, and/or substitutions, FGDVLGDVRMAHCNIS (SEQ ID NO: 81) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, or FGDVLGDVDMAKCTIS (SEQ ID NO: 83) which may comprise 0, 1, 2, 3, 4, or 5 insertions, deletions, and/or substitutions; and
- (d) a β19 sheet which may comprise positions 413-419, wherein the β19 sheet may comprise an amino acid sequence of SITLPCR (SEQ ID NO: 84) which may comprise 0, 1, 2, 3, 4, or 5 insertions, deletions, and/or substitutions, SIVLPCR (SEQ ID NO: 85) which may comprise 0, 1, 2, 3, 4, or 5 insertions, deletions, and/or substitutions, SLILPCR (SEQ ID NO: 86) which may comprise 0, 1, 2, 3, 4, or 5 insertions, deletions, and/or substitutions, or SLILPCW (SEQ ID NO: 87) which may comprise 0, 1, 2, 3, 4, or 5 insertions, deletions, and/or substitutions;

wherein HIV Env gp120 polypeptide positions correspond to the HXB2 reference (SEQ ID NO: 1).

In some embodiments, a variant HIV Env gp120 polypeptide described herein may comprise one or more of
- (a) a V1 loop which may comprise positions 131-154, wherein the V1 loop may comprise an amino acid sequence of CTNVTNNITDDMRGEL (SEQ ID NO: 71), CTNYAPNLLSNMRGEL (SEQ ID NO: 72), CTNYAPNLLSNMRGEI (SEQ ID NO: 73), CTNYAPKLLSNMRGEI (SEQ ID NO: 74), CTNYAPKLRSMMRGEI (SEQ ID NO: 75), or CTNYAPNLRSDMRGEI (SEQ ID NO: 76);
- (b) a V3 loop which may comprise positions 297-334, wherein positions 297-303 of the V3 loop may comprise an amino acid sequence of TRPNNNT (SEQ ID NO: 77), or TRPSNNT (SEQ ID NO: 78);
- (c) a V3 loop which may comprise positions 297-334, wherein positions 319-334 of the V3 loop may comprise an amino acid sequence of TGDIIGDIRQAHCNVS (SEQ ID NO: 79), FGDIIGDIRMAHCNVS (SEQ ID NO: 80), FGDVLGDVRMAHCNIS (SEQ ID NO: 81), FGDVLGHVRMAHCNIS (SEQ ID NO: 82), or FGDVLGDVDMAKCTIS (SEQ ID NO: 83); and
- (d) a β19 sheet which may comprise positions 413-419, wherein the β19 sheet may comprise an amino acid sequence of SITLPCR (SEQ ID NO: 84), SIVLPCR (SEQ ID NO: 85), SLILPCR (SEQ ID NO: 86), or SLILPCW (SEQ ID NO: 87);

wherein HIV Env gp120 polypeptide positions correspond to the HXB2 reference (SEQ ID NO: 1).

In some embodiments, a variant HIV Env gp120 polypeptide described herein may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of
- CTNYAPKLLSNMRGEI (SEQ ID NO: 74), TRPNNNT (SEQ ID NO: 77), FGDVLGHVRMAHCNIS (SEQ ID NO: 82), and SLILPCR (SEQ ID NO: 86), respectively,
- CTNYAPKLRSMMRGEI (SEQ ID NO: 75), TRPNNNT (SEQ ID NO: 77), FGDVLGDVRMAHCNIS (SEQ ID NO: 81), and SLILPCR (SEQ ID NO: 86), respectively,
- CTNYAPKLRSMMRGEI (SEQ ID NO: 75), TRPNNNT (SEQ ID NO: 77), FGDVLGHVRMAHCNIS (SEQ ID NO: 82), and SLILPCR (SEQ ID NO: 86), respectively,
- CTNYAPKLRSMMRGEI (SEQ ID NO: 75), TRPSNNT (SEQ ID NO: 78), FGDVLGHVRMAHCNIS (SEQ ID NO: 82), and SLILPCR (SEQ ID NO: 86), respectively,
- CTNYAPKLRSMMRGEI (SEQ ID NO: 75), TRPSNNT (SEQ ID NO: 78), FGDVLGHVRMAHCNIS (SEQ ID NO: 82), and SLILPCW (SEQ ID NO: 87), respectively,
- CTNYAPNLRSDMRGEI (SEQ ID NO: 76), TRPNNNT (SEQ ID NO: 77), FGDVLGDVDMAKCTIS (SEQ ID NO: 83), and SLILPCR (SEQ ID NO: 86), respectively,
- CTNYAPKLLSNMRGEI (SEQ ID NO: 74) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively,
- CTNYAPKLRSMMRGEI (SEQ ID NO: 75) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGDVRMAHCNIS (SEQ ID NO: 81) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively, CTNYAPKLRSMMRGEI (SEQ ID NO: 75) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively, CTNYAPKLRSMMRGEI (SEQ ID NO: 75) which may comprise 0, 1, 2, 3, 4, or 5 insertions, deletions, and/or substitutions, TRPSNNT (SEQ ID NO: 78) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively, CTNYAPKLRSMMRGEI (SEQ ID NO: 75) which may comprise 0, 1, 2, 3, 4, or 5 insertions, deletions, and/or substitutions, TRPSNNT (SEQ ID NO: 78) which may comprise 0, 1, 2, 3, 4, or 5 insertions, deletions, and/or substitutions, FGDVLGHVRMAHCNIS (SEQ ID NO: 82) which may comprise 0, 1, 2, 3, 4, or 5 insertions, deletions, and/or substitutions, and SLILPCW (SEQ ID NO: 87) which may comprise 0, 1, 2, 3, 4, or 5 insertions, deletions, and/or substitutions, respectively, or CTNYAPNLRSDMRGEI (SEQ ID NO: 76) which may comprise 0, 1, 2, 3, 4, or 5 insertions, deletions, and/or substitutions, TRPNNNT (SEQ ID NO: 77) which may comprise 0, 1, 2, 3, 4, or 5 insertions, deletions, and/or substitutions, FGDVLGDVDMAKCTIS (SEQ ID NO: 83) which may comprise 0, 1, 2, 3, 4, or 5 insertions, deletions, and/or substitutions, and SLILPCR (SEQ ID NO: 86) which may comprise 0, 1, 2, 3, 4, or 5 insertions, deletions, and/or substitutions, respectively, wherein HIV Env gp120 polypeptide positions correspond to the HXB2 reference (SEQ ID NO: 1).

In some embodiments, a variant HIV Env gp120 polypeptide described herein may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLLSNMRGEI (SEQ ID NO: 74), TRPNNNT (SEQ ID NO: 77), FGDVLGHVRMAHCNIS (SEQ ID NO: 82), and SLILPCR (SEQ ID NO: 86), respectively, wherein HIV Env gp120 polypeptide positions correspond to the HXB2 reference (SEQ ID NO: 1). In some embodiments, a variant HIV Env gp120 polypeptide described herein may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPNNNT (SEQ ID NO: 77), FGDVLGDVRMAHCNIS (SEQ ID NO: 81), and SLILPCR (SEQ ID NO: 86), respectively, wherein HIV Env gp120 polypeptide positions correspond to the HXB2 reference. In some embodiments, a variant HIV Env gp120 polypeptide described herein may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPNNNT (SEQ ID NO: 77), FGDVLGHVRMAHCNIS (SEQ ID NO: 82), and SLILPCR (SEQ ID NO: 86), respectively, wherein HIV Env gp120 polypeptide positions correspond to the HXB2 reference. In some embodiments, a variant HIV Env gp120 polypeptide described herein may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPSNNT (SEQ ID NO: 78), FGDVLGHVRMAHCNIS (SEQ ID NO: 82), and SLILPCR (SEQ ID NO: 86), respectively, wherein HIV Env gp120 polypeptide positions correspond to the HXB2 reference. In some embodiments, a variant HIV Env gp120 polypeptide described herein may comprise a V1 loop which may comprise positions 131-154, a V3 loop which may comprise positions 297-334, and a β19 sheet which may comprise positions 413-419, wherein the V1 loop, positions 297-303 of the V3 loop, positions 319-334 of the V3 loop, and the β19 sheet may comprise the amino acid sequence of CTNYAPKLRSMMRGEI (SEQ ID NO: 75), TRPSNNT (SEQ ID NO: 78), FGDVLGHVRMAHCNIS (SEQ ID NO: 82), and SLILPCW (SEQ ID NO: 87), respectively, wherein HIV Env gp120 polypeptide positions correspond to the HXB2 reference.

In some embodiments, a variant HIV Env gp120 polypeptide described herein may comprise N332.

In some embodiments, a variant HIV Env gp120 polypeptide described herein may comprise an N-terminal residue of one of HIV Env positions 1-35. In some embodiments, a variant HIV Env gp120 polypeptide described herein may comprise an N-terminal residue of one of HIV Env positions 1-10. In some embodiments, a variant HIV Env gp120 polypeptide described herein may comprise an N-terminal residue of one of HIV Env positions 10-20. In some embodiments, a variant HIV Env gp120 polypeptide described herein may comprise an N-terminal residue of one of HIV Env positions 20-35. In some embodiments, a variant HIV Env gp120 polypeptide described herein may comprise an N-terminal residue of one of HIV Env position 25, 26, 27, 28, 29, 30, 31, 32, 33, 34, and 35. In some embodiments, a variant HIV Env gp120 polypeptide described herein may comprise an N-terminal residue of HIV Env position 30. In some embodiments, a variant HIV Env gp120 polypeptide described herein may comprise an N-terminal residue of HIV Env position 31. In some embodiments, a variant HIV Env gp120 polypeptide described herein may comprise an N-terminal residue of HIV Env position 32. HIV Env polypeptide positions correspond to the HXB2 reference (SEQ ID NO: 1).

In some embodiments, a variant HIV Env gp120 polypeptide described herein may comprise a C-terminal residue of one of HIV Env positions 503-512. In some embodiments, a variant HIV Env gp120 polypeptide described herein may comprise a C-terminal residue of one of HIV Env positions 503-508. In some embodiments, a variant HIV Env gp120 polypeptide described herein may comprise a C-terminal residue of one of HIV Env positions 508-512. In some embodiments, a variant HIV Env gp120 polypeptide described herein may comprise a C-terminal residue of HIV Env position 512. HIV Env polypeptide positions correspond to the HXB2 reference (SEQ ID NO: 1).

In some embodiments, a variant HIV Env gp120 polypeptide described herein is a variant of the BG505, BG505 N332, BG505 MD39, BG505 MD64, BG505 MD39 N332, BG505 MD39 11mutB, or BG505 MD39 17mutE gp120 polypeptide. In some embodiments, a variant HIV Env gp120 polypeptide described herein is a variant of the BG505 MD39 N332 polypeptide. In some embodiments, a variant HIV Env gp120 polypeptide described herein is a variant of the BG505 MD64 N332 polypeptide.

In some embodiments, a variant HIV Env gp120 polypeptide described herein may comprise K137 and H325. In some embodiments, a variant HIV Env gp120 polypeptide described herein may comprise K137 and P325. In some embodiments, a variant HIV Env gp120 polypeptide described herein may comprise K137, M141 and H325. In some embodiments, a variant HIV Env gp120 polypeptide described herein may comprise K137, R139, M141, and H325. In some embodiments, a variant HIV Env gp120 polypeptide described herein may comprise K137 and P325. In some embodiments, a variant HIV Env gp120 polypeptide described herein may comprise K137, M141, and P325. In some embodiments, a variant HIV Env gp120 polypeptide described herein may comprise K137, R139, M141, and P325. HIV Env polypeptide positions correspond to the HXB2 reference (SEQ ID NO: 1).

In some embodiments, an isolated polypeptide described herein may comprise
an amino acid sequence having at least about 80%, at least about 90%, at least about 95%, at least about 97%, at least about 99%, or 100% sequence identity to the amino acid sequence of BG505 MD39 N332-GT1,
an amino acid sequence having at least about 80%, at least about 90%, at least about 95%, at least about 97%, at least about 99%, or 100% sequence identity to the amino acid sequence of BG505 MD39 N332-GT2,
an amino acid sequence having at least about 80%, at least about 90%, at least about 95%, at least about 97%, at least about 99%, or 100% sequence identity to the amino acid sequence of BG505 MD39 N332-GT3,
an amino acid sequence having at least about 80%, at least about 90%, at least about 95%, at least about 97%, at least about 99%, or 100% sequence identity to the amino acid sequence of BG505 MD39 N332-GT4,
an amino acid sequence having at least about 80%, at least about 90%, at least about 95%, at least about 97%, at least about 99%, or 100% sequence identity to the amino acid sequence of BG505 MD39 N332-GT5, or
an amino acid sequence having at least about 80%, at least about 90%, at least about 95%, at least about 97%, at least about 99%, or 100% sequence identity to the amino acid sequence of BG505 MD39 N332-GT2-KO.

In some embodiments, an isolated polypeptide described herein may comprise an amino acid sequence having at least about 80%, at least about 90%, at least about 95%, at least about 97%, at least about 99%, or 100% sequence identity to the amino acid sequence of BG505 MD39 N332-GT1. In some embodiments, an isolated polypeptide described herein may comprise an amino acid sequence having at least about 80%, at least about 90%, at least about 95%, at least about 97%, at least about 99%, or 100% sequence identity to the amino acid sequence of BG505 MD39 N332-GT2. In some embodiments, an isolated polypeptide described herein may comprise an amino acid sequence having at least about 80%, at least about 90%, at least about 95%, at least about 97%, at least about 99%, or 100% sequence identity to the amino acid sequence of BG505 MD39 N332-GT3. In some embodiments, an isolated polypeptide described herein may comprise an amino acid sequence having at least about 80%, at least about 90%, at least about 95%, at least about 97%, at least about 99%, or 100% sequence identity to the amino acid sequence of BG505 MD39 N332-GT4. In some embodiments, an isolated polypeptide described herein may comprise an amino acid sequence having at least about 80%, at least about 90%, at least about 95%, at least about 97%, at least about 99%, or 100% sequence identity to the amino acid sequence of BG505 MD39 N332-GT5. In some embodiments, an isolated polypeptide described herein may comprise an amino acid sequence having at least about 80%, at least about 90%, at least about 95%, at least about 97%, at least about 99%, or 100% sequence identity to the amino acid sequence of BG505 MD64 N332-GT2.

In some embodiments, an isolated polypeptide described herein may comprise the amino acid sequence of BG505 MD39 N332-GT1, BG505 MD39 N332-GT2, BG505 MD39 N332-GT3, BG505 MD39 N332-GT4, BG505 MD39 N332-GT5, or BG505 MD39 N332-GT2-KO. In some embodiments, an isolated polypeptide described herein may comprise the amino acid sequence of BG505 MD39 N332-GT1. In some embodiments, an isolated polypeptide described herein may comprise the amino acid sequence of BG505 MD39 N332-GT2. In some embodiments, an isolated polypeptide described herein may comprise the amino acid sequence of BG505 MD39 N332-GT3. In some embodiments, an isolated polypeptide described herein may comprise the amino acid sequence of BG505 MD39 N332-GT4. In some embodiments, an isolated polypeptide described herein may comprise the amino acid sequence of BG505 MD39 N332-GT5.

In some embodiments, an isolated polypeptide described herein may comprise the amino acid sequence of BG505 MD39 N332-GT1. In some embodiments, an isolated polypeptide described herein may comprise the amino acid sequence of BG505 MD39 N332-GT2. In some embodiments, an isolated polypeptide described herein may comprise the amino acid sequence of BG505 MD39 N332-GT3. In some embodiments, an isolated polypeptide described herein may comprise the amino acid sequence of BG505 MD39 N332-GT4. In some embodiments, an isolated polypeptide described herein may comprise the amino acid sequence of BG505 MD39 N332-GT5. In some embodiments, an isolated polypeptide described herein may comprise the amino acid sequence of BG505 MD64 N332-GT2. In some embodiments, an isolated polypeptide described herein may comprise K137 and H325. In some embodiments, an isolated polypeptide described herein may comprise K137 and P325. In some embodiments, an isolated polypeptide described herein may comprise K137, M141 and H325. In some embodiments, an isolated polypeptide described herein may comprise K137, R139, M141, and H325. In some embodiments, an isolated polypeptide described herein may comprise K137 and P325. In some embodiments, an isolated polypeptide described herein may comprise K137, M141, and P325. In some embodiments, an isolated polypeptide described herein may comprise K137, R139, M141, and P325. In some embodiments, an isolated polypeptide described herein may comprise N332. HIV Env polypeptide positions correspond to the HXB2 reference (SEQ ID NO: 1).

In some embodiments, an isolated polypeptide described herein specifically binds to the BG18 antibody. In some embodiments, an isolated polypeptide described herein specifically binds to an antibody selected from the group consisting of BG18.11 and BG18.6. In some embodiments, an isolated polypeptide described herein specifically binds to an antibody selected from the group consisting of BG18 iGL0, BG18 iGL1, and BG18 iGL2. In some embodiments, an isolated polypeptide described herein specifically binds to BG18 iGL0. In some embodiments, an isolated polypeptide described herein specifically binds to BG18 iGL1. In some embodiments, an isolated polypeptide described herein specifically binds to BG18 iGL2. In some embodiments, an isolated polypeptide described herein specifically binds to an antibody selected from the group consisting of PRE1, PRE2, PRE3, PRE4, PRE5, PRE6, PRE7, PRE8, PRE9, PRE10, PRE11, PRE12, PRE13, PRE14, and PRE15. In some embodiments, an isolated polypeptide described herein specifically binds to the PG121 iGL antibody.

In some embodiments, an isolated polypeptide described herein specifically binds to an antibody which may comprise the VH and VL of
VH4-59 and BG18 iGL, respectively;
VH1-69 and BG18 iGL, respectively;
VH5-51 and BG18 iGL, respectively;
VH3-33 and BG18 iGL, respectively;
VH3-23 and BG18 iGL, respectively;
BG18 iGL1 and VL3-19, respectively;
BG18 iGL1 and VL3-10, respectively;
BG18 iGL1 and VL3-1, respectively;
BG18 iGL1 and VL3-21, respectively; or
BG18 iGL1 and VL2-8, respectively.

The affinity of an isolated polypeptide disclosed for an antibody described herein (e.g., BG18 iGL0) can be determined experimentally using any suitable method well-known in the art, e.g., flow cytometry, enzyme-linked immunoabsorbent assay (ELISA), biolayer interferometry (BLI) assay, radioimmunoassay (MA), or kinetics (e.g., BIA-CORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art and such as the buffer described herein.

In some embodiments, an isolated polypeptide described herein may comprise a gp140. In some embodiments, an isolated polypeptide described herein may comprise a gp120.

In one aspect, provided herein are recombinant HIV Env trimers which may comprise an isolated polypeptide described herein. In some embodiments, a recombinant HIV Env trimer described herein is a homotrimer. In some embodiments, a recombinant HIV Env trimer described herein a heterotrimer. In some embodiments, a recombinant HIV Env trimer described herein may comprise gp120-gp41 heterodimers. In some embodiments, a recombinant HIV Env trimer described herein may comprise gp120-gp41 heterodimers wherein the heterodimers are covalently linked. In some embodiments, a recombinant HIV Env trimer described herein may comprise gp120-gp41 fusions. In some embodiments, a recombinant HIV Env trimer described herein is a stabilized trimer. In some embodiments, a recombinant HIV Env trimer described herein is an SOSIP, NFL or UFO trimer. In some embodiments, a recombinant HIV Env trimer described herein is an SOSIP trimer.

In some embodiments, a recombinant HIV Env trimer described herein may comprise a variant gp120 polypeptide described herein.

In some embodiments, a recombinant HIV Env trimer described herein may comprise the amino acid sequence of BG505 MD39 N332-GT1, BG505 MD39 N332-GT2, BG505 MD39 N332-GT3, BG505 MD39 N332-GT4, BG505 MD39 N332-GT5, or BG505 MD39 N332-GT2-KO. In some embodiments, a recombinant HIV Env trimer described herein may comprise the amino acid sequence of BG505 MD39 N332-GT1. In some embodiments, a recombinant HIV Env trimer described herein may comprise the amino acid sequence of BG505 MD39 N332-GT2. In some embodiments, a recombinant HIV Env trimer described herein may comprise the amino acid sequence of BG505 MD39 N332-GT3. In some embodiments, a recombinant HIV Env trimer described herein may comprise the amino acid sequence of BG505 MD39 N332-GT4. In some embodiments, a recombinant HIV Env trimer described herein may comprise the amino acid sequence of BG505 MD39 N332-GT5. In some embodiments, a recombinant HIV Env trimer described herein may comprise the amino acid sequence of BG505 MD64 N332-GT2. In some embodiments, a recombinant HIV Env trimer described herein may comprise K137 and H325. In some embodiments, a recombinant HIV Env trimer described herein may comprise K137 and P325. In some embodiments, a recombinant HIV Env trimer described herein may comprise K137, M141 and H325. In some embodiments, a recombinant HIV Env trimer described herein may comprise K137, R139, M141, and H325. In some embodiments, a recombinant HIV Env trimer described herein may comprise K137 and P325. In some embodiments, a recombinant HIV Env trimer described herein may comprise K137, M141, and P325. In some embodiments, a recombinant HIV Env trimer described herein may comprise K137, R139, M141, and P325. HIV Env polypeptide positions correspond to the HXB2 reference (SEQ ID NO: 1).

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci US All 1(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-I primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci US A 109(30):12111-12116; Nkolola J P, et al. (2014) Comparison of multiple adjuvants on the stability and immunogenicity of a clade C HIV-I gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bnAbs, (GE148 and GE136) generated following immunization of uncleaved gp140 trimers (YU2 gp140-foldon) in non-human primates (NHP). Non-bnAbs, represented by GE136 and 148, can only neutralize the sensitive so-called "tier I viruses" that are not representative of the more neutralization resistant tier 2-like primary isolates circulating in the human population. Using crystallography, EM reconstructions, paratope scanning and molecular modeling, Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci US A 111(7):E738-747).

The cumulative historical data have led to the hypothesis that a more faithful mimic of the HIV-I spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNHI 144 SOSIP is also available but does not provide atomic level details (Bartesaghi A, Merk A, Borgnia M J, Milne J L, & Subramaniam S (2013) Nat Struct Mol Biol 20(12):1352-1357). The BG505 SOSIP and KNH1144 SOSIP trimers are derived from the Env sequences of the subtype A BG505 and KNHI 144 strains. These soluble trimers possess an engineered disulfide linkage between the gp120 and gp41 (at residues 501C and 605C, respectively) and an additional mutation in the heptad repeat I (HRI) of gp41 (I559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-I primary strains were attempted over the past decade, the BG505- and KNHI 144-derived SOSIP trimers are the two limited examples of SOSIPs that yield homogeneous trimers suitable for high resolution biophysical and structural analysis. The structural explanation for the difficulty to readily transfer the SOSIP design to other HIV-I strain-derived sequences is not yet fully understood and would be valuable information to broaden the trimer design horizon.

Since the initial soluble native-like BG505 SOPIP.664 Env trimer was confirmed to adopt a near-native conformation by high-resolution structural analysis, multiple efforts to produce stable, soluble Env mimetics derived from multiple HIV-1 strains were pursued. Multiple solutions to this objective include the improved cleavage-independent NFL trimers, UFOs and modified SOSIPs. Both the SOSIP and NFL well-ordered trimers are efficiently recognized by broadly neutralizing antibodies (bnAbs) which arise sporadically during the course of natural infection. In some cases, including the important advances described here, have been used to isolate such bnAbs. One approach to elicit tier 2 neutralizing Abs has been to immunize the existing well-ordered trimers using prime:boosting in selected animal models. For BG505 and 16055 native-like trimers this approach does elicit tier 2 neutralizing antibodies, but of limited cross-reactive breadth.

Most cross-conserved sites on the HIV Env spike are occluded by evolved, incorporated self-N-glycans, limiting naïve B cell recognition of the underlying polypeptide surface. The exceptions are the protein surfaces of the primary receptor CD4 binding site (CD4bs) and the furin cleavage site (proximal to the gp120:41 interface). Infrequently, during the course of the natural HIV infection process, bnAbs are elicited to these aforementioned sites of vulnerability. In addition, other bnAbs directed to the V2 apex, the 332N-glycan supersite and to the fusion peptide or the high-mannose patch are elicited during the course of chronic HIV infection.

After decades of development, advances in soluble HIV-1 Env mimics design permits the generation of a diverse array of native-like trimers (Ward and Wilson, 2017. The HIV-1 envelope glycoprotein structure: nailing down a moving target. Immunol Rev 275:21-32; Karlsson et al., 2017. Evolution of B cell analysis and Env trimer redesign. Immunol Rev 275:183-202). The successful development of the soluble SOSIP trimers provided proof-of-principle (Sanders et al, 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618) forming a prefusion native-like conformation (Lyumkis et al., 2013. Cryo-EM structure of a fully glycosylated soluble cleaved HIV-1 envelope trimer. Science 342:1484-1490; Julien et al, 2013. Crystal structure of a soluble cleaved HIV-1 envelope trimer. Science 342:1477-1483; Garces et al., 2015. Affinity Maturation of a Potent Family of HIV Antibodies Is Primarily Focused on Accommodating or Avoiding Glycans. Immunity 43:1053-1063; Pancera et al., 2014. Structure and immune recognition of trimeric pre-fusion HIV-1 Env. Nature 514:455-461). The SOSIP gp140 trimer is proteolytically cleaved by cellular furins to gp120 and gp41 subunits and covalently linked by an engineered intra-protomer disulfide bond A501C-T605C (SOS). These trimers also require mutation (I559P) in the gp41 heptad repeat 1 (HR1) to maintain well-ordered oligomers, as well as expression of exogenous furin for full conformational integrity (Sanders et al., 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618; Guenaga et al., 2015. Well-Ordered Trimeric HIV-1 Subtype B and C Soluble Spike Mimetics Generated by Negative Selection Display Native-like Properties. PLoS Pathog 11:e1004570; Julien et al., 2015. Design and structure of two HIV-1 clade C SOSIP.664 trimers that increase the arsenal of native-like Env immunogens. Proc Natl Acad Sci USA 112:11947-11952; de Taeye et al. 2015. Immunogenicity of Stabilized HIV-1 Envelope Trimers with Reduced Exposure of Non-neutralizing Epitopes. Cell 163:1702-1715; Pugach et al. 2015. A native-like SOSIP.664 trimer based on an HIV-1 subtype B env gene. J Virol 89:3380-3395; Ringe et al. 2013. Cleavage strongly influences whether soluble HIV-1 envelope glycoprotein trimers adopt a native-like conformation. Proc Natl Acad Sci USA 110:18256-18261; Ringe et al. 2015. Influences on the Design and Purification of Soluble, Recombinant Native-Like HIV-1 Envelope Glycoprotein Trimers. J Virol 89:12189-12210; Ringe et al. 2017. Reducing V3 Antigenicity and Immunogenicity on Soluble, Native-Like HIV-1 Env SOSIP Trimers. J Virol 91; Ahmed et al. 2017. Stabilization of a soluble, native-like trimeric form of an efficiently cleaved Indian HIV-1 clade C envelope glycoprotein. J Biol Chem 292:8236-8243; Sanders et al. 2002. Stabilization of the soluble, cleaved, trimeric form of the envelope glycoprotein complex of human immunodeficiency virus type 1. J Virol 76:8875-8889; Binley et al. 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 74:627-643). In the past years, Applicants developed an improved native-like trimer design, generating well-ordered soluble Env mimics that are fully cleavage-independent, termed native flexibly linked (NFL) trimers. This design uses a flexible linker (two copies of Gly4-Ser, "G4S") to replace the natural cleavage site and sequence (Sharma et al. 2015. Cleavage-independent HIV-1 Env trimers engineered as soluble native spike mimetics for vaccine design. Cell Rep 11:539-550). The flexible linker between the natural C-terminus of gp120 and N-terminus of gp41, allows the un-cleaved trimers to achieve a native-like conformation without the need of furin for precursor processing. However, the original NFL trimer design contains the I559P mutation (Sharma et al. 2015. Cleavage-independent HIV-1 Env trimers engineered as soluble native spike mimetics for vaccine design. Cell Rep 11:539-550) that was initially identified in the SOSIP context to disfavor the post fusion state (Sanders et al. 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618). Both the original SOSIP and NFL designs do not form a high percentage of well-ordered trimers in all Env contexts. In the original NFL design, it is relatively inefficient in generating high yields of trimers derived from clade C strains, such as 16055 (Guenaga et al. 2015. Structure-Guided Redesign Increases the Propensity of HIV Env To Generate Highly Stable Soluble Trimers. J Virol 90:2806-2817). To improve trimer design, Applicants incorporated residues from BG505 (called trimer-derived (TD) residues) into 16055 NFLs, substantially improving the propensity to form native-like trimers (Guenaga et al. 2015. Structure-Guided Redesign Increases the Propensity of HIV Env To Generate Highly Stable Soluble Trimers. J Virol 90:2806-2817) and the elicitation of tier 2 clade C neutralizing antibodies (Martinez-Murillo et al., GB. 2017. Particulate Array of Well-Ordered HIV Clade C Env Trimers Elicits Neutralizing Antibodies that Display a Unique V2 Cap Approach. Immunity 46:804-817 e807; Dubrovskaya et al. 2017. Targeted N-glycan deletion at the receptor-binding site retains HIV Env NFL trimer integrity and accelerates the elicited antibody response. PLoS Pathog 13:e1006614). Further improvements on the TD design by targeted glycine substitutions at helix-to-coil transitions that disfavor the post-fusion state of Env (TD CC+, namely "TD+"), significantly improve trimer homogeneity, yield, stability and antigenicity, resulting in the first high-resolution clade C Env structure (Guenaga et al. 2017. Glycine Substitution at Helix-to-Coil Transitions Facilitates the Structural Determination of a Stabilized Subtype C HIV Envelope Glycoprotein. Immunity 46:792-803 e793).

In one aspect, provided herein are nanoparticles which may comprise an isolated polypeptide described herein. In some embodiments, a nanoparticle described herein is a ferritin nanoparticle, an encapsulin nanoparticle, a Sulfur Oxygenase Reductase (SOR) nanoparticle, a lumazine synthase nanoparticle or a pyruvate dehydrogenase nanoparticle. In some embodiments, a nanoparticle described herein is a ferritin nanoparticle. In some embodiments, a nanoparticle described herein may comprise an amino acid sequence having at least about 80%, at least about 90%, at least about 95%, at least about 97%, at least about 99%, or 100% sequence identity to the amino acid sequence of N332-GT1, N332-GT2, N332-GT3, N332-GT4, or N332-GT5. In some embodiments, a nanoparticle described herein may comprise an amino acid sequence having at least about 80%, at least about 90%, at least about 95%, at least about 97%, at least about 99%, or 100% sequence identity to the amino acid sequence of N332-GT1, N332-GT2, N332-GT3, N332-GT4, or N332-GT5. In some embodiments, a nanoparticle described herein may comprise N332-GT1, N332-GT2, N332-GT3, N332-GT4, or N332-GT5. In some embodiments, a nanoparticle described herein may comprise N332-GT2. In some embodiments, a nanoparticle described herein may comprise N332-GT5. In some embodiments, a nanoparticle described herein has at least about 80%, at least about 90%, at least about 95%, at least about 97%, at least about 99%, or 100% sequence identity to the amino acid sequence of SEQ ID NO: 13 or 15. In some embodiments, a nanoparticle described herein is a ferritin nanoparticle which may comprise the amino acid sequence of SEQ ID NO. 13 or 15.

The nanoparticle formulations may be a carbohydrate nanoparticle which may comprise a carbohydrate carrier and a modified nucleic acid molecule (e.g., mmRNA). As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; herein incorporated by reference in its entirety).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

The average diameter of the nanoparticle employed in the compositions of the invention can be at least one member selected from the group consisting of about 20 nanometers, about 25 nanometers, about 30 nanometers, about 40 nanometers, about 50 nanometers, about 75 nanometers, about 100 nanometers, about 125 nanometers, about 150 nanometers, about 175 nanometers and about 200 nanometers. In another embodiment, the average diameter of the particle is at least one member selected from the group consisting of between about 10 to about 200 nanometers, between about 0.5 to about 5 microns and between about 5 to about 10 microns. In another embodiment, the average diameter of the microparticle is selected from the group consisting of about 0.1 μm, about 0.2 μm, about 0.4 μm, about 0.5 μm, about 1 μm and about 2

Nanoparticles for use in the compositions of the invention can be made from lipids or other fatty acids (see, for example, U.S. Pat. Nos. 5,709,879; 6,342,226; 6,090,406; Lian, et al., J. of Pharma. Sci. 90:667-680 (2001) and van Slooten, et al., Pharm Res. 17:42-48 (2000)) and non-lipid compositions (see, for example, Kreuter, J. Anat. 189:503-505 (1996), the teachings of all of which are hereby incorporated by reference in their entirety). The compositions can be bilayer or multilamellar liposomes and phospholipid based. Polymerized nanoparticles, as described, for example, in U.S. Pat. No. 7,285,289, the teachings of which are incorporated by reference in their entirety.

Metallic oxide nanoparticles for use in the compositions of the invention can be chemically substituted with at least one reactive moiety capable of forming a thioether bond employing conventionally techniques as described herein and in U.S. Pat. No. 6,086,881, the teachings of which are hereby incorporated by reference in their entirety. The antigen described herein can be coupled in a single step onto the metallic oxide particles by the formation of at least one thioether bond or it may be synthesized or assembled stepwise onto the metallic oxide particles after the initial thioether bond formation. The chemical derivatization reagents for the metallic oxide particles can include organosilane reagents that provide thioalkane functionality or other groups that may readily be converted into thiols or thiol-reactive moieties. Organosilane reagents which may be utilized for this purpose may be, but are not limited to, 3-mercaptopropyltrimethoxysilane, 3-aminopropyltriethoxysilane, 3-iodopropyltrimethoxysilane, 2-chloroethyltrichlorosilane, 3-glycidoxypropyltrimethoxysilane, vinyltrichlorosilane and 3-acryloxypropyltrimethoxysilane. Moieties that include one or more disulfide components may also be joined to the metallic oxide particle surface and thereby provide the corresponding reactive moiety able to enter into and form a thioether bond and juncture. Exemplary nanoparticles for use in the compositions of the invention include at least one member selected from the group consisting of poly (D,L-lactide-co-glycolide, also referred to as "poly(lactic-co-glycolic acid) and bisacyloxypropylcysteine.

Nanoparticles for use in the compositions of the invention can be made of inorganic material. Nanoparticles for use in the compositions of the invention can be made of a polymer material, such as at least one member selected from the group consisting of polystyrene, brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, a carbohydrate, carboxymethyl cellulose, hydroxyethyl cellulose, agar, gel, proteinaceous polymer, polypeptide, eukaryotic and prokaryotic cells, viruses, lipid, metal, resin, latex, rubber, silicone (e.g., polydimethyldiphenyl siloxane), glass, ceramic, charcoal, kaolinite and bentonite.

In one aspect, provided herein are virus-like particles (VLPs) which may comprise an isolated polypeptide described herein.

It should be understood that in some embodiments, the polypeptides (e.g., Env trimers, nanoparticles, and other antigens) described herein can differ from the exact sequences illustrated and described herein. Thus, the invention contemplates deletions, additions and substitutions to the sequences shown, so long as the sequences function in accordance with the methods described herein. In this regard, in some embodiments, substitutions are conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, praline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention As disclosed and exemplified herein, germline reverted antibodies can be designed by comparing the heavy and light chains of an isolated bnAb (e.g., BG18) that binds to an epitope of interest to nucleotide sequences and/or the amino acid sequences potentially encoded by germline V gene segments. For example, one can obtain a germline reverted antibody starting from the amino acid sequence of an antibody directed to an antigen or epitope of choice and identifying germline encoded antibody segments (i.e., heavy chain V, D, and J gene segments and light chain V and J gene segments) close in sequence to the starting antibody. Germline variable genes are cataloged, for example at VBASE2 (Retter I, Althaus H H, Münch R, Müller W: VBASE2, an integrative V gene database. Nucleic Acids Res. 2005 Jan. 1; 33(Database issue):D671-4.). Starting from a known or preselected antibody and moving to such a database can be advantageous as the paired heavy and light chains will be compatible and likely to be well represented in the repertoire of expressed germline genes.

Germline antibody genes or inferred germline genes can be identified by analyzing NGS dataset obtained from HIV-uninfected human subjects, as discussed in the Examples below. Germline antibody genes or inferred germline genes that bind to an epitope of interest can also be identified by screening libraries of human heavy and light chain genes, for example by phage display. Another method is by immunization and preparation of monoclonal antibodies from a mouse that expresses human antibody genes. Preferably hybridomas are prepared before there is substantial somatic mutation and selection. It can be advantageous to select germline antibody gene segments that are well represented in the repertoire of expressed human antibodies, also taking into account compatibility of various heavy chain-light chain pairings. In certain embodiments, it is advantageous to select V-D, D-J, V-D-J (heavy chain) or V-J (light chain) combinations that are well represented.

In one aspect, provided herein are germline reverted and inferred-germline (iGL) variant heavy and light chain variable domains, including heavy and light chain CDR regions of BG18 that bind to an HIV Env polypeptide disclosed herein (e.g., N332-GT1, N332-GT2, N332-GT3, N332-GT4, or N332-GT5).

Germline reverted and inferred-germline antibodies disclosed herein are suitable for the selection of candidate vaccine molecules according to methods disclosed herein.

In one aspect, provided herein are isolated antibodies which may comprise the VHCDR1, VH CDR2, and VH CDR3 of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE1S, VH4-595, VH1-69, VH5-51, VH3-33, or VH3-23; and the VL CDR1, VL CDR2, and VL CDR3 of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE1S, VL3-10, VL3-19, VL3-1, VL3-21, or VL2-8. In some embodiments, an isolated antibody described herein may comprise the VH CDR1, VH CDR2, VH CDR3, VL CDR1, VL CDR2, and VL CDR3 of BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, or PRE15. In some embodiments, an isolated antibody described herein may comprise the 3 VH CDRs and 3 VL CDRs of VH4-59 and BG18 iGL, respectively;
VH1-69 and BG18 iGL, respectively;
VH5-51 and BG18 iGL, respectively;
VH3-33 and BG18 iGL, respectively;
VH3-23 and BG18 iGL, respectively;
BG18 iGL1 and VL3-19, respectively;
BG18 iGL1 and VL3-10, respectively;
BG18 iGL1 and VL3-1, respectively;
BG18 iGL1 and VL3-21, respectively; or
BG18 iGL1 and VL2-8, respectively In some embodiments, the CDR sequences are identified according to Kabat.

In some embodiments, an isolated antibody described herein may comprise the VH of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VH4-595, VH1-69, VH5-51, VH3-33, or VH3-23; and the VL of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VL3-10, VL3-19, VL3-1, VL3-21, or VL2-8. In some embodiments, an isolated antibody described herein may comprise the VH and VL of BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, or PRE15. In some embodiments, an isolated antibody described herein may comprise the VH and VL of VH4-59 and BG18 iGL, respectively;
VH1-69 and BG18 iGL, respectively;
VH5-51 and BG18 iGL, respectively;
VH3-33 and BG18 iGL, respectively;
VH3-23 and BG18 iGL, respectively;
BG18 iGL1 and VL3-19, respectively;
BG18 iGL1 and VL3-10, respectively;
BG18 iGL1 and VL3-1, respectively;
BG18 iGL1 and VL3-21, respectively; or
BG18 iGL1 and VL2-8, respectively.

In one aspect, provided herein are isolated polynucleotides encoding an isolated polypeptide described herein, a variant HIV Env gp120 polypeptide described herein, a recombinant HIV Env trimer described herein, a VLP described herein, or a nanoparticle described herein. In some embodiments, an isolated polynucleotide described herein is a DNA. In some embodiments, an isolated polynucleotide described herein is an mRNA. In some embodiments, an isolated polynucleotide described herein is an mRNA which may comprise a modified nucleotide.

Further provided herein are vectors which may comprise a polynucleotide described herein. In some embodiments, a vector described herein can be used for recombinant expression of an isolated polypeptide described herein, a variant HIV Env gp120 polypeptide described herein, a recombinant HIV Env trimer described herein, a VLP described herein, or a nanoparticle described herein. In one embodiment, a vector described herein can be used for administration of an isolated polypeptide described herein, a variant HIV Env gp120 polypeptide described herein, a recombinant HIV Env trimer described herein, or a nanoparticle described herein to a patient in need thereof.

In one aspect, provided herein are RNA replicons which may comprise an isolated polynucleotide described herein.

In some embodiments, an isolated polynucleotide described herein encodes an isolated polypeptide described herein. In some embodiments, the isolated polypeptide described herein may comprise the amino acid sequence of BG505 MD39 N332-GT1, BG505 MD39 N332-GT2, BG505 MD39 N332-GT3, BG505 MD39 N332-GT4, BG505 MD39 N332-GT5, or BG505 MD39 N332-GT2-KO.

In some embodiments, an isolated polynucleotide described herein encodes a nanoparticle described herein. In some embodiments, a nanoparticle described herein may comprise N332-GT1, N332-GT2, N332-GT3, N332-GT4, or N332-GT5. In some embodiments, a nanoparticle described herein may comprise N332-GT2. In some embodiments, a nanoparticle described herein may comprise N332-GT5. In some embodiments, a nanoparticle described herein is a ferritin nanoparticle which may comprise the SEQ ID NO. of 13 or 15.

In some embodiments, an isolated polynucleotide described herein encodes a recombinant HIV Env trimer described herein. In some embodiments, the recombinant HIV Env trimer described herein may comprise the amino acid sequence of BG505 MD39 N332-GT1, BG505 MD39 N332-GT2, BG505 MD39 N332-GT3, BG505 MD39 N332-GT4, BG505 MD39 N332-GT5, or BG505 MD39 N332-GT2-KO.

In some embodiments, an isolated polynucleotide described herein encodes an antibody described herein. In some embodiments, an isolated polynucleotide described herein encodes BG18.11, BG18.6. In some embodiments, an isolated polynucleotide described herein encodes BG18 iGL0, BG18 iGL1, or BG18 iGL2. In some embodiments, an isolated polynucleotide described herein encodes PRE1, PRE2, PRE3, PRE4, PRE5, PRE6, PRE7, PRE8, PRE9, PRE10, PRE11, PRE12, PRE13, PRE14, or PRE1S. In some embodiments, an isolated polynucleotide described herein encodes VH4-595, VH1-69, VH5-51, VH3-33, VH3-23, VL3-10, VL3-19, VL3-1, VL3-21, or VL2-8.

In one embodiment, an isolated polynucleotide described herein encodes a polypeptide (e.g., recombinant HIV Env trimer or nanoparticle) described herein and may comprise an mRNA. In one embodiment, the mRNA may comprise at least one modified nucleotide. In one embodiment, a modified mRNA encoding a polypeptide (e.g., recombinant HIV Env trimer or nanoparticle) described herein is for administering to a subject to treat or prevent HIV infection.

As used herein, an "isolated" polynucleotide or nucleic acid molecule is one, which is separated from other nucleic acid molecules, which are present in the natural source (e.g., in a mouse or a human) of the nucleic acid molecule.

Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a polypeptide (e.g., recombinant HIV Env trimer or nanoparticle) described herein is isolated or purified.

In yet another specific embodiment, a polynucleotide provided herein may comprise a nucleotide sequence encoding a polypeptide (e.g., recombinant HIV Env trimer or nanoparticle) described herein that is optimized, e.g., by codon/RNA optimization, replacement with heterologous signal sequences, and elimination of mRNA instability elements. Methods to generate optimized nucleic acids for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

The term "nucleic acid," in its broadest sense, includes any compound and/or substance that is or can be incorporated into an oligonucleotide chain. Exemplary nucleic acids for use in accordance with the present invention include, but are not limited to, one or more of DNA, RNA, hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

Provided are modified nucleic acids containing a translatable region encoding a peptide described herein, and one, two, or more than two different nucleoside modifications. In some embodiments, the modified nucleic acid exhibits reduced degradation in a cell into which the nucleic acid is introduced, relative to a corresponding unmodified nucleic acid. For example, the degradation rate of the nucleic acid is reduced by at least 10%, 20%, 30%, 40%, 50%, 60%, 70%, 80%, or 90%, compared to the degradation rate of the corresponding unmodified nucleic acid. Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or a hybrid thereof. In preferred embodiments, the modified nucleic acid includes messenger RNAs (mRNAs). As described herein, the nucleic acids of the invention do not substantially induce an innate immune response of a cell into which the mRNA is introduced.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In certain embodiments it is desirable to intracellularly degrade a modified nucleic acid introduced into the cell, for example if precise timing of protein production is desired. Thus, the invention provides a modified nucleic acid containing a degradation domain, which is capable of being acted on in a directed manner within a cell.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

Other components of nucleic acid are optional, and are beneficial in some embodiments. For example, a 5' untranslated region (UTR) and/or a 3'UTR are provided, wherein either or both may independently contain one or more different nucleoside modifications. In such embodiments, nucleoside modifications may also be present in the translatable region. Also provided are nucleic acids containing a Kozak sequence.

Further, nucleic acids encoding a peptide described herein, and containing an internal ribosome entry site (IRES) are provided herein. An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When nucleic acids are provided with an IRES, further optionally provided is a second translatable region. Examples of IRES sequences that can be used according to the invention include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

The therapeutic mRNAs as described, for example, in U.S. Pat. Nos. 9,464,124; 9,447,164; 9,428,535; 9,334,328; 9,303,079; 9,301,993; 9,295,689; 9,283,287; 9,271,996; 9,255,129; 9,254,311; 9,233,141; 9,221,891; 9,220,792; 9,220,755; 9,216,205; 9,192,651; 9,186,372; 9,181,319; 9,149,506; 9,114,113; 9,107,886; 9,095,552; 9,089,604; 9,061,059; 9,050,297; 8,999,380; 8,980,864; 8,822,663; 8,754,062; 8,710,200; 8,680,069 and 8,664,194 may be utilized for the present invention.

In certain embodiments, an optimized polynucleotide sequence encoding a polypeptide (e.g., recombinant HIV Env trimer or nanoparticle) described herein can hybridize to an antisense (e.g., complementary) polynucleotide of a n unoptimized polynucleotide sequence encoding polypeptide described herein or a fragment thereof (e.g., VL domain or VH domain). In specific embodiments, an optimized nucleotide sequence encoding a polypeptide (e.g., recombinant HIV Env trimer or nanoparticle) described herein or a fragment hybridizes under high stringency conditions to antisense polynucleotide of an unoptimized polynucleotide sequence encoding a polypeptide (e.g., recombinant HIV Env trimer or nanoparticle) described herein or a fragment thereof. In a specific embodiment, an optimized nucleotide sequence encoding a polypeptide (e.g., recombinant HIV Env trimer or nanoparticle) described herein hybridizes under high stringency, intermediate or lower stringency hybridization conditions to an antisense polynucleotide of an unoptimized nucleotide sequence encoding a polypeptide (e.g., recombinant HIV Env trimer or nanoparticle) described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, and modified versions of these antibodies can be determined using methods well-known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-246), which, briefly, involves the synthesis of overlapping oligonucleotides containing portions of the sequence encoding the antibody, annealing and ligating of those oligonucleotides, and then amplification of the ligated oligonucleotides by PCR.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a polypeptide (e.g., recombinant HIV Env trimer or nanoparticle) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

In one aspect, provided herein are isolated vectors which may comprise a polynucleotide described herein. In some embodiments, an isolated vector described herein is a viral vector.

In one aspect, provided herein are recombinant viruses which may comprise a polynucleotide described herein. In some embodiments, a recombinant virus described herein is a recombinant adeno-associated virus (AAV).

In one aspect, provided herein are host cells which may comprise a polynucleotide described herein, or a vector described herein. In some embodiments, a host cell described herein is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

In one aspect, provided herein are methods of producing an isolated polypeptide described herein, a recombinant HIV Env trimer described herein, or a nanoparticle described herein which may comprise, culturing the host cell described herein so that the polynucleotide is expressed and the isolated polypeptide, recombinant HIV Env trimer, or the nanoparticle is produced.

In certain aspects, provided herein are cells (e.g., host cells) expressing (e.g., recombinantly) polypeptides described herein and related polynucleotides and expression vectors. Provided herein are vectors (e.g., expression vectors) which may comprise polynucleotides which may comprise nucleotide sequences encoding polypeptides described herein. In one embodiment, the vectors can be used for recombinant expression of a polypeptide described herein in host cells (e.g., mammalian cells). In one embodiment, the vectors can be used for administration of a polypeptide described herein to a patient in need thereof. Also provided herein are host cells which may comprise such vectors for recombinantly expressing polypeptides described herein. In a particular aspect, provided herein are methods for producing a polypeptide described herein, which may comprise expressing such polypeptides in a host cell.

In certain aspects, provided herein is an isolated vector which may comprise a polynucleotide described herein. In one embodiment, the vector is a viral vector.

In certain aspects, provided herein is a recombinant virus which may comprise a polynucleotide described herein. In one embodiment, the recombinant virus encodes a polypeptide described herein. In one embodiment, the recombinant virus encodes a variant HIV Env polypeptide described herein. In one embodiment, the recombinant virus is a replication defective virus. Suitable replication defective viral vectors are known to those skilled in the art, for example, as disclosed in U.S. Pat. Nos. 7,198,784, 9,408, 905, 9,862,931, 8,067,156, U.S. Pat. Appl. Pub. Nos. 20150291935, 20120220492, 20180291351, and 20170175137, each of which is incorporated herein by reference in its entirety. In one embodiment, the recombinant virus is a retrovirus or retroviral vector, for example, a lentivirus or lentiviral vector. In one embodiment, the recombinant virus is an adenovirus or adenoviral vector, HSV or HSV vector, or influenza virus or viral vector. In one embodiment, the recombinant virus is an adeno-associated virus (AAV). In one embodiment, the recombinant virus is for administration to a subject to prevent or treat HIV infection. In one embodiment, the recombinant virus is an adeno-associated virus (AAV) for administration to a subject to prevent or treat HIV infection. Recombinant AAV particles encoding a polypeptide described herein and methods for producing thereof are known to one skilled in the art, for example, as disclosed in U.S. Pat. No. 8,865,881 and US20190031740, each of which is incorporated by reference herein in its entirety for all purposes. See also, Lin and Balazs, Retrovirology 15:66 (2018) and van den Berg et al., Molecular Therapy: Methods & Clinical Development 14:100-112 (2019), each of which is incorporated by reference herein in its entirety for all purposes.

In certain aspects, provided herein is a host cell which may comprise a polynucleotide described herein, or a vector described herein. In one embodiment, the vector encodes a polypeptide described herein.

In one embodiment, the host cell is selected from the group consisting of *E. coli, Pseudomonas, Bacillus, Streptomyces*, yeast, CHO, YB/20, NS0, PER-C6, HEK-293T, NIH-3T3, Helga, BHK, Hep G2, SP2/0, R1.1, B-W, L-M, COS 1, COS 7, BSC1, BSC40, BMT10 cell, plant cell, insect cell, and human cell in tissue culture. In one embodiment, the host cell is CHO.

In certain aspects, provided herein is a method of producing a polypeptide described herein which may comprise culturing a host cell described herein so that the polynucleotide is expressed and the polypeptide is produced. In one embodiment, the method further may comprise recovering the polypeptide.

The isolated polypeptides (e.g., recombinant HIV Env trimer or nanoparticle) described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding polypeptides of interest. Recombinant expression vectors are replicable DNA constructs, which have synthetic or cDNA-derived DNA fragments encoding a polypeptide operatively linked to suitable transcriptional or translational regulatory elements derived from mammalian, microbial, viral or insect genes. A transcriptional unit generally may comprise an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor, which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A variety of host-expression vector systems can be utilized to express polypeptide molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express a polypeptide molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces pichia*) transformed with recombinant yeast expression vectors containing polypeptide coding sequences; insect cell systems infected with recombinant virus expression vectors (e.g., baculovirus) containing polypeptide coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing polypeptide coding sequences; or mammalian cell systems (e.g., COS (e.g., COS1 or COS), CHO, BHK, MDCK, HEK 293, NS0, PER.C6, VERO, CRL7O3O, HsS78Bst, Helga, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing polypeptides described herein are CHO cells, for example CHO cells from the CHO GS System™ (Lonza). In a particular embodiment, cells for expressing polypeptides described herein are human cells, e.g., human cell lines. In a specific embodiment, a mammalian expression vector is pOptiVEC™ or pcDNA3.3. In a particular embodiment, bacterial cells such as *E. coli*, or eukaryotic cells (e.g., mammalian cells) are used for the expression of a recombinant polypeptide molecule. For example, mammalian cells such as Chinese hamster ovary (CHO) cells in conjunction with a vector such as the major intermediate early gene promoter element from human cytomegalovirus is an effective expression system for polypeptides. In a specific embodiment, the expression of nucleotide sequence encoding polypeptides described herein is regulated by a constitutive promoter, inducible promoter or tissue specific promoter.

For applications where it is desired that the polypeptides described herein be expressed in vivo, for example in a subject in need of treatment with a polypeptide described herein, any vector that allows for the expression of the polypeptides and is safe for use in vivo can be used. In one embodiment, the vector is a viral vector. Viral vectors can include poxvirus (vaccinia), including vaccinia Ankara and canarypox; adenoviruses, including adenovirus type 5 (Ad5); rubella; sendai virus; rhabdovirus; alphaviruses; and adeno-associated viruses. In one embodiment, the viral vector is an adeno-associated virus. Alternatively, a polynucleotide encoding the polypeptide could be delivered as DNA or RNA to the subject for in vivo expression of the polypeptide.

Suitable host cells for expression of a polypeptide of interest such as a polypeptide described herein include prokaryotes, yeast, insect or higher eukaryotic cells under the control of appropriate promoters. Prokaryotes include gram negative or gram-positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express a recombinant protein such as a polypeptide described herein. Expression of recombinant proteins in mammalian cells can be performed because such proteins are generally correctly folded, appropriately modified and completely functional. Examples of suitable mammalian host cell lines include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza HA peptide sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems, which secrete recombinant protein, e.g., a polypeptide, into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices which may comprise sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further an agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In specific embodiments, a polypeptide (e.g., recombinant HIV Env trimer or nanoparticle) described herein is isolated or purified. Generally, an isolated polypeptide is one that is substantially free of other polypeptides. For example, in a particular embodiment, a preparation of a polypeptide described herein is substantially free of cellular material and/or chemical precursors. The language "substantially free of cellular material" includes preparations of a polypeptide in which the polypeptide is separated from cellular components of the cells from which it is isolated or recombinantly produced. Thus, a polypeptide that is substantially free of cellular material includes preparations having less than about 30%, 20%, 10%, 5%, 2%, 1%, 0.5%, or 0.1% (by dry weight) of heterologous protein (also referred to herein as a "contaminating protein") and/or variants of a polypeptide, for example, different post-translational modified forms of a polypeptide. When the polypeptide (e.g., recombinant HIV Env trimer or nanoparticle described herein) is recombinantly produced, it is also generally substantially free of culture medium, i.e., culture medium represents less than about 20%, 10%, 2%, 1%, 0.5%, or 0.1% of the volume of the protein preparation. When the polypeptide (e.g., recombinant HIV Env trimer or nanoparticle described herein) is produced by chemical synthesis, it is generally substantially free of chemical precursors or other chemicals, i.e., it is separated from chemical precursors or other chemicals, which are involved in the synthesis of the protein. Accordingly, such preparations of the polypeptide (e.g., recombinant HIV Env trimer or nanoparticle described herein) have less than about 30%, 20%, 10%, or 5% (by dry weight) of chemical precursors or compounds other than the polypeptide of interest. In one embodiment, polypeptides described herein are isolated or purified.

Compositions which may comprise polypeptides described herein (e.g., recombinant HIV Env trimer or nanoparticle) are also provided. Further provided herein are compositions which may comprise a polynucleotide encoding a polypeptide described herein. In some embodiments, the polynucleotide may comprise mRNA. In some embodiments, the composition is a pharmaceutical composition. In some embodiments, the composition is an immunogenic composition.

In one aspect, provided herein are pharmaceutical compositions which may comprise an isolated polypeptide described herein, recombinant HIV Env trimer described herein, nanoparticle described herein, polynucleotide described herein, recombinant virus described herein, VLP described herein, or liposome described herein and a pharmaceutically acceptable excipient. In some embodiments, the composition is an immunogenic composition. In some embodiments, the composition is a vaccine. In some embodiments, an immunogenic composition or vaccine further may comprise an adjuvant. In some embodiments, the composition (e.g., immunogenic composition) is formulated for subcutaneous administration. In some embodiments, the composition (e.g., immunogenic composition) is formulated for intramuscular administration. In some embodiments, the composition (e.g., immunogenic composition) is formulated for topical administration, and in certain embodiments the composition is formulated for vaginal or rectal administration.

In one aspect, provided herein are immunogenic compositions which may comprise an isolated polypeptide described herein, recombinant HIV Env trimer described herein, nanoparticle described herein, polynucleotide described herein, recombinant virus described herein, VLP described herein, or liposome described herein and a pharmaceutically acceptable excipient.

In some embodiments, an immunogenic composition described herein further may comprise an adjuvant. In some embodiments, the adjuvant may comprise lecithin. In some embodiments, the adjuvant may comprise alum. In some embodiments, the adjuvant may comprise saponin, cholesterol and phospholipid. In some embodiments, the adjuvant may comprise ISCOMATRIX™. In some embodiments, the adjuvant may comprise carbomer homopolymer and lecithin. In some embodiments, the adjuvant may comprise Adjuplex™

In some embodiments, an immunogenic composition described herein is capable of eliciting a BG18 like response. In some embodiments, an immunogenic composition described herein is capable of eliciting a BG18 like response in a human subject. In some embodiments, an immunogenic composition described herein is capable of eliciting a BG18 like response in BG18$^{gH}$ B cell adoptive transfer recipient mice. In some embodiments, an immunogenic composition described herein is capable of eliciting the production of an antibody that binds to N332-GT2. In some embodiments, an immunogenic composition described herein is capable of eliciting the production of an antibody that binds to N332-GT2 with a higher affinity than to N332-GT2-KO. In some embodiments, an immunogenic composition described herein is capable of eliciting the production of a broadly neutralizing antibody in a subject.

In one aspect, provided herein are liposomes which may comprise an isolated polypeptide described herein.

Compositions described herein which may comprise a polypeptide described herein are intended for prevention and treatment of HIV infection. In some embodiments, compositions described herein (e.g., immunogenic composition) are for eliciting an immune reaction in a subject against HIV. In some embodiments, compositions described herein (e.g., immunogenic composition) are for eliciting a protective immune reaction in a subject against HIV.

In further embodiments of the present disclosure, a composition which may comprise a polypeptide described herein can additionally be combined with other compositions for the treatment of HIV infection or the prevention of HIV transmission.

In some embodiments, a polypeptide described herein can be administered within a pharmaceutically acceptable diluent, carrier, or excipient, in unit dose form. Conventional pharmaceutical practice can be employed to provide suitable formulations or compositions for administration to individuals. In some embodiments, the administration is prophylactic. Any appropriate route of administration can be employed, for example, administration can be parenteral, intravenous, intra-arterial, subcutaneous, intramuscular, intraperitoneal, intranasal, aerosol, suppository, oral administration, vaginal, or anal.

In some embodiments, the polypeptides and polynucleotides described herein are administered as a component of an immunogenic composition which may comprise the polypeptides and/or polynucleotides described herein in admixture with a pharmaceutically acceptable carrier. The immunogenic compositions described herein are useful to stimulate an immune response against HIV-1 and can be used as one or more components of a prophylactic or therapeutic vaccine against HIV-1 for the prevention, amelioration or treatment of AIDS. The polynucleotides and vectors described herein are particularly useful for providing genetic vaccines, i.e. vaccines for delivering the polynucleotides encoding the antigenic polypeptides described herein to a subject, such as a human, such that the antigenic polypeptides are then expressed in the subject to elicit an immune response.

In some embodiments, immunogenic compositions described herein comprise injectable suspensions, solutions, sprays, lyophilized powders, syrups, elixirs and the like. Any suitable form of composition can be used. To prepare such a composition, a polypeptide and/or polynucleotide described herein, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof; buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol. In some embodiments, immunogenic compositions described herein are formulated in the form of an oil-in-water emulsion. In some embodiments, the oil-in-water emulsion is based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. In some embodiments, the oil is used in combination with an emulsifier to form the emulsion. In some embodiments, the emulsifier may comprise a nonionic surfactant, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. In some embodiments, the adjuvant can be a mixture of emulsifier(s), micelle-forming agent, and oil such as that which is commercially available under the name Provax® (IDEC Pharmaceuticals, San Diego, CA). (PEG).

In some embodiments, an immunogenic composition described herein may comprise additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

In some embodiments, an immunogenic composition described herein may comprise an adjuvant. Suitable adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC3 1; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D fromMycobacterium tuberculosis, substances found in Cornyebacterium parvum, Bordetella pertussis, or members of the genus Brucella), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-0-acylated monophosphoryl lipid A (3D-MPL), imiquimod (also known in the art as IQM and commercially available as Aldara®; U.S. Pat. Nos. 4,689,338; 5,238,944; Zuber, A K. et al (2004) 22(13-14): 1791-8), and the CCR5 inhibitor CMPD167 (see Veazey, R S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A M. et al (2001) J. Immunol. 167(6): 3398-405), polyphosphazenes (Allcock, H.R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or a-galactosyl ceramide; see Green, T. D. et al, (2003) J. Virol. 77(3): 2046-2055), immunostimulatory fusion proteins such as IL-2 fused to the Fe fragment of immunoglobulins (Barouch et al., Science 290:486-492, 2000) and co-stimulatory molecules B7. 1 and B7.2 (Boyer), all of which can be administered either as proteins or in the form of DNA, on the same expression vectors as those encoding the antigens described herein or on separate expression vectors. In some embodiments, the adjuvant may comprise lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced Bio-Adjuvants (ABA)).

In some embodiments, an immunogenic composition described herein is formulated to introduce the polypeptides and polynucleotides disclosed herein (collectively, the immunogens) to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Pharmaceutical compositions described herein can be, for example, in unit dose form, such as in the form of ampoules, vials, suppositories, tablets, pills, or capsules. The formulations can be administered to human individuals in therapeutically or prophylactic effective amounts (e.g., amounts which prevent, eliminate, or reduce a pathological condition) to provide therapy or prophylaxis for a disease or condition (e.g., HIV infection). The preferred dosage of therapeutic or prophylactic agent to be administered is likely to depend on such variables as the type and extent of the disorder, the overall health status of the particular patient, the formulation of the compound excipients, and its route of administration. Suitable dosages of the polypeptides and polynucleotides disclosed herein (collectively, the immunogens) in the immunogenic composition disclosed herein can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

In one aspect, provided herein are methods for eliciting an immune response to HIV Env gp120 in a subject, which may comprise administering to the subject an effective amount of an immunogenic composition described herein, thereby generating the immune response. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the subject is a BG18$^{gH}$ B cell adoptive transfer recipient mouse. In some embodiments, the subject is a mouse. In some embodiments, the immunogenic composition may comprise an isolated polypeptide described herein. In some embodiments, the immunogenic composition may comprise a recombinant HIV Env trimer described herein. In some embodiments, the immunogenic composition may comprise a nanoparticle described herein. In some embodiments, the immunogenic composition may comprise a nucleic acid described herein. In some embodiments, the pharmaceutical composition may comprise a recombinant virus described herein. In some embodiments, an immunogenic composition further may comprise an adjuvant. In some embodiments, the immunogenic composition is formulated for subcutaneous administration. In some embodiments, the immunogenic composition is formulated for intramuscular administration.

In one aspect, provided herein are methods of reducing the likelihood of HIV infection in a subject exposed to HIV which may comprise administering to the subject an effective amount of an immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition may comprise an isolated polypeptide described herein. In some embodiments, the immunogenic composition may comprise a recombinant HIV Env trimer described herein. In some embodiments, the immunogenic composition may comprise a nanoparticle described herein. In some embodiments, the immunogenic composition may comprise a nucleic acid described herein. In some embodiments, the pharmaceutical composition may comprise a recombinant virus described herein. In some embodiments, an immunogenic composition further may comprise an adjuvant. In some embodiments, the immunogenic composition is formulated for subcutaneous administration. In some embodiments, the immunogenic composition is formulated for intramuscular administration.

In one aspect, provided herein are methods of reducing the risk of a subject becoming infected with HIV which may comprise administering to the subject in need thereof an effective amount of an immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition may comprise an isolated polypeptide described herein. In some embodiments, the immunogenic composition may comprise a recombinant HIV Env trimer described herein. In some embodiments, the immunogenic composition may comprise a nanoparticle described herein. In some embodiments, the immunogenic composition may comprise a nucleic acid described herein. In some embodiments, the pharmaceutical composition may comprise a recombinant virus described herein. In some embodiments, an immunogenic composition further may comprise an adjuvant. In some embodiments, the immunogenic composition is formulated for subcutaneous administration. In some embodiments, the immunogenic composition is formulated for intramuscular administration.

In one aspect, provided herein are methods of preventing HIV infection which may comprise administering to a subject in need thereof an effective amount of the immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition may comprise an isolated polypeptide described herein. In some embodiments, the immunogenic composition may comprise a recombinant HIV Env trimer described herein. In some embodiments, the immunogenic composition may comprise a nanoparticle described herein.

In some embodiments, the immunogenic composition may comprise a nucleic acid described herein. In some embodiments, the pharmaceutical composition may comprise a recombinant virus described herein. In some embodiments, an immunogenic composition further may comprise an adjuvant. In some embodiments, the immunogenic composition is formulated for subcutaneous administration. In some embodiments, the immunogenic composition is formulated for intramuscular administration.

In one aspect, provided herein are methods of treating HIV/AIDS which may comprise administering to a subject in need thereof an effective amount of the immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition may comprise an isolated polypeptide described herein. In some embodiments, the immunogenic composition may comprise a recombinant HIV Env trimer described herein. In some embodiments, the immunogenic composition may comprise a nanoparticle described herein. In some embodiments, the immunogenic composition may comprise a nucleic acid described herein. In some embodiments, the pharmaceutical composition may comprise a recombinant virus described herein. In some embodiments, an immunogenic composition further may comprise an adjuvant. In some embodiments, the immunogenic composition is formulated for subcutaneous administration. In some embodiments, the immunogenic composition is formulated for intramuscular administration.

In some embodiments, the immunogenic composition may comprise an isolated polypeptide described herein. In some embodiments, the immunogenic composition may comprise a recombinant HIV Env trimer described herein. In some embodiments, the immunogenic composition may comprise a nanoparticle described herein. In some embodiments, the immunogenic composition may comprise a nucleic acid described herein. In some embodiments, the pharmaceutical composition may comprise a recombinant virus described herein. In some embodiments, the immunogenic composition may comprise an isolated polypeptide described herein. In some embodiments, the immunogenic composition may comprise a recombinant HIV Env trimer described herein. In some embodiments, the immunogenic composition may comprise a nanoparticle described herein. In some embodiments, the immunogenic composition may comprise a nucleic acid described herein. In some embodiments, the pharmaceutical composition may comprise a recombinant virus described herein. In some embodiments, an immunogenic composition further may comprise an adjuvant. In some embodiments, the immunogenic composition is formulated for subcutaneous administration. In some embodiments, the immunogenic composition is formulated for intramuscular administration.

In some embodiments, a method described herein further may comprise administering at least one additional therapeutic agent. In some embodiments, the additional therapeutic agent is an antiretroviral agent. In some embodiments, the additional therapeutic agent may comprise an antiretroviral therapy (ART) agent, a reservoir activator, an immunomodulator, a second antibody, or a broadly neutralizing anti-BIV antibody.

In one embodiment, the administering to the subject is by at least one mode selected from oral, parenteral, subcutaneous, intramuscular, intravenous, vaginal, rectal, buccal, sublingual, and transdermal.

In certain embodiments, the subject is at risk for exposure to HIV. In some embodiments, the subject is infected with HIV. In some embodiments, the subject is diagnosed with AIDS. In certain embodiments, the subject at risk for exposure to HIV is a health care worker. In certain embodiments, the subject at risk for exposure to HIV is a sex worker. In certain embodiments, the subject at risk for exposure to HIV is a sexual partner of an HIV infected individual. In certain embodiments, the subject at risk for exposure to HIV is a newborn.

In some embodiments, the polypeptides and/or polynucleotides described herein are administered in vivo, for example where the aim is to produce an immunogenic response in a subject. In some embodiments, the "subject" may be any animal. In some embodiments, it will be desirable to express the antigens described herein in human subjects, such as in clinical trials and for actual clinical use of the immunogenic compositions and vaccine of the invention. In some embodiments, the subject is a human, for example a human that is infected with, or is at risk of infection with, HIV-1.

For such in vivo applications the polypeptides and/or polynucleotides described herein can be administered as a component of an immunogenic composition which may comprise the polypeptides and/or polynucleotides described herein in admixture with a pharmaceutically acceptable carrier. The immunogenic compositions described herein are useful to stimulate an immune response against HIV-1 and can be used as one or more components of a prophylactic or therapeutic vaccine against HIV-1 for the prevention, amelioration or treatment of AIDS. The polynucleotides described herein are particularly useful for providing genetic vaccines, i.e. vaccines for delivering the polynucleotides encoding the polypeptides described herein to a subject, such as a human, such that the polypeptides are then expressed in the subject to elicit an immune response.

When provided prophylactically, the immunogenic compositions described herein can be administered to a subject in advance of HIV infection, or evidence of HIV infection, or in advance of any symptom due to AIDS, especially in high-risk subjects. The prophylactic administration of the immunogenic compositions described herein can serve to provide protective immunity of a subject against HIV-1 infection or to prevent or attenuate the progression of AIDS in a subject already infected with HIV-1. When provided therapeutically, the immunogenic compositions described herein can serve to ameliorate and treat AIDS symptoms and can be used as soon after infection as possible, for example, before appearance of any symptoms of AIDS, but can also be used at (or after) the onset of the disease symptoms.

Immunization schedules (or regimens) are well known for animals (including humans) and can be readily determined for the particular subject and immunogenic composition. Hence, the immunogens can be administered one or more times to the subject. In some embodiments, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but can have as few as one or two or four. The methods of inducing an immune response described herein can also include administration of an adjuvant with the immunogens. In some instances, annual, biannual or other long interval (5-10 years) booster immunization can supplement the initial immunization protocol.

The methods described herein also include a variety of prime-boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). In some embodiments, the prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using a polypeptide (e.g., Env trimer or nanoparticle) described herein to provide priming and boosting regimens.

In some embodiments, a method of inducing an immune response against HIV in a subject described herein may comprise administering an immunogenic composition of the invention which may comprise an adenovirus vector containing DNA encoding one or more of the polypeptides described herein, one or more times to a subject wherein the polypeptides are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In some embodiments, the other HIV immunogen is Env, for example, an HIV Env trimer.

Provided herein are methods for identifying vaccines capable of eliciting a broadly neutralizing antibody (bnAb) response in a subject (e.g., a human subject).

In one aspect, provided herein are methods for identifying a vaccine candidate variant HIV Env polypeptide (e.g., gp120 polypeptide or HIV Env trimer), the method which may comprise providing a library which may comprise a plurality of variant HIV Env polypeptides; contacting the library with an antibody described herein; and identifying a variant HIV Env polypeptide that specifically binds to the antibody. In some embodiments of a method for identifying a vaccine candidate variant HIV Env polypeptide described herein the plurality of variant HIV Env polypeptides comprise variants of a parental HIV Env polypeptide which may comprise one or more amino acid substitutions at a region selected from the V1 loop which may comprise positions 131-154, V3 loop which may comprise positions 297-334, and β19 sheet which may comprise positions 413-419, wherein HIV Env polypeptide positions correspond to the HXB2 reference (SEQ ID NO: 1). In some embodiments of a method for identifying a vaccine candidate variant HIV Env polypeptide described herein the parental HIV Env polypeptide may comprise BG505, BG505 N332, BG505 MD39, BG505 MD39 N332, BG505 MD39 11mutB, or BG505 MD39 17mutE Env polypeptide. In some embodiments, the Env polypeptide is a gp160 polypeptide, a gp120 polypeptide, or an Env trimer polypeptide.

The nanoparticle formulations may be a carbohydrate nanoparticle which may comprise a carbohydrate carrier and a modified nucleic acid molecule (e.g., mmRNA). As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; herein incorporated by reference in its entirety).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

The average diameter of the nanoparticle employed in the compositions of the invention can be at least one member selected from the group consisting of about 20 nanometers, about 25 nanometers, about 30 nanometers, about 40 nanometers, about 50 nanometers, about 75 nanometers, about 100 nanometers, about 125 nanometers, about 150 nanometers, about 175 nanometers and about 200 nanometers. In another embodiment, the average diameter of the particle is at least one member selected from the group consisting of between about 10 to about 200 nanometers, between about 0.5 to about 5 microns and between about 5 to about 10 microns. In another embodiment, the average diameter of the microparticle is selected from the group consisting of about 0.1 μm, about 0.2 μm, about 0.4 μm, about 0.5 μm, about 1 nm and about 2 μm.

Nanoparticles for use in the compositions of the invention can be made from lipids or other fatty acids (see, for example, U.S. Pat. Nos. 5,709,879; 6,342,226; 6,090,406; Lian, et al., J. of Pharma. Sci. 90:667-680 (2001) and van Slooten, et al., Pharm Res. 17:42-48 (2000)) and non-lipid compositions (see, for example, Kreuter, J. Anat. 189:503-505 (1996), the teachings of all of which are hereby incorporated by reference in their entirety). The compositions can be bilayer or multilamellar liposomes and phospholipid based. Polymerized nanoparticles, as described, for example, in U.S. Pat. No. 7,285,289, the teachings of which are incorporated by reference in their entirety.

Metallic oxide nanoparticles for use in the compositions of the invention can be chemically substituted with at least one reactive moiety capable of forming a thioether bond employing conventionally techniques as described herein and in U.S. Pat. No. 6,086,881, the teachings of which are hereby incorporated by reference in their entirety. The antigen described herein can be coupled in a single step onto the metallic oxide particles by the formation of at least one thioether bond or it may be synthesized or assembled stepwise onto the metallic oxide particles after the initial thioether bond formation. The chemical derivatization reagents for the metallic oxide particles can include organosilane reagents that provide thioalkane functionality or other groups that may readily be converted into thiols or thiol-reactive moieties. Organosilane reagents which may be utilized for this purpose may be, but are not limited to, 3-mercaptopropyltrimethoxysilane, 3-aminopropyltriethoxysilane, 3-iodopropyltrimethoxysilane, 2-chloroethyltrichlorosilane, 3-glycidoxypropyltrimethoxysilane, vinyltrichlorosilane and 3-acryloxypropyltrimethoxysilane. Moieties that include one or more disulfide components may also be joined to the metallic oxide particle surface and thereby provide the corresponding reactive moiety able to enter into and form a thioether bond and juncture. Exemplary nanoparticles for use in the compositions of the invention include at least one member selected from the group consisting of poly (D,L-lactide-co-glycolide, also referred to as "poly(lactic-co-glycolic acid) and bisacyloxypropylcysteine.

Nanoparticles for use in the compositions of the invention can be made of inorganic material. Nanoparticles for use in the compositions of the invention can be made of a polymer material, such as at least one member selected from the group consisting of polystyrene, brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, a carbohydrate, carboxymethyl cellulose, hydroxyethyl cellulose, agar, gel, proteinaceous polymer, polypeptide, eukaryotic and prokaryotic cells, viruses, lipid, metal, resin, latex, rubber, silicone (e.g., polydimethyldiphenyl siloxane), glass, ceramic, charcoal, kaolinite and bentonite.

It is noted that these therapeutics may be a chemical compound, a composition which may comprise a polypeptide of the present invention and/or antibody elicited by such a chemical compound and/or portion thereof or a pharmaceutically acceptable salt or a composition which may comprise a polypeptide of the invention, and may be administered alone or as an active ingredient in combination with pharmaceutically acceptable carriers, diluents, and vehicles, as well as other active ingredients.

The compounds or compositions may be administered orally, subcutaneously or parenterally including intravenous, intraarterial, intramuscular, intraperitoneally, and intranasal administration as well as intrathecal and infusion techniques.

It is noted that humans are treated generally longer than the mice or other experimental animals which treatment has a length proportional to the length of the disease process and drug effectiveness. The doses may be single doses or multiple doses over a period of several days, but single doses are preferred. Thus, one may scale up from animal experiments, e.g., rats, mice, and the like, to humans, by techniques from this disclosure and documents cited herein and the knowledge in the art, without undue experimentation.

In a particularly advantageous embodiment, the mRNAs of the present invention are administered in combinations of a prime dose followed by one or more boost doses over time. mRNA doses of about 100 µg are advantageous, however, dosages of about 10 µg to about 1000 µg, about 20 µg to about 900 µg, about 30 µg to about 800 µg, about 40 µg to about 700 µg, about 50 µg to about 600 µg, about 60 µg to about 500 µg, about 70 µg to about 400 µg, about 80 µg to about 300 µg, or about 900 µg to about 200 µg, are contemplated. Varying combinations are presented below as non-limiting examples.

The treatment generally has a length proportional to the length of the disease process and drug effectiveness and the patient being treated.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier may be a solvent or dispersing medium containing, for example, water, ethanol, polyol (for example, glycerol, propylene glycol, liquid polyethylene glycol, and the like), suitable mixtures thereof, and vegetable oils.

Proper fluidity may be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, may be added. Prevention of the action of microorganisms may be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form may be brought about by the use of agents delaying absorption, for example, aluminum monostearate and gelatin. According to the present invention, however, any vehicle, diluent, or additive used would have to be compatible with the compounds.

Sterile injectable solutions may be prepared by incorporating the compounds utilized in practicing the present invention in the required amount of the appropriate solvent with various amounts of the other ingredients, as desired.

A pharmacological formulation of the present invention, e.g., which may comprise a therapeutic compound or polypeptide of the present invention, may be administered to the patient in an injectable formulation containing any compatible carrier, such as various vehicles, adjuvants, additives, and diluents; or the compounds utilized in the present invention may be administered parenterally to the patient in the form of slow-release subcutaneous implants or targeted delivery systems such as monoclonal antibodies, iontophoretic, polymer matrices, liposomes, and microspheres.

A pharmacological formulation of the compound and composition which may comprise a polypeptide utilized in the present invention may be administered orally to the patient. Conventional methods such as administering the compounds in tablets, suspensions, solutions, emulsions, capsules, powders, syrups and the like are usable. Known techniques, which deliver the compound orally or intravenously and retain the biological activity, are preferred.

In one embodiment, a formulation of the present invention may be administered initially, and thereafter maintained by further administration. For instance, a formulation of the invention may be administered in one type of composition and thereafter further administered in a different or the same type of composition. For example, a formulation of the invention may be administered by intravenous injection to bring blood levels to a suitable level. The patient's levels are then maintained by an oral dosage form, although other forms of administration, dependent upon the patient's condition, may be used. In the instance of a vaccine composition, the vaccine may be administered as a single dose, or the vaccine may incorporate set booster doses. For example, booster doses may comprise variants in order to provide protection against multiple clades of HIV.

The quantity to be administered will vary for the patient being treated and whether the administration is for treatment or prevention and will vary from a few micrograms to a few milligrams for an average 70 kg patient, e.g., 5 micrograms to 5 milligrams such as 500 micrograms, or about 100 ng/kg of body weight to 100 mg/kg of body weight per administration and preferably will be from 10 pg/kg to 10 mg/kg per administration. Typically, however, the antigen is present in an amount on, the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and LD50 in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations may be ascertained without undue experimentation. For instance, dosages may be readily ascertained by those skilled in the art from this disclosure and the knowledge in the art. Thus, the skilled artisan may readily determine the amount of compound and optional additives, vehicles, and/or carrier in compositions and to be administered in methods of the invention. Typically, an adjuvant or additive is commonly used as 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Such determinations do not require undue experimentation from the knowledge of the skilled artisan, this disclosure and the documents cited herein. And, the time for sequential administrations may be ascertained without undue experimentation.

Examples of compositions which may comprise a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions may also be lyophilized. The compositions may contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention may be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers may preferably dispense a metered dose or, a dose having a particular particle size.

Compositions of the invention may contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions may approach solid or gelatin forms, which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally. Viscous compositions, on the other hand, may be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions may be isotonic, i.e., it may have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative may be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems may be readily avoided by reference to standard texts or by simple experiments (not involving undue experimentation), from this disclosure and the documents cited herein.

It is generally envisaged that compounds and compositions of the invention will be administered by injection, as such compounds are to elicit anti-HIV antibodies, and the skilled artisan may, from this disclosure and the knowledge in the art, formulate compounds and compositions identified by herein methods for administration by injection and administer such compounds and compositions by injection.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions may be administered in dosages and by techniques well known to those skilled in the medical arts taking into consideration such factors as the age, sex, weight, and condition of the particular patient, and the composition form used for administration (e.g., solid vs. liquid). Dosages for humans or other mammals may be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Experimental Design

Next generation sequencing (NGS) and bioinformatics was used to identify HCDR3s sharing key properties with the HCDR3-dependent bnAb BG18 in 14 of 14 HIV-uninfected donors. Then, BG18 inferred-germline (iGL) variants with NGS-derived HCDR3 loops were used as targets for structural-model-guided, multitarget mammalian-display selection of a series of Env trimers (N332-GT trimers) that bind to diverse BG18 potential precursors. Sorting of human B cells from HIV-uninfected donors using N332-GT trimer probes revealed BG18-like naive B cells with long HCDR3 loops and light chains similar to those in BG18. Cryo-electron microscopy complexes of a native-like trimer bound to BG18, and of N332-GT trimers bound to either BG18 iGL or human naive B cell sorting-derived Abs, all showed a similar binding epitope and orientation, supporting the bnAb precursor potential of the sorting-derived Abs. N332-GT trimer-based nanoparticles were constructed. It was found that nanoparticle immunization initiated responses from rare BG18-like B cells in mice hosting transferred BG18 iGL heavy chain B cells. This study demonstrated the potential for vaccine targeting of rare HCDR3-dependent bnAb precursors and suggested that N332-GT-trimer-based nanoparticles have promise for priming BG18-like bnAb responses in humans.

Germline-targeting (GT) HIV vaccine design is a strategy that aims to induce bnAbs by first priming the precursor B cells of known bnAbs and then shepherding B cell affinity maturation with a series of rationally designed boosting immunogens. There have been many advances in developing and testing germline-targeting immunogens to prime precursors of VRC01-class bnAbs with an Env-binding mode that is dependent on the human VH1-2 gene but permissive for a wide variety of HCDR3 loops[1-10], and at least one such immunogen is entering human clinical testing. However, VRC01-class bnAbs represent a specialized case in which non-HCDR3 features dominate the binding modality. In contrast, most HIV bnAbs and most Abs in general employ the HCDR3 as a major determinant for epitope interaction. Hence, an optimally effective HIV vaccine that induces multiple bnAbs for optimal coverage, and a general solution to germline-targeting vaccine design, will need to include HCDR3-dependent bnAbs. The enormous junctional diversity within long HCDR3s (at junctions between $V_H$ and $D_H$, and $D_H$ and $J_H$ genes) presents a key difficulty for developing GT immunogens to initiate HCDR3-dependent bnAb responses consistently. This diversity in the human B cell repertoire makes any single HCDR3 sequence an impractical vaccine target and requires that a pool of potential precursors sharing a minimal set of bnAb-associated genetic features should be identified and targeted.

Figure 10:
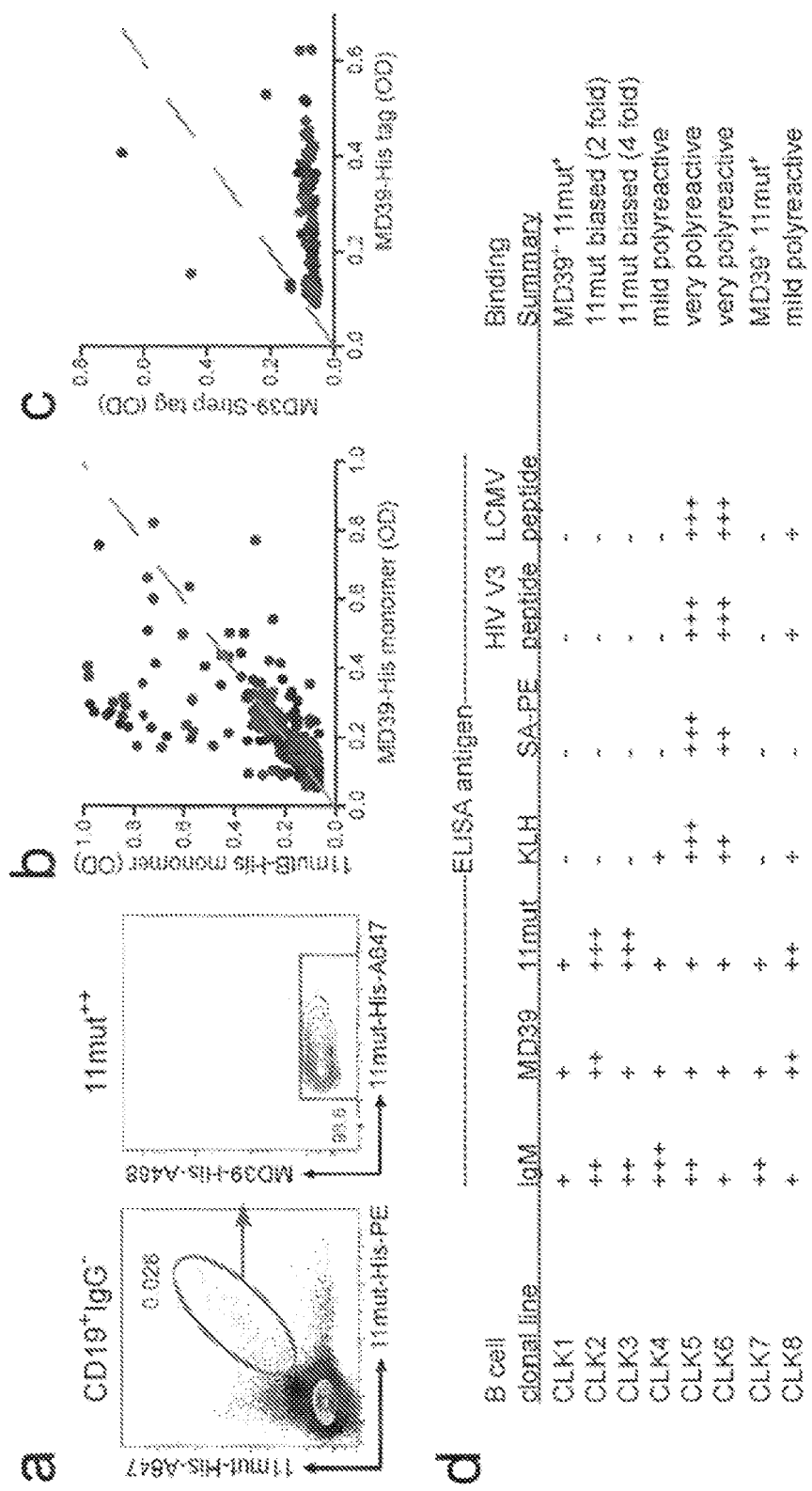
FIG. 10. Naive human B cell repertoire screening of 11mutB, N332-GT1 and N332-GT2. In total, 57 million B cells were screened from 4 donors using 11mutB as a sorting probe. a) Gating strategy for 11mutB epitope-specific sorting of naive human B cells. b) 11mutB+11mutB+MD39neg B cells were sorted and clonal B cell lines were generated. Culture supernatants from >1000 clonal B cell lines were tested by ELISA for specificity to 11mutB and MD39. c) Many clonal lines did not show binding to MD39 with a strep tag, but did show specificity MD39 with a His tag, implying that many of the clonal lines were not MD39-specific. d) Summary ELISA results for eight representative B cell clonal lines with differing polyreactivity profiles, but all positive for 11mutB and MD39. KLH (keyhole limpet hemocyanin), SA-PE (streptavidin-phycoerythrin), HIV V3 peptide (CTRPNNNTRKSIRIGPGQAFYATG-DIIGDIRQAHC), and LCMV peptide (DIYKGVYQFKSV) were used to test for polyreactivity. e) B cell lines were sequenced for HC and LC. e) Frequency of N332-GT probe double positive (N332-GT+N332-GT+) of total IgG negative B cells as shown in FIG. 2a left. f) Frequency of N332 epitope-specific B cells among N332-GT probe double positive B cells (MD39neg of N332-GT1+N332-GT1+ or N332-GT2KOneg of N332-GT2+N332-GT2+) as shown in FIG. 2a right. g) Frequency of N332 epitope-specific B cells of total IgG negative B cells (N332-GT1+N332-GT1+MD39neg or N332-GT2+N332-GT2+N332-GT2KOneg) as shown in FIG. 2a right. h) Epitope classification among 45 HMP Fabs from naive human B cells. 17 HMP Fabs showed epitope-specific binding to N332-GT trimers (red). Three Fabs showed epitope-specificity to non-N332 epitopes on N332-GT trimers (white). The remaining Fabs had weak/undetectable binding to N332-GT trimers (gray). i) Genetic features of Ab H-L paired sequences and expressed Fabs isolated from N332-GT1 and N332-GT2 B cell sorting.
Figure 10:
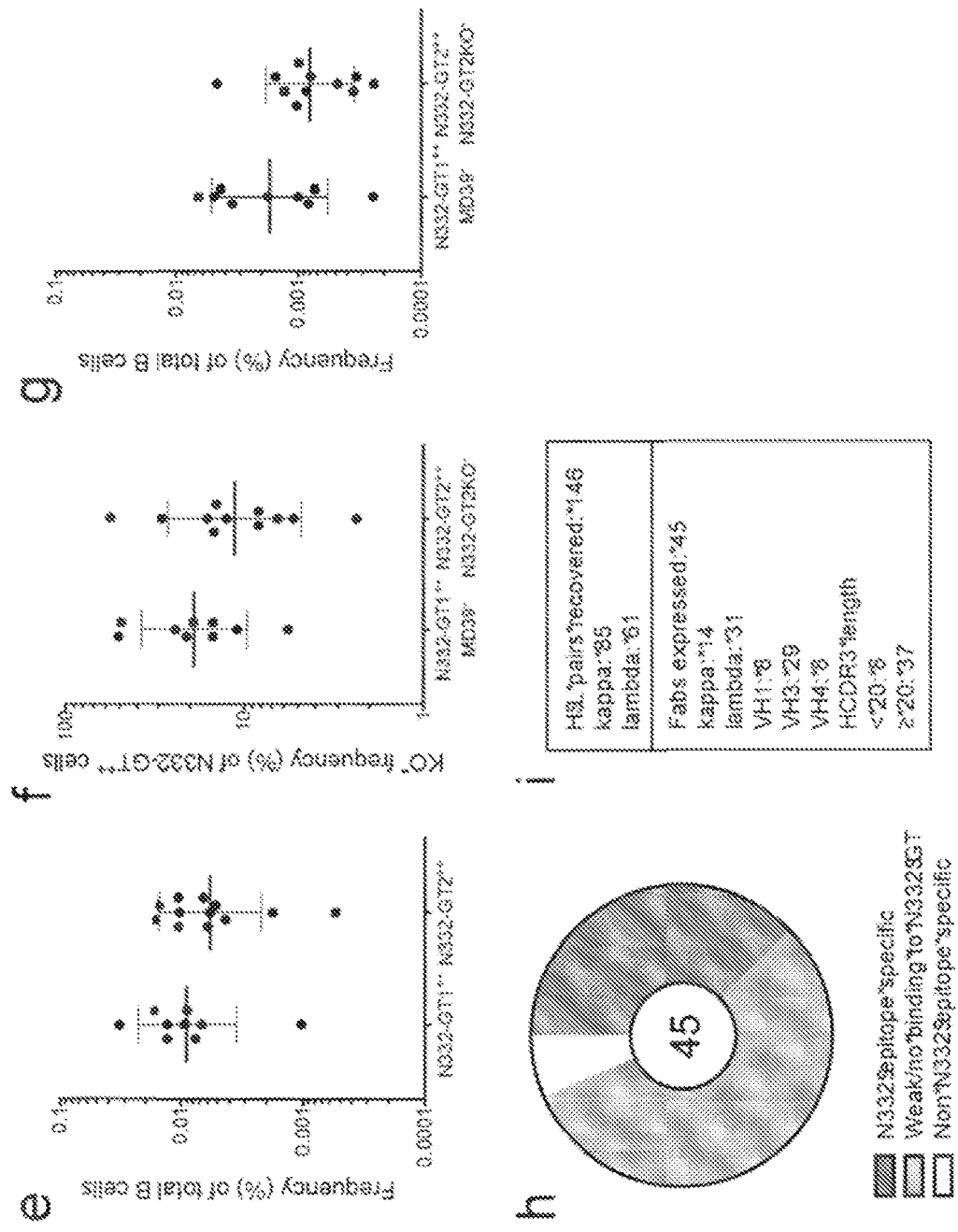

GT Env trimers with affinity for iGL precursors of the HCDR3-dependent bnAb PGT121[11] that binds to the N332 glycan supersite, also known as the high mannose patch or V3-glycan epitope, on the trimer[12,13] were previously engineered. These GT trimers (10mut, 11mut$_B$) were able to prime B cells in a PGT121 iGL homozygous B cell receptor (BCR) knock-in mouse. Immunization with a GT prime followed by a series of our shepherding boosts elicited PGT121-class bnAbs in this mouse model, providing proof principle that HIV bnAbs can be elicited starting from B cells bearing human iGL BCRs[11,14]. Despite this success, human clinical testing of this immunization regimen was not pursued, primarily because 10mut and 11mutB trimers had low affinity for PGT121 iGL variants, suggesting that bona fide naive precursors lacking bnAb junctional regions may have very low or no detectable affinity. Correspondingly, attempts to isolate PGT121 precursors from naive human B cells by using 11mutB trimers as bait did not succeed (FIG. 10).

Figure 4:
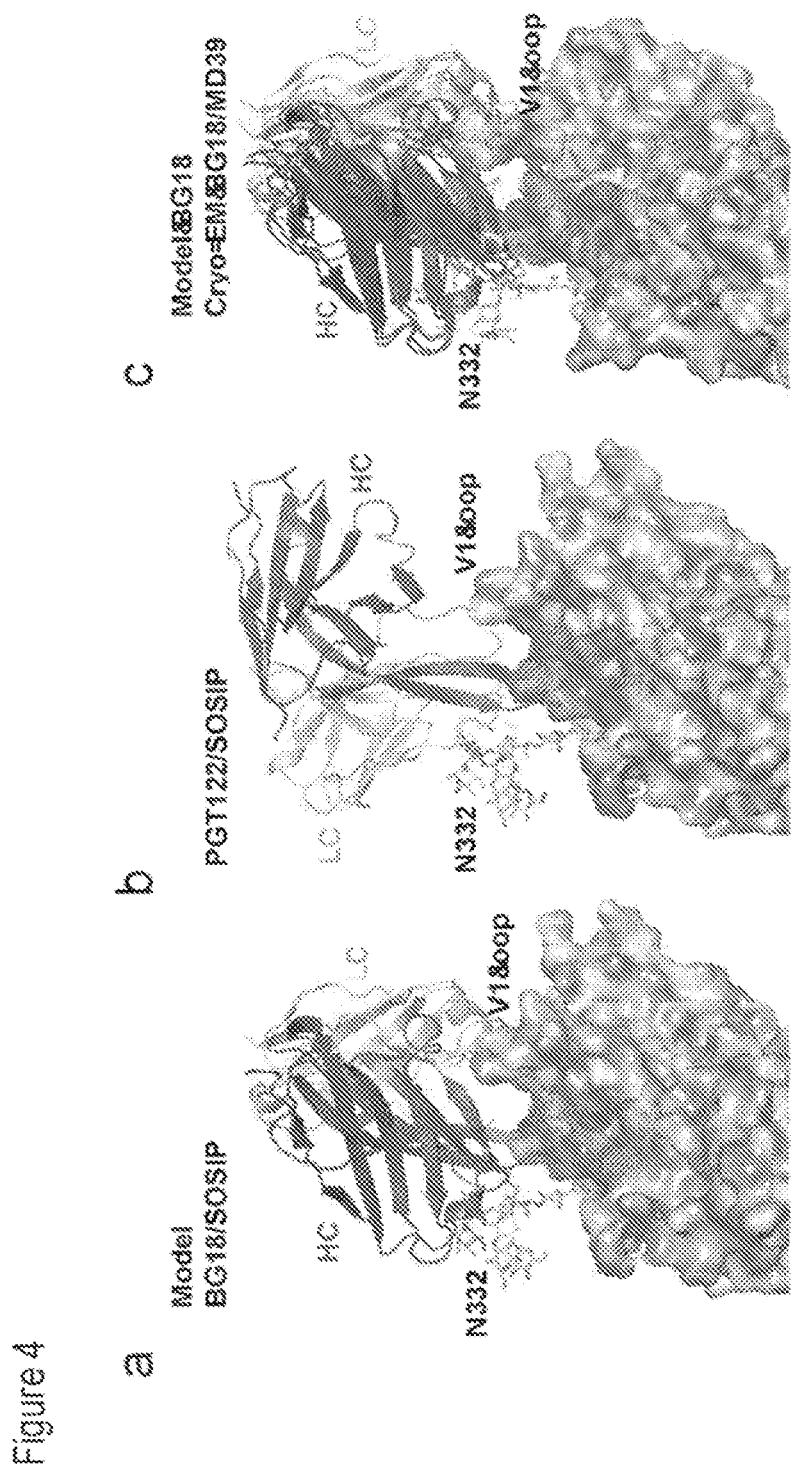
FIG. 4. Model of BG18 bound to BG505 SOSIP that was used to guide GT design. a) Model of BG18 bound to BG505 SOSIP obtained by HCDR3 alignment of unliganded BG18 (PDB:5UD9) to PGT122 bound to BG505 SOSIP (PDB: 4TVP). BG505 SOSIP, gray; BG18 HC purple; BG18 LC, cyan; N332 glycan, green sticks. Conserved residues contacted by the HCDR3 (G324, D325, I326, R327, Q328, H330, T415, and P417) are colored red. b) PGT122 complexed with BG505 SOSIP shown for comparison. BG505 SOSIP, gray; PGT122 HC, purple; PGT122 LC, cyan; N332 glycan, green sticks. Conserved residues contacted by the HCDR3 are colored red as in a). c) Model of BG18 bound to BG505 SOSIP aligned to the cryo-EM derived structure of BG18 bound to BG505 MD39 from FIG. 1b. BG505 SOSIP is not shown in this alignment. MD39, gray; BG18 HC, purple; BG18 LC, cyan; N332 glycan, green sticks. Conserved residues contacted by the HCDR3 are colored red as in a). d) BG18/SOSIP model indicates that the HCDR1 R29 interacts with the N332 glycan. SOSIP, gray; BG18 HC, purple; N332 glycan, green sticks. e) HCDR1 somatic mutation R29 was reverted to germline Isoleucine and tested for neutralization on a panel of 24 BG18-sensitive pseudoviruses. *IC50 values for BG18 were taken from Freund et al 15.
Figure 4:
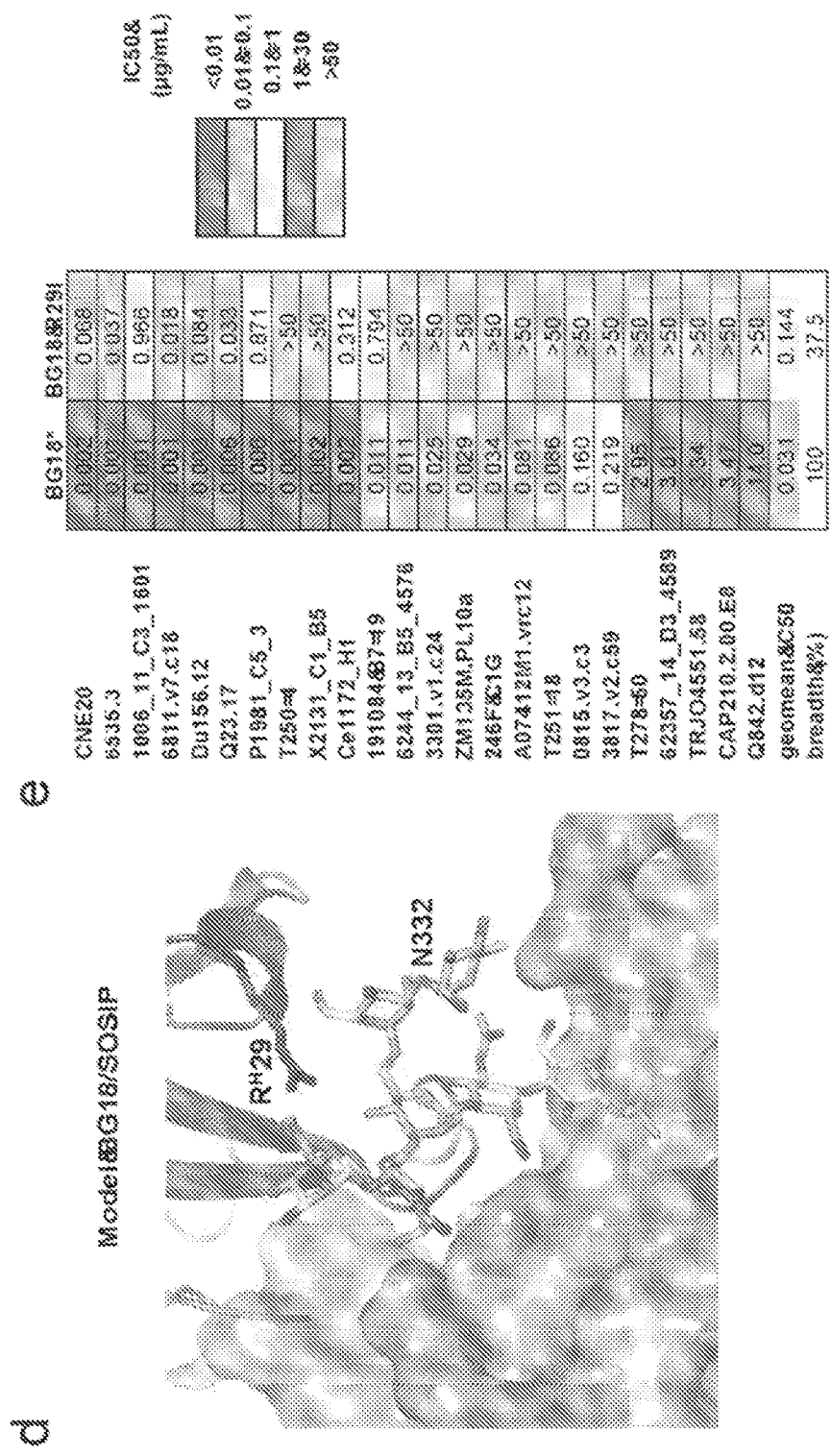

It was considered that BG18, a more recently described N332 glycan-dependent bnAb[15], may be a superior vaccine target to PGT121. BG18 has higher potency and similar breadth, a shorter HCDR3 suggesting a higher precursor frequency, and a potentially simpler maturation pathway lacking insertions or deletions (indels), whereas PGT21 activity requires indels. As with PGT121, BG18 iGL does not bind to WT BG505 Env (T332N), indicating that protein design would be required to develop an effective priming immunogen. To enable structure-guided immunogen design, how BG18 engages the Env protein was studied. Alignment of the HCDR3 from the crystal structure of unliganded BG18[15] to the structure of PGT122 (a somatic variant of PGT121) bound to BG505 SOSIP[16], revealed that the HCDR3s are in a highly similar conformation with identical or chemically similar side chains at epitope contact positions (FIG. 1a). The structural alignment suggested a BG18 binding mode in which the HCDR3 engages the conserved GDIR motif like PGT121, while the HCDR1 contacts the relatively conserved N332 glycan, and the light chain (LC) straddles the V1 loop of gp120, unlike PGT121 (FIG. 4a-c). Mutagenesis studies (FIG. 4d-e), structural model-guided design of a minimally mutated BG18 bnAb (minBG18) (FIG. 5), and a 4.4 Å resolution cryo-electron microscopy (cryo-EM) derived structure of BG18 bound to the BG505 MD39 trimer[11] (FIG. 1b), confirmed this HCDR3 binding mode, in agreement with recently published crystal structures of BG18 bound to BG505 and B41 SOSIP trimers[17].

Example 2. Identification of BG18-Like HCDR3s

To assess whether BG18-like HCDR3s are present in the HIV-uninfected population, a bioinformatics approach was used to search an NGS dataset of $1.1 \times 10^9$ unique sequences of human BCR heavy chains (HCs) from 14 healthy, HIV-uninfected donors (from ref.[18] and this work). Informed by Applicants' structural model for the BG18-Env interaction, HCDR3s with the same length as BG18, the same D gene in the same reading frame and position within the HCDR3, and the same JH gene were searched for. Such HCDR3s were identified in all 14 donors (FIG. 6), encouraging us to proceed with vaccine design.

Example 3. GT Immunogen Design

Figure 2:
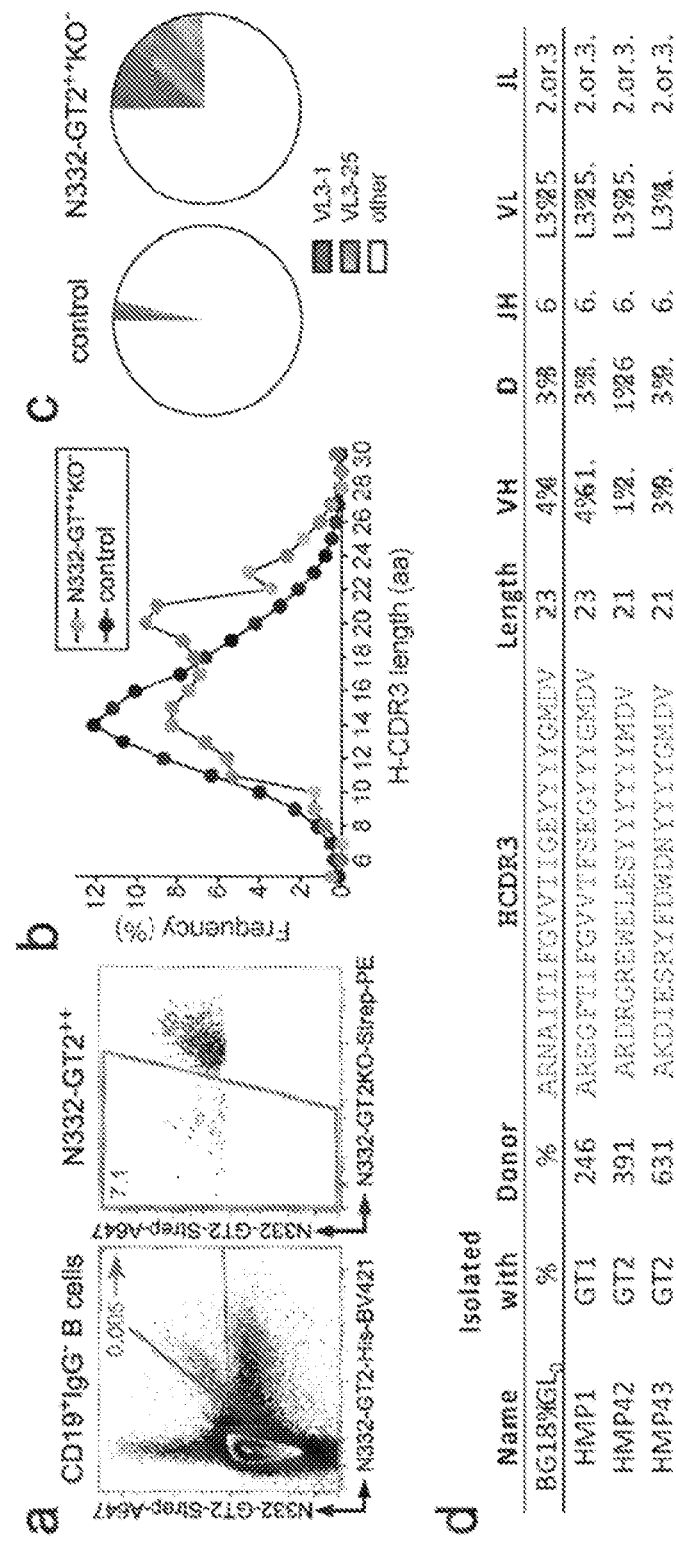
FIG. 2. Naive human B cell sorting with N332-GT trimers. a) Gating strategy for N332-GT epitope-specific sorting of naive human B cells. b) HCDR3 length distribution in N332-GT sorted naive B cells compared to control B cells from DeKosky et al38 and Jardine et al39. c) Frequency of VL3-25/VL3-1 LCs from N332-GT2 sorted naive B cells relative to control B cells from DeKosky et al. 38 and Jardine et al39. d) HCDR3 sequence and gene usage of three BG18-like precursors for which cryo-EM structures were determined. The BG18 iGL0, HMP1. HMP42, and HMP43 HCDR3 sequences shown are SEQ ID NO: 88-91, respectively. e) SPR binding dissociation constants of HMP epitope-specific FAbs from naive B cells isolated with N332-GT1 and -GT2. Dashed line indicates the limit of detection. f) Low resolution cryo-EM reconstructions of BG18-like precursors HMP1, HMP42, and HMP43 bound to N332-GT5 trimer with a low-pass filtered reconstruction of BG18-iGL0 (yellow) bound to N332-GT2 (gray) shown for reference. The approximate densities of the HMP Fabs are colored green, purple and blue for HMP1, HMP42, and HMP43, respectively based on comparison to BG18 iGL0. The approximate densities of the trimers are colored gray.
Figure 2:
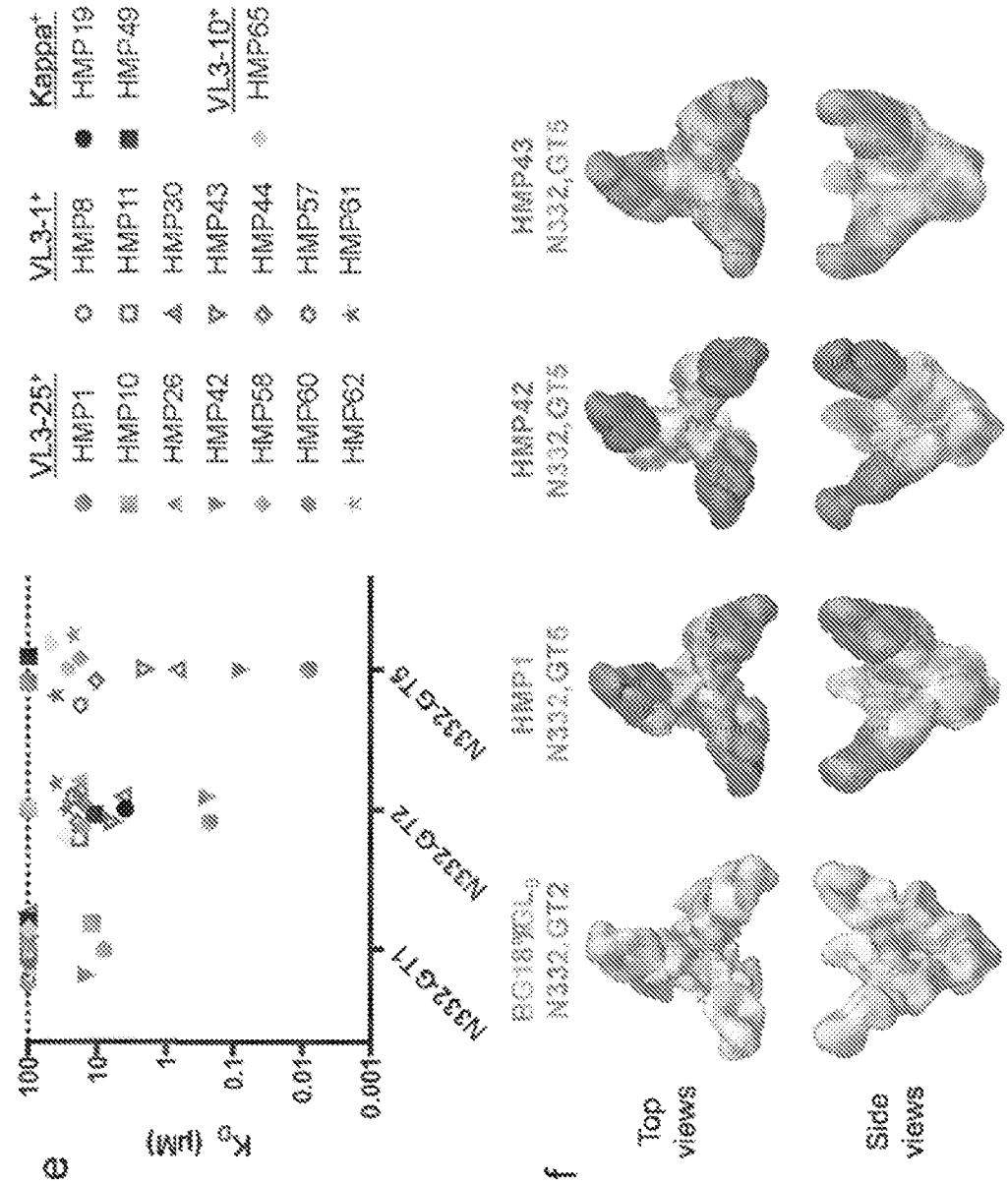

GT immunogen design was initiated using Applicants' directed evolution methodology for engineering trimers on the surface of mammalian cells that previously proved capable of producing stabilized native-like trimers with affinity for PGT121 iGL variants[11,19]. However, this case was an attempt to overcome the limitations of using only iGL variants to represent the pool of potential bnAb precursors in the human repertoire. Inferred-germline Abs contain bnAb HCDR3 junctions that have been selected and possibly somatically mutated for high affinity Env binding during bnAb development, hence such iGL Abs under-represent both the diversity of potential precursors and the difficulty of engineering high affinity antigens to target those precursors. A set of 15 Abs were designed that use BG18 germline-reverted genes but contain naive human BG18-like HCDR3s with diverse junction regions identified in Applicants' search of HC NGS data described above (FIG. 6b). It was also hypothesized that BG18-like bnAbs that interact with Env in a mode similar to that of BG18 can utilize alternate $V_H$ or $V_L$ genes. This idea was supported by Applicants' finding that BG18-like bnAbs can derive from at least 3 alternate LCs (FIG. 5a), as well as the fact that the key $V_H$ contact residues in BG18 are somatic mutations (FIGS. 5b-c and 8a-b). Therefore, 12 other variants of BG18 iGL were produced that use common human germline $V_H$ and $V_L$ genes. This gave 28 potential BG18-like precursors, including three iGL variants (BG18 iGL$_{0-2}$), that could be used as selection reagents for multitarget optimization[4]. Structure-guided libraries were designed to screen by mammalian cell surface display using 11mutB as the starting construct. Five libraries were screened iteratively with selection against the least challenging antibody targets first (i.e. BG18 iGL) followed by selection against more difficult targets (i.e. NGS-derived and alternate $V_H$/$V_L$ precursors) in the last three libraries (FIG. 1d). This directed evolution design process resulted in two GT trimers (N332-GT1 and -GT2; FIG. 1*d* and FIG. 7). N332-GT2 bound with a $K_D$ of 213 pM to BG18 $iGL_1$, which represented a 130,000-fold improvement over $11mut_B$. 11 of 15 NGS-derived precursors bound to N332-GT2 with a geomean $K_D$ of 519 nM, and all $V_H/V_L$ variants bound to N332-GT2. Overall, 17 of 28 precursors had submicromolar KDs for N332-GT2 (FIG. 1*e*), a potential benchmark for generating robust germinal center responses from rare B cell precursors in vivo[20].

Example 4. Cryo-EM Derived Structure of GT Immunogen-Antibody Complexes

Applicants' 3.9 Å resolution cryo-EM derived structure of BG18 $iGL_0$ complexed with N332-GT2 (FIG. 1*c*) showed that the HCDR3 makes a similar interaction to the base of the V3 as mature BG18 (FIG. 1*b*) and PGT121, and most of the additional interactions come from V1 mutations that fill a groove in the light chain and contact the HCDR3 (FIG. 8). The HCDR3 dominated the interaction in the BG18 $iGL_0$ complex, burying 64% of the total buried surface area. In the mature BG18 complex, the HCDR3 maintained the same key interactions and contributed 35% of the total buried area as the Ab made substantially increased contacts to glycans (FIG. 9*b*). Overall, Applicants' cryo-EM structures showed that N332-GT2 binds to BG18 $iGL_0$ with a similar HCDR3-dependent, V1-straddling binding mode as BG505 MD39 binds to BG18.

Example 5. Identification of BG18-Like Precursors in the Human Naive B Cell Repertoire To identify BG18-like precursors in the human naive B cell repertoire that recognize N332-GT trimers, N332-GT1 and N332-GT2 were used as sorting reagents and either BG505-MD39 (containing a native N332 epitope) or N332-GT2-KO (an epitope knockout) as negative sorting probes (FIG. 2*a*). Approximately 47 million naive B cells from 6 donors were probed with N332-GT1, and 112 million naive B cells from 10 donors were probed with N332-GT2, after accounting for PCR and sorting efficiencies. Epitope-specific naive B cells, isolated at a frequency of 0.001% (FIG. 10), were enriched for long HCDR3s (FIG. 2b) and highly enriched for $V_L$3-25 and $V_L$3-1 LCs (FIG. 2c) corresponding to the BG18 LC and a LC with similar binding properties, respectively (FIG. 1e and FIG. 5). Of 146 HC-LC pairs sequenced, one precursor, high mannose patch-1 (HMP1) was a near perfect match to BG18 iGL, with the same HCDR3 length, D gene, D gene position within the HCDR3, and $J_H$, $V_L$ and $J_L$ genes (FIG. 2d). The isolation of one ideal BG18-like precursor in 159 million B cells is approximately consistent (within a factor of 3) with Applicants' bioinformatic estimate of 1 in 54 million human B cells (see Methods and FIG. 6). Fabs of 45 HMP naive B cell clones were expressed and purified (FIG. 10i) and binding affinities to native-like and GT Env trimers were measured. 17 HMP Fabs bound to N332-GT1 and/or GT2 and did not bind detectably to the MD39 native-like trimer, indicate proper epitope specificity (FIG. 2e). HMP1 bound to N332-GT2 with a $K_D$ of 220 nM and was the highest affinity HMP Fab tested. Four of the five highest affinity naive Abs isolated (HMP1, HMP30, HMP42, and HMP43), used $V_L$3-25 or $V_L$3-1 LCs and have long HCDR3 loops (>20 AA) (FIG. 2d-e). Initial attempts to determine low resolution EM structures of HMP Fabs bound to N332-GT2 were not successful. However, in the late stages of this study, a higher affinity GT trimer (N332-GT5, FIG. 2e and FIG. 7) was developed, and this trimer proved capable of forming stable complexes with HMP1, HMP42, and HMP43 that were amenable to cryo-EM structural analysis. At ~15 Å resolution, the binding orientations of all three HMP precursors were indistinguishable from BG18 iGL$_0$ complexed with N332-GT2 (FIG. 2f), suggesting that these naive Abs use a BG18-like binding mode to engage the N332-GT trimer.

Example 6. Ferritin Nanoparticle Design

Figure 11:
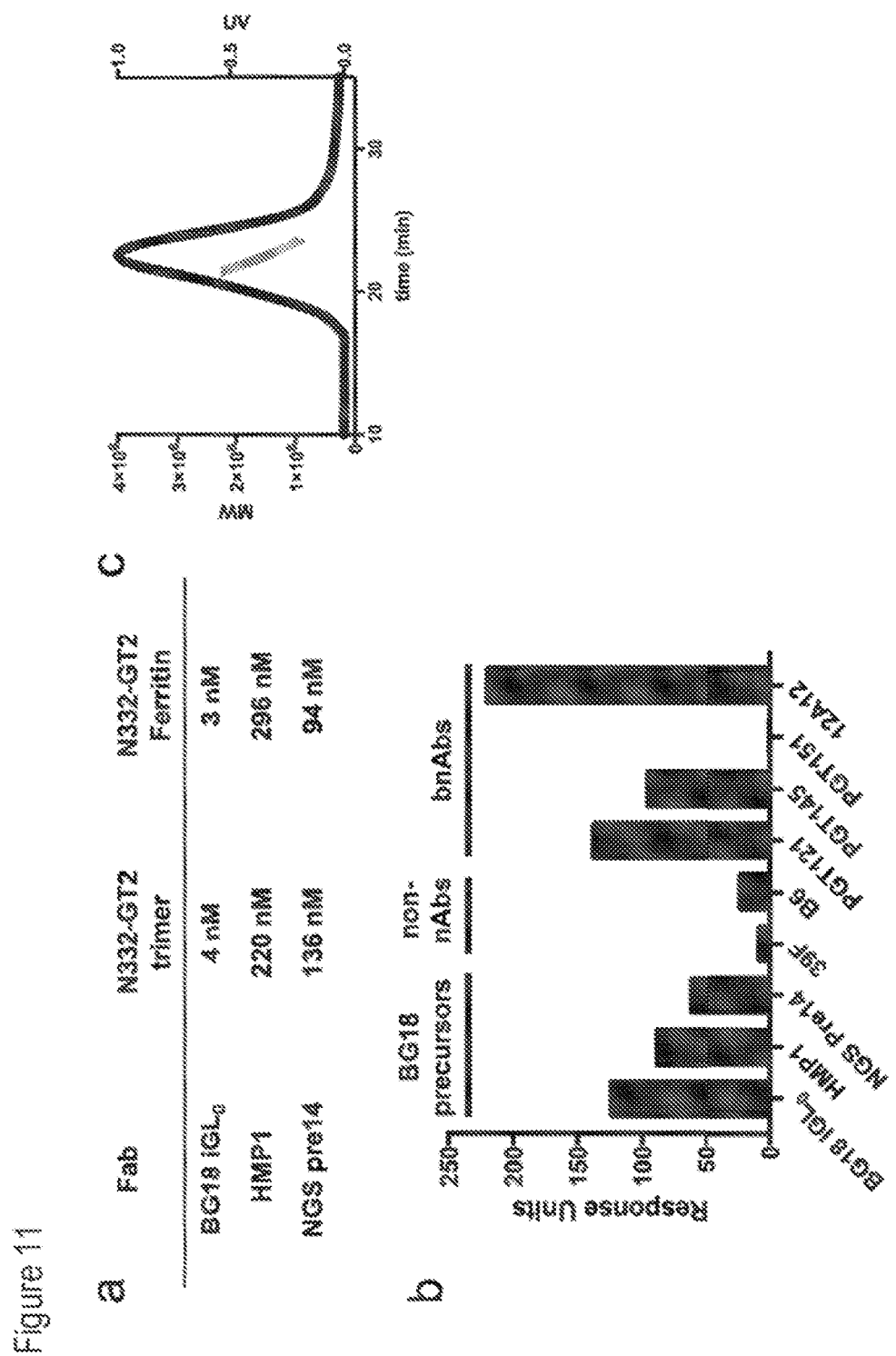
FIG. 11. Biophysical characterization of N332-GT2 nanoparticles. a) SPR KDs for N332-GT2 trimer and NP binding to BG18 precursors. The NP was captured as ligand with PGT128, and Fabs were flowed as analytes. b) SPR analysis of N332-GT2 NP binding to a panel of non-nAb and bnAbs. The format of the experiment was the same as in a). c) SECMALS analysis of N332-GT2 NPs. The black line indicates the UV trace and the red line indicates the protein molecular weight.

In separate work[21], ferritin nanoparticles (NPs)[22,23] were constructed that displayed up to 8 copies of MD39 native-like trimers, and it was found that in mouse immunization studies that such NPs were superior to MD39 trimers in trafficking to follicular dendritic cell networks, concentrating in germinal centers, and eliciting IgG responses. To gain such immunogenicity enhancements here, similar ferritin NPs displaying N332-GT2 trimers were engineered (FIG. 11).

Example 7. BG18$^{gH}$ Knock-in Mouse

Figure 3:
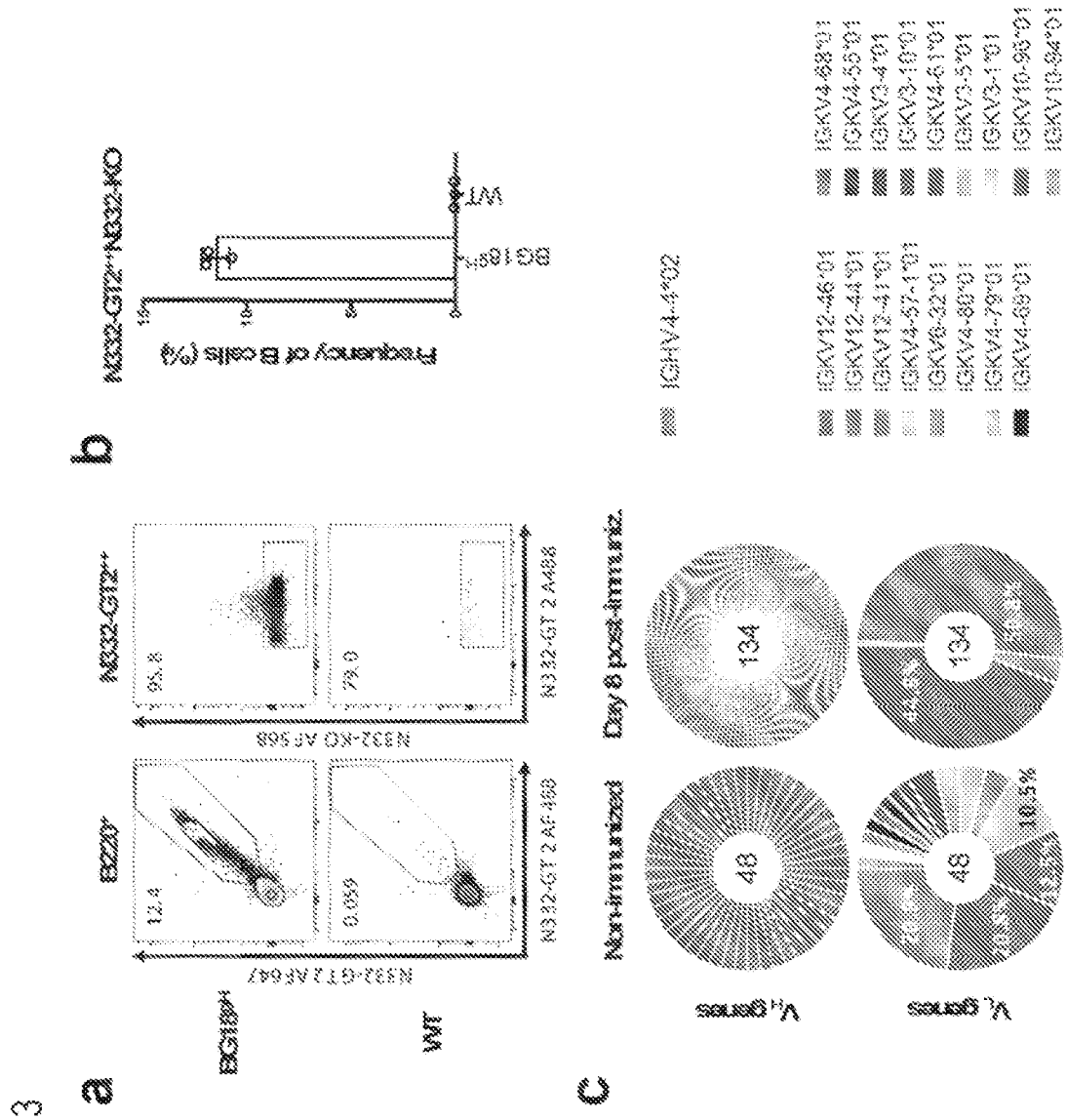
FIG. 3. Immunization of BG18$^{gH}$ B cell adoptive transfer recipient mice with N332-GT NPs. a) Representative examples of fluorescence-activated cell sorting (FACS) gating to identify epitope-specific (N332-GT2++/N332-GT2-KO-) B cells in BG18gH and WT mice. b) Frequency of epitope-specific B cells in non-immunized BG18gH and WT mice. c) Pie charts showing the distribution of VH and VL genes in epitope-specific naive B cells in non-immunized BG18gH mice (left) and epitope-specific GC (CD38lowCD95+) B cells 8 days after immunization of BG18gH B cell adoptive transfer recipient mice (right). d) Representative examples of FACS gating to identify epitope-specific CD45.2+GC B cells 8 days after immunization of mouse recipients of either BG18gH (top) or WT B cells (bottom). e) Frequency of GC B cells (left) or CD45.2+ GC B cells (right) in four immunization conditions. f) Frequency of CD45.2+(left) or CD45.1+(right) epitope-specific B cells in four immunization conditions. g) Serum ELISA 50% equilibrium dilution values for GT2 and GT2-KO at day 14 after immunization for four immunization conditions. h) Dissociation constants measured by SPR for the interaction of N332-GT2 trimer with Fabs derived from epitope-specific naive B cells in non-immunized BG18gH mice (left) and epitope-specific GC B cells 8 days after immunization of BG18gH B cell adoptive transfer recipient mice (right). Statistical significance tests in e), f), and g) were unpaired t tests, with * indicating p=0.024 and *** indicating p<0.001.
Figure 3:
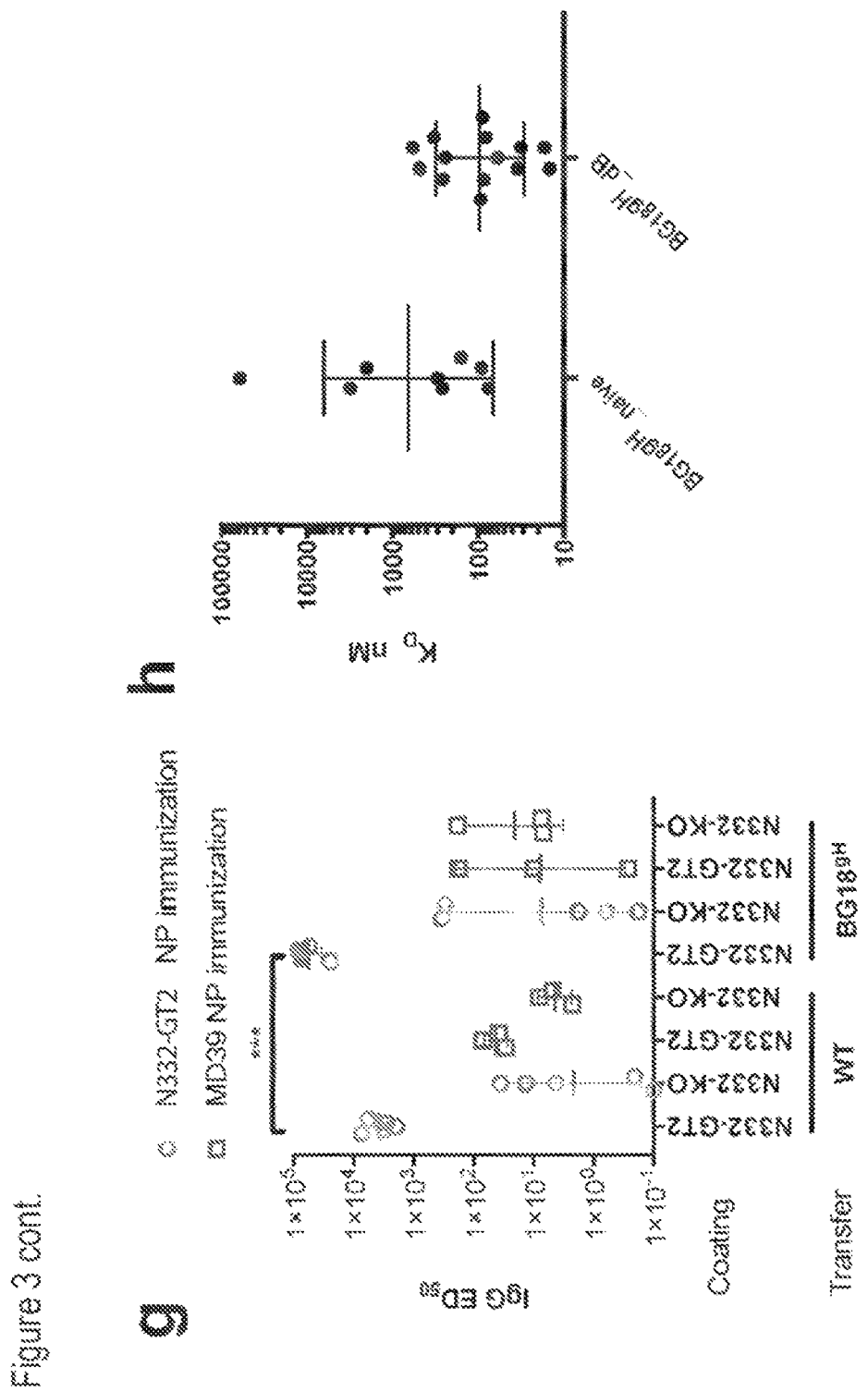

To test the immunogenicity of these N332-GT2-NPs, a BG18$^{gH}$ knock-in mouse engineered via a CRISPR/Cas9 rapid targeting strategy was employed, in which ~30% of B cells express the BG18 iGL2 HC variable region and mouse constant region paired with mouse LCs[24]. N332-GT2 but not MD39 bound to 12±1% of naive B cells in this mouse compared to 0.06±0.01% in WT (C57BL/6) mice, demonstrating N332-GT2 specificity for BG18$^{gH}$ naive B cells (FIG. 3a,b). Antigen-specific single B cell sorting and BCR sequencing demonstrated that the N332-GT2-specific naive BG18$^{gH}$ B cells carry a variety of mouse LCs paired with BG18$^{gH}$ (FIG. 3c).

Example 8. Immunization Studies

Figure 12:
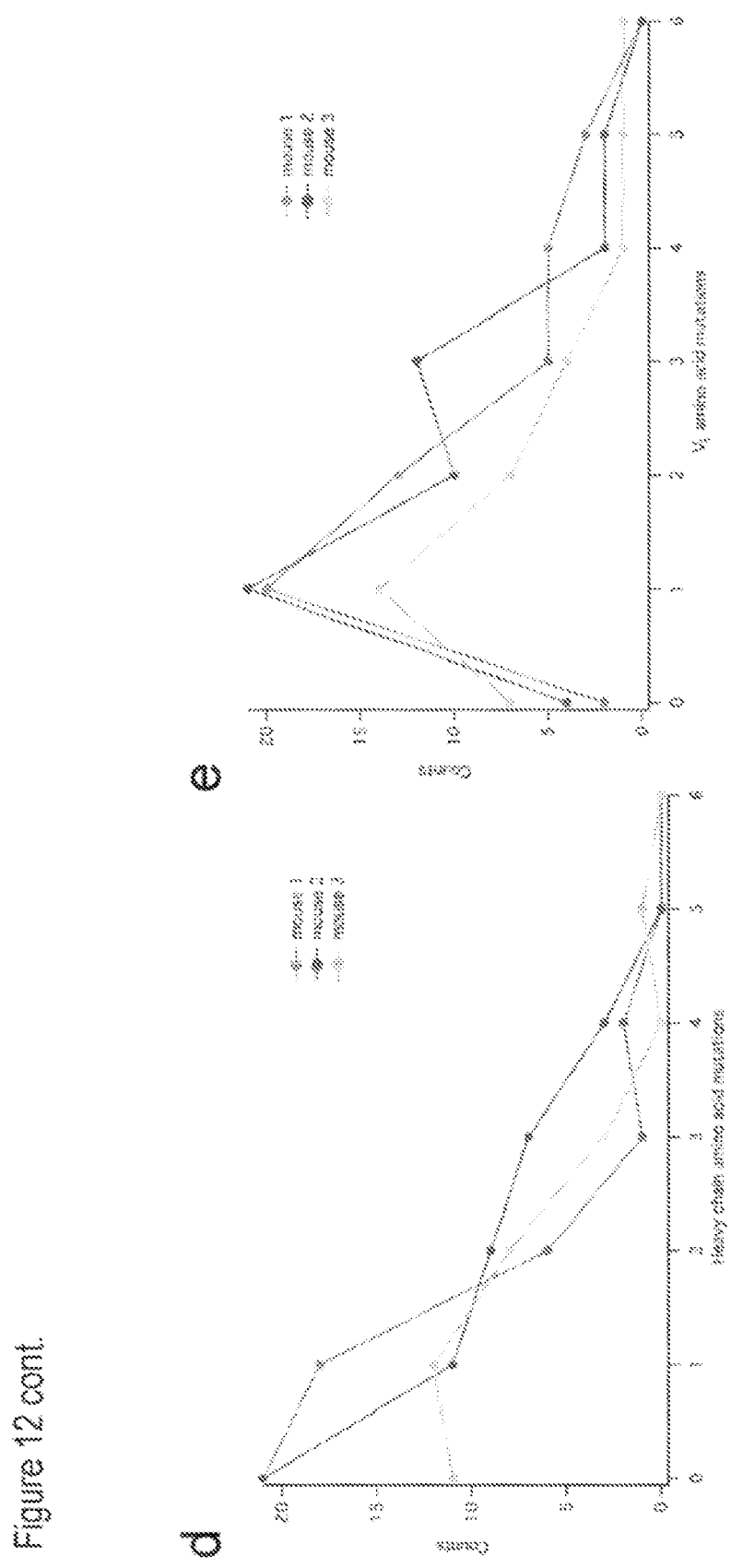
FIG. 12. Calibration of transferred CD45.2 B cells into CD45.1 recipient mice. Splenocytes from transferred recipient mice were analyzed by flow cytometry. CountBright Beads (Invitrogen) were added to the samples (5×106 splenocytes—quantified by Nucleocounter, ChemoMetec USA) to determine exact cell population numbers. a) The raw data acquired at the flow cytometer. b) The normalized values in the stained samples, obtained by multiplying the raw data by the beads multiplication factor (starting beads/beads measured). c) The total cell numbers for the mouse spleens, obtained by multiplying the values for 5×106 splenocytes by the spleen multiplication factor (total splenocytes/5). d+e) Histograms of HC amino acid mutations d) and LC VL amino acid mutations e) for the 136 Abs derived from epitope-specific GC B cells 8 days after immunization of BG18gH B cell adoptive transfer recipient mice.

To generate a mouse model with rare bnAb precursor B cells, adoptive transfer experiments were carried out in which 5,000 CD45.2 BG18$^{gH}$ B cells were transferred to CD45.1 WT mice on day −1, establishing a frequency of ~7 GT2$^{++}$/KO$^-$ BG18$^{gH}$ CD45.2 B cells per million CD45.1 B cells by day 0 (FIG. 12a-c). Control transfers were 50,000 CD45.2 WT B cells. Recipient mice were immunized at day 0 with either N332-GT2-NPs or control NPs displaying MD39 trimers lacking GT mutations, for a total of four immunization conditions (BG18$^{gH}$ or WT B cells transferred, N332-GT2- or MD39-NPs immunized). Splenocytes were analyzed by cytometry at day 8 (FIG. 3d-f). Germinal center (GC) B cells (CD38$^{low}$CD95$^+$) were detected in all four immunization conditions, but CD45.2 GC B cells were detected only in the case of N332-GT2-NP immunization of BG18$^{gH}$ B cell recipients, demonstrating that N332-GT2-NPs activated rare BG18$^{gH}$ B cells in vivo but MD39-NPs did not (FIG. 3e). N332-GT2-NP-induced CD45.2 GC B cells bound to N332-GT2 and not to N332-GT2-KO (FIG. 3f), consistent with a BG18-like response. In contrast, host CD45.1 GC B cells showed negligible binding to N332-GT2 (FIG. 3f), suggesting that the day 8 CD45.1 GC responses were directed either to the ferritin nanoparticle base or to the adjuvant. In day 14 serum binding analyses, GT2-NPs induced strong epitope-specific responses (strong binding to N332-GT2 and weak binding to N332-GT2-KO) in BG18$^{gH}$ B cell recipients and 15-fold weaker epitope-specific responses in WT B cell recipients (FIG. 3g), demonstrating that activation of rare BG18$^{gH}$ precursor B cells led to potent serum responses but also showing that WT B cells responded to the BG18 epitope on N332-GT2. In contrast, MD39-NPs induced negligible epitope-specific serum responses in either BG18$^{gH}$ or WT B cell recipients (FIG. 3g). Together these results demonstrated that N332-GT2-NPs elicited GC and antibody responses from rare BG18$^{gH}$ B cells.

By single cell sorting and BCR sequencing CD45.2$^+$/N332-GT2$^{++}$/KO$^-$ GC B cells from 3 BG18$^{gH}$ recipient mice immunized with N332-GT2-NPs, 134 HC-LC pairs were obtained. 100% of the HCs were derived from BG18$^{gH}$, formally proving that these GC responses utilized the knockin HC. In contrast to the wide variety of mouse IGKV genes used in LCs of GT2-specific naive BG18$^{gH}$ B cells, the LCs from day 8 GC B cells were highly enriched for two mouse kappa genes: IGKV12-46 and IGKV12-44 (FIG. 3c). The amino-acid mutation levels in the day 8 GC BCRs were 1.1±1.2 in the HCs and 1.8±1.3 in the $V_L$ genes (FIG. 12d-e), whereas naive B cells from unimmunized mice showed no BCR mutations. 14 of the most mutated GT2-NP-induced Fabs were expressed and it was found that they had KDs for N332-GT2 ranging from 15 to 580 nM (geomean 97 nM), whereas 8 Fabs produced from N332-GT2$^+$KO$^-$ naive B cells in un-immunized BG18$^{gH}$ mice bound more weakly by an average factor of 6.8, with geomean 655 nM (FIG. 3h). This showed that N332-GT-NPs can induce affinity maturation of rare BG18-like precursors.

Example 9: Discussion

Figure 13:
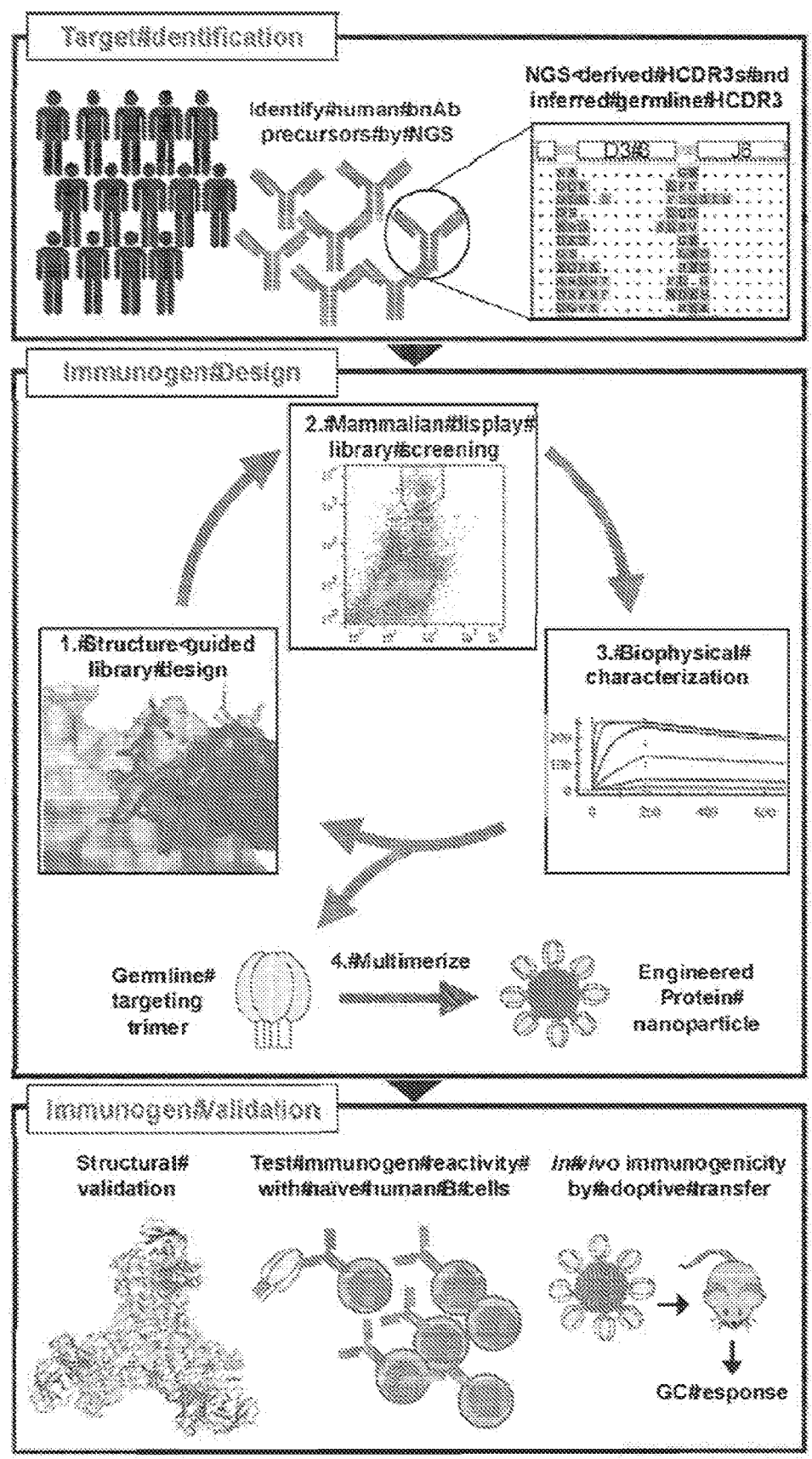
FIG. 13. Overall strategy for designing GT immunogens to prime precursors of HCDR3-dependent antibodies. The BCR HC repertoires of 14 HIV-negative donors were sequenced and queried bioinformatically to identify HCDR3s with key features similar to a known bnAb indicating that such HCDR3s have potential to contribute to bnAb precursors. That process validated the bnAb for germline targeting immunogen design. In the top panel, the human repertoire is shown in green with HCDR3-dependent bnAb precursors shown in red. The second panel shows the iterative immunogen design process. To design a GT immunogen capable of binding to human naive potential precursor B cells, potential bnAb precursor antibodies containing NGS-derived HCDR3s were used for multi-target iterative immunogen library screening. Key aspects of preclinical immunogen validation are summarized in the third panel. Structural analyses confirmed the expected binding orientation between GT immunogen and iGL Ab. Sorting naive human B cells with the GT immunogens was employed to isolate bona fide potential precursors that have features matching the target precursors. Cryo-EM and sequence analysis of isolated epitope-specific precursors can serve to refine and broaden the definition of potential bnAb precursors, enabling iterative design improvements. Adoptive transfer immunization experiments with inferred-germline bnAb knock-in B cells demonstrated that a GT immunogen can prime rare target precursor B cells.

Most antibodies recognize their target in a strongly HCDR3-dependent manner. This includes most HIV and influenza bnAbs. A central challenge of GT vaccine design is the large paratope sequence and structural complexity possible for any set of Abs targeting a conserved epitope via a shared HCDR3-dependent binding modality. Here the successful design of a GT immunogen for this general class of Ab recognition was demonstrated (FIG. 13). The strategy was to use the human repertoire as a guide to identify potential bnAb precursors and then to design an immunogen that has affinity for a representative set of those precursors. This procedure was validated by the isolation of an authentic BG18-class precursor (HMP1) from naive human B cells with N332-GT trimers and the demonstration that N332-GT nanoparticles drive a robust BG18-class B cell and GC response in an animal model with rare BG18 precursors. Furthermore, Applicants' findings that N332-GT trimer-sorted human naive B cells are enriched for $V_L3$-25 and $V_L3$-1 light chains with long HCDR3s, and that high affinity clones of this type exhibit a BG18-like binding mode, indicate that the pool of potential BG18 human naive precursors is larger and more diverse than originally expected. This study lays out a pathway for the development and pre-clinical validation of HCDR3-dependent GT immunogens, a pathway that could potentially be expanded to other HIV epitopes or other vaccine targets.

Example 10: Methods

BG18/BG505 SOSIP structural model. The HCDR3 loop of unliganded BG18 was aligned to PGT122 (PDB: 4TVP) and several features suggested this as a plausible binding mode. First, $Arg^L54$ in the LCDR2 would be positioned in a similar space as the LCDR3 $Arg^L94$ in PGT122, a known critical contact residue for PGT122. Second, $Arg^H29$ was positioned close to the N332 glycan, and it was confirmed that $Arg^H29$ was important for neutralization, by mutagenesis (FIG. 4d-e). Finally, analysis of the V1 conformation suggested that the LC could plausibly avoid clashing with the N137 glycan.

Design of minimally mutated versions of BG18 and alternate $V_L$ variants. Design of minimally mutated versions of BG18 was guided by analysis of the structural model of BG18 bound to BG505 SOSIP (FIG. 4a). Framework mutations and CDR mutations were reverted to germline if structural inspection indicated they were not contributing to the binding interaction. Several HC and LC variants were tested. BG18.11, which is referred to as "minBG18", was the least mutated variant that showed >50% breadth compared to BG18 and maintained similar potency as BG18. BG18.6 was the least mutated variant that showed any neutralization. To make the $V_L$ variants shown in FIG. 5, the indicated $V_L$ gene was substituted for the BG18 $V_L$ gene and BG18 mutations were incorporated.

Immunogen design. BG18 iGL2 had detectable affinity to the $11mut_B$ (PGT121 germline targeting) trimer but no detectable affinity to BG505 MD39 containing a native N332 epitope, therefore $11mut_B$ was used as a base construct to begin the BG18 iGL GT design process. The following libraries were screened using a previously described mammalian cell surface display method[11]. Library 1 was an NNK codon scan of positions 294, 297, 298, 299, 300, 302, 304, 305, 326, 329, 330, 333, 386, 413, 414, 415, 416, 417, 419, 420. NNK codons were introduced into BG505-$11mut_B$-gp120 using the QuikChange Site-Directed Mutagensis Kit (Agilent). Library 1 was screened for binding to BG18 $iGL_2$ and PGT121-$GL_{CDR3rev4}$. Library 2 was a combinatorial library with amino acids F/I/LN introduced at positions 154, 322, 323, 326, 333, 414, 415, and 416. The library insert was assembled with overlapping ultramers (IDT DNA) followed by Gibson cloning (NEB) into BG505-$11mut_B$-gp120. Library 2 was screened for binding to BG18 iGL2 and PGT121-$GL_{CDR3rev4}$. Library 3 was a combinatorial library with NNK codons introduced at positions 137, 325, and (F/I/L/V) at position 326. The library insert was assembled with overlapping ultramers (IDT DNA) followed by Gibson cloning (NEB) into BG505-MD39-17mutE. Library 3 was screened for binding to the following 24 Abs: BG18 $iGL_0$, BG18 $iGL_1$, pre1-pre6, pre8, pre10-pre15, $V_L2$-8, $V_L2$-14, $V_L3$-21, $V_H1$-69, $V_H3$-33, $V_H4$-59, $V_H5$-51, PGT121-$GL_{CDR3mat}$, PGT121-$GL_{CDR3rev1}$. Library 4 was a combinatorial library with NNK codons introduced at positions 138 and 141 and (P/H/A/D) at position 325. The library insert was assembled with overlapping ultramers (IDT DNA) followed by Gibson cloning (NEB) into BG505-MD39-17mutE-N137K. Library 4 was screened for binding to BG18 $iGL_0$, pre3, pre14, $V_L3$-21, $V_L2$-8, $V_L2$-14, $V_H3$-33. Library 5 was a combinatorial library with NNK codons introduced at positions 138 and 139 and (P/H/A/D) at position 325. The library insert was assembled with overlapping ultramers (IDT DNA) followed by Gibson cloning (NEB) into BG505-MD39-17mutE-N137K. Library 5 was screened for binding to BG18 $iGL_0$, $V_L3$-21, $V_L2$-8, $V_L2$-14, $V_H1$-69, $V_H5$-51. Library 6 was an NNK scan of positions 167 to 308. The insert was synthesized at SGI-DNA and Gibson cloned (NEB) into BG505-MD39-N332-GT3. Library 6 was screened for binding to BG18 $iGL_0$, $V_L2$-8. Library 7 was an NNK scan of positions 309 to 443. The insert was synthesized at SGI-DNA and Gibson cloned (NEB) into BG505-MD39-N332-GT3. Library 7 was screened for binding to BG18 $iGL_0$, pre1, pre2, pre4, pre10, pre15, $V_L2$-8. All constructs contained a C-terminal myc tag and were anchored to the cell membrane via a C-terminal PDGFR transmembrane domain. Staining of the cell populations was typically done with IgG until saturated binding was obtained at low nanomolar IgG concentrations, and then Fabs were used for staining to maintain selection pressure. Typically, libraries were sorted 3 to 5 times, and the enriched cell populations were frozen until sequencing could be carried out as described previously[11]. The most enriched clones were synthesized at Genscript either as C-terminal His tagged gp120s or MD39/MD64 trimers in the pHLsec vector and expressed and purified as described previously[11].

Nanoparticle design and purification. To obtain multivalent immunogens, trimers were genetically fused to ferritin from *Helicobacter pylori* using a short flexible linker. Genes were codon optimized for HEK293 cells and cloned into the pHLsec plasmid (GenScript). MD39-NP DNA was co-transfected with a plasmid encoding human Furin protease into FreeStyle 293F cells (Invitrogen, Cat no. R79007) using 293Fectin (ThermoFisher) and proteins were expressed at 37° C. for four days. NPs were purified either using snow drop lectin-conjugated agarose beads (Vector laboratories) or HiTrap NHS-Activated HP affinity columns (GE Healthcare) conjugated with PGT145 (kindly provided by the Dennis Burton lab), each followed by gel-filtration using a Superose 6 sixe-exclusion chromatography column (GE Healthcare). N332-GT2 NP has the Furin cleavage site removed and was not co-transfected with Furin. NP-assembly was assessed by negative-stain EM and SEC+multi-angle light scattering (SEC-MALS) using a Superose 6 10/300 column (GE Healthcare) at a flow rate of 0.5 mL/min followed by DAWN HELEOS II and Optilab T-rEX detectors (Wyatt Technology), correcting for the glycan molecular mass by applying the built-in protein-conjugate analysis (ASTRA).

Neutralization Activity. Neutralizing activity of monoclonal antibodies (mAbs) was assessed using single round of replication in TZM-b1 target cells, in the absence of DEAE-dextran as described previously[25]. Briefly, pseudoviruses were generated by co-transfection of HEK293T cells with an Env-expressing plasmid and an Env-deficient genomic backbone plasmid (pSG3ΔEnv)

Cryo-EM structure determination. Trimers were incubated with a 10× molar excess of Fab overnight at room temperature. The following morning, each complex was purified using a HiLoad 16/600 Superdex 200 pg size exclusion column (GE Healthcare) with Tris-buffered saline (50 mM Tris pH 7.4, 150 mM NaCl) as the running buffer, and the peak corresponding to trimer-fab complex was pooled and concentrated to ~8 mg/mL. 18 μL of complex were mixed with 3 μL of 0.42 mM n-dodecyl β-D-maltoside (DDM; Anatrace), such that final DDM concentration (0.06 mM) is below the critical micellar concentration (CMC). A 3 μL aliquot of the complex was applied to a C-Flat grid (CF-2/2-4C, Electron Microscopy Sciences, Protochips, Inc.) which had been plasma cleaned for 10 s using a mixture of $Ar/O_2$ (Gatan Solarus 950 Plasma system), and following a 10 s incubation, the grid was blotted between 4-5 s and plunged into liquid ethane using the FEI Vitrobot system (100% relative humidity, 10° C.).

The samples were imaged using an FEI Titan Krios electron microscope (Thermo Fisher) operating at 300 kV and a Gatan K2 Summit direct electron director operating in counting mode. Automated data collection was performed using the Leginon software suite[26]. Each micrograph movie (250 ms exposure per frame) was collected at a magnification of 29,000, which resulted in a pixel size of 1.03 Å in the specimen plane. Data collection statistics for each sample are summarized in FIG. 9a. Micrograph movie frames were aligned and dose-weighted using MotionCor2[27], and CTF models were calculated using GCTF[28].

Initial negative-stain EM attempts of HMP-GT5 Fab complexes suffered from severe preferred orientation, so samples were instead prepared for low resolution cryoEM in a similar fashion as above except that the size exclusion step was omitted to prevent antibody dissociation due to faster off-rates. The samples were imaged using an FEI Talos Arctica electron microscope (Thermo Fisher) operating at 200 kV and an FEI Ceta 16M CMOS camera (Thermo Fisher). Single frame exposures were collected with a total dose of ~50 $e^-/Å^2$ at a magnification of 73,000, resulting in a pixel size of 1.98 Å at the specimen plane. CTF models were calculated as above.

Single particles were selected using DoGPicker[29] from the whole-frame aligned and summed micrographs, and particles extracted using Relion 2.1[30] using a box size of 288 pixels. After numerous rounds of 2D and 3D classification, final reconstructions were performed in Relion 2.1 with C3 symmetry imposed, and after post-processing, the final resolution estimates (FSC 0.143) are ~3.9 Å for BG505-MD64-N332-GT2 in complex with BG18 iGL$_0$ and ~4.4 Å for BG505-MD39 in complex with mature BG18. Additional data processing statistics are summarized in FIG. 9a. The low resolution cryoEM datasets of HMP complexes were processed in a similar manner except that the final combined map did not undergo post-processing and final resolution estimates are ~15 Å for each complex.

Atomic models were built and refined into the high-resolution reconstructions by creating homology models based off deposited coordinates of BG505 SOSIP.664 (PDB 5cez) and 354BG18 fab (PDB 5ud9), followed by an iterative cycle of manual building in COOT[31] and real space refinement in Phenix 1.13[32]. Glycans were validated by CARP[33] and Privateer[34], and overall structures were evaluated using EMRinger[35] and Molprobity[36].

ELISA. N332-GT2-specific antibody titers were detected by ELISA, using anti-His Ab (2 μg/ml) to capture N332-GT2 or N332-GT2-KO antigen (2 μg/ml) on the plate. Mouse sera were incubated for two hours and alkaline phosphatase conjugated anti-mouse IgG (Jackson ImmunoResearch, #115-055-071) was incubate another hour. Titers were determined from the dilution curve in the linear range of absorbance. All non-commercial ELISA plates were developed with p-Nitrophenyl Phosphate (Sigma, #N2770). Absorbance at 405 nm was determined with a plate reader (BioTek).

Surface plasmon resonance (SPR). Kinetics and affinities of antibody/antigen interactions were measured on a ProteOn XPR36 (Bio-Rad) using GLC Sensor Chip (Bio-Rad) or Biacore4000 (GE) with Series S Sensor Chip CMS (GE). 1×HBS-EP+pH 7.4 running buffer (20× stock from Teknova, Cat. No H8022) supplemented with BSA at 1 mg/ml was used. Following manufacturer's instructions for Human Antibody Capture Kit (Cat. No BR-1008-39 from GE) about six thousand RUs of capture mAb were immobilized onto each flow cell of GLC Sensor Chip or about ten thousand RUs in case of CMS Sensor Chip. In a typical experiment on ProteOn XPR36 system, approximately 300-400 RUs of mAbs were captured onto each flow cell and analytes were passed over the flow cell at 50 μL/min for 3 min followed by a 5 min dissociation time. Regeneration was accomplished using 3M Magnesium Chloride with 180 seconds contact time and injected four times per cycle. Raw sensograms were analyzed using ProteOn Manager software (Bio-Rad), including interspot and column double referencing, and either Equilibrium fits or Kinetic fits with Langmuir model, or both, were employed when applicable. For Biacore4000 instrument similar conditions were used but lower ligand capture levels. In the case of Fab-fragment/antigen kinetic and affinity measurements on ProteOn XPR36 or Biacore4000 similar ligand-capture technique with several modifications was used. The capture reagent was His-tag Rabbit pAb (GenScript Cat. No. A00174). It was amine coupled to Sensor Chip surface using the same protocol from GE Human Antibody Capture Kit referenced above. Applicants' regeneration solution was Phosphoric Acid 0.85% with 30 seconds contact time, four injections per cycle. In the case of ferritin nanoparticle experiment ProteOn XPR36 system and Human Antibody Capture protocol described above was used with one additional step. PGT128 IgG was captured at 1300 RU level in all channels including reference followed by NP (as ligand) capture at 1600 RU. All other steps were the same as in Human Antibody Capture protocol. Analyte concentrations were measured on a NanoDrop 2000c Spectrophotometer using Absorption signal at 280 $nm^3$.

NGS dataset of human BCR HCs. This work utilized a large NGS dataset of $1.1 \times 10^9$ unique amino acid sequences of BCR HCs from 14 healthy, HIV-uninfected donors. In this dataset, 255 million sequences from 10 donors were obtained from ref.[18] which used the HiSeq sequencing platform and an amplification strategy including unique identifiers (UIDs) to enable discrimination of unique mRNA transcripts from PCR artifacts. These sequences were collapsed by UID, assigned to VDJ gene segments with Abstar[18], and then rendered unique by clustering at the 99% amino acid identity level within each of six biological replicates per donor. JSON output files from Abstar were converted to parquet format and uploaded to the Amazon S3 storage cloud. To query databases, Amazon Elastic Map Reduce (EMR) 5.15.5 was used to configure a Spark cluster, and PySpark was used to query the database with custom Python scripts. Sequences for 4 additional donors were obtained here by both HiSeq and NextSeq sequencing platforms without the use of UIDs, as described below.

BCR HC sequencing for 4 donors. Full leukopaks (3 blood volumes) were obtained from four human subjects (AllCells LLC or Hemacare, Inc) under a protocol approved by the Institutional Review Board of the respective commercial provider. All subjects were healthy, HIV-negative adults with no reported acute illness in the 14 days prior to leukapheresis, and samples were de-identified prior to shipment. The Institutional Review Board of The Scripps Research Institute determined that research with these samples did not constitute human subjects research. Immediately upon receipt of the leukopak, peripheral blood mononuclear cells (PBMCs) were purified by gradient centrifugation and cryopreserved in aliquots of approximately $5 \times 10^8$ PBMCs. The junctional regions of antibody heavy chain libraries were amplified as in Willis et al., 2015[37]. SPRI-purified sequencing libraries were initially quantified using fluorometry (Qubit, Thermo Fisher Scientific) before size determination using a bioanalyzer (Agilent 2100). Libraries were re-quantified using qPCR (KAPA Biosystems) before sequencing on either an Illumina HiSeq (2×150 bp chemistry) or NextSeq (2×150 bp chemistry). Sequences were merged with PANDAseq using the default (symple_bayesian) merging algorithm before annotation with Abstar[18].

Figure 6:
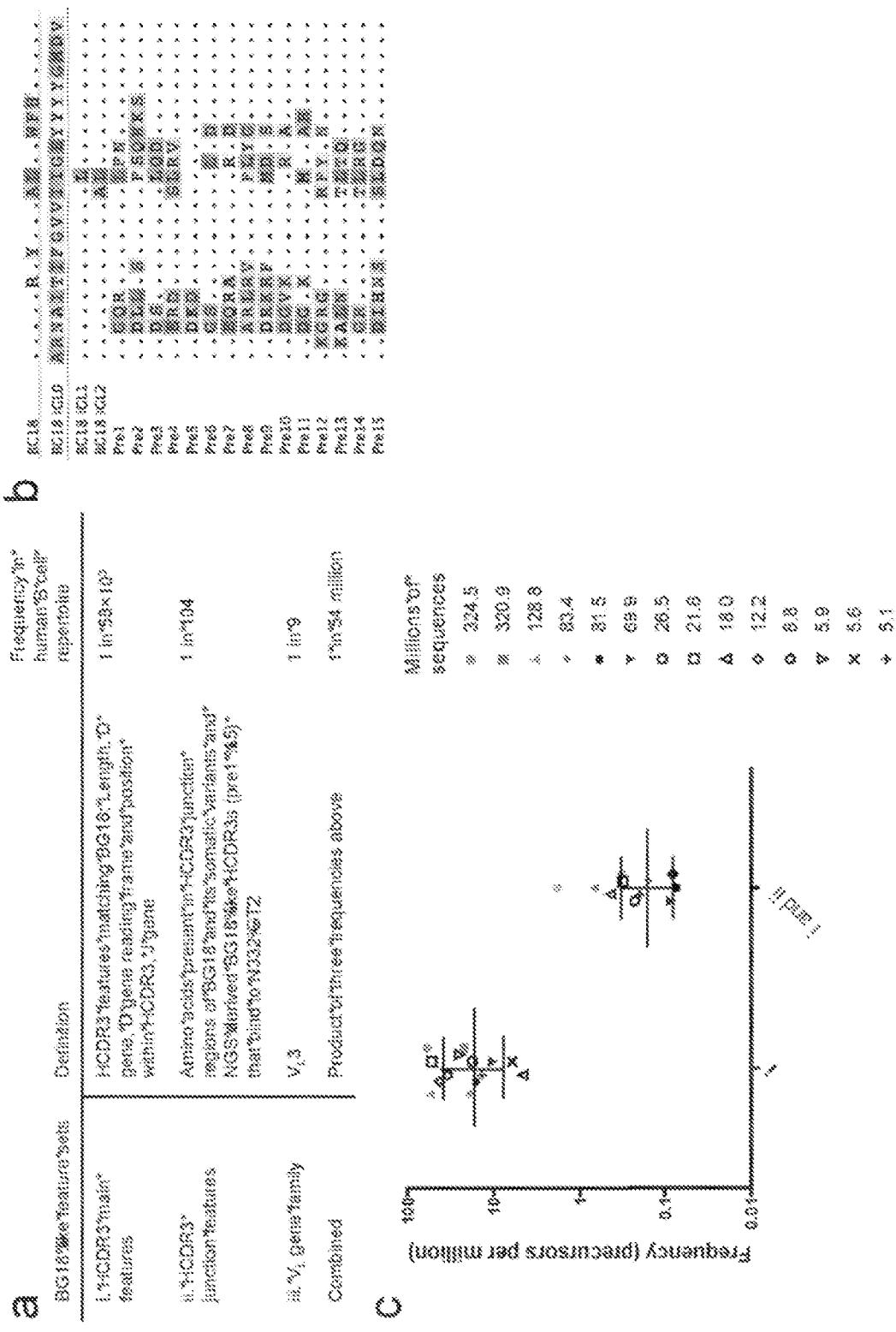
FIG. 6. Identifying BG18-like HCDR3s and estimating the BG18 precursor frequency in the human B cell repertoire. a) Table defining key BG18-like features and their frequencies in NGS datasets of BCR HCs from HIV-uninfected donors. Frequencies for BG18-like feature sets i (HCDR3 main features) and ii (HCDR3 junction features) were measured from NGS data from Briney et al. 18 for 10 donors for which sequencing used UIDs to discriminate PCR artifacts from true unique mRNA transcripts. On average, ~80% of the sequences from these 10 donors were IgM, and of those, ~50% had two or fewer nucleotide mutations in the VH gene indicating that they were enriched for naive B cells18. Sequences of BG18 somatic variants are described in Freund et al. 15 The frequency for feature set iii (VL family) was measured from the HC-LC paired sequences in DeKosky et al38. b) HCDR3 amino acid sequence alignment for BG18, BG18 iGL0-2, and 15 NGS-derived BG18-like HCDR3s. VH CDR3 of BG18, BG18 iGL0-iGL2, and Pre1 to 15 have the amino acid sequence of SEQ ID NO: 94, 88, and 95-111, respectively. c) Graph of the frequencies for Feature Sets i or (i and ii), as defined in a), for all 14 donors. Each symbol represents one donor, and the total number of sequences for each donor in the NGS dataset is given in the key. Black symbols are for the 10 donors from Briney et al. 18 sequenced using UIDs, and red symbols are for the 4 donors sequenced here without the use of UIDs. Bars denote geometric mean and geometric standard deviation measured over the 10 UID donors only. Also see Methods for a detailed explanation of the BG18-like precursor frequency estimate.
Figure 7:
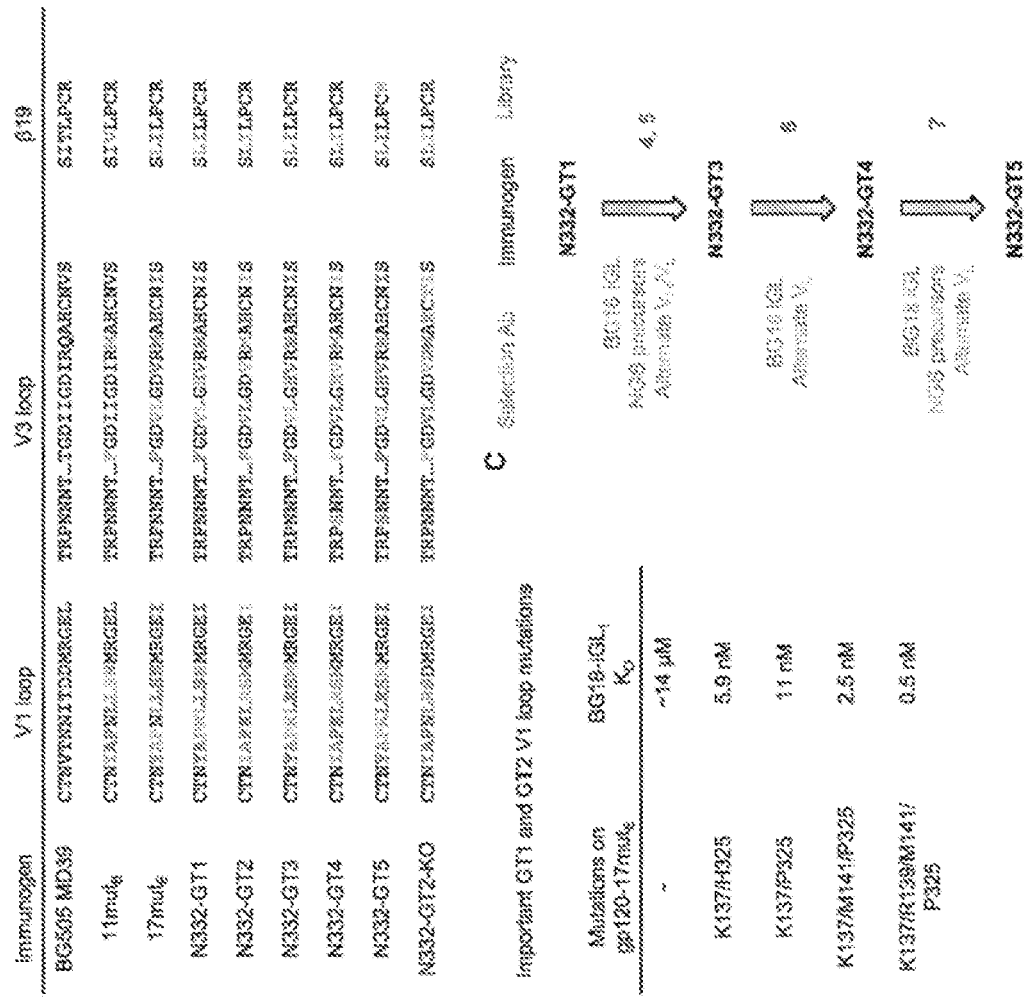
FIG. 7. Mutations in N332-GT trimers and strategy for designing N332-GT5. a) GT mutations present in N332-GT trimers are localized to the V1, V3, and I319. Amino acid changes relative to BG505-MD39 are shown in red. Sequences shown are CTNVTNNITDDMRGEL (SEQ ID NO: 71), CTNYAPNLLSNMRGEL (SEQ ID NO: 72), CTNYAPNLLSNMRGEI (SEQ ID NO: 73), CTNYAPKLLSNMRGEI (SEQ ID NO: 74), CTNYAPKLRSMMRGEI (SEQ ID NO: 75), CTNYAPNLRSDMRGEI (SEQ ID NO: 76), TRPNNNT (SEQ ID NO: 77), TRPSNNT (SEQ ID NO: 78), TGDIIGDIRQAHCNVS (SEQ ID NO: 79), FGDIIGDIRMAHCNVS (SEQ ID NO: 80), FGDVLGDVRMAHCNIS (SEQ ID NO: 81), FGDVLGHVRMAHCNIS (SEQ ID NO: 82), FGDVLGDVDMAKCTIS (SEQ ID NO: 83), SITLPCR (SEQ ID NO: 84), SIVLPCR (SEQ ID NO: 85), SLILPCR (SEQ ID NO: 86), SLILPCW (SEQ ID NO: 87). b) SPR binding KDs demonstrating that mutations in the V1 loop provide large gains in affinity for binding to BG18 iGL1. c) Schematic showing the flow of iterative directed evolution for the design of N332-GT5.
Figure 8:
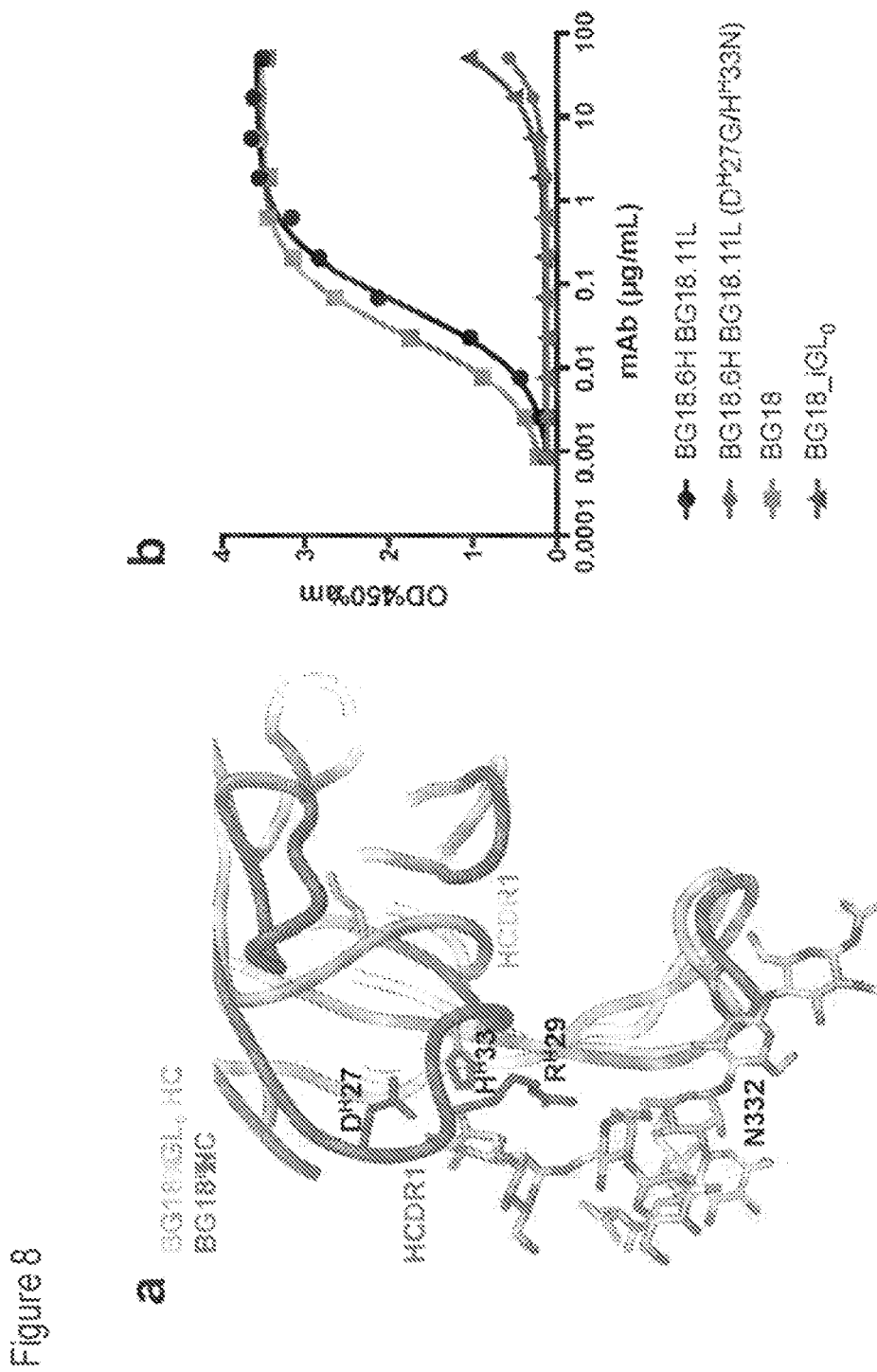
FIG. 8. Structural comparison of BG18 and BG18 iGL0 complexes. a) HCDR3 alignment of BG18 (purple) and BG18 iGL0 (pink) shows that there is a large conformational change in the HCDR1 of BG18 that brings it into proximity to the N332 glycan (green sticks). Despite limited resolution, the density map suggests that this rearrangement allows interaction with the N332 glycan through numerous HCDR1 side chain interactions, all of which are somatic mutations. b) Effect of reverting HCDR1 residues D32 and H33 to germline in a less mutated variant of BG18 measured by ELISA binding to BG505-MD39. c) The LC of BG18 (cyan) straddles the V1 loop (tan), but residues 142-152 of V1 are disordered, suggesting that this loop is utilized differently by mature BG18 compared to BG18 iGL0. Notably, the LCDR2 R54 is inserted into a cleft formed by the GDIR motif at the base of V3 (yellow), and the N-acetylglucosamine residues at N137 and N156 (tan sticks). d) There is a rearrangement of the LCDR2 in BG18 relative to BG18 iGL0, which allows the mature BG18 LC to accommodate the topology of the V1 loop. The malleability of the LCDR2 loop is accentuated by the observation that it is fully resolved when in complex with the trimer but disordered in the published ligand-free crystal structure of the Fab alone 15. e) The V1 loop of BG505 MD64 N332-GT2 is shown in tan with the side chains of the most important mutations shown as sticks. The side chain of K137 in V1 fits a groove in the LC (dark blue) LCDR1, with the aliphatic portion forming a CH-π interaction with LCDR1 Y32 and the ε-amino group a salt bridge with LCDR2 D51, as well as potential hydrogen bonding with nearby backbone carbonyls and the side chain of LFR3 S66. Additionally, the HCDR3 (pink) packs against V1, with the side chain of R139 situated between the variable light and heavy chains of the antibody. The mutation of the V1 residue D141 to methionine further stabilizes this region, as it interacts favorably with HCDR3 I100e.

BG18 precursor frequency estimate. The NGS dataset of human BCR HCs was queried by bioinformatic searches to gain information on the frequency of BG18-like HCDR3s in the human B cell repertoire (FIG. 6). HCDR3s meeting the definition of BG18-like feature set i in FIG. 6a, constituting a broad set of potential BG18-like HCDR3 precursors, were identified in 14 of 14 donors (FIG. 6c). The geomean frequency was 1 in 58,000 among the 10 donors sequenced by Briney et al.[18] using UIDs. To refine this frequency estimate, it was considered that only 11 of 14 BG18 iGL variants with NGS-derived HCDR3s differing in the HCDR3 junctions (FIG. 6b) exhibited binding to N332-GT2 (FIG. 1e). BG18-like feature set ii (HCDR3 junction features) in FIG. 6a characterized amino acids present in the non-templated junction regions of BG18 and its somatic variants[15] and in the 11 precursors that bound to N332-GT2. The frequency of HCDR3s meeting the definitions for both feature sets i and ii was found to be lower than those within set i by a factor of 104. Because the $V_L$ gene plays an important role In the BG18 V1-loop straddling binding mode, $V_L$ gene usage was incorporated into the frequency estimate, as feature set iii ("$V_L$ gene family"). The conservative assumption was that only $V_L3$ LCs can support the BG18-class binding mode, as all $V_L3$ LCs tested bound with high affinity to N332-GT2. The frequency of all $V_L3$-derived Abs in the HC-LC paired sequences in DeKosky et al[38] was 1 in 9 (13845 $V_L3$s in 127701 sequences). It was also assumed that any $V_H$ gene can support this binding mode, because when five of the most common human $V_H$ genes were substituted into BG18 iGL$_1$, all five variants showed low nanomolar binding to N332-GT2 (FIG. 1e). Therefore no frequency factor was imposed for $V_H$ gene usage. Multiplying the frequencies of all three feature sets together gave Applicants' best estimate for the frequency in the human B cell repertoire of BG18-like precursors that could be targeted by N332-GT2: 1 in 54 million.

N332-GT specific naive human B cell sorting and BCR sequencing. LRS (leukoreduction) tubes were obtained from the San Diego Blood Bank from healthy, HIV-seronegative human donors. These studies do not constitute human subjects research, as determined by the Institutional Review Boards of both La Jolla Institute and The Scripps Research Institute. More than 1 billion peripheral blood mononuclear cells were regularly recovered. CD19$^+$ B cells were isolated using a positive selection magnetic bead separation kit (Miltenyi Biotec) and resuspended in complete RPMI media with 10% FBS.

Avi-tagged protein immunogens were biotinylated using the Bulk BirA kit (Avidity, LLC). N332-GT2 and N332-GT2KO probes were used in N332-GT2 sorting experiments. N332-GT1 and MD39 probes were used in N332-GT1 sorting experiments. 11mut$_B$ and MD39 probes were used in 11mut$_B$ sorting experiments. Biotinylated protein immunogens were individually premixed with fluorescently labeled streptavidin to form tetramer probes. Multiple tactics were used to avoid false positives: 1) used two "positive" probes, 2) each "positive" probe used a different protein tag (His-tag or Strep-tag) to avoid tag specific B cells, 3) used a "negative" probe to identify N332-epitope specific B cells, 4) choose independent (no tandems) fluorochromes for all probes to avoid fluorochrome specific B cells. For example, N332-GT2 sorting experiments used the follow probes: N332-GT2-Histag-biotin+streptavidin Alexa Fluor 647, N332-GT2-streptag-biotin+streptavidin Brilliant Violet 421, and N332-GT2KO biotin+streptavidin phycoerythrin.

Cells were incubated with N332-GT probes for 20 min at 4° C. Without washing, anti-CD19 (PE-Cy7,ThermoFisher, clone HIB19) and anti-CD20 (PE-Cy7, ThermoFisher, clone 2H7), in addition to anti-IgG (APC-Cy7, Biolegend, clone HP6017), anti-CD3 (APC eFluor®780, ThermoFisher, clone UCHT1), anti-CD14 (APC eFluor®780, ThermoFisher, clone 61D3), anti-CD16 (APC eFluor®780, ThermoFisher, clone eBioCB16), and Live/Dead (APC eFluor®780, ThermoFisher) for exclusion, were added for an additional 20 min. A BD FACSAria was used for all cell sorting. Cells were sorted at a flow rate of 1500 events/second using an 85-μm nozzle. Sorting stringency was set to a strict setting to obtain one cell per well. Single B cells were sorted directly into cold lysis buffer or N332-specific clonal B cell lines were generated and interrogated as in[4]. cDNA synthesis, nested BCR PCR, Sanger sequencing and sequence analysis was carried out as in[10]. Sorting was done with FACSDiva (BD) software and post-sort analyses were done with FlowJo (FlowJo, LLC).

Adoptive transfer experiments and immunization. For adoptive transfer experiments, B cells were isolated from CD45.2 C57BL/6J ("WT") or BG18$^{gH}$ KI mice of 8-10 weeks of age, and cells were resuspended in 150 μl of PBS and injected i.v. into CD45.1 B6. SJL-Ptprc$^a$ Pepc$^b$/BoyJ recipient animals ($5 \times 10^3$ cells per mouse for BG18$^{gH}$ transfers and $50 \times 10^3$ cells per mouse for C57BL/6 transfers). One day later, recipient mice were injected i.p. with 10 μg GT2- or MD39-NPs with Sigma adjuvant (Sigma, #S6322 SIGMA). After eight days, mice were sacrificed to harvest spleen samples. Blood samples were taken from the sub-mandibular vein on day 0 and 14 after immunization. Four immunization conditions were tested in two independent experiments, with the following total number of mice in each condition: (1) BG18$^{gH}$ B cell transfer, N332-GT2 NP immunization (N=6 for day 8 GC analysis, N=5 for day 14 ELISA); (2) BG18$^{gH}$ B cell transfer, MD39 NP immunization (N=3 for day 8 GC analysis, N=3 for day 14 ELISA); (3) WT B cell transfer, N332-GT2 NP immunization (N=5 for day 8 GC analysis, N=5 for day 14 ELISA); (4) WT B cell transfer, MD39 NP immunization (N=3 for day 8 GC analysis, N=3 for day 14 ELISA).

Antigen specific single cell sorting for BCR sequencing in mouse experiments. Antigen tetramers were prepared by conjugating for 1 hour (room temp.) biotinylated N332-GT2 and N332-GT2-KO trimers with fluorescently labeled streptavidins (Alexa Fluor 488, Alexa Fluor 647, eBioscience; Alexa Fluor 568, Thermo Fisher Scientific) in a 4:1 molar ratio. The same streptavidins conjugated with biotinylated Fab anti-IgM and biotinylated BSA were used as positive and negative staining controls, respectively (data not shown). Single cell suspensions generated from spleen samples were depleted of red blood cells by ACK lysis, Fc blocked (BD Biosciences) and stained in FACS buffer (2% FCS/PBS) with antigen tetramers for 30 min at 4C, 50 nM concentration. Next, a cocktail of mAbs was added for 30 minutes at 4 C. For staining of splenocytes from naive mice (FIG. 3a), the cocktail was: B220 PerCP-Cy5.5 (Clone RA3-6B2, Biolegend), IgD PE-Cy7 (Clone 11-26c.2a, Biolegend), CD4 APC-eFluor780 (Clone RM4-5, eBioscience), CD8a APC-eFluor780 (Clone 53-6.7, eBioscience), F4/80 APC-eFluor780 (Clone BM8, eBioscience), Ly-6G APC-eFluor780 (Clone RB6-8C5, eBioscience). For staining of splenocytes from immunized mice (FIG. 3d), the cocktail was: CD38 Alexa Fluor 700 (Clone 90, Invitrogen), CD45.2 PE (Clone 104, Biolegend), CD45.1 PerCP-Cy5.5 (Clone A20, Biolegend), B220 PB (Clone RA3-6B2, Biolegend), CD95 PE-Cy7 (Clone Jo2, BD Bioscience), CD4 APC-eFluor780 (Clone RM4-5, eBioscience), CD8a APC-eFluor780 (Clone 53-6.7, eBioscience), F4/80 APC-eFluor780 (Clone BM8, eBioscience), Ly-6G APC-eFluor780 (Clone RB6-8C5, eBioscience). Live-Dead staining kits (Thermo Scientific) were used to identify dead cells for exclusion from the analysis. Data acquisition and single cell sorting were performed on FACS ARIA II (BD Bioscience) and analyzed with FlowJo v. 10 (Tree Star). Single cell sorting and single cell PCR was carried out as described previously[24].

REFERENCES

1 Jardine, J. et al. Rational HIV immunogen design to target specific germline B cell receptors. *Science* 340, 711-716, doi:10.1126/science.1234150 (2013).
2 McGuire, A. T. et al. Engineering HIV envelope protein to activate germline B cell receptors of broadly neutralizing anti-CD4 binding site antibodies. *J Exp Med* 210, 655-663, doi:10.1084/jem.20122824 (2013).
3 Jardine, J. G. et al. HIV-1 VACCINES. Priming a broadly neutralizing antibody response to HIV-1 using a germline-targeting immunogen. *Science* 349, 156-161, doi:10.1126/science.aac5894 (2015).
4 Jardine, J. G. et al. HIV-1 broadly neutralizing antibody precursor B cells revealed by germline-targeting immunogen. *Science* 351, 1458-1463, doi:10.1126/science.aad9195 (2016).
5 McGuire, A. T. et al. Specifically modified Env immunogens activate B-cell precursors of broadly neutralizing HIV-1 antibodies in transgenic mice. *Nat Commun* 7, 10618, doi:10.1038/ncomms10618 (2016).
6 Briney, B. et al. Tailored Immunogens Direct Affinity Maturation toward HIV Neutralizing Antibodies. *Cell* 166, 1459-1470 e1411, doi:10.1016/j.cell.2016.08.005 (2016).
7 Tian, M. et al. Induction of HIV Neutralizing Antibody Lineages in Mice with Diverse Precursor Repertoires. *Cell* 166, 1471-1484 e1418, doi:10.1016/j.cell.2016.07.029 (2016).
8 Sok, D. et al. Priming HIV-1 broadly neutralizing antibody precursors in human Ig loci transgenic mice. *Science* 353, 1557-1560, doi:10.1126/science.aah3945 (2016).
9 Medina-Ramirez, M. et al. Design and crystal structure of a native-like HIV-1 envelope trimer that engages multiple broadly neutralizing antibody precursors in vivo. *J Exp Med* 214, 2573-2590, doi:10.1084/jem.20161160 (2017).
10 Havenar-Daughton, C. et al. The human naive B cell repertoire contains distinct subclasses for a germline-targeting HIV-1 vaccine immunogen. *Sci Transl Med* 10, doi:10.1126/scitranslmed.aat0381 (2018).
11 Steichen, J. M. et al. HIV Vaccine Design to Target Germline Precursors of Glycan-Dependent Broadly Neutralizing Antibodies. *Immunity* 45, 483-496, doi:10.1016/j.immuni.2016.08.016 (2016).
12 Julien, J. P. et al. Broadly neutralizing antibody PGT121 allosterically modulates CD4 binding via recognition of the HIV-1 gp120 V3 base and multiple surrounding glycans. *PLoS pathogens* 9, e1003342, doi:10.1371/journal.ppat.1003342 (2013).
13 Julien, J. P. et al. Crystal structure of a soluble cleaved HIV-1 envelope trimer. *Science* 342, 1477-1483, doi:10.1126/science.1245625 (2013).
14 Escolano, A. et al. Sequential Immunization Elicits Broadly Neutralizing Anti-HIV-1 Antibodies in Ig Knockin Mice. *Cell* 166, 1445-1458 e1412, doi:10.1016/j.cell.2016.07.030 (2016).
15 Freund, N. T. et al. Coexistence of potent HIV-1 broadly neutralizing antibodies and antibody-sensitive viruses in a viremic controller. *Sci Transl Med* 9, doi:10.1126/scitranslmed.aal2144 (2017).
16 Pancera, M. et al. Structure and immune recognition of trimeric pre-fusion HIV-1 Env. *Nature* 514, 455-461, doi:10.1038/nature13808 (2014).
17 Barnes, C. O. et al. Structural characterization of a highly-potent V3-glycan broadly neutralizing antibody bound to natively-glycosylated HIV-1 envelope. *Nat Commun* 9, 1251, doi:10.1038/s41467-018-03632-y (2018).
18 Briney, B. I., A.; Joyce, C.; Burton, D. R. Uniqueness, commonality and exceptional diversity in the baseline human antibody repertoire. (submitted)
19 Kulp, D. W. et al. Structure-based design of native-like HIV-1 envelope trimers to silence non-neutralizing epitopes and eliminate CD4 binding. *Nat Commun* 8, 1655, doi:10.1038/s41467-017-01549-6 (2017).
20 Abbott, R. K. et al. Precursor Frequency and Affinity Determine B Cell Competitive Fitness in Germinal Centers, Tested with Germline-Targeting HIV Vaccine Immunogens. *Immunity* 48, 133-146 e136, doi:10.1016/j.immuni.2017.11.023 (2018).
21 Tokatlian, T. et al. Innate immune recognition of glycans targets nanoparticle immunogens to germinal centers. (submitted).
22 Kanekiyo, M. et al. Self-assembling influenza nanoparticle vaccines elicit broadly neutralizing H1N1 antibodies. *Nature* 499, 102-106, doi:10.1038/nature12202 (2013).
23 Sliepen, K. et al. Presenting native-like HIV-1 envelope trimers on ferritin nanoparticles improves their immunogenicity. *Retrovirology* 12, 82, doi:10.1186/s12977-015-0210-4 (2015).
24 Lin, Y.-C. P., S.; Steichen, J. M.; Kratochvil, S.; Melzi, E.; Arnold, J., Dougan, S. K.; Wu, L.; Hirsch, K. H.; Nair, U.; Schief, W. R.; Batista, F. D. One-step CRISPR/Cas9 method for the rapid generation of human antibody heavy chain knock-in mice. *The EMBO Journal*, doi:10.15252 (2018).
25 Landais, E. et al. Broadly Neutralizing Antibody Responses in a Large Longitudinal Sub-Saharan HIV Primary Infection Cohort. *PLoS pathogens* 12, e1005369, doi:10.1371/journal.ppat.1005369 (2016).

26 Suloway, C. et al. Automated molecular microscopy: the new Leginon system. *Journal of structural biology* 151, 41-60, doi:10.1016/j.jsb.2005.03.010 (2005).

27 Zheng, S. Q. et al. MotionCor2: anisotropic correction of beam-induced motion for improved cryo-electron microscopy. *Nat Methods* 14, 331-332, doi:10.1038/nmeth.4193 (2017).

28 Zhang, K. Gctf: Real-time CTF determination and correction. *Journal of structural biology* 193, 1-12, doi:10.1016/j.jsb.2015.11.003 (2016).

29 Voss, N. R., Yoshioka, C. K., Radermacher, M., Potter, C. S. & Carragher, B. DoG Picker and TiltPicker: software tools to facilitate particle selection in single particle electron microscopy. *Journal of structural biology* 166, 205-213 (2009).

30 Kimanius, D., Forsberg, B. O., Scheres, S. H. & Lindahl, E. Accelerated cryo-EM structure determination with parallelisation using GPUs in RELION-2. *Elife* 5, doi:10.7554/eLife.18722 (2016).

31 Emsley, P., Lohkamp, B., Scott, W. G. & Cowtan, K. Features and development of Coot. *Acta Crystallogr D Biol Crystallogr* 66, 486-501, doi:10.1107/S0907444910007493 (2010).

32 Adams, P. D. et al. PHENIX: a comprehensive Python-based system for macromolecular structure solution. *Acta Crystallogr D Biol Crystallogr* 66, 213-221, doi:10.1107/S0907444909052925 (2010).

33 Lutteke, T., Frank, M. & von der Lieth, C. W. Carbohydrate Structure Suite (CSS): analysis of carbohydrate 3D structures derived from the PDB. *Nucleic Acids Res* 33, D242-246, doi:10.1093/nar/gki013 (2005).

34 Winn, M. D. et al. Overview of the CCP4 suite and current developments. *Acta Crystallogr D Biol Crystallogr* 67, 235-242, doi:10.1107/S0907444910045749 (2011).

35 Barad, B. A. et al. EMRinger: side chain-directed model and map validation for 3D cryo-electron microscopy. *Nat Methods* 12, 943-946, doi:10.1038/nmeth.3541 (2015).

36 Chen, V. B. et al. MolProbity: all-atom structure validation for macromolecular crystallography. *Acta Crystallogr D Biol Crystallogr* 66, 12-21, doi:10.1107/S0907444909042073 (2010).

37 Willis, J. R. et al. Redesigned HIV antibodies exhibit enhanced neutralizing potency and breadth. *J Clin Invest* 125, 2523-2531, doi:10.1172/JCI80693 (2015).

38 DeKosky, B. J. et al. High-throughput sequencing of the paired human immunoglobulin heavy and light chain repertoire. *Nat Biotechnol* 31, 166-169, doi:10.1038/nbt.2492 (2013).

39 Jardine, J. G. et al. Minimally Mutated HIV-1 Broadly Neutralizing Antibodies to Guide Reductionist Vaccine Design. *PLoS pathogens* 12, e1005815, doi:10.1371/journal.ppat.1005815 (2016).s SEQUENCES
HXB2 Env

SEQ ID NO: 1

MRVKEKYQHLWRWGWRWGTMLLGMLMICSATEKLWVTVYYGVPVWKEATTTLF

CASDAKAYDTEVHNVWATHACVPTDPNPQEVVLVNVTENFNMWKNDMVEQMHED

IISLWDQSLKPCVKLTPLCVSLKCTDLKNDTNTNSSSGRMIMEKGEIKNCSFNISTSIRG

KVQKEYAFFYKLDIIPIDNDTTSYKLTSCNTSVITQACPKVSEEPIPIHYCAPAGFAILKC

NNKTFNGTGPCTNVSTVQCTHGIRPVVSTQLLLNGSLAEEEVVIRSVNFTDNAKTIIVQ

LNTSVEINCTRPNNNTRKRIRIQRGPGRAFVTIGKIGNIVIRQAHCNISRAKWNNTLKQIA

SKLREQFGNNKTIIFKQSSGGDPEIVTHSFNCGGEFFYCNSTQLFNSTWFNSTWSTEGS

NNTEGSDTITLPCRIKQIINMWQKVGKAMYAPPISGQIRCSSNITGLLLTRDGGNSNNE

SEIFRPGGGDMRDNWRSELYKYKVVKIEPLGVAPTKAKRRVVQREKRAVGIGALFLG

FLGAAGSTMGAASMTLTVQARQLLSGIVQQQNNLLRAIEAQQHLLQLTVWGIKQLQ

ARILAVERYLKDQQLLGIWGCSGKLICTTAVPWNASWSNKSLEQIWNHTTWMEWDR

EINNYTSLIHSLIEESQNQQEKNEQELLELDKWASLWNWFNITNWLWYIKLFIMIVGG

LVGLRIVFAVLSIVNRVRQGYSPLSFQTHLPTPRGPDRPEGIEEEGGERDRDRSIRLVNG

SLALIWDDLRSLCLFSYHRLRDLLLIVTRIVELLGRRGWEALKYWWNLLQYWSQELK

NSAVSLLNATAIAVAEGTDRVIEVVQGACRAIRHIPRRIRQGLERILL;

BG505 Env

SEQ ID NO: 2

MRVMGIQRNCQHLFRWGTMILGMIIICSAAENLWVTVYYGVPVWKDAETTLFCASD

AKAYETEKHNVWATHACVPTDPNPQEIHLENVTEEFNIVIWKNNMVEQMHTDIISLWD

QSLKPCVKLTPLCVTLQCTNVTNNITDDMRGELKNCSFNMTTELRDKKQKVYSLFYR

LDVVQINENQGNRSNNSNKEYRLINCNTSAITQACPKVSFEPIPIHYCAPAGFAILKCK

DKKENGTGPCPSVSTVQCTHGIKPVVSTQLLLNGSLAEEEVMIRSENITNNAKNILVQF

NTPVQINCTRPNNNTRKSIRIGPGQAFYATGDIIGDIRQAHCTVSKATWNETLGKVVK

-continued

QLRKEIFGNNTIIRFANSSGGDLEVTTHSFNCGGEFFYCNTSGLENSTWISNTSVQGSNS

TGSNDSITLPCRIKQIINMWQRIGQAMYAPPIQGVIRCVSNITGLILTRDGGSTNSTTETE

RPGGGDMRDNWRSELYKYKVVKIEPLGVAPTRAKRRVVGREKRAVGIGAVFLGFLG

AAGSTMGAASMTLTVQARNLLSGIVQQQSNLLRAIEAQQHLLKLTVWGIKQLQARVL

AVERYLRDQQLLGIWGCSGKLICTTNVPWNSSWSNRNLSEIWDNMTWLQWDKEISN

YTQIIYGLLEESQNQQEKNEQDLLALDKWASLWNWFDISNWLWYIKIFIMIVGGLIGL

RIVFAVLSVIHRVRQGYSPLSFQTHTPNPRGLDRPERIEEEDGEQDRGRSTRLVSGFLA

LAWDDLRSLCLFCYHRLRDFILIAARIVELLGHSSLKGLRLGWEGLKYLWNLLAYWG

RELKISAINLFDTIAIAVAEWTDRVIEIGQRLCRAFLHIPRRIRQGLERALL;

BG505 MD39
SEQ ID NO: 3
AENLWVTVYYGVPVWKDAETTLFCASDAKAYETEKHNVWATHACVPTDPNPQEIHL

ENVTEEFNMWKNNMVEQMHEDIISLWDQSLKPCVKLTPLCVTLQCTNVTNNITDDM

RGELKNCSFNMTTELRDKKQKVYSLFYRLDVVQINENQGNRSNNSNKEYRLINCNTS

AITQACPKVSFEPIPIHYCAPAGFAILKCKDKKFNGTGPCPSVSTVQCTHGIKPVVSTQL

LLNGSLAEEEVIIRSENITNNAKNILVQLNTPVQINCTRPNNNTVKSIRIGPGQAFYYTG

DIIGDIRQAHCNVSKATWNETLGKVVKQLRKHFGNNTIIRFAQSSGGDLEVTTHSFNC

GGEFFYCNTSGLENSTWISNTSVQGSNSTGSNDSITLPCRIKQIINMWQRIGQAMYAPPI

QGVIRCVSNITGLILTRDGGSTNSTTETFRPGGGDMRDNWRSELYKYKVVKIEPLGVA

PTRCKRRVVGRRRRRRAVGIGAVSLGFLGAAGSTMGAASMTLTVQARNLLSGIVQQ

QSNLLRAPEPQQHLLKDTHWGIKQLQARVLAVEHYLRDQQLLGIWGCSGKLICCTNV

PWNSSWSNRNLSEIWDNMTWLQWDKEISNYTQIIYGLLEESQNQQEKNEQDLLALD;

BG505 MD39 11mutB
SEQ ID NO: 4
V;

BG505 MD39 17mutE
SEQ ID NO: 5
AENLWVTVYYGVPVWKDAETTLFCASDAKAYETEKHNVWATHACVPTDPNPQEIHL

ENVTEEFNMWKNNMVEQMHEDIISLWDQSLKPCVKLTPLCVTLQCTNYAPNLLSNM

RGEIKNCSFNMTTELRDKKQKVYSLFYRLDVVQINENQGNRSNNSNKEYRLINCNTS

AITQACPKVSFEPIPIHYCAPAGFAILKCKDKKENGTGPCPSVSTVQCTHGIKPVVSTQL

LLNGSLAEEEVIIRSENTTNNAKNILVQLNTPVQINCTRPNNNTVKSIRIGPGQAFYYFG

DVLGDVRMAHCNISKATWNETLGKVVKQLRKEIFGNNTIIRFAQSSGGDLEVTTHSFN

CGGEFFYCNTSGLENSTWISNTSVQGSNSTGSNDSLILPCRIKQIINMWQRIGQAMYAP

PIQGVIRCVSNITGLILTRDGGSTNSTTETFRPGGGDMRDNWRSELYKYKVVKIEPLGV

APTRCKRRVVGRRRRRRAVGIGAVSLGFLGAAGSTMGAASMTLTVQARNLLSGIVQ

QQSNLLRAPEPQQHLLKDTHWGIKQLQARVLAVEHYLRDQQLLGIWGCSGKLICCTN

VPWNSSWSNRNLSEIWDNMTWLQWDKEISNYTQIIYGLLEESQNQQEKNEQDLLALD;

BG505 MD39 N332 GT1
SEQ ID NO: 6
AENLWVTVYYGVPVWKDAETTLFCASDAKAYETEKHNVWATHACVPTDPNPQEIHL

ENVTEEFNMWKNNMVEQMHEDIISLWDQSLKPCVKLTPLCVTLQCTNYAPKLLSNM

RGEIKNCSFNMTTELRDKKQKVYSLFYRLDVVQINENQGNRSNNSNKEYRLINCNTS

AITQACPKVSFEPIPIHYCAPAGFAILKCKDKKENGTGPCPSVSTVQCTHGIKPVVSTQL

LLNGSLAEEEVIIRSENTTNNAKNILVQLNTPVQINCTRPNNNTVKSIRIGPGQAFYYFG

-continued

DVLGHVRMAHCNISKATWNETLGKVVKQLRKEIFGNNTIIRFAQSSGGDLEVTTHSFN
CGGEFFYCNTSGLFNSTWISNTSVQGSNSTGSNDSLILPCRIKQIINMWQRIGQAMYAP
PIQGVIRCVSNITGLILTRDGGSTNSTTETFRPGGGDMRDNWRSELYKYKVVKIEPLGV
APTRCKRRVVGRRRRRRAVGIGAVSLGFLGAAGSTMGAASMTLTVQARNLLSGIVQ
QQSNLLRAPEPQQHLLKDTHWGIKQLQARVLAVEHYLRDQQLLGIWGCSGKLICCTN
VPWNSSWSNRNLSEIWDNMTWLQWDKEISNYTQIIYGLLEESQNQQEKNEQDLLALD;

BG505 MD39 N332 GT2

SEQ ID NO: 7

AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENTTNNAKNILVQLNTPVQINCTRPNNNTVKSIRIGPGQAFYYFG
DVLGDVRMAHCNISKATWNETLGKVVKQLRKHFGNNTIIRFAQSSGGDLEVTTHSFN
CGGEFFYCNTSGLFNSTWISNTSVQGSNSTGSNDSLILPCRIKQIINMWQRIGQAMYAP
PIQGVIRCVSNITGLILTRDGGSTNSTTETFRPGGGDMRDNWRSELYKYKVVKIEPLGV
APTRCKRRVVGRRRRRRAVGIGAVSLGFLGAAGSTMGAASMTLTVQARNLLSGIVQ
QQSNLLRAPEPQQHLLKDTHWGIKQLQARVLAVEHYLRDQQLLGIWGCSGKLICCTN
VPWNSSWSNRNLSEIWDNMTWLQWDKEISNYTQIIYGLLEESQNQQEKNEQDLLALD;

BG505 MD39 N332 GT3

SEQ ID NO: 8

AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENTTNNAKNILVQLNTPVQINCTRPNNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCRIKQIINMWQRIGQAMYAP
PIQGVIRCVSNITGLILTRDGGSTNSTTETFRPGGGDMRDNWRSELYKYKVVKIEPLGV
APTRCKRRVVGRRRRRRAVGIGAVSLGFLGAAGSTMGAASMTLTVQARNLLSGIVQ
QQSNLLRAPEPQQHLLKDTHWGIKQLQARVLAVEHYLRDQQLLGIWGCSGKLICCTN
VPWNSSWSNRNLSEIWDNMTWLQWDKEISNYTQIIYGLLEESQNQQEKNEQDLLALD;

BG505 MD39 N332 GT4

SEQ ID NO: 9

AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENTTNNAKNILVQLNTPVQINCTRPSNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCRIKQIINMWQRIGQAMYAP
PIQGVIRCVSNITGLILTRDGGSTNSTTETFRPGGGDMRDNWRSELYKYKVVKIEPLGV
APTRCKRRVVGRRRRRRAVGIGAVSLGFLGAAGSTMGAASMTLTVQARNLLSGIVQ

```
QQSNLLRAPEPQQHLLKDTHWGIKQLQARVLAVEHYLRDQQLLGIWGCSGKLICCTN

VPWNSSWSNRNLSEIWDNMTWLQWDKEISNYTQIIYGLLEESQNQQEKNEQDLLALD;

BG505 MD39 N332 GT5
                                                    SEQ ID NO: 10
AENLWVTVYYGVPVWKDAETTLFCASDAKAYETEKHNVWATHACVPTDPNPQEIHL

ENVTEEFNIVIWKNNMVEQMHEDIISLWDQSLKPCVKLTPLCVTLQCTNYAPKLRSMM

RGEIKNCSFNMTTELRDKKQKVYSLFYRLDVVQINENQGNRSNNSNKEYRLINCNTS

AITQACPKVSFEPIPIHYCAPAGFAILKCKDKKFNGTGPCPSVSTVQCTHGIKPVVSTQL

LLNGSLAEEEVIIRSENTTNNAKNILVQLNTPVQINCTRPSNNTVKSIRIGPGQAFYYFG

DVLGHVRMAHCNISKATWNETLGKVVKQLRKHFGNNTIIRFAQSSGGDLEVTTHSFN

CGGEFFYCNTSGLFNSTWISNTSVQGSNSTGSNDSLILPCWIKQIINMWQRIGQAMYAP

PIQGVIRCVSNITGLILTRDGGSTNSTTETFRPGGGDMRDNWRSELYKYKVVKIEPLGV

APTRCKRRVVGRRRRRRAVGIGAVSLGFLGAAGSTMGAASMTLTVQARNLLSGIVQ

QQSNLLRAPEPQQHLLKDTHWGIKQLQARVLAVEHYLRDQQLLGIWGCSGKLICCTN

VPWNSSWSNRNLSEIWDNMTWLQWDKEISNYTQIIYGLLEESQNQQEKNEQDLLALD;

BG505 MD39 N332 GT2 KO
                                                    SEQ ID NO: 11
AENLWVTVYYGVPVWKDAETTLFCASDAKAYETEKHNVWATHACVPTDPNPQEIHL

ENVTEEFNMWKNNMVEQMHEDIISLWDQSLKPCVKLTPLCVTLQCTNYAPNLRSDM

RGEIKNCSFNMTTELRDKKQKVYSLFYRLDVVQINENQGNRSNNSNKEYRLINCNTS

AITQACPKVSFEPIPIHYCAPAGFAILKCKDKKFNGTGPCPSVSTVQCTHGIKPVVSTQL

LLNGSLAEEEVIIRSENTTNNAKNILVQLNTPVQINCTRPNNNTVKSIRIGPGQAFYYFG

DVLGDVDMAKCTISKATWNETLGKVVKQLRKHFGNNTIIRFAQSSGGDLEVTTHSFN

CGGEFFYCNTSGLFNSTWISNTSVQGSNSTGSNDSLILPCRIKQIINMWQRIGQAMYAP

PIQGVIRCVSNITGLILTRDGGSTNSTTETFRPGGGDMRDNWRSELYKYKVVKIEPLGV

APTRCKRRVVGRRRRRRAVGIGAVSLGFLGAAGSTMGAASMTLTVQARNLLSGIVQ

QQSNLLRAPEPQQHLLKDTHWGIKQLQARVLAVEHYLRDQQLLGIWGCSGKLICCTN

VPWNSSWSNRNLSEIWDNMTWLQWDKEISNYTQIIYGLLEESQNQQEKNEQDLLALD;

BG505 MD64 N332 GT2
                                                    SEQ ID NO: 12
AENLWVTVYYGVPVWKDAETTLFCASDAKAYETEKHNVWATHECVPTDPNPQEIHL

ENVTEEFNMWKNNMVEQMHTDIIELWDQSLKPCVKLTPLCVTLQCTNYAPKLRSMM

RGEIKNCSFNMTTELRDKKQKVYSLFYRLDVVQINENQGNRSNNSNKEYRLINCNTS

AITQACPKVSFEPIPIHYCAPAGFAILKCKDKKFNGTGPCPSVSTVQCTHGIKPVVSTQL

LLNGSLAEEEVIIRSENTTNNAKNILVQLNTPVQINCTRPNNNTVKSIRIGPGQAFYYFG

DVLGDVRMAHCNISKATWNETLGKVVKQLRKHFGNNTIIRFAQSSGGDLEVTTHSFN

CGGEFFYCNTSGLFNSTWISNTSVQGSNSTGSNDSLILPCRIKQIINMWQRIGQAMYAP

PIQGVIRCVSNITGLILTRDGGSTNSTTETFRPGGGDMRDNWRSELYKYKVVKIEPLGV

APTRCKRRVVGRRRRRRAVGIGAVSLGFLGAAGSTMGAASMTLTVQARNLLSGIVQ

QQSNLLRAPEPQQHLLKLTVWGIKQLQARVLAVEHYLRDQQLLGIWGCSGKLICCTN

VPWNSSWSNRNLSEIWDNMTWLQWDKEISNYTQIIYGLLEESQNQQEKNEQDLLALD;

N332-GT2 NP (ferritin)
                                                    SEQ ID NO: 13
AENLWVTVYYGVPVWKDAETTLFCASDAKAYETEKHNVWATHACVPTDPNPQEIHL

ENVTEEFNMWKNNMVEQMHEDIISLWDQSLKPCVKLTPLCVTLQCTNYAPKLRSMM
```

-continued

RGEIKNCSFNMTTELRDKKQKVYSLFYRLDVVQINENQGNRSNNSNKEYRLINCNTS

AITQACPKVSFEPIPIHYCAPAGFAILKCKDKKFNGTGPCPSVSTVQCTHGIKPVVSTQL

LLNGSLAEEEVIIRSENTTNNAKNILVQLNTPVQINCTRPNNNTVKSIRIGPGQAFYYFG

DVLGDVRMAHCNISKATWNETLGKVVKQLRKHFGNNTIIRFAQSSGGDLEVTTHSFN

CGGEFFYCNTSGLFNSTWISNTSVQGSNSTGSNDSLILPCRIKQIINMWQRIGQAMYAP

PIQGVIRCVSNITGLILTRDGGSTNSTTETFRPGGGDMRDNWRSELYKYKVVKIEPLGV

APTRCKRRVVGSHSGSGGSGSGGHAAVGIGAVSLGFLGAAGSTMGAASMTLTVQAR

NLPSGIVQQQSNLLRAPEPQQHLLKDTHWGIKQLQARVLAVEHYLRDQQLLGIWGCS

GKLICCTNVPWNSSWSNRNLSEIWDNMTWLQWDKEISNYTQIIYGLLEESQNQQEKN

EQDLLALDGSGGLSERMLKALNDQLNRELYSAYLYFAMAAYFEDLGLEGFANWMK

AQAEEEIGHALRFYNYIYDKNGRVELDEIPKPPKEWESPLKAFEAAYEHEKFISKSIYE

LAALAEEEKDYSTRAFLEWFINEQVEEEASVKKILDKLKFAKDSPQILFMLDKELSAR

APKLPGLLMQGGE;

MD39 NP (ferritin)

SEQ ID NO: 14

AENLWVTVYYGVPVWKDAETTLFCASDAKAYETEKHNVWATHACVPTDPNPQEIHL

ENVTEEFNMWKNNMVEQMHEDIISLWDQSLKPCVKLTPLCVTLQCTNVTNNITDDM

RGELKNCSFNMTTELRDKKQKVYSLFYRLDVVQINENQGNRSNNSNKEYRLINCNTS

AITQACPKVSFEPIPIHYCAPAGFAILKCKDKKFNGTGPCPSVSTVQCTHGIKPVVSTQL

LLNGSLAEEEVIIRSENITNNAKNILVQLNTPVQINCTRPNNNTVKSIRIGPGQAFYYTG

DIIGDIRQAHCNVSKATWNETLGKVVKQLRKHFGNNTIIRFAQSSGGDLEVTTHSFNC

GGEFFYCNTSGLFNSTWISNTSVQGSNSTGSNDSITLPCRIKQIINMWQRIGQAMYAPPI

QGVIRCVSNITGLILTRDGGSTNSTTETFRPGGGDMRDNWRSELYKYKVVKIEPLGVA

PTRCKRRVVGRRRRRRAVGIGAVSLGFLGAAGSTMGAASMTLTVQARNLLSGIVQQ

QSNLLRAPEPQQHLLKDTHWGIKQLQARVLAVEHYLRDQQLLGIWGCSGKLICCTNV

PWNSSWSNRNLSEIWDNMTWLQWDKEISNYTQIIYGLLEESQNQQEKNEQDLLALDG

SGGLSERMLKALNDQLNRELYSAYLYFAMAAYFEDLGLEGFANWMKAQAEEEIGHA

LRFYNYIYDKNGRVELDEIPKPPKEWESPLKAFEAAYEHEKFISKSIYELAALAEEEKD

YSTRAFLEWFINEQVEEEASVKKILDKLKFAKDSPQILFMLDKELSARAPKLPGLLMQ

GGE;

N332-GT5 NP (ferritin 3bve)

SEQ ID NO: 15

AENLWVTVYYGVPVWKDAETTLFCASDAKAYETEKHNVWATHACVPTDPNPQEIHL

ENVTEEFNIVIWKNNMVEQMHEDIISLWDQSLKPCVKLTPLCVTLQCTNYAPKLRSMM

RGEIKNCSFNMTTELRDKKQKVYSLFYRLDVVQINENQGNRSNNSNKEYRLINCNTS

AITQACPKVSFEPIPIHYCAPAGFAILKCKDKKFNGTGPCPSVSTVQCTHGIKPVVSTQL

LLNGSLAEEEVIIRSENITNNAKNILVQLNTPVQINCTRPSNNTVKSIRIGPGQAFYYFG

DVLGHVRMAHCNISKATWNETLGKVVKQLRKHFGNNTIIRFAQSSGGDLEVTTHSFN

CGGEFFYCNTSGLFNSTWISNTSVQGSNSTGSNDSLILPCWIKQIINMWQRIGQAMYAP

PIQGVIRCVSNITGLILTRDGGSTNSTTETFRPGGGDMRDNWRSELYKYKVVKIEPLGV

APTRCKREVVGRRRRRRAVGIGAVSLGFLGAAGSTMGAASMTLTVQARNLLSGIVQQ

QSNLLRAPEPQQHLLKDTHWGIKQLQARVLAVEHYLRDQQLLGIWGCSGKLICCTNV

```
PWNSSWSNRNLSEIWDNMTWLQWDKEISNYTQIIYGLLEESQNQQEKNEQDLLALDG

SGGLSKDIIKLLNEQVNKEMQSSNLYMSMSSWCYTHSLDGAGLFLFDHAAEEYEHAK

KLIIFLNENNVPVQLTSISAPEHKFEGLTQIFQKAYEHEQHISESINNIVDHAIKSKDHAT

FNFLQWYVAEQHEEEVLFKDILDKIELIGNENHGLYLADQYVKGIAKSRKS;

BG505 MD65 congly N332-GTS
                                         SEQ ID NO: 16
AENLWVTVYYGVPVWKDAETTLFCASDAKAYETEKHNVWATHACVPTDPNPQEIHL

ENVTEEFNIVIWKNNMVEQMHEDIISLWDQSLKPCVKLTPLCVTLQCTNYAPKLRSMM

RGEIKNCSFNMTTELRDKKQKVYSLFYRLDVVQINENQGNRSNNSNKEYRLINCNTS

AITQACPKVSFEPIPIHYCAPAGFAILKCKDKKFNGTGPCQNVSTVQCTHGIKPVVSTQ

LLLNGSLAEEEVIIRSENITNNAKNILVQLNTSVQINCTRPSNNTVKSIRIGPGQAFYYFG

DVLGHVRMAHCNISKATWNETLGKVVKQLRKHFGNNTIIRFAQSSGGDLEVTTHSFN

CGGEFFYCNTSGLFNSTWISNTSVQGSNSTGSNDSLILPCWIKQIINMWQRIGQAMYAP

PIQGVIRCVSNITGLILTRDGGSTNSTTETFRPGGGDMRDNWRSELYKYKVVKIEPLGV

APTRCKRRTVGRRRRRAAGIGASSDGFLGAAGSTMGAASMTLTVQARNLLSGIVQQ

QSNLLRAPEPQQHLLKDTHWGIKQLQARVLAVEHYLRDQQLLGIWGCSGKLICCTNV

PWNSSWSNRNLSEIWDNMTWLQWDKEISNYTQIIYGLLEESQNQQEKNEQDLLALD;

VH BG18
                                         SEQ ID NO: 17
QVQLRESGPGLVKPSETLSLSCTVSNDSRPSDHSWTWVRQSPGKALEWIGDIHYNGAT

TYNPSLRSRVRIELDQSIPRFSLKMTSMTAADTGMYYCARNAIRIYGVVALGEWFHYG

MDVWGQGTAVTVSS;

VL BG18
                                         SEQ ID NO: 18
SSELTQPPSVSVSPGQTARITCSGAPLTSRFTYWYRQKPGQAPVLIISRSSQRSSGWSGR

FSASWSGTTVTLTIRGVQADDEADYYCQSSDTSDSYKMFGGGTKLTVL;

VH BG18.11
                                         SEQ ID NO: 19
QVQLQESGPGLVKPSGTLSLTCAVSNDSRPSDHSWSWVRQPPGKGLEWIGDIHYSGST

TYNPSLKSRVTISVDKSKNQFSLKLSSVTAADTAVYYCARNAIRIYGVVALGEWFHYG

MDVWGQGTTVTVSS;

VL BG18.11
                                         SEQ ID NO: 20
SYELTQPPSVSVSPGQTARITCSGDALPSRYAYWYQQKPGQAPVLVISRDSQRSSGISG

RFSGSWSGTTVTLTISGVQAEDEADYYCQSSDSSDTYKVFGGGTKLTVL;

VH BG18.6
                                         SEQ ID NO: 21
QVQLQESGPGLVKPSGTLSLTCAVSGDSRPSDHSWSWVRQPPGKGLEWIGEIYYSGST

NYNPSLKSRVTISVDKSKNQFSLKLSSVTAADTAVYYCARNAIRIYGVVALGEWFHY

GMDVWGQGTTVTVSS;

VL BG18.6
                                         SEQ ID NO: 22
SYELTQPPSVSVSPGQTARITCSGDALPKQYAYWYQQKPGQAPVLVIYRDSQRPSGIS

GRFSGSSSGTTVTLTISGVQAEDEADYYCQSADSSDTYKVFGGGTKLTVL;
```

```
VH BG18 iGL0
                                          SEQ ID NO: 23
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARNAITIFGVVIIGEYYYYG

MDVWGQGTTVTVSS;

VL BG18 iGL0
                                          SEQ ID NO: 24
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH BG18 iGL1
                                          SEQ ID NO: 25
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARNAITIFGVVILGEYYYYG

MDVWGQGTTVTVSS;

VL BG18 iGL1 (Same as VL BG18 iGL0)
                                          SEQ ID NO: 26
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH BG18 iGL2
                                          SEQ ID NO: 27
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARNAITIFGVVALGEYYYYG

MDVWGQGTTVTVSS;

VL BG18 iGL2 (Same as VL BG18 iGL0)
                                          SEQ ID NO: 28
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH VH4-59
                                          SEQ ID NO: 29
QVQLQESGPGLVKPSETLSLTCTVSGGSISSYYWSWIRQPPGKGLEWIGYIYYSGSTNY

NPSLKSRVTISVDTSKNQFSLKLSSVTAADTAVYYCARNAITIFGVVALGEYYYYGMD

VWGQGTTVTVSS;

VH VH1-69
                                          SEQ ID NO: 30
QVQLVQSGAEVKKPGSSVKVSCKASGGTFSSYAISWVRQAPGQGLEWMGGIIPIFGTA

NYAQKFQGRVTITADESTSTAYMELSSLRSEDTAVYYCARNAITIFGVVALGEYYYYG

MDVWGQGTTVTVSS;

VH VH5-51
                                          SEQ ID NO: 31
EVQLVQSGAEVKKPGESLKISCKGSGYSFTSYWIGWVRQMPGKGLEWMGIIYPGDSD

TRYSPSFQGQVTISADKSISTAYLQWSSLKASDTAMYYCARNAITIFGVVALGEYYYY

GMDVWGQGTTVTVSS;

VH VH3-33
                                          SEQ ID NO: 32
QVQLVESGGGVVQPGRSLRLSCAASGFTFSSYGMHWVRQAPGKGLEWVAVIWYDGS

NKYYADSVKGRFTISRDNSKNTLYLQMNSLRAEDTAVYYCARNAITIFGVVALGEYY

YYGMDVWGQGTTVTVSS;
```

```
VH VH3-23
                                         SEQ ID NO: 33
EVQLLESGGGLVQPGGSLRLSCAASGFTFSSYAMSWVRQAPGKGLEWVSAISGSGGS

TYYADSVKGRFTISRDNSKNTLYLQMNSLRAEDTAVYYCAKNAITIFGVVALGEYYY

YGMDVWGQGTTVTVSS;

VL VL3-19
                                         SEQ ID NO: 34
SSELTQDPAVSVALGQTVRITCQGDSLRSYYASWYQQKPGQAPVLVIYGKNNRPSGIP

DRFSGSSSGNTASLTITGAQAEDEADYYCNSRDSSGNHWVFGGGTKLTVL;

VL VL3-10
                                         SEQ ID NO: 35
SYELTQPPSVSVSPGQTARITCSGDALPKKYAYWYQQKSGQAPVLVIYKDSKRPSGIP

ERFSGSSSGTMATLTISGAQVEDEDDYYCYSADYSGNHWVFGGGTKLTVL;

VL VL3-1
                                         SEQ ID NO: 36
SYELTQPPSVSVSPGQTASITCSGDKLGDKYACWYQQKPGQSPVLVIYQDSKRPSGIPE

RFSGSNSGNTATLTISGTQAMDEADYYCQAWDSSTAWVFGGGTKLTVL;

VL VL3-21
                                         SEQ ID NO: 37
SYVLTQPPSVSVAPGQTARITCGGNNIGSKSVHWYQQKPGQAPVLVVYDDSDRPSGIP

ERFSGSNSGNTATLTISRVEAGDEADYYCQVWDSSSDHWVFGGGTKLTVL;

VL VL2-8
                                         SEQ ID NO: 38
QSALTQPPSASGSPGQSVTISCTGTSSDVGGYNYVSWYQQHPGKAPKLMIYEVSKRPS

GVPDRFSGSKSGNTASLTVSGLQAEDEADYYCSSYAGSNNFWVFGGGTKLTVL;

VH PRE1
                                         SEQ ID NO: 39
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARGQRTIFGVVILFNYYYYG

MDVWGQGTTVTVSS;

VL PRE1 (Same as VL BG18 iGL0)
                                         SEQ ID NO: 40
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE2
                                         SEQ ID NO: 41
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARDLLTSFGVVIFSQHKSYG

MDVWGQGTTVTVSS;

VL PRE2 (Same as VL BG18 iGL0)
                                         SEQ ID NO: 42
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE3
                                         SEQ ID NO: 43
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARDSITIFGVVILQDYYYG

MDVWGQGTTVTVSS;
```

-continued

VL PRE3 (Same as VL BG18 iGL0)
SEQ ID NO: 44
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE4
SEQ ID NO: 45
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARERDTIFGVVSLRVYYYYG

MDVWGQGTTVTVSS;

VL PRE4 (Same as VL BG18 iGL0)
SEQ ID NO: 46
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE5
SEQ ID NO: 47
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARDKDTIFGVVIIGEYYYYG

MDVWGQGTTVTVSS;

VL PRE5 (Same as VL BG18 iGL0)
SEQ ID NO: 48
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE6
SEQ ID NO: 49
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARGSITIFGVVIILEDYYYGM

DVWGQGTTVTVSS;

VL PRE6 (Same as VL BG18 iGL0)
SEQ ID NO: 50
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE7
SEQ ID NO: 51
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCAREQRAIFGVVIIREDYYYG

MDVWGQGTTVTVSS;

VL PRE7 (Same as VL BG18 iGL0)
SEQ ID NO: 52
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE8
SEQ ID NO: 53
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARARLRVFGVVIFLYGYYY

GMDVWGQGTTVTVSS;

VL PRE8 (Same as VL BG18 iGL0)
SEQ ID NO: 54
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE9
                                      SEQ ID NO: 55
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARDRKRFFGVVIMDESYYY

GMDVWGQGTTVTVSS;

VL PRE9 (Same as VL BG18 iGL0)
                                      SEQ ID NO: 56
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE10
                                      SEQ ID NO: 57
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARDGVKIFGVVIIREAYYYG

MDVWGQGTTVTVSS;

VL PRE10 (Same as VL BG18 iGL0)
                                      SEQ ID NO: 58
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE11
                                      SEQ ID NO: 59
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARDGIKIFGVVIMGEAHYYG

MDVWGQGTTVTVSS;

VL PRE11 (Same as VL BG18 iGL0)
                                      SEQ ID NO: 60
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE12
                                      SEQ ID NO: 61
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCAKGRGTIFGVVRFYENYYY

GMDVWGQGTTVTVSS;

VL PRE12 (Same as VL BG18 iGL0)
                                      SEQ ID NO: 62
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE13
                                      SEQ ID NO: 63
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCAKALNTIFGVVTLTQYYYY

GMDVWGQGTTVTVSS;

VL PRE13 (Same as VL BG18 iGL0)
                                      SEQ ID NO: 64
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE14
                                      SEQ ID NO: 65
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARGRITIFGVVTLRGYYYG

MDVWGQGTTVTVSS;

-continued

VL PRE14 (Same as VL BG18 iGL0)
SEQ ID NO: 66
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PRE15
SEQ ID NO: 67
QVQLQESGPGLVKPSGTLSLTCAVSGGSISSSNWWSWVRQPPGKGLEWIGEIYHSGST

NYNPSLKSRVTISVDKSKNQFSLKLSSVTAADTAVYYCARDIHNSFGVVSLDQNYYY

GMDVWGQGTTVTVSS;

VL PRE15 (Same as VL BG18 iGL0)
SEQ ID NO: 68
SYELTQPPSVSVSPGQTARITCSGDALPKQYAYWYQQKPGQAPVLVIYKDSERPSGIPE

RFSGSSSGTTVTLTISGVQAEDEADYYCQSADSSGTYWVFGGGTKLTVL;

VH PG121 iGL
SEQ ID NO: 69
QVQLQESGPGLVKPSETLSLTCTVSGGSISSYYWSWIRQPPGKGLEWIGYIYYSGSTNY

NPSLKSRVTISVDTSKNQFSLKLSSVTAADTAVYYCARTQQGKRIYGVVSFGDYYYY

YYMDVWGKGTTVTVSS;

VL PG121 iGL
SEQ ID NO: 70
SYVLTQPPSVSVAPGQTARITCGGNNIGSKSVHWYQQKPGQAPVLVVYDDSDRPSGIP

ERFSGSNSGNTATLTISRVEAGDEADYYCQVWDSSSDHPWVFGGGTKLTVL;

SEQ ID NO: 71
CTNVTNNITDDMRGEL

SEQ ID NO: 72
CTNYAPNLLSNMRGEL

SEQ ID NO: 73
CTNYAPNLLSNMRGEI

SEQ ID NO: 74
CTNYAPKLLSNMRGEI

SEQ ID NO: 75
CTNYAPKLRSMMRGEI

SEQ ID NO: 76
CTNYAPNLRSDMRGEI

SEQ ID NO: 77
TRPNNNT

SEQ ID NO: 78
TRPSNNT

SEQ ID NO: 79
TGDIIGDIRQAHCNVS

SEQ ID NO: 80
FGDIIGDIRMAHCNVS

SEQ ID NO: 81
FGDVLGDVRMAHCNIS

SEQ ID NO: 82
FGDVLGHVRMAHCNIS

SEQ ID NO: 83
FGDVLGDVDMAKCTIS

SEQ ID NO: 84
SITLPCR

SEQ ID NO: 85
SIVLPCR

-continued

```
                                    SEQ ID NO: 86
SLILPCR

SEQ ID NO: 87
SLILPCW

HCDR3 of BG18 iGL0
                                    SEQ ID NO: 88
ARNAITIFGVVIIGEYYYYGMDV;

HCDR3 of HMP1
                                    SEQ ID NO: 89
AREGFTIFGVVTFSEGYYYYGMDV;

HCDR3 of HMP42
                                    SEQ ID NO: 90
ARDRGREWELESYYYYYMDV;

HCDR3 of HMP43
                                    SEQ ID NO: 91
AKDIESRYFDWDNYYYYGMDV;

VH4-4
                                    SEQ ID NO: 92

VL3-25
                                    SEQ ID NO: 93

BG18 VH CDR3
                                    SEQ ID NO: 94
ARNAIRIYGVVALGEWFHYGMDV;

BG18 iGL1 VH CDR3
                                    SEQ ID NO: 95
ARNAITIFGVVILGEYYYYGMDV;

BG18 iGL2 VH CDR3
                                    SEQ ID NO: 96
ARNAITIFGVVALGEYYYYGMDV;

Pre1 VH CDR3
                                    SEQ ID NO: 97
ARGQRTIFGVVILFNYYYYGMDV;

Pre2 VH CDR3
                                    SEQ ID NO: 98
ARDLLTSFGVVIFSQHKSYGMDV;

Pre3 VH CDR3
                                    SEQ ID NO: 99
ARDSITIFGVVILQDYYYYGMDV;

Pre4 VH CDR3
                                    SEQ ID NO: 100
ARERDTIFGVVSLRVYYYYGMDV;

Pre5 VH CDR3
                                    SEQ ID NO: 101
ARDKDTIFGVVIIGEYYYYGMDV;

Pre6 VH CDR3
                                    SEQ ID NO: 102
ARGSITIFGVVIILEDYYYYGMDV;

Pre7 VH CDR3
                                    SEQ ID NO: 103
AREQRAIFGVVIIREDYYYGMDV;

Pre8 VH CDR3
                                    SEQ ID NO: 104
ARARLRVFGVVIFLYGYYYGMDV;

Pre9 VH CDR3
                                    SEQ ID NO: 105
ARDRKRFFGVVIMDESYYYGMDV;

Pre10 VH CDR3
                                    SEQ ID NO: 106
ARDGVKIFGVVIIREAYYYGMDV;
```

-continued

Pre11 VH CDR3
SEQ ID NO: 107
ARDGIKIFGVVIMGEAHYYGMDV;

Pre12 VH CDR3
SEQ ID NO: 108
AKGRGTIFGVVRFYENYYYGMDV;

Pre13 VH CDR3
SEQ ID NO: 109
AKALNTIFGVVTLTQYYYYGMDV;

Pre14 VH CDR3
SEQ ID NO: 110
ARGRITIFGVVTLRGYYYYGMDV;

Pre15 VH CDR3
SEQ ID NO: 111
ARDIHNSFGVVSLDQNYYYGMDV;

The invention is further described by the following numbered paragraphs:

1. An isolated polypeptide comprising a variant HIV Env gp120 polypeptide, wherein the variant HIV Env gp120 polypeptide comprises one or more of
   (a) a V1 loop comprising positions 131-154, wherein the V1 loop comprises an amino acid sequence of
      (i) CTNVTNNITDDMRGEL (SEQ ID NO: 71) comprising 0, 1, 2, 3, 4, or 5 insertion, deletion, or substitution,
      (ii) CTNYAPNLLSNMRGEL (SEQ ID NO: 72) comprising 0, 1, 2, 3, 4, or 5 insertion, deletion, or substitution,
      (iii) CTNYAPNLLSNMRGEI (SEQ ID NO: 73) comprising 0, 1, 2, 3, 4, or 5 insertion, deletion, or substitution,
      (iv) CTNYAPKLLSNMRGEI (SEQ ID NO: 74) comprising 0, 1, 2, 3, 4, or 5 insertion, deletion, or substitution,
      (v) CTNYAPKLRSMMRGEI (SEQ ID NO: 75) comprising 0, 1, 2, 3, 4, or 5 insertion, deletion, or substitution, or
      (vi) CTNYAPNLRSDMRGEI (SEQ ID NO: 76) comprising 0, 1, 2, 3, 4, or 5 insertion, deletion, or substitution;
   (b) a V3 loop comprising positions 297-334, wherein positions 297-303 of the V3 loop comprises an amino acid sequence of
      (i) TRPNNNT (SEQ ID NO: 77) comprising 0, 1, 2, 3, 4, or 5 insertion, deletion, or substitution, or
      (ii) TRPSNNT (SEQ ID NO: 78) comprising 0, 1, 2, 3, 4, or 5 insertion, deletion, or substitution;
   (c) a V3 loop comprising positions 297-334, wherein positions 319-334 of the V3 loop comprises an amino acid sequence of
      (i) TGDIIGDIRQAHCNVS (SEQ ID NO: 79) comprising 0, 1, 2, 3, 4, or 5 insertion, deletion, or substitution,
      (ii) FGDIIGDIRMAHCNVS (SEQ ID NO: 80) comprising 0, 1, 2, 3, 4, or 5 insertion, deletion, or substitution,
      (iii) FGDVLGDVRMAHCNIS (SEQ ID NO: 81) comprising 0, 1, 2, 3, 4, or 5 insertion, deletion, or substitution,
      (iv) FGDVLGHVRMAHCNIS (SEQ ID NO: 82) comprising 0, 1, 2, 3, 4, or 5 insertion, deletion, or substitution, or
      (v) FGDVLGDVDMAKCTIS (SEQ ID NO: 83) comprising 0, 1, 2, 3, 4, or 5 insertion, deletion, or substitution; and
   (d) a β19 sheet comprising positions 413-419, wherein the β19 sheet comprises an amino acid sequence of
      (i) SITLPCR (SEQ ID NO: 84) comprising 0, 1, 2, 3, 4, or 5 insertion, deletion, or substitution,
      (ii) SIVLPCR (SEQ ID NO: 85) comprising 0, 1, 2, 3, 4, or 5 insertion, deletion, or substitution,
      (iii) SLILPCR (SEQ ID NO: 86) comprising 0, 1, 2, 3, 4, or 5 insertion, deletion, or substitution, or
      (iv) SLILPCW (SEQ ID NO: 87) comprising 0, 1, 2, 3, 4, or 5 insertion, deletion, or substitution;
   wherein HIV Env gp120 polypeptide positions correspond to the HXB2 reference.

2. An isolated polypeptide comprising a variant HIV Env gp120 polypeptide, wherein the variant HIV Env gp120 polypeptide comprises
   (a) a V1 loop comprising positions 131-154, wherein the V1 loop comprises an amino acid sequence of
      (i) CTNVTNNITDDMRGEL (SEQ ID NO: 71) comprising 0, 1, 2, 3, 4, or 5 insertion, deletion, or substitution,
      (ii) CTNYAPNLLSNMRGEL (SEQ ID NO: 72) comprising 0, 1, 2, 3, 4, or 5 insertion, deletion, or substitution,
      (iii) CTNYAPNLLSNMRGEI (SEQ ID NO: 73) comprising 0, 1, 2, 3, 4, or 5 insertion, deletion, or substitution,
      (iv) CTNYAPKLLSNMRGEI (SEQ ID NO: 74) comprising 0, 1, 2, 3, 4, or 5 insertion, deletion, or substitution,
      (v) CTNYAPKLRSMMRGEI (SEQ ID NO: 75) comprising 0, 1, 2, 3, 4, or 5 insertion, deletion, or substitution, or
      (vi) CTNYAPNLRSDMRGEI (SEQ ID NO: 76) comprising 0, 1, 2, 3, 4, or 5 insertion, deletion, or substitution;
   (b) a V3 loop comprising positions 297-334, wherein positions 297-303 of the V3 loop comprises an amino acid sequence of
      (i) TRPNNNT (SEQ ID NO: 77) comprising 0, 1, 2, 3, 4, or 5 insertion, deletion, or substitution, or
      (ii) TRPSNNT (SEQ ID NO: 78) comprising 0, 1, 2, 3, 4, or 5 insertion, deletion, or substitution;
   (c) a V3 loop comprising positions 297-334, wherein positions 319-334 of the V3 loop comprises an amino acid sequence of (i) TGDIIGDIRQAHCNVS (SEQ ID NO: 79) comprising 0, 1, 2, 3, 4, or 5 insertion, deletion, or substitution,
(ii) FGDIIGDIRMAHCNVS (SEQ ID NO: 80) comprising 0, 1, 2, 3, 4, or 5 insertion, deletion, or substitution,
(iii) FGDVLGDVRMAHCNIS (SEQ ID NO: 81) comprising 0, 1, 2, 3, 4, or 5 insertion, deletion, or substitution,
(iv) FGDVLGHVRMAHCNIS (SEQ ID NO: 82) comprising 0, 1, 2, 3, 4, or 5 insertion, deletion, or substitution, or
(v) FGDVLGDVDMAKCTIS (SEQ ID NO: 83) comprising 0, 1, 2, 3, 4, or 5 insertion, deletion, or substitution; and
(d) a β19 sheet comprising positions 413-419, wherein the β19 sheet comprises an amino acid sequence of
(i) SITLPCR (SEQ ID NO: 84) comprising 0, 1, 2, 3, 4, or 5 insertion, deletion, or substitution,
(ii) SIVLPCR (SEQ ID NO: 85) comprising 0, 1, 2, 3, 4, or 5 insertion, deletion, or substitution,
(iii) SLILPCR (SEQ ID NO: 86) comprising 0, 1, 2, 3, 4, or 5 insertion, deletion, or substitution, or
(iv) SLILPCW (SEQ ID NO: 87) comprising 0, 1, 2, 3, 4, or 5 insertion, deletion, or substitution;
wherein HIV Env gp120 polypeptide positions correspond to the HXB2 reference.

3. An isolated polypeptide comprising a variant HIV Env gp120 polypeptide, wherein the variant HIV Env gp120 polypeptide comprises one or more of
(a) a V1 loop comprising positions 131-154, wherein the V1 loop comprises an amino acid sequence of

```
(i)
                                    (SEQ ID NO: 71)
CTNVTNNITDDMRGEL, (ii)
                                    (SEQ ID NO: 72)
CTNYAPNLLSNMRGEL, (iii)
                                    (SEQ ID NO: 73)
CTNYAPNLLSNMRGEI, (iv)
                                    (SEQ ID NO: 74)
CTNYAPKLLSNMRGEI, (v)
                                    (SEQ ID NO: 75)
CTNYAPKLRSMMRGEI,
or (vi)
                                    (SEQ ID NO: 76)
CTNYAPNLRSDMRGEI;
```

(b) a V3 loop comprising positions 297-334, wherein positions 297-303 of the V3 loop comprises an amino acid sequence of

```
(i)
                                    (SEQ ID NO: 77)
TRPNNNT,
or (ii)
                                    (SEQ ID NO: 78)
TRPSNNT;
```

(c) a V3 loop comprising positions 297-334, wherein positions 319-334 of the V3 loop comprises an amino acid sequence of

```
(i)
                                    (SEQ ID NO: 79)
TGDIIGDIRQAHCNVS, (ii)
                                    (SEQ ID NO: 80)
FGDIIGDIRMAHCNVS, (iii)
                                    (SEQ ID NO: 81)
FGDVLGDVRMAHCNIS, (iv)
                                    (SEQ ID NO: 82)
FGDVLGHVRMAHCNIS,
or (v)
                                    (SEQ ID NO: 83)
FGDVLGDVDMAKCTIS;
``` and
(d) a β19 sheet comprising positions 413-419, wherein the β19 sheet comprises an amino acid sequence of

```
(i)
                                    (SEQ ID NO: 84)
SITLPCR, (ii)
                                    (SEQ ID NO: 85)
SIVLPCR, (iii)
                                    (SEQ ID NO: 86)
SLILPCR,
or (iv)
                                    (SEQ ID NO: 87)
SLILPCW;
``` wherein HIV Env gp120 polypeptide positions correspond to the HXB2 reference.

4. An isolated polypeptide comprising a variant HIV Env gp120 polypeptide, wherein the variant HIV Env gp120 polypeptide comprises
(a) a V1 loop comprising positions 131-154, wherein the V1 loop comprises an amino acid sequence of

```
(i)
                                    (SEQ ID NO: 71)
CTNVTNNITDDMRGEL, (ii)
                                    (SEQ ID NO: 72)
CTNYAPNLLSNMRGEL, (iii)
                                    (SEQ ID NO: 73)
CTNYAPNLLSNMRGEI, (iv)
                                    (SEQ ID NO: 74)
CTNYAPKLLSNMRGEI, (v)
```

```
                                              (SEQ ID NO: 75)
CTNYAPKLRSMMRGEI,
or (vi)
                                              (SEQ ID NO: 76)
CTNYAPNLRSDMRGEI;
```

(b) a V3 loop comprising positions 297-334, wherein positions 297-303 of the V3 loop comprises an amino acid sequence of

```
(i)
                                              (SEQ ID NO: 77)
TRPNNNT,
or (ii)
                                              (SEQ ID NO: 78)
TRPSNNT;
```

(c) a V3 loop comprising positions 297-334, wherein positions 319-334 of the V3 loop comprises an amino acid sequence of

```
(i)
                                              (SEQ ID NO: 79)
TGDIIGDIRQAHCNVS, (ii)
                                              (SEQ ID NO: 80)
FGDIIGDIRMAHCNVS, (iii)
                                              (SEQ ID NO: 81)
FGDVLGDVRMAHCNIS, (iv)
                                              (SEQ ID NO: 82)
FGDVLGHVRMAHCNIS,
or (v)
                                              (SEQ ID NO: 83)
FGDVLGDVDMAKCTIS;
``` and (d) a β19 sheet comprising positions 413-419, wherein the β19 sheet comprises an amino acid sequence of

```
(i)
                                              (SEQ ID NO: 84)
SITLPCR, (ii)
                                              (SEQ ID NO: 85)
SIVLPCR, (iii)
                                              (SEQ ID NO: 86)
SLILPCR,
or (iv)
                                              (SEQ ID NO: 87)
SLILPCW;
``` wherein HIV Env gp120 polypeptide positions correspond to the HXB2 reference.

5. An isolated polypeptide comprising a variant HIV Env gp120 polypeptide, wherein the variant HIV Env gp120 polypeptide comprises a V1 loop comprising positions 131-154, a V3 loop comprising positions 297-334, and a β19 sheet comprising positions 413-419, wherein the V1 loop, positions 297-303 of the V3 loop, positions 319-334 of the V3 loop, and the β19 sheet comprises the amino acid sequence of (a) CTNYAPKLLSNMRGEI (SEQ ID NO: 74), TRPNNNT (SEQ ID NO: 77), FGDVLGHVRMAHCNIS (SEQ ID NO: 82), and SLILPCR (SEQ ID NO: 86), respectively, (b) CTNYAPKLRSMMRGEI (SEQ ID NO: 75), TRPNNNT (SEQ ID NO: 77), FGDVLGDVRMAHCNIS (SEQ ID NO: 81), and SLILPCR (SEQ ID NO: 86), respectively, (c) CTNYAPKLRSMMRGEI (SEQ ID NO: 75), TRPNNNT (SEQ ID NO: 77), FGDVLGHVRMAHCNIS (SEQ ID NO: 82), and SLILPCR (SEQ ID NO: 86), respectively, (d) CTNYAPKLRSMMRGEI (SEQ ID NO: 75), TRPSNNT (SEQ ID NO: 78), FGDVLGHVRMAHCNIS (SEQ ID NO: 82), and SLILPCR (SEQ ID NO: 86), respectively, (e) CTNYAPKLRSMMRGEI (SEQ ID NO: 75), TRPSNNT (SEQ ID NO: 78), FGDVLGHVRMAHCNIS (SEQ ID NO: 82), and SLILPCW (SEQ ID NO: 87), respectively, (f) CTNYAPNLRSDMRGEI (SEQ ID NO: 76), TRPNNNT (SEQ ID NO: 77), FGDVLGDVDMAKCTIS (SEQ ID NO: 83), and SLILPCR (SEQ ID NO: 86), respectively, (g) CTNYAPKLLSNMRGEI (SEQ ID NO: 74) comprising 0, 1, 2, 3, 4, or 5 insertion, deletion, or substitution, TRPNNNT (SEQ ID NO: 77) comprising 0, 1, 2, 3, 4, or 5 insertion, deletion, or substitution, FGDVLGHVRMAHCNIS (SEQ ID NO: 82) comprising 0, 1, 2, 3, 4, or 5 insertion, deletion, or substitution, and SLILPCR (SEQ ID NO: 86) comprising 0, 1, 2, 3, 4, or 5 insertion, deletion, or substitution, respectively, (h) CTNYAPKLRSMMRGEI (SEQ ID NO: 75) comprising 0, 1, 2, 3, 4, or 5 insertion, deletion, or substitution, TRPNNNT (SEQ ID NO: 77) comprising 0, 1, 2, 3, 4, or 5 insertion, deletion, or substitution, FGDVLGDVRMAHCNIS (SEQ ID NO: 81) comprising 0, 1, 2, 3, 4, or 5 insertion, deletion, or substitution, and SLILPCR (SEQ ID NO: 86) comprising 0, 1, 2, 3, 4, or 5 insertion, deletion, or substitution, respectively, (i) CTNYAPKLRSMMRGEI (SEQ ID NO: 75) comprising 0, 1, 2, 3, 4, or 5 insertion, deletion, or substitution, TRPNNNT (SEQ ID NO: 77) comprising 0, 1, 2, 3, 4, or 5 insertion, deletion, or substitution, FGDVLGHVRMAHCNIS (SEQ ID NO: 82) comprising 0, 1, 2, 3, 4, or 5 insertion, deletion, or substitution, and SLILPCR (SEQ ID NO: 86) comprising 0, 1, 2, 3, 4, or 5 insertion, deletion, or substitution, respectively, (j) CTNYAPKLRSMMRGEI (SEQ ID NO: 75) comprising 0, 1, 2, 3, 4, or 5 insertion, deletion, or substitution, TRPSNNT (SEQ ID NO: 78) comprising 0, 1, 2, 3, 4, or 5 insertion, deletion, or substitution, FGDVLGHVRMAHCNIS (SEQ ID NO: 82) comprising 0, 1, 2, 3, 4, or 5 insertion, deletion, or substitution, and SLILPCR (SEQ ID NO: 86) comprising 0, 1, 2, 3, 4, or 5 insertion, deletion, or substitution, respectively, (k) CTNYAPKLRSMMRGEI (SEQ ID NO: 75) comprising 0, 1, 2, 3, 4, or 5 insertion, deletion, or substitution, TRPSNNT (SEQ ID NO: 78) comprising 0, 1, 2, 3, 4, or 5 insertion, deletion, or substitution, FGDVLGHVRMAHCNIS (SEQ ID NO: 82) comprising 0, 1, 2, 3, 4, or 5 insertion, deletion, or substitution, and SLILPCW (SEQ ID NO: 87) comprising 0, 1, 2, 3, 4, or 5 insertion, deletion, or substitution, respectively, or (l) CTNYAPNLRSDMRGEI (SEQ ID NO: 76) comprising 0, 1, 2, 3, 4, or 5 insertion, deletion, or substitution, TRPNNNT (SEQ ID NO: 77) comprising 0, 1, 2, 3, 4, or 5 insertion, deletion, or substitution, FGDVLGDVDMAKCTIS (SEQ ID NO: 83) comprising 0, 1, 2, 3, 4, or 5 insertion, deletion, or substitution, and SLILPCR (SEQ ID NO: 86) comprising 0, 1, 2, 3, 4, or 5 insertion, deletion, or substitution, respectively, and wherein HIV Env gp120 polypeptide positions correspond to the HXB2 reference.

6. An isolated polypeptide comprising a variant HIV Env gp120 polypeptide, wherein the variant HIV Env gp120 polypeptide comprises a V1 loop comprising positions 131-154, a V3 loop comprising positions 297-334, and a β19 sheet comprising positions 413-419, wherein the V1 loop, positions 297-303 of the V3 loop, positions 319-334 of the V3 loop, and the β19 sheet comprises the amino acid sequence of CTNYAPKLLSNMRGEI (SEQ ID NO: 74), TRPNNNT (SEQ ID NO: 77), FGDVLGHVRMAHCNIS (SEQ ID NO: 82), and SLILPCR (SEQ ID NO: 86), respectively, and wherein HIV Env gp120 polypeptide positions correspond to the HXB2 reference.

7. An isolated polypeptide comprising a variant HIV Env gp120 polypeptide, wherein the variant HIV Env gp120 polypeptide comprises a V1 loop comprising positions 131-154, a V3 loop comprising positions 297-334, and a β19 sheet comprising positions 413-419, wherein the V1 loop, positions 297-303 of the V3 loop, positions 319-334 of the V3 loop, and the β19 sheet comprises the amino acid sequence of CTNYAPKLRSMMRGEI (SEQ ID NO: 75), TRPNNNT (SEQ ID NO: 77), FGDVLGDVRMAHCNIS (SEQ ID NO: 81), and SLILPCR (SEQ ID NO: 86), respectively, and wherein HIV Env gp120 polypeptide positions correspond to the HXB2 reference.

8. An isolated polypeptide comprising a variant HIV Env gp120 polypeptide, wherein the variant HIV Env gp120 polypeptide comprises a V1 loop comprising positions 131-154, a V3 loop comprising positions 297-334, and a β19 sheet comprising positions 413-419, wherein the V1 loop, positions 297-303 of the V3 loop, positions 319-334 of the V3 loop, and the β19 sheet comprises the amino acid sequence of CTNYAPKLRSMMRGEI (SEQ ID NO: 75), TRPNNNT (SEQ ID NO: 77), FGDVLGHVRMAHCNIS (SEQ ID NO: 82), and SLILPCR (SEQ ID NO: 86), respectively, and wherein HIV Env gp120 polypeptide positions correspond to the HXB2 reference.

9. An isolated polypeptide comprising a variant HIV Env gp120 polypeptide, wherein the variant HIV Env gp120 polypeptide comprises a V1 loop comprising positions 131-154, a V3 loop comprising positions 297-334, and a β19 sheet comprising positions 413-419, wherein the V1 loop, positions 297-303 of the V3 loop, positions 319-334 of the V3 loop, and the β19 sheet comprises the amino acid sequence of CTNYAPKLRSMMRGEI (SEQ ID NO: 75), TRPSNNT (SEQ ID NO: 78), FGDVLGHVRMAHCNIS (SEQ ID NO: 82), and SLILPCR (SEQ ID NO: 86), respectively, and wherein HIV Env gp120 polypeptide positions correspond to the HXB2 reference.

10. An isolated polypeptide comprising a variant HIV Env gp120 polypeptide, wherein the variant HIV Env gp120 polypeptide comprises a V1 loop comprising positions 131-154, a V3 loop comprising positions 297-334, and a β19 sheet comprising positions 413-419, wherein the V1 loop, positions 297-303 of the V3 loop, positions 319-334 of the V3 loop, and the β19 sheet comprises the amino acid sequence of CTNYAPKLRSMMRGEI (SEQ ID NO: 75), TRPSNNT (SEQ ID NO: 78), FGDVLGHVRMAHCNIS (SEQ ID NO: 82), and SLILPCW (SEQ ID NO: 87), respectively, and wherein HIV Env gp120 polypeptide positions correspond to the HXB2 reference.

11. The isolated polypeptide of any one of paragraphs 1 to 10, wherein the variant HIV Env gp120 polypeptide comprises N332.

12. The isolated polypeptide of any one of paragraphs 1 to 11, wherein the N-terminal residue of the variant HIV Env gp120 polypeptide is one of HIV Env positions 1-35.

13. The isolated polypeptide of any one of paragraphs 1 to 12, wherein the C-terminal residue of the variant HIV Env gp120 polypeptide is one of HIV Env positions 503-512.

14. The isolated polypeptide of any one of paragraphs 1 to 13, wherein the variant HIV Env gp120 polypeptide is a variant of the BG505, BG505 N332, BG505 MD39, BG505 MD64, BG505 MD39 N332, BG505 MD39 11mutB, or BG505 MD39 17mutE gp120 polypeptide.

15. The isolated polypeptide of any one of paragraphs 1 to 13, wherein the variant HIV Env gp120 polypeptide is a variant of the BG505 MD39 N332 gp120 polypeptide.

16. The isolated of any one of paragraphs 1 to 13 wherein the variant HIV Env gp120 polypeptide is a variant of the BG505 MD64 N332 gp120 polypeptide.

17. An isolated polypeptide comprising
   (a) an amino acid sequence having at least about 80%, at least about 90%, at least about 95%, at least about 97%, at least about 99%, or 100% sequence identity to the amino acid sequence of BG505 MD39 N332-GT1,
   (b) an amino acid sequence having at least about 80%, at least about 90%, at least about 95%, at least about 97%, at least about 99%, or 100% sequence identity to the amino acid sequence of BG505 MD39 N332-GT2,
   (c) an amino acid sequence having at least about 80%, at least about 90%, at least about 95%, at least about 97%, at least about 99%, or 100% sequence identity to the amino acid sequence of BG505 MD39 N332-GT3,
   (d) an amino acid sequence having at least about 80%, at least about 90%, at least about 95%, at least about 97%, at least about 99%, or 100% sequence identity to the amino acid sequence of BG505 MD39 N332-GT4,
   (e) an amino acid sequence having at least about 80%, at least about 90%, at least about 95%, at least about 97%, at least about 99%, or 100% sequence identity to the amino acid sequence of BG505 MD39 N332-GT5, or
   (f) an amino acid sequence having at least about 80%, at least about 90%, at least about 95%, at least about 97%, at least about 99%, or 100% sequence identity to the amino acid sequence of BG505 MD39 N332-GT2-KO.
18. An isolated polypeptide comprising an amino acid sequence having at least about 80%, at least about 90%, at least about 95%, at least about 97%, at least about 99%, or 100% sequence identity to the amino acid sequence of BG505 MD39 N332-GT1.
19. An isolated polypeptide comprising an amino acid sequence having at least about 80%, at least about 90%, at least about 95%, at least about 97%, at least about 99%, or 100% sequence identity to the amino acid sequence of BG505 MD39 N332-GT2.
20. An isolated polypeptide comprising an amino acid sequence having at least about 80%, at least about 90%, at least about 95%, at least about 97%, at least about 99%, or 100% sequence identity to the amino acid sequence of BG505 MD39 N332-GT3.
21. An isolated polypeptide comprising an amino acid sequence having at least about 80%, at least about 90%, at least about 95%, at least about 97%, at least about 99%, or 100% sequence identity to the amino acid sequence of BG505 MD39 N332-GT4.
22. An isolated polypeptide comprising an amino acid sequence having at least about 80%, at least about 90%, at least about 95%, at least about 97%, at least about 99%, or 100% sequence identity to the amino acid sequence of BG505 MD39 N332-GT5.
23. An isolated polypeptide comprising an amino acid sequence having at least about 80%, at least about 90%, at least about 95%, at least about 97%, at least about 99%, or 100% sequence identity to the amino acid sequence of BG505 MD64 N332-GT2.
24. An isolated polypeptide comprising a variant HIV Env polypeptide, wherein the variant HIV Env polypeptide comprises
    (a) the amino acid sequence of BG505 MD39 N332-GT1,
    (b) the amino acid sequence of BG505 MD39 N332-GT2,
    (c) the amino acid sequence of BG505 MD39 N332-GT3,
    (d) the amino acid sequence of BG505 MD39 N332-GT4,
    (e) the amino acid sequence of BG505 MD39 N332-GT5, or
    (f) the amino acid sequence of BG505 MD39 N332-GT2-KO.
25. An isolated polypeptide comprising a variant HIV Env polypeptide, wherein the variant HIV Env gp120 polypeptide comprises the amino acid sequence of BG505 MD39 N332-GT1.
26. An isolated polypeptide comprising a variant HIV Env polypeptide, wherein the variant HIV Env gp120 polypeptide comprises the amino acid sequence of BG505 MD39 N332-GT2.
27. An isolated polypeptide comprising a variant HIV Env polypeptide, wherein the variant HIV Env gp120 polypeptide comprises the amino acid sequence of BG505 MD39 N332-GT3.
28. An isolated polypeptide comprising a variant HIV Env polypeptide, wherein the variant HIV Env gp120 polypeptide comprises the amino acid sequence of BG505 MD39 N332-GT4.
29. An isolated polypeptide comprising a variant HIV Env polypeptide, wherein the variant HIV Env gp120 polypeptide comprises the amino acid sequence of BG505 MD39 N332-GT5.
30. An isolated polypeptide comprising a variant HIV Env polypeptide, wherein the variant HIV Env gp120 polypeptide comprises the amino acid sequence of BG505 MD64 N332-GT2.
31. The isolated polypeptide of any one of paragraphs 1 to 30, wherein the variant HIV Env polypeptide comprises K137 and H325.
32. The isolated polypeptide of any one of paragraphs 1 to 30, wherein the variant HIV Env polypeptide comprises K137 and P325.
33. The isolated polypeptide of any one of paragraphs 1 to 30, wherein the variant HIV Env polypeptide comprises K137, M141 and H325.
34. The isolated polypeptide of any one of paragraphs 1 to 30, wherein the variant HIV Env polypeptide comprises K137, R139, M141, and H325.
35. The isolated polypeptide of any one of paragraphs 1 to 30, wherein the variant HIV Env polypeptide comprises K137 and P325.
36. The isolated polypeptide of any one of paragraphs 1 to 30, wherein the variant HIV Env polypeptide comprises K137, M141, and P325.
37. The isolated polypeptide of any one of paragraphs 1 to 30, wherein the variant HIV Env polypeptide comprises K137, R139, M141, and P325.
38. The isolated polypeptide of any one of paragraphs 1 to 37 that specifically binds to the BG18 antibody.
39. The isolated polypeptide of any one of paragraphs 1 to 38 that specifically binds to an antibody selected from the group consisting of BG18.11 and BG18.6.
40. The isolated polypeptide of any one of paragraphs 1 to 39 that specifically binds to an antibody selected from the group consisting of BG18 iGL0, BG18 iGL1, and BG18 iGL2.
41. The isolated polypeptide of any one of paragraphs 1 to 40 that specifically binds to an antibody selected from the group consisting of PRE1, PRE2, PRE3, PRE4, PRE5, PRE6, PRE7, PRE8, PRE9, PRE10, PRE11, PRE12, PRE13, PRE14, and PRE1S.
42. The isolated polypeptide of any one of paragraphs 1 to 41 that specifically binds to the PG121 iGL antibody.
43. The isolated polypeptide of any one of paragraphs 1 to 42 that specifically binds to an antibody comprising the VH and VL of
    (a) VH4-59 and BG18 iGL, respectively;
    (b) VH1-69 and BG18 iGL, respectively;
    (c) VH5-51 and BG18 iGL, respectively;
    (d) VH3-33 and BG18 iGL, respectively;
    (e) VH3-23 and BG18 iGL, respectively;
    (f) BG18 iGL1 and VL3-19, respectively;
    (g) BG18 iGL1 and VL3-10, respectively;
    (h) BG18 iGL1 and VL3-1, respectively;
    (i) BG18 iGL1 and VL3-21, respectively; or
    (j) BG18 iGL1 and VL2-8, respectively.
44. The isolated polypeptide of any one of paragraphs 1 to 43 that comprises a gp140.
45. The isolated polypeptide of any one of paragraphs 1 to 43 that comprises a gp160.
46. A recombinant HIV Env trimer comprising the isolated polypeptide of any one of paragraphs 1 to 45.
47. The recombinant HIV Env trimer of paragraph 46 that is a homotrimer.

48. The recombinant HIV Env trimer of paragraph 46 that is a heterotrimer.
49. The recombinant HIV Env trimer of any one of paragraphs 46 to 48 that comprises gp120-gp41 heterodimers.
50. The recombinant HIV Env trimer of any one of paragraphs 46 to 48 that comprises gp120-gp41 heterodimers wherein the heterodimers are covalently linked.
51. The recombinant HIV Env trimer of any one of paragraphs 46 to 48 that comprises gp120-gp41 fusions.
52. The recombinant HIV Env trimer of any one of paragraphs 46 to 48 that is a stabilized trimer.
53. The recombinant HIV Env trimer of any one of paragraphs 46 to 48 that is an SOSIP, NFL or UFO trimer.
54. The recombinant HIV Env trimer of any one of paragraphs 46 to 48 that is an SOSIP trimer.
55. A nanoparticle comprising the isolated polypeptide of any one of paragraphs 1 to 45.
56. The nanoparticle of paragraph 55, wherein the nanoparticle is a ferritin nanoparticle, an encapsulin nanoparticle, a Sulfur Oxygenase Reductase (SOR) nanoparticle, a lumazine synthase nanoparticle or a pyruvate dehydrogenase nanoparticle.
57. The nanoparticle of paragraph 55, wherein the nanoparticle comprises N332-GT1, N332-GT2, N332-GT3, N332-GT4, or N332-GT5.
58. The nanoparticle of paragraph 55, wherein the nanoparticle is a ferritin nanoparticle.
59. The nanoparticle of paragraph 55, wherein the nanoparticle is a ferritin nanoparticle having at least about 80%, at least about 90%, at least about 95%, at least about 97%, at least about 99%, or 100% sequence identity to the amino acid sequence of the amino acid sequence of SEQ ID NO. 13 or 15.
60. The nanoparticle of paragraph 55, wherein the nanoparticle is a ferritin nanoparticle comprising the amino acid sequence of SEQ ID NO. 13 or 15.
61. An isolated polynucleotide encoding the isolated polypeptide of any one of paragraphs 1 to 45, recombinant HIV Env trimer of any one of paragraphs 46 to 54, or the nanoparticle of paragraph 55 to 60.
62. The isolated polynucleotide of paragraph 61, which is a DNA.
63. The isolated polynucleotide of paragraph 61, which is an mRNA.
64. The isolated polynucleotide of paragraph 63, wherein the mRNA comprises a modified nucleotide.
65. An RNA replicon comprising the isolated polynucleotide of paragraph 61.
66. An isolated vector comprising the polynucleotide of paragraph 61.
67. The isolated vector of paragraph 66, wherein the vector is a viral vector.
68. A recombinant virus comprising the polynucleotide of paragraph 61.
69. The recombinant virus of paragraph 68, which is a recombinant adeno-associated virus (AAV).
70. A host cell comprising the polynucleotide of any one of paragraphs 61 to 64, or the vector of paragraph 66 or paragraph 67.
71. The host cell of paragraph 70, which is selected from the group consisting of E. coli, Pseudomonas, Bacillus, Streptomyces, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.
72. A method of producing the isolated polypeptide of any one of paragraphs 1 to 45, recombinant HIV Env trimer of any one of paragraphs 46 to 54, or the nanoparticle of paragraph 55 to 60 comprising, culturing the host cell of paragraph 71 so that the polynucleotide is expressed and the isolated polypeptide, recombinant HIV Env trimer, or nanoparticle is produced.
73. A VLP comprising the polypeptide of any one of paragraphs 1 to 45.
74. A liposome comprising the polypeptide of any one of paragraphs 1 to 45.
75. A pharmaceutical composition comprising the isolated polypeptide of any one of paragraphs 1 to 45, recombinant HIV Env trimer of any one of paragraphs 46 to 54, the nanoparticle of paragraph any one of paragraphs 55 to 60, the polynucleotide of any one of paragraphs 61 to 64, the vector of paragraph 66 or paragraph 67, the recombinant virus of paragraph 68 or paragraph 69, VLP of paragraph 73, or the liposome of paragraph 74 and a pharmaceutically acceptable excipient.
76. An immunogenic composition comprising the isolated polypeptide of any one of paragraphs 1 to 45, recombinant HIV Env trimer of any one of paragraphs 46 to 54, the nanoparticle of paragraph any one of paragraphs 55 to 60, the polynucleotide of any one of paragraphs 61 to 64, the vector of paragraph 66 or paragraph 67, the recombinant virus of paragraph 68 or paragraph 69, VLP of paragraph 73, or the liposome of paragraph 74 and a pharmaceutically acceptable excipient.
77. The immunogenic composition of paragraph 76, further comprising an adjuvant.
78. The immunogenic composition of paragraph 77, wherein the adjuvant comprises lecithin.
79. The immunogenic composition of paragraph 77, wherein the adjuvant comprises alum.
80. The immunogenic composition of paragraph 77, wherein the adjuvant comprises saponin, cholesterol and phospholipid.
81. The immunogenic composition of paragraph 7, wherein the adjuvant comprises carbomer homopolymer and lecithin.
82. The immunogenic composition of any one of paragraphs 76 to 81 that is capable of eliciting a BG18 like response.
83. The immunogenic composition of any one of paragraphs 76 to 81 that is capable of eliciting a BG18 like response in a human subject.
84. The immunogenic composition of any one of paragraphs 76 to 81 that is capable of eliciting a BG18 like response in BG18$^{gH}$ B cell adoptive transfer recipient mice.
85. The immunogenic composition of any one of paragraphs 76 to 81 that is capable of eliciting the production of an antibody that binds to N332-GT2.
86. The immunogenic composition of any one of paragraphs 76 to 81 that is capable of eliciting the production of an antibody that binds to N332-GT2 with a higher affinity than to N332-GT2-KO.
87. The immunogenic composition of any one of paragraphs 76 to 81 that is capable of eliciting the production of a broadly neutralizing antibody in a subject.
88. A method for eliciting an immune response to HIV Env gp120 in a subject, comprising administering to the subject an effective amount of the immunogenic composition of any one of paragraphs 76 to 81, thereby generating the immune response.
89. The method of paragraph 88, wherein the subject is a human.

90. The method of paragraph 88, wherein the subject is a non-human primate.

91. The method of paragraph 88, wherein the subject is a BG18$^{gH}$ B cell adoptive transfer recipient mouse.

92. The method of paragraph 88, wherein the subject is a mouse.

93. A method of reducing the likelihood of HIV infection in a subject exposed to HIV comprising administering to the subject an effective amount of the immunogenic composition of any one of paragraphs 76 to 81, or the pharmaceutical composition of paragraph 75.

94. A method of reducing the risk of a subject becoming infected with HIV comprising administering to the subject in need thereof an effective amount of the immunogenic composition of any one of paragraphs 76 to 81, or the pharmaceutical composition of paragraph 75.

95. A method of preventing HIV infection comprising administering to a subject in need thereof an effective amount of the immunogenic composition of any one of paragraphs 76 to 81, or the pharmaceutical composition of paragraph 75.

96. A method of treating HIV/AIDS comprising administering to a subject in need thereof an effective amount of the immunogenic composition of any one of paragraphs 76 to 81, or the pharmaceutical composition of paragraph 75.

97. The method of any one of paragraphs 88 to 96, wherein the immunogenic composition comprises the isolated polypeptide of any one of paragraphs 1 to 45.

98. The method of any one of paragraphs 88 to 96, wherein the immunogenic composition comprises the recombinant HIV Env trimer of any one of paragraphs 46 to 54.

99. The method of any one of paragraphs 88 to 96, wherein the immunogenic composition comprises the nanoparticle of any one of paragraphs 55 to 60.

100. The method of any one of paragraphs 88 to 96, wherein the immunogenic composition comprises the polynucleotide of any one of paragraphs 61 to 64.

101. The method of any one of paragraphs 88 to 96, wherein the immunogenic composition comprises the vector of any one of paragraphs 66 to 67.

102. The method of any one of paragraphs 88 to 96, wherein the pharmaceutical composition comprises the recombinant virus of any one of paragraphs 68 to 69.

103. The method of any one of paragraphs 88 to 102, further comprising administering at least one additional therapeutic agent.

104. The method of paragraph 103, wherein the additional therapeutic agent comprises an antiretroviral agent.

105. The method of paragraph 103 or 104, wherein the additional therapeutic agent comprises a broadly neutralizing anti-HIV antibody.

106. The method of any one of paragraphs 88 to 105, wherein the subject is a human.

107. The method of any one of paragraphs 88 to 105, wherein the subject is a non-human primate.

108. An isolated antibody comprising
(a) the VHCDR1, VH CDR2, and VH CDR3 of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE1S, VH4-595, VH1-69, VH5-51, VH3-33, or VH3-23; and
(b) the VL CDR1, VL CDR2, and VL CDR3 of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE1S, VL3-10, VL3-19, VL3-1, VL3-21, or VL2-8.

109. An isolated antibody comprising the VH CDR1, VH CDR2, VH CDR3, VL CDR1, VL CDR2, and VL CDR3 of BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, or PRE15.

110. An isolated antibody comprising the 3 VH CDRs and 3 VL CDRs of
(a) VH4-59 and BG18 iGL, respectively;
(b) VH1-69 and BG18 iGL, respectively;
(c) VH5-51 and BG18 iGL, respectively;
(d) VH3-33 and BG18 iGL, respectively;
(e) VH3-23 and BG18 iGL, respectively;
(f) BG18 iGL1 and VL3-19, respectively;
(g) BG18 iGL1 and VL3-10, respectively;
(h) BG18 iGL1 and VL3-1, respectively;
(i) BG18 iGL1 and VL3-21, respectively; or
(j) BG18 iGL1 and VL2-8, respectively.

111. An isolated antibody comprising
(a) the VH of BG18,BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VH4-595, VH1-69, VH5-51, VH3-33, or VH3-23; and
(b) the VL of BG18, BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, PRE15, VL3-10, VL3-19, VL3-1, VL3-21, or VL2-8.

112. An isolated antibody comprising the VH and VL of BG18.11, BG18.6, BG18 iGL0, BG18 iGL1, BG18 iGL2, PRE1, PRE2, PRE3, PRE4, PRE5, PRE6, PRE7, PRE8, PRE9, PRE10, PRE11, PRE12, PRE13, PRE14, or PRE15.

113. An isolated antibody comprising the VH and VL of
(a) VH4-59 and BG18 iGL, respectively;
(b) VH1-69 and BG18 iGL, respectively;
(c) VH5-51 and BG18 iGL, respectively;
(d) VH3-33 and BG18 iGL, respectively;
(e) VH3-23 and BG18 iGL, respectively;
(f) BG18 iGL1 and VL3-19, respectively;
(g) BG18 iGL1 and VL3-10, respectively;
(h) BG18 iGL1 and VL3-1, respectively;
(i) BG18 iGL1 and VL3-21, respectively; or
(j) BG18 iGL1 and VL2-8, respectively.

114. A method for identifying a vaccine candidate variant HIV Env gp120 polypeptide, the method comprising
(a) providing a library comprising a plurality of variant HIV Env gp120 polypeptides;
(b) contacting the library with an antibody according to any one of paragraphs 107 to 109; and
(c) identifying a variant HIV Env gp120 polypeptide that specifically binds to the antibody.

115. The method of paragraph 110, wherein the plurality of variant HIV Env gp120 polypeptides comprise variants of a parental HIV Env gp120 polypeptide comprising one or more amino acid substitutions at a region selected from the V1 loop comprising positions 131-154, V3 loop comprising positions 297-334, and β19 sheet comprising positions 413-419, wherein HIV Env gp120 polypeptide positions correspond to the HXB2 reference.

116. The method of paragraph 111, wherein the parental HIV Env gp120 polypeptide comprises BG505, BG505 N332, BG505 MD39, BG505 MD39 N332, BG505 MD39 11mutB, or BG505 MD39 17mutE gp120 polypeptide.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated polypeptide comprising a variant HIV Env gp120 polypeptide, wherein the variant HIV Env gp120 polypeptide comprises
a V1 loop comprising positions 131-154,
a V3 loop -continued SLILPCR,
respectively, or (z)

CTNYAPKLRSMMRGEI, (SEQ ID NO: 75)

TRPNNNT, (SEQ ID NO: 77)

FGDVLGDVRMAHCNIS, and (SEQ ID NO: 81)

SLILPCR, (SEQ ID NO: 86)
respectively, and wherein HIV Env gp120 polypeptide positions correspond to the HXB2 reference.

2. The isolated polypeptide of claim 1, wherein the variant HIV Env gp120 polypeptide comprises N332.

3. The isolated polypeptide of claim 1, wherein the N-terminal residue of the variant HIV Env gp120 polypeptide is one of HIV Env positions 1-35, wherein HIV Env gp120 polypeptide positions correspond to the HXB2 reference.

4. The isolated polypeptide of claim 1, wherein the C-terminal residue of the variant HIV Env gp120 polypeptide is one of HIV Env positions 503-512, wherein HIV Env gp120 polypeptide positions correspond to the HXB2 reference.

5. The isolated polypeptide of claim 1, wherein the variant HIV Env gp120 polypeptide is a variant of the BG505 MD39 N332 gp120 polypeptide having the sequence of SEQ ID NO: 6, 7, 8, 9, 10, or 11.

6. The isolated polypeptide of claim 1, wherein the variant HIV Env gp120 polypeptide is a variant of the BG505 MD64 N332 gp120 polypeptide having the sequence of SEQ ID NO: 12.

7. A recombinant HIV Env trimer comprising the isolated polypeptide of claim 1.

8. The recombinant HIV Env trimer of claim 7, wherein the recombinant HIV Env trimer is:
a homotrimer or a heterotrimer;
wherein the heterotrimer comprises:
gp120-gp41 heterodimers,
wherein the gp120-gp41 heterodimers are covalently linked; or
gp120-gp41 fusions.

9. A nanoparticle comprising the isolated polypeptide of claim 1.

10. The nanoparticle of claim 9, wherein the nanoparticle is a ferritin nanoparticle having at least about 80%, at least about 90%, at least about 95%, at least about 97%, at least about 99%, or 100% sequence identity to the amino acid sequence of the amino acid sequence of SEQ ID NO. 13 or 15.

11. The nanoparticle of claim 9, wherein the nanoparticle is an encapsulin nanoparticle, a Sulfur Oxygenase Reductase (SOR) nanoparticle, a lumazine synthase nanoparticle or a pyruvate dehydrogenase nanoparticle.

12. The nanoparticle of claim 9, wherein the nanoparticle comprises N332-GT1, N332-GT2, N332-GT3, N332-GT4, or N332-GT5.

13. A pharmaceutical composition comprising the isolated polypeptide of claim 1 and a pharmaceutically acceptable excipient.

14. An immunogenic composition comprising the isolated polypeptide of claim 1 and a pharmaceutically acceptable excipient.

15. The immunogenic composition of claim 14, further comprising an adjuvant comprising lecithin, alum, saponin, cholesterol, phospholipid, or carbomer homopolymer.

16. The recombinant HIV Env trimer of claim 7, wherein the recombinant HIV Env trimer is a SOSIP, NFL or UFO trimer.

* * * * *